United States Patent
Hirayama et al.

(10) Patent No.: US 9,957,251 B2
(45) Date of Patent: May 1, 2018

(54) HETEROCYCLIC COMPOUND

(71) Applicant: Takeda Pharmaceutical Company Limited, Osaka (JP)

(72) Inventors: Takaharu Hirayama, Fujisawa (JP); Jun Fujimoto, Fujisawa (JP); Douglas Robert Cary, Fujisawa (JP); Masanori Okaniwa, Cambridge, MA (US); Yasuhiro Hirata, Fujisawa (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days. days.

(21) Appl. No.: 15/304,623

(22) PCT Filed: Apr. 16, 2015

(86) PCT No.: PCT/JP2015/061660
§ 371 (c)(1),
(2) Date: Oct. 17, 2016

(87) PCT Pub. No.: WO2015/159938
PCT Pub. Date: Oct. 22, 2015

(65) Prior Publication Data
US 2017/0044132 A1 Feb. 16, 2017

(30) Foreign Application Priority Data
Apr. 18, 2014 (JP) ................. 2014-086927

(51) Int. Cl.
| | |
|---|---|
| C07D 401/04 | (2006.01) |
| C07D 401/14 | (2006.01) |
| C07D 405/14 | (2006.01) |
| C07D 413/14 | (2006.01) |
| C07D 491/08 | (2006.01) |
| A61K 31/4439 | (2006.01) |
| A61K 31/444 | (2006.01) |
| A61K 31/4545 | (2006.01) |
| A61K 31/4704 | (2006.01) |
| A61K 31/4725 | (2006.01) |
| A61K 31/496 | (2006.01) |
| A61K 31/4985 | (2006.01) |
| A61K 31/499 | (2006.01) |
| A61K 31/5377 | (2006.01) |
| A61K 31/5386 | (2006.01) |
| A61K 31/541 | (2006.01) |
| A61K 31/553 | (2006.01) |
| C07D 409/04 | (2006.01) |
| C07D 409/14 | (2006.01) |
| C07D 417/04 | (2006.01) |
| C07D 417/14 | (2006.01) |
| C07D 471/04 | (2006.01) |
| C07D 487/04 | (2006.01) |
| C07D 487/08 | (2006.01) |

(Continued)

(52) U.S. Cl.
CPC .......... *C07D 401/04* (2013.01); *A61K 31/444* (2013.01); *A61K 31/4439* (2013.01); *A61K 31/4545* (2013.01); *A61K 31/4704* (2013.01); *A61K 31/4725* (2013.01); *A61K 31/496* (2013.01); *A61K 31/499* (2013.01); *A61K 31/4985* (2013.01); *A61K 31/5377* (2013.01); *A61K 31/5386* (2013.01); *A61K 31/541* (2013.01); *A61K 31/553* (2013.01); *C07D 213/64* (2013.01); *C07D 401/14* (2013.01); *C07D 405/14* (2013.01); *C07D 409/04* (2013.01); *C07D 409/14* (2013.01); *C07D 413/14* (2013.01); *C07D 417/04* (2013.01); *C07D 417/14* (2013.01); *C07D 471/04* (2013.01); *C07D 487/04* (2013.01); *C07D 487/08* (2013.01); *C07D 491/08* (2013.01); *C07D 491/107* (2013.01); *C07D 498/08* (2013.01)

(58) Field of Classification Search
CPC .................................................. C07D 401/04
USPC ......................................................... 546/329
See application file for complete search history.

(56) References Cited

U.S. PATENT DOCUMENTS

2007/0037807 A1 2/2007 Oi et al.
2012/0071477 A1 3/2012 Porter et al.
(Continued)

FOREIGN PATENT DOCUMENTS

WO WO 2005/042488 A1 5/2005
WO WO 2007/077861 A1 7/2007
(Continued)

OTHER PUBLICATIONS

King, Med. Chem., Principle and Practice (1994), pp. 206-208.*
(Continued)

*Primary Examiner* — Taofiq A Solola
(74) *Attorney, Agent, or Firm* — Foley & Lardner LLP

(57) ABSTRACT

The present invention provides a heterocyclic compound having a CDK8 and/or CDK19 inhibitory effect. The present invention provides a compound represented by formula (I)

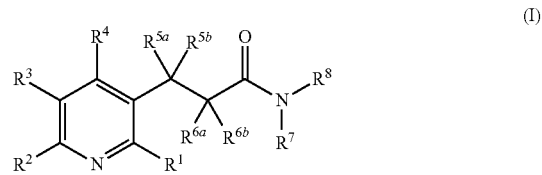

(in the formula, the symbols are as defined in the description) or a salt thereof.

10 Claims, No Drawings

(51) Int. Cl.
*C07D 491/107* (2006.01)
*C07D 498/08* (2006.01)
*C07D 213/64* (2006.01)

(56) References Cited

U.S. PATENT DOCUMENTS

2013/0116214 A1 5/2013 Ujikawa et al.
2014/0343029 A1 11/2014 Lan et al.

FOREIGN PATENT DOCUMENTS

| WO | WO 2012/008549 A1 | 1/2012 |
| WO | WO 2013/040059 A1 | 3/2013 |
| WO | WO 2013/116786 A1 | 8/2013 |

OTHER PUBLICATIONS

Joyce et al., Cytokine and Growth factor Revs (2001), vol. 12, pp. 73-90.*
Nozaki et al., Eds., "Hydride Displacement Law," Medicinal Chemistry, Jul. 1, 1995, 98-99, with partial English translation.
Umezawa et al,. "Inhibition of tumor growth by NF-κβ inhibitors," Cancer Science, 2006, 97(10):990-995.
Wermuth, C.G., Ed., "D. Erlenmeyer's extension of the concept of equivalence," The Practice of Medicinal Chemistry, Aug. 15, 1998, 1:235-265, with partial English translation.
Zhang et al., "Oligomannurarate sulfate blocks tumor growth by inhibiting NFκβ activation," Acta Pharmacologica Sinica, 2010, 31:375-381.

\* cited by examiner

HETEROCYCLIC COMPOUND

CROSS-REFERENCE TO RELATED APPLICATIONS

This application is a National Stage application of PCT/JP2015/061660, filed Apr. 16, 2015, which claims priority from Japanese application no. JP 2014-086927, filed Apr. 18, 2014.

TECHNICAL FIELD

The present invention relates to a novel compound or salts thereof which possesses inhibitory activity against cyclin-dependent kinase (hereinafter, also abbreviated to CDK) 8 and/or CDK19. The present invention further relates to a medicament for prevention or treatment of diseases associated with CDK8 and/or CDK19, such as cancer, comprising the compound or salts thereof.

BACKGROUND OF INVENTION

Cyclin-dependent kinases (CDKs) are phosphorylating enzymes that are activated through complex formation with cyclin proteins, and were discovered as factors regulating the cell cycle. At least 21 types of CDKs (CDK1 to 10, 11A, 11B, and 12 to 20) are known for humans.

Human CDK8 (GenBank Accession No.: NM_001260) was discovered as an enzyme that forms a complex with cyclin C and in turn phosphorylates the RNA polymerase C-terminal domain, etc., and is considered to be a factor involved in transcriptional regulation. Human CDK19 (GenBank Accession No.: NM_015076) is a protein having an amino acid sequence of approximately 80% identity to human CDK8.

Patent Reference 1 suggests the possibility that CDK8 and/or CDK19 inhibitory compounds are useful for the treatment or prevention of cancer.

Patent References 2 to 4 disclose a pyridine compound.

CITATION LIST

Patent Literature

[Patent Reference 1] U.S. Patent Publication No. US2012/0071477
[Patent Reference 2] International Publication No. WO2012/008549
[Patent Reference 3] International Publication No. WO2013/040059
[Patent Reference 4] International Publication No. WO2005/042488

SUMMARY OF INVENTION

Technical Problem

The object of the present invention is to provide a compound that possesses potent CDK8 and/or CDK19 inhibitory activity and is suitable for use as a medicament.

Solution to Problem

The present inventors have conducted extensive studies to address the above issues and found that a compound represented by the formula given below possesses CDK8 and/or CDK19 inhibitory activity, resulting in completion of the present invention. Accordingly, the present invention is as follows:

[1] A compound represented by the formula:

[Formula 1]

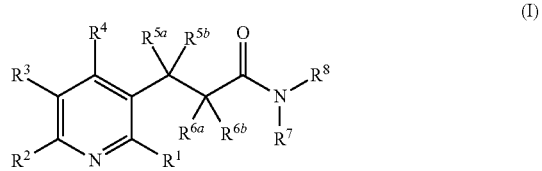

wherein
$R^1$, $R^2$ and $R^3$ each independently represent a hydrogen atom or a substituent;
$R^4$ represents an optionally substituted aromatic heterocyclic group;
$R^{5a}$ and $R^{6a}$ each independently represent a hydrogen atom or a substituent;
$R^{5b}$ and $R^{6b}$ together (i) form a double bond or (ii) form an optionally substituted $C_{3-4}$ cycloalkyl together including the carbon atom to which they are mutually bound, or each independently represent a hydrogen atom or a substituent; and
$R^7$ and $R^8$ each independently represent a hydrogen atom or a substituent, or form an optionally substituted nitrogen-containing heterocycle together including the nitrogen atom to which they are mutually bound,
or a salt thereof (in the present specification, the compound or the salt is also referred to as "compound (I)").

[2] A compound according to the above-mentioned [1] or a salt thereof, wherein $R^1$ is a hydrogen atom.

[3] A compound according to the above-mentioned [1] or [2] or a salt thereof, wherein $R^2$ is a hydrogen atom, a halogen atom, an amino group or a hydroxy group.

[4] A compound according to any of the above-mentioned [1] to [3] or a salt thereof, wherein $R^3$ is a hydrogen atom or a halogen atom.

[5] A compound according to any of the above-mentioned [1] to [4] or a salt thereof, wherein
$R^4$ is pyrazolyl optionally substituted by 1 to 3 substituents selected from the following substituents (1) to (3):
(1) a $C_{1-6}$ alkyl group optionally having 1 to 3 halogen atoms,
(2) a $C_{1-6}$ alkyl group substituted by 1 to 3 halogenated $C_{3-10}$ cycloalkyl groups, and
(3) a $C_{3-10}$ cycloalkyl group.

[6] A compound according to any of the above-mentioned [1] to [5] or a salt thereof, wherein
both of $R^{5a}$ and $R^{6a}$ are both hydrogen atoms, and
$R^{5b}$ and $R^{6b}$ together form a double bond.

[7] A compound according to any of the above-mentioned [1] to [6] or a salt thereof, wherein
either $R^7$ or $R^8$ is a hydrogen atom, and the other is
(I) a $C_{6-14}$ aryl group optionally having 1 to 3 substituents selected from the following (i) and (ii):
(i) a halogen atom, and
(ii) a $C_{1-6}$ alkyl group optionally having 1 to 3 substituents selected from the following (1) to (4):
(1) a halogen atom,
(2) a 3- to 14-membered non-aromatic heterocyclic group optionally having 1 to 3 substituents selected from a halogen atom and a $C_{1-6}$ alkoxy group, (3) a 5- to 14-membered aromatic heterocyclic group, and
(4) a 7- to 10-membered bridged heterocyclic group
(II) a 5- to 14-membered aromatic heterocyclic group optionally having 1 to 3 substituents of the following (i):
    (i) an optionally halogenated $C_{1-6}$ alkyl group; or
(III) a 3- to 14-membered non-aromatic heterocyclic group optionally having 1 to 3 substituents of the following (i):
    (i) a $C_{1-6}$ alkyl group optionally having 1 to 3 halogen atoms.

[8] A compound according to the above-mentioned [1] or a salt thereof, wherein
$R^1$ is a hydrogen atom;
$R^2$ is a hydrogen atom, a halogen atom, an amino group or a hydroxy group;
$R^3$ is a hydrogen atom or a halogen atom;
$R^4$ is a 5- or 6-membered monocyclic aromatic heterocyclic group or an 8- to 14-membered fused polycyclic aromatic heterocyclic group, optionally substituted by 1 to 3 substituents selected from the following substituents (1) to (11):
(1) a $C_{1-6}$ alkyl group optionally having 1 to 7 halogen atoms,
(2) a $C_{1-6}$ alkyl group substituted by 1 to 7 substituents selected from
    (i) a hydroxy group,
    (ii) an amino group,
    (iii) a $C_{1-6}$ alkoxy group,
    (iv) an optionally halogenated $C_{3-10}$ cycloalkyl group,
    (v) a 5- to 14-membered aromatic heterocyclic group,
    (vi) a 3- to 14-membered non-aromatic heterocyclic group,
    (vii) a $C_{1-6}$ alkoxy-carbonyl group, and
    (viii) a carbamoyl group,
(3) a $C_{3-10}$ cycloalkyl group,
(4) a $C_{7-16}$ aralkyl group optionally substituted by 1 to 7 substituents selected from the following (i) to (iii):
    (i) a halogen atom,
    (ii) an optionally halogenated $C_{1-6}$ alkyl group, and
    (iii) a cyano group,
(5) a 3- to 14-membered non-aromatic heterocyclic group,
(6) a $C_{1-6}$ alkyl-carbonyl group,
(7) a $C_{1-6}$ alkoxy group,
(8) a $C_{1-6}$ alkoxy-carbonyl group,
(9) a carbamoyl group,
(10) a cyano group, and
(11) a halogen atom;
$R^{5a}$ and $R^{6a}$ are each independently a hydrogen atom or a $C_{1-6}$ alkyl group;
$R^{5b}$ and $R^{6b}$ are both hydrogen atoms, or $R^{5b}$ and $R^{6b}$ together (i) form a double bond or (ii) form a $C_{3-4}$ cycloalkyl including the carbon atom to which they are mutually bound; and
either $R^7$ or $R^8$ is a hydrogen atom, and the other is a substituent, wherein the substituent is
(I) a $C_{6-14}$ aryl group optionally having 1 to 3 substituents selected from the following (i) to (xvii):
    (i) a halogen atom,
    (ii) a cyano group,
    (iii) a hydroxy group,
    (iv) a $C_{1-6}$ alkoxy group optionally having 1 to 3 substituents selected from a halogen atom, a $C_{1-6}$ alkoxy group, a mono- or di-$C_{1-6}$ alkyl-amino group and a $C_{3-10}$ cycloalkyl group,
    (v) a 5- to 14-membered aromatic heterocyclyloxy group,
    (vi) a 3- to 14-membered non-aromatic heterocyclic group optionally having 1 to 5 halogen atoms,
    (vii) a 5- to 14-membered aromatic heterocyclic group optionally having 1 to 3 optionally halogenated $C_{1-6}$ alkyl groups,
    (viii) a 3- to 14-membered non-aromatic heterocyclyl-carbonyl group,
    (ix) a $C_{1-6}$ alkoxy-carbonyl group,
    (x) a carbamoyl group,
    (xi) a $C_{1-6}$ alkylsulfonyl group,
    (xii) a $C_{1-6}$ alkyl-carbonylamino group,
    (xiii) a ($C_{1-6}$ alkyl)($C_{1-6}$ alkyl-carbonyl)amino group,
    (xiv) a $C_{1-6}$ alkylsulfonylamino group,
    (xv) a sulfamoyl group,
    (xvi) a $C_{3-10}$ cycloalkyl group, and
    (xvii) a $C_{1-6}$ alkyl group optionally having 1 to 7 substituents selected from the following (1) to (10):
        (1) a halogen atom,
        (2) a cyano group,
        (3) a hydroxy group,
        (4) a 3- to 14-membered non-aromatic heterocyclic group optionally having 1 to 5 substituents selected from an optionally hydroxy group-substituted $C_{1-6}$ alkyl group, a halogen atom, a hydroxy group, a carboxy group, a carbamoyl group, a $C_{1-6}$ alkoxy group and an oxo group,
        (5) an optionally halogenated $C_{1-6}$ alkoxy group,
        (6) a $C_{1-6}$ alkylsulfonyl group,
        (7) 2-oxa-7-azaspiro[3.5]nonyl or 2-oxa-6-azaspiro[3.3]heptanyl,
        (8) a 5- to 14-membered aromatic heterocyclic group optionally having 1 to 3 substituents selected from an amino group and a $C_{1-6}$ alkyl group,
        (9) a 7- to 10-membered bridged heterocyclic group optionally having 1 to 3 $C_{1-6}$ alkyl groups, and
        (10) an amino group optionally mono- or di-substituted by a substituent selected from the following (a) to (0:
            (a) a $C_{1-6}$ alkyl-carbonyl group,
            (b) a $C_{1-6}$ alkoxy-carbonyl group,
            (c) a $C_{1-6}$ alkyl group optionally having 1 to 5 substituents selected from a halogen atom, a cyano group, a hydroxy group, a $C_{1-6}$ alkoxy group, a carboxy group, a $C_{1-6}$ alkylsulfonyl group, a $C_{1-6}$ alkyl-carbonylamino group, a $C_{1-6}$ alkyl-sulfamoyl group and a 3- to 14-membered non-aromatic heterocyclic group,
            (d) an optionally halogenated $C_{3-10}$ cycloalkyl group,
            (e) a 5- to 14-membered aromatic heterocyclic group, and
            (f) a 3- to 14-membered non-aromatic heterocyclic group optionally having 1 to 3 substituents selected from a $C_{1-6}$ alkyl group and an oxo group;
(II) a 5- to 14-membered aromatic heterocyclic group optionally having 1 to 3 substituents selected from the following (i) to (iv):
    (i) a carbamoyl group,
    (ii) an optionally halogenated $C_{1-6}$ alkyl group,
    (iii) a $C_{3-10}$ cycloalkyl-$C_{1-6}$ alkyl group, and
    (iv) a 3- to 14-membered non-aromatic heterocyclyl-$C_{1-6}$ alkyl group;
(III) a 3- to 14-membered non-aromatic heterocyclic group optionally having 1 to 3 substituents selected from the following (i) to (viii):
    (i) a halogen atom,
    (ii) an oxo group,
    (iii) a $C_{1-6}$ alkyl group optionally having 1 to 5 substituents selected from a halogen atom, a hydroxy group and a $C_{1-6}$ alkoxy group,
    (iv) a $C_{3-10}$ cycloalkyl-$C_{1-6}$ alkyl group optionally having 1 to 5 halogen atoms,
    (v) an optionally halogenated $C_{1-6}$ alkyl-carbonyl group,
    (vi) a $C_{1-6}$ alkoxy-carbonyl group, (vii) a $C_{3-10}$ cycloalkyl-carbonyl group, and
(viii) a 3- to 14-membered non-aromatic heterocyclyl-carbonyl group optionally having 1 to 3 $C_{1-6}$ alkyl groups;
(IV) a $C_{6-14}$ aryl-$C_{3-10}$ cycloalkyl group;
(V) a $C_{7-16}$ aralkyl group optionally having 1 to 3 substituents selected from the following (i) to (iii):
  (i) a cyano group,
  (ii) an optionally hydroxy group-substituted $C_{1-6}$ alkyl group, and
  (iii) an optionally halogenated $C_{1-6}$ alkoxy group;
(VI) a 5- to 14-membered aromatic heterocyclyl-$C_{1-6}$ alkyl group;
(VII) a 3- to 14-membered non-aromatic heterocyclyl-$C_{1-6}$ alkyl group optionally having 1 to 3 $C_{1-6}$ alkyl groups; or
(VIII) dihydroindenyl or tetrahydronaphthalenyl optionally having a substituent selected from a $C_{1-6}$ alkyl group and an oxo group.

[9] (2E)-3-(4-(1-Methyl-1H-pyrazol-4-yl)pyridin-3-yl)-N-(2-(2,2,2-trifluoroethyl)-2,3-dihydro-1H-isoindol-5-yl)acrylamide or a salt thereof.

[10] (2E)-3-(4-(1-Cyclopropyl-1H-pyrazol-4-yl)pyridin-3-yl)-N-(4-((3,3-difluoroazetidin-1-yl)methyl)phenyl)acrylamide or a salt thereof.

[11] (2E)-3-(4-(1-Cyclopropyl-1H-pyrazol-4-yl)-5-fluoropyridin-3-yl)-N-(2-fluoro-4-((3-methoxyazetidin-1-yl)methyl)phenyl)acrylamide or a salt thereof.

[12] (2E)-3-(4-(1-Cyclopropyl-1H-pyrazol-4-yl)-5-fluoropyridin-3-yl)-N-(4-((3-methoxyazetidin-1-yl)methyl)phenyl)acrylamide or a salt thereof.

[13] (2E)-N-(4-((3,3-Difluoroazetidin-1-yl)methyl)phenyl)-3-(5-fluoro-4-(1-methyl-1H-pyrazol-4-yl)pyridin-3-yl)acrylamide or a salt thereof.

[14] A medicament comprising a compound according to any of the above-mentioned [1] to [13] or a salt thereof.

[15] A medicament according to the above-mentioned [14], wherein the medicament is an inhibitor of CDK8 and/or CDK19.

[16] A medicament according to the above-mentioned [14] or [15], wherein the medicament is a preventive or therapeutic agent for cancer.

[17] A method for inhibiting CDK8 and/or CDK19 in a mammal, comprising administering an effective amount of a compound according to any of the above-mentioned [1] to [13] or a salt thereof to the mammal.

[18] A method for preventing or treating cancer in a mammal, comprising administering an effective amount of a compound according to any of the above-mentioned [1] to [13] or a salt thereof to the mammal.

[19] A compound according to any of the above-mentioned [1] to [13] or a salt thereof for use in prevention or treatment of cancer.

[20] Use of a compound according to any of the above-mentioned [1] to [13] or a salt thereof for production of a preventive or therapeutic agent for cancer.

Effects of the Invention

The compound or the medicament of the present invention possesses potent inhibitory activity against CDK8 and/or CDK19 enzyme activity. Thus, the compound or the medicament of the present invention can be used as a CDK8 and/or CDK19 inhibitor and is useful against diseases that may be influenced by CDK8 and/or CDK19, for example, as a preventive or therapeutic agent for cancer.

DETAILED DESCRIPTION OF THE INVENTION

A compound of the present invention, a method for producing the same, and use thereof are described in detail in the following.

The definition of each substituent used in the present specification is described in detail in the following. Unless otherwise specified, each substituent has the following definition.

In the present specification, examples of the "halogen atom" include fluorine, chlorine, bromine and iodine.

In the present specification, examples of the "$C_{1-6}$ alkyl group" include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl and 2-ethylbutyl.

In the present specification, examples of the "optionally halogenated $C_{1-6}$ alkyl group" include a $C_{1-6}$ alkyl group optionally having 1 to 7, preferably 1 to 5, halogen atoms. Specific examples thereof include methyl, chloromethyl, difluoromethyl, trichloromethyl, trifluoromethyl, ethyl, 2-bromoethyl, 2,2,2-trifluoroethyl, tetrafluoroethyl, pentafluoroethyl, propyl, 2,2-difluoropropyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl and 6,6,6-trifluorohexyl.

In the present specification, examples of the "$C_{2-6}$ alkenyl group" include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl and 5-hexenyl.

In the present specification, examples of the "$C_{2-6}$ alkynyl group" include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and 4-methyl-2-pentynyl.

In the present specification, examples of the "$C_{3-10}$ cycloalkyl group" include cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl and adamantyl.

In the present specification, examples of the "optionally halogenated $C_{3-10}$ cycloalkyl group" include a $C_{3-10}$ cycloalkyl group optionally having 1 to 7, preferably 1 to 5, halogen atoms. Specific examples thereof include cyclopropyl, 2,2-difluorocyclopropyl, 2,3-difluorocyclopropyl, cyclobutyl, difluorocyclobutyl, cyclopentyl, cyclohexyl, cycloheptyl and cyclooctyl.

In the present specification, examples of the "$C_{3-10}$ cycloalkenyl group" include cyclopropenyl, cyclobutenyl, cyclopentenyl, cyclohexenyl, cycloheptenyl and cyclooctenyl.

In the present specification, examples of the "$C_{6-14}$ aryl group" include phenyl, 1-naphthyl, 2-naphthyl, 1-anthryl, 2-anthryl and 9-anthryl.

In the present specification, examples of the "$C_{7-16}$ aralkyl group" include benzyl, phenethyl, naphthylmethyl and phenylpropyl.

In the present specification, examples of the "$C_{1-6}$ alkoxy group" include methoxy, ethoxy, propoxy, isopropoxy, butoxy, isobutoxy, sec-butoxy, tert-butoxy, pentyloxy and hexyloxy.

In the present specification, examples of the "optionally halogenated $C_{1-6}$ alkoxy group" include a $C_{1-6}$ alkoxy group optionally having 1 to 7, preferably 1 to 5, halogen atoms.

Specific examples thereof include methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy and hexyloxy.

In the present specification, examples of the "$C_{3\text{-}10}$ cycloalkyloxy group" include cyclopropyloxy, cyclobutyloxy, cyclopentyloxy, cyclohexyloxy, cycloheptyloxy and cyclooctyloxy.

In the present specification, examples of the "$C_{1\text{-}6}$ alkylthio group" include methylthio, ethylthio, propylthio, isopropylthio, butylthio, sec-butylthio, tert-butylthio, pentylthio and hexylthio.

In the present specification, examples of the "optionally halogenated $C_{1\text{-}6}$ alkylthio group" include a $C_{1\text{-}6}$ alkylthio group optionally having 1 to 7, preferably 1 to 5, halogen atoms. Specific examples thereof include methylthio, difluoromethylthio, trifluoromethylthio, ethylthio, propylthio, isopropylthio, butylthio, 4,4,4-trifluorobutylthio, pentylthio and hexylthio.

In the present specification, examples of the "$C_{1\text{-}6}$ alkyl-carbonyl group" include acetyl, propanoyl, butanoyl, 2-methylpropanoyl, pentanoyl, 3-methylbutanoyl, 2-methylbutanoyl, 2,2-dimethylpropanoyl, hexanoyl and heptanoyl.

In the present specification, examples of the "optionally halogenated $C_{1\text{-}6}$ alkyl-carbonyl group" include a $C_{1\text{-}6}$ alkyl-carbonyl group optionally having 1 to 7, preferably 1 to 5, halogen atoms. Specific examples thereof include acetyl, chloroacetyl, trifluoroacetyl, trichloroacetyl, propanoyl, butanoyl, pentanoyl and hexanoyl.

In the present specification, examples of the "$C_{1\text{-}6}$ alkoxy-carbonyl group" include methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl and hexyloxycarbonyl.

In the present specification, examples of the "$C_{6\text{-}14}$ aryl-carbonyl group" include benzoyl, 1-naphthoyl and 2-naphthoyl.

In the present specification, examples of the "$C_{7\text{-}16}$ aralkyl-carbonyl group" include phenylacetyl and phenylpropionyl.

In the present specification, examples of the "5- to 14-membered aromatic heterocyclyl-carbonyl group" include nicotinoyl, isonicotinoyl, thenoyl and furoyl.

In the present specification, examples of the "3- to 14-membered non-aromatic heterocyclyl-carbonyl group" include morpholinylcarbonyl, piperidinylcarbonyl and pyrrolidinylcarbonyl.

In the present specification, examples of the "mono- or di-$C_{1\text{-}6}$ alkyl-carbamoyl group" include methylcarbamoyl, ethylcarbamoyl, dimethylcarbamoyl, diethylcarbamoyl and N-ethyl-N-methylcarbamoyl.

In the present specification, examples of the "mono- or di-$C_{7\text{-}16}$ aralkyl-carbamoyl group" include benzylcarbamoyl and phenethylcarbamoyl.

In the present specification, examples of the "$C_{1\text{-}6}$ alkyl-sulfonyl group" include methylsulfonyl, ethylsulfonyl, propylsulfonyl, isopropylsulfonyl, butylsulfonyl, sec-butylsulfonyl and tert-butylsulfonyl.

In the present specification, examples of the "optionally halogenated $C_{1\text{-}6}$ alkyl-sulfonyl group" include a $C_{1\text{-}6}$ alkyl-sulfonyl group optionally having 1 to 7, preferably 1 to 5, halogen atoms. Specific examples thereof include methylsulfonyl, difluoromethylsulfonyl, trifluoromethylsulfonyl, ethylsulfonyl, propylsulfonyl, isopropylsulfonyl, butylsulfonyl, 4,4,4-trifluorobutylsulfonyl, pentylsulfonyl and hexylsulfonyl.

In the present specification, examples of the "$C_{6\text{-}14}$ arylsulfonyl group" include phenylsulfonyl, 1-naphthylsulfonyl and 2-naphthylsulfonyl.

In the present specification, examples of the "substituent" include a halogen atom, a cyano group, a nitro group, an optionally substituted hydrocarbon group, an optionally substituted heterocyclic group, an acyl group, an optionally substituted amino group, an optionally substituted carbamoyl group, an optionally substituted thiocarbamoyl group, an optionally substituted sulfamoyl group, an optionally substituted hydroxy group, an optionally substituted sulfanyl (SH) group and an optionally substituted silyl group.

In the present specification, examples of the "hydrocarbon group" (including the "hydrocarbon group" of the "optionally substituted hydrocarbon group") include a $C_{1\text{-}6}$ alkyl group, a $C_{2\text{-}6}$ alkenyl group, a $C_{2\text{-}6}$ alkynyl group, a $C_{3\text{-}10}$ cycloalkyl group, a $C_{3\text{-}10}$ cycloalkenyl group, a $C_{6\text{-}14}$ aryl group and a $C_{7\text{-}16}$ aralkyl group.

In the present specification, examples of the "optionally substituted hydrocarbon group" include a hydrocarbon group optionally having substituent(s) selected from the following substituent group A.

[Substituent Group A]
(1) a halogen atom,
(2) a nitro group,
(3) a cyano group,
(4) an oxo group,
(5) a hydroxy group,
(6) an optionally halogenated $C_{1\text{-}6}$ alkoxy group,
(7) a $C_{6\text{-}14}$ aryloxy group (e.g., phenoxy, naphthoxy),
(8) a $C_{7\text{-}16}$ aralkyloxy group (e.g., benzyloxy),
(9) a 5- to 14-membered aromatic heterocyclyloxy group (e.g., pyridyloxy),
(10) a 3- to 14-membered non-aromatic heterocyclyloxy group (e.g., morpholinyloxy, piperidinyloxy),
(11) a $C_{1\text{-}6}$ alkyl-carbonyloxy group (e.g., acetoxy, propanoyloxy),
(12) a $C_{6\text{-}14}$ aryl-carbonyloxy group (e.g., benzoyloxy, 1-naphthoyloxy, 2-naphthoyloxy),
(13) a $C_{1\text{-}6}$ alkoxy-carbonyloxy group (e.g., methoxycarbonyloxy, ethoxycarbonyloxy, propoxycarbonyloxy, butoxycarbonyloxy),
(14) a mono- or di-$C_{1\text{-}6}$ alkyl-carbamoyloxy group (e.g., methylcarbamoyloxy, ethylcarbamoyloxy, dimethylcarbamoyloxy, diethylcarbamoyloxy),
(15) a $C_{6\text{-}14}$ aryl-carbamoyloxy group (e.g., phenylcarbamoyloxy, naphthylcarbamoyloxy),
(16) a 5- to 14-membered aromatic heterocyclyl-carbonyloxy group (e.g., nicotinoyloxy),
(17) a 3- to 14-membered non-aromatic heterocyclyl-carbonyloxy group (e.g., morpholinylcarbonyloxy, piperidinylcarbonyloxy),
(18) an optionally halogenated $C_{1\text{-}6}$ alkyl-sulfonyloxy group (e.g., methylsulfonyloxy, trifluoromethylsulfonyloxy),
(19) a $C_{6\text{-}14}$ aryl-sulfonyloxy group optionally substituted by a $C_{1\text{-}6}$ alkyl group (e.g., phenylsulfonyloxy, toluenesulfonyloxy),
(20) an optionally halogenated $C_{1\text{-}6}$ alkylthio group,
(21) a 5- to 14-membered aromatic heterocyclic group,
(22) a 3- to 14-membered non-aromatic heterocyclic group,
(23) a formyl group,
(24) a carboxy group,
(25) an optionally halogenated $C_{1\text{-}6}$ alkyl-carbonyl group,
(26) a $C_{6\text{-}14}$ aryl-carbonyl group,
(27) a 5- to 14-membered aromatic heterocyclyl-carbonyl group,

(28) a 3- to 14-membered non-aromatic heterocyclyl-carbonyl group,
(29) a $C_{1-6}$ alkoxy-carbonyl group,
(30) a $C_{6-14}$ aryloxy-carbonyl group (e.g., phenyloxycarbonyl, 1-naphthyloxycarbonyl, 2-naphthyloxycarbonyl),
(31) a $C_{7-16}$ aralkyloxy-carbonyl group (e.g., benzyloxycarbonyl, phenethyloxycarbonyl),
(32) a carbamoyl group,
(33) a thiocarbamoyl group,
(34) a mono- or di-$C_{1-6}$ alkyl-carbamoyl group,
(35) a $C_{6-14}$ aryl-carbamoyl group (e.g., phenylcarbamoyl),
(36) a 5- to 14-membered aromatic heterocyclyl-carbamoyl group (e.g., pyridylcarbamoyl, thienylcarbamoyl),
(37) a 3- to 14-membered non-aromatic heterocyclyl-carbamoyl group (e.g., morpholinylcarbamoyl, piperidinylcarbamoyl),
(38) an optionally halogenated $C_{1-6}$ alkyl-sulfonyl group,
(39) a $C_{6-14}$ aryl-sulfonyl group,
(40) a 5- to 14-membered aromatic heterocyclyl-sulfonyl group (e.g., pyridylsulfonyl, thienylsulfonyl),
(41) an optionally halogenated $C_{1-6}$ alkyl-sulfinyl group,
(42) a $C_{6-14}$ arylsulfinyl group (e.g., phenylsulfinyl, 1-naphthylsulfinyl, 2-naphthylsulfinyl),
(43) a 5- to 14-membered aromatic heterocyclyl-sulfinyl group (e.g., pyridylsulfinyl, thienylsulfinyl),
(44) an amino group,
(45) a mono- or di-$C_{1-6}$ alkylamino group (e.g., methylamino, ethylamino, propylamino, isopropylamino, butylamino, dimethylamino, diethylamino, dipropylamino, dibutylamino, N-ethyl-N-methylamino),
(46) a mono- or di-$C_{6-14}$ arylamino group (e.g., phenylamino),
(47) a 5- to 14-membered aromatic heterocyclylamino group (e.g., pyridylamino),
(48) a $C_{7-16}$ aralkylamino group (e.g., benzylamino),
(49) a formylamino group,
(50) a $C_{1-6}$ alkyl-carbonylamino group (e.g., acetylamino, propanoylamino, butanoylamino),
(51) a ($C_{1-6}$ alkyl)($C_{1-6}$ alkyl-carbonyl)amino group (e.g., N-acetyl-N-methylamino),
(52) a $C_{6-14}$ aryl-carbonylamino group (e.g., phenylcarbonylamino, naphthylcarbonylamino),
(53) a $C_{1-6}$ alkoxy-carbonylamino group (e.g., methoxycarbonylamino, ethoxycarbonylamino, propoxycarbonylamino, butoxycarbonylamino, tert-butoxycarbonylamino),
(54) a $C_{7-16}$ aralkyloxy-carbonylamino group (e.g., benzyloxycarbonylamino),
(55) a $C_{1-6}$ alkyl-sulfonylamino group (e.g., methylsulfonylamino, ethylsulfonylamino),
(56) a $C_{6-14}$ aryl-sulfonylamino group optionally substituted by a $C_{1-6}$ alkyl group (e.g., phenylsulfonylamino, toluenesulfonylamino),
(57) an optionally halogenated $C_{1-6}$ alkyl group,
(58) a $C_{2-6}$ alkenyl group,
(59) a $C_{2-6}$ alkynyl group,
(60) a $C_{3-10}$ cycloalkyl group,
(61) a $C_{3-10}$ cycloalkenyl group and
(62) a $C_{6-14}$ aryl group.

The number of the above-mentioned substituents in the "optionally substituted hydrocarbon group" is, for example, 1 to 5, preferably 1 to 3. When the number of the substituents is two or more, the respective substituents may be the same or different.

In the present specification, examples of the "heterocyclic group" (including the "heterocyclic group" of the "optionally substituted heterocyclic group") include (i) an aromatic heterocyclic group, (ii) a non-aromatic heterocyclic group and (iii) a 7- to 10-membered bridged heterocyclic group, each containing, as a ring-constituting atom besides carbon atom, 1 to 4 hetero atoms selected from nitrogen, sulfur and oxygen atoms.

In the present specification, examples of the "aromatic heterocyclic group" (including the "5- to 14-membered aromatic heterocyclic group") include a 5- to 14-membered (preferably 5- to 10-membered) aromatic heterocyclic group containing, as a ring-constituting atom besides carbon atom, 1 to 4 hetero atoms selected from nitrogen, sulfur and oxygen atoms.

Preferable examples of the "aromatic heterocyclic group" include 5- or 6-membered monocyclic aromatic heterocyclic groups such as thienyl, furyl, pyrrolyl, imidazolyl, pyrazolyl, thiazolyl, isothiazolyl, oxazolyl, isoxazolyl, pyridyl, pyrazinyl, pyrimidinyl, pyridazinyl, 1,2,4-oxadiazolyl, 1,3,4-oxadiazolyl, 1,2,4-thiadiazolyl, 1,3,4-thiadiazolyl, triazolyl, tetrazolyl, triazinyl and the like; and 8- to 14-membered fused polycyclic (preferably bi or tricyclic) aromatic heterocyclic groups such as benzothiophenyl, benzofuranyl, benzimidazolyl, benzoxazolyl, benzisoxazolyl, benzothiazolyl, benzisothiazolyl, benzotriazolyl, imidazopyridinyl, thienopyridinyl, furopyridinyl, pyrrolopyridinyl, pyrazolopyridinyl, oxazolopyridinyl, thiazolopyridinyl, imidazopyrazinyl, imidazopyrimidinyl, thienopyrimidinyl, furopyrimidinyl, pyrrolopyrimidinyl, pyrazolopyrimidinyl, oxazolopyrimidinyl, thiazolopyrimidinyl, pyrazolotriazinyl, naphtho[2,3-b]thienyl, phenoxathiinyl, indolyl, isoindolyl, 1H-indazolyl, purinyl, isoquinolyl, quinolyl, phthalazinyl, naphthyridinyl, quinoxalinyl, quinazolinyl, cinnolinyl, carbazolyl, β-carbolinyl, phenanthridinyl, acridinyl, phenazinyl, phenothiazinyl, phenoxazinyl and the like.

In the present specification, examples of the "non-aromatic heterocyclic group" (including the "3- to 14-membered non-aromatic heterocyclic group") include a 3- to 14-membered (preferably 4- to 10-membered) non-aromatic heterocyclic group containing, as a ring-constituting atom besides carbon atom, 1 to 4 hetero atoms selected from nitrogen, sulfur and oxygen atoms.

Preferable examples of the "non-aromatic heterocyclic group" include 3- to 8-membered monocyclic non-aromatic heterocyclic groups such as aziridinyl, oxiranyl, thiiranyl, azetidinyl, oxetanyl, thietanyl, tetrahydrothienyl, tetrahydrofuranyl, pyrrolinyl, pyrrolidinyl, imidazolinyl, imidazolidinyl, oxazolinyl, oxazolidinyl, pyrazolinyl, pyrazolidinyl, thiazolinyl, thiazolidinyl, tetrahydroisothiazolyl, tetrahydrooxazolyl, tetrahydroisooxazolyl, piperidinyl, piperazinyl, tetrahydropyridinyl, dihydropyridinyl, dihydrothiopyranyl, tetrahydropyrimidinyl, tetrahydropyridazinyl, dihydropyranyl, tetrahydropyranyl, tetrahydrothiopyranyl, morpholinyl, thiomorpholinyl, azepanyl, diazepanyl, azepinyl, oxepanyl, azocanyl, diazocanyl and the like; and 9- to 14-membered fused polycyclic (preferably bi or tricyclic) non-aromatic heterocyclic groups such as dihydrobenzofuranyl, dihydrobenzimidazolyl, dihydrobenzoxazolyl, dihydrobenzothiazolyl, dihydrobenzisothiazolyl, dihydronaphtho[2,3-b]thienyl, tetrahydroisoquinolyl, tetrahydroquinolyl, 4H-quinolizinyl, indolinyl, isoindolinyl, tetrahydrothieno[2,3-c]pyridinyl, tetrahydrobenzazepinyl, tetrahydroquinoxalinyl, tetrahydrophenanthridinyl, hexahydrophenothiazinyl, hexahydrophenoxazinyl, tetrahydrophthalazinyl, tetrahydronaphthyridinyl, tetrahydroquinazolinyl, tetrahydrocinnolinyl, tetrahydrocarbazolyl, tetrahydro-β-carbolinyl, tetrahydroacrydinyl, tetrahydrophenazinyl, tetrahydrothioxanthenyl, octahydroisoquinolyl and the like.

In the present specification, preferable examples of the "7- to 10-membered bridged heterocyclic group" include quinuclidinyl and 7-azabicyclo[2.2.1]heptanyl.

In the present specification, examples of the "nitrogen-containing heterocyclic group" include a "heterocyclic group" containing at least one nitrogen atom as a ring-constituting atom.

In the present specification, examples of the "optionally substituted heterocyclic group" include a heterocyclic group optionally having substituent(s) selected from the aforementioned substituent group A.

The number of the substituents in the "optionally substituted heterocyclic group" is, for example, 1 to 3. When the number of the substituents is two or more, the respective substituents may be the same or different.

In the present specification, examples of the "acyl group" include a formyl group, a carboxy group, a carbamoyl group, a thiocarbamoyl group, a sulfino group, a sulfo group, a sulfamoyl group and a phosphono group, each optionally having "1 or 2 substituents selected from a $C_{1-6}$ alkyl group, a $C_{2-6}$ alkenyl group, a $C_{3-10}$ cycloalkyl group, a $C_{3-10}$ cycloalkenyl group, a $C_{6-14}$ aryl group, a $C_{7-16}$ aralkyl group, a 5- to 14-membered aromatic heterocyclic group and a 3- to 14-membered non-aromatic heterocyclic group, each of which optionally has 1 to 3 substituents selected from a halogen atom, an optionally halogenated $C_{1-6}$ alkoxy group, a hydroxy group, a nitro group, a cyano group, an amino group and a carbamoyl group".

Examples of the "acyl group" also include a hydrocarbon-sulfonyl group, a heterocyclyl-sulfonyl group, a hydrocarbon-sulfinyl group and a heterocyclyl-sulfinyl group.

Here, the hydrocarbon-sulfonyl group means a hydrocarbon group-bonded sulfonyl group, the heterocyclyl-sulfonyl group means a heterocyclic group-bonded sulfonyl group, the hydrocarbon-sulfinyl group means a hydrocarbon group-bonded sulfinyl group and the heterocyclyl-sulfinyl group means a heterocyclic group-bonded sulfinyl group.

Preferable examples of the "acyl group" include a formyl group, a carboxy group, a $C_{1-6}$ alkyl-carbonyl group, a $C_{2-6}$ alkenyl-carbonyl group (e.g., crotonoyl), a $C_{3-10}$ cycloalkyl-carbonyl group (e.g., cyclobutanecarbonyl, cyclopentanecarbonyl, cyclohexanecarbonyl, cycloheptanecarbonyl), a $C_{3-10}$ cycloalkenyl-carbonyl group (e.g., 2-cyclohexenecarbonyl), a $C_{6-14}$ aryl-carbonyl group, a $C_{7-16}$ aralkyl-carbonyl group, a 5- to 14-membered aromatic heterocyclyl-carbonyl group, a 3- to 14-membered non-aromatic heterocyclyl-carbonyl group, a $C_{1-6}$ alkoxy-carbonyl group, a $C_{6-14}$ aryloxy-carbonyl group (e.g., phenyloxycarbonyl, naphthyloxycarbonyl), a $C_{7-16}$ aralkyloxy-carbonyl group (e.g., benzyloxycarbonyl, phenethyloxycarbonyl), a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl), a mono- or di-$C_{6-14}$ aryl-carbamoyl group (e.g., phenylcarbamoyl), a mono- or di-$C_{7-16}$ aralkyl-carbamoyl group, a 5- to 14-membered aromatic heterocyclyl-carbamoyl group (e.g., pyridylcarbamoyl), a thiocarbamoyl group, a mono- or di-$C_{1-6}$ alkyl-thiocarbamoyl group (e.g., methylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a 5- to 14-membered aromatic heterocyclyl-thiocarbamoyl group (e.g., pyridylthiocarbamoyl), a sulfino group, a $C_{1-6}$ alkyl-sulfinyl group (e.g., methylsulfinyl, ethylsulfinyl), a sulfo group, a $C_{1-6}$ alkyl-sulfonyl group, a $C_{6-14}$ aryl-sulfonyl group, a phosphono group and a mono- or di-$C_{1-6}$ alkyl-phosphono group (e.g., dimethylphosphono, diethylphosphono, diisopropylphosphono, dibutylphosphono).

In the present specification, examples of the "optionally substituted amino group" include an amino group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclyl-carbonyl group, a 3- to 14-membered non-aromatic heterocyclyl-carbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkyl-sulfonyl group and a $C_{6-14}$ aryl-sulfonyl group, each of which optionally has 1 to 3 substituents selected from substituent group A".

Preferable examples of the optionally substituted amino group include an amino group, a mono- or di-(optionally halogenated $C_{1-6}$ alkyl)amino group (e.g., methylamino, trifluoromethylamino, dimethylamino, ethylamino, diethylamino, propylamino, dibutylamino), a mono- or di-$C_{2-6}$ alkenylamino group (e.g., diallylamino), a mono- or di-$C_{3-10}$ cycloalkylamino group (e.g., cyclopropylamino, cyclohexylamino), a mono- or di-$C_{6-14}$ arylamino group (e.g., phenylamino), a mono- or di-$C_{7-16}$ aralkylamino group (e.g., benzylamino, dibenzylamino), a mono- or di-(optionally halogenated $C_{1-6}$ alkyl)-carbonylamino group (e.g., acetylamino, propionylamino), a mono- or di-$C_{6-14}$ aryl-carbonylamino group (e.g., benzoylamino), a mono- or di-$C_{7-16}$ aralkyl-carbonylamino group (e.g., benzylcarbonylamino), a mono- or di-5- to 14-membered aromatic heterocyclyl-carbonylamino group (e.g., nicotinoylamino, isonicotinoylamino), a mono- or di-3- to 14-membered non-aromatic heterocyclyl-carbonylamino group (e.g., piperidinylcarbonylamino), a mono- or di-$C_{1-6}$ alkoxy-carbonylamino group (e.g., tert-butoxycarbonylamino), a 5- to 14-membered aromatic heterocyclylamino group (e.g., pyridylamino), a carbamoylamino group, a (mono- or di-$C_{1-6}$ alkyl-carbamoyl)amino group (e.g., methylcarbamoylamino), a (mono- or di-$C_{7-16}$ aralkyl-carbamoyl)amino group (e.g., benzylcarbamoylamino), a $C_{1-6}$ alkyl-sulfonylamino group (e.g., methylsulfonylamino, ethylsulfonylamino), a $C_{6-14}$ aryl-sulfonylamino group (e.g., phenylsulfonylamino), a ($C_{1-6}$ alkyl)($C_{1-6}$ alkyl-carbonyl)amino group (e.g., N-acetyl-N-methylamino) and a ($C_{1-6}$ alkyl)($C_{6-14}$ aryl-carbonyl)amino group (e.g., N-benzoyl-N-methylamino).

In the present specification, examples of the "optionally substituted carbamoyl group" include a carbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclyl-carbonyl group, a 3- to 14-membered non-aromatic heterocyclyl-carbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from substituent group A".

Preferable examples of the optionally substituted carbamoyl group include a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl, cyclohexylcarbamoyl), a mono- or di-$C_{6-14}$ aryl-carbamoyl group (e.g., phenylcarbamoyl), a mono- or di-$C_{7-16}$ aralkyl-carbamoyl group, a mono- or di-$C_{1-6}$ alkyl-carbonyl-carbamoyl group (e.g., acetylcarbamoyl, propionylcarbamoyl), a mono- or di-$C_{6-14}$ aryl-carbonyl-carbamoyl group (e.g., benzoylcarbamoyl) and a 5- to 14-membered aromatic heterocyclyl-carbamoyl group (e.g., pyridylcarbamoyl).

In the present specification, examples of the "optionally substituted thiocarbamoyl group" include a thiocarbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclyl-carbonyl group, a 3- to 14-membered non-aromatic heterocyclyl-carbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from substituent group A".

Preferable examples of the optionally substituted thiocarbamoyl group include a thiocarbamoyl group, a mono- or di-$C_{1-6}$ alkyl-thiocarbamoyl group (e.g., methylthiocarbamoyl, ethylthiocarbamoyl, dimethylthiocarbamoyl, diethylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a mono- or di-$C_{1-6}$ alkyl-carbonyl-thiocarbamoyl group (e.g., acetylthiocarbamoyl, propionylthiocarbamoyl), a mono- or di-$C_{6-14}$ aryl-carbonyl-thiocarbamoyl group (e.g., benzoylthiocarbamoyl) and a 5- to 14-membered aromatic heterocyclyl-thiocarbamoyl group (e.g., pyridylthiocarbamoyl).

In the present specification, examples of the "optionally substituted sulfamoyl group" include a sulfamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclyl-carbonyl group, a 3- to 14-membered non-aromatic heterocyclyl-carbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from substituent group A".

Preferable examples of the optionally substituted sulfamoyl group include a sulfamoyl group, a mono- or di-$C_{1-6}$ alkyl-sulfamoyl group (e.g., methylsulfamoyl, ethylsulfamoyl, dimethylsulfamoyl, diethylsulfamoyl, N-ethyl-N-methylsulfamoyl), a mono- or di-$C_{2-6}$ alkenyl-sulfamoyl group (e.g., diallylsulfamoyl), a mono- or di-$C_{3-10}$ cycloalkyl-sulfamoyl group (e.g., cyclopropylsulfamoyl, cyclohexylsulfamoyl), a mono- or di-$C_{6-14}$ aryl-sulfamoyl group (e.g., phenylsulfamoyl), a mono- or di-$C_{7-16}$ aralkyl-sulfamoyl group (e.g., benzylsulfamoyl, phenethylsulfamoyl), a mono- or di-$C_{1-6}$ alkyl-carbonyl-sulfamoyl group (e.g., acetylsulfamoyl, propionylsulfamoyl), a mono- or di-$C_{6-14}$ aryl-carbonyl-sulfamoyl group (e.g., benzoylsulfamoyl) and a 5- to 14-membered aromatic heterocyclyl-sulfamoyl group (e.g., pyridylsulfamoyl).

In the present specification, examples of the "optionally substituted hydroxy group" include a hydroxyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclyl-carbonyl group, a 3- to 14-membered non-aromatic heterocyclyl-carbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkyl-sulfonyl group and a $C_{6-14}$ aryl-sulfonyl group, each of which optionally has 1 to 3 substituents selected from substituent group A".

Preferable examples of the optionally substituted hydroxy group include a hydroxy group, a $C_{1-6}$ alkoxy group, a $C_{2-6}$ alkenyloxy group (e.g., allyloxy, 2-butenyloxy, 2-pentenyloxy, 3-hexenyloxy), a $C_{3-10}$ cycloalkyloxy group (e.g., cyclohexyloxy), a $C_{6-14}$ aryloxy group (e.g., phenoxy, naphthyloxy), a $C_{7-16}$ aralkyloxy group (e.g., benzyloxy, phenethyloxy), a $C_{1-6}$ alkyl-carbonyloxy group (e.g., acetyloxy, propionyloxy, butyryloxy, isobutyryloxy, pivaloyloxy), a $C_{6-14}$ aryl-carbonyloxy group (e.g., benzoyloxy), a $C_{7-16}$ aralkyl-carbonyloxy group (e.g., benzylcarbonyloxy), a 5- to 14-membered aromatic heterocyclyl-carbonyloxy group (e.g., nicotinoyloxy), a 3- to 14-membered non-aromatic heterocyclyl-carbonyloxy group (e.g., piperidinylcarbonyloxy), a $C_{1-6}$ alkoxy-carbonyloxy group (e.g., tert-butoxycarbonyloxy), a 5- to 14-membered aromatic heterocyclyloxy group (e.g., pyridyloxy), a carbamoyloxy group, a $C_{1-6}$ alkyl-carbamoyloxy group (e.g., methylcarbamoyloxy), a $C_{7-16}$ aralkyl-carbamoyloxy group (e.g., benzylcarbamoyloxy), a $C_{1-6}$ alkyl-sulfonyloxy group (e.g., methylsulfonyloxy, ethylsulfonyloxy) and a $C_{6-14}$ aryl-sulfonyloxy group (e.g., phenylsulfonyloxy).

In the present specification, examples of the "optionally substituted sulfanyl group" include a sulfanyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group and a 5- to 14-membered aromatic heterocyclic group, each of which optionally has 1 to 3 substituents selected from substituent group A" and a halogenated sulfanyl group.

Preferable examples of the optionally substituted sulfanyl group include a sulfanyl (—SH) group, a $C_{1-6}$ alkylthio group, a $C_{2-6}$ alkenylthio group (e.g., allylthio, 2-butenylthio, 2-pentenylthio, 3-hexenylthio), a $C_{3-10}$ cycloalkylthio group (e.g., cyclohexylthio), a $C_{6-14}$ arylthio group (e.g., phenylthio, naphthylthio), a $C_{7-16}$ aralkylthio group (e.g., benzylthio, phenethylthio), a $C_{1-6}$ alkyl-carbonylthio group (e.g., acetylthio, propionylthio, butyrylthio, isobutyrylthio, pivaloylthio), a $C_{6-14}$ aryl-carbonylthio group (e.g., benzoylthio), a 5- to 14-membered aromatic heterocyclylthio group (e.g., pyridylthio) and a halogenated thio group (e.g., pentafluorothio).

In the present specification, examples of the "optionally substituted silyl group" include a silyl group optionally having "1 to 3 substituents selected from a $C_{1-6}$ alkyl group, a $C_{2-6}$ alkenyl group, a $C_{3-10}$ cycloalkyl group, a $C_{6-14}$ aryl group and a $C_{7-16}$ aralkyl group, each of which optionally has 1 to 3 substituents selected from substituent group A".

Preferable examples of the optionally substituted silyl group include a tri-$C_{1-6}$ alkylsilyl group (e.g., trimethylsilyl, tert-butyl(dimethyl)silyl).

In the present specification, examples of the "$C_{1-6}$ alkylene group" include —$CH_2$—, —$(CH_2)_2$—, —$(CH_2)_3$—, —$(CH_2)_4$—, —$(CH_2)_5$—, —$(CH_2)_6$—, —$CH(CH_3)$—, —$C(CH_3)_2$—, —$CH(C_2H_5)$—, —$CH(C_3H_7)$—, —$CH(CH(CH_3)_2)$—, —$(CH(CH_3))_2$—, —$CH_2$—$CH(CH_3)$—, —$CH(CH_3)$—$CH_2$—, —$CH_2$—$CH_2$—$C(CH_3)_2$—, —$C(CH_3)_2$—$CH_2$—$CH_2$—, —$CH_2$—$CH_2$—$CH_2$—$C(CH_3)_2$— and —$C(CH_3)_2$—$CH_2$—$CH_2$—$CH_2$—.

In the present specification, examples of the "$C_{2-6}$ alkenylene group" include —CH=CH—, —$CH_2$—CH=CH—, —CH=CH—$CH_2$—, —$C(CH_3)_2$—CH=CH—, —CH=CH—$C(CH_3)_2$—, —$CH_2$—CH=CH—$CH_2$—, —$CH_2$—$CH_2$—CH=CH—, —CH=CH—$CH_2$—$CH_2$—, —CH=CH—CH=CH—, —CH=CH—$CH_2$—$CH_2$—$CH_2$— and —$CH_2$—$CH_2$—$CH_2$—CH=CH—.

In the present specification, examples of the "$C_{2-6}$ alkynylene group" include —C≡C—, —$CH_2$—C≡C—, —C≡C—$CH_2$—, —$C(CH_3)_2$—C≡C—, —C≡C—$C(CH_3)_2$—, —$CH_2$—C≡C—$CH_2$—, —$CH_2$—$CH_2$—C≡C—, —C≡C—$CH_2$—$CH_2$—, —C≡C—C≡C—, —C≡C—$CH_2$—$CH_2$—$CH_2$— and —$CH_2$—$CH_2$—$CH_2$—C≡C—.

In the present specification, examples of the "hydrocarbon ring" include a $C_{6-14}$ aromatic hydrocarbon ring, $C_{3-10}$ cycloalkane and $C_{3-10}$ cycloalkene.

In the present specification, examples of the "$C_{6-14}$ aromatic hydrocarbon ring" include benzene and naphthalene.

In the present specification, examples of the "$C_{3-10}$ cycloalkane" include cyclopropane, cyclobutane, cyclopentane, cyclohexane, cycloheptane and cyclooctane.

In the present specification, examples of the "$C_{3-10}$ cycloalkene" include cyclopropene, cyclobutene, cyclopentene, cyclohexene, cycloheptene and cyclooctene.

In the present specification, examples of the "heterocycle" include an aromatic heterocycle and a non-aromatic heterocycle, each containing, as a ring-constituting atom besides carbon atom, 1 to 4 hetero atoms selected from nitrogen, sulfur and oxygen atoms.

In the present specification, examples of the "aromatic heterocycle" include a 5- to 14-membered (preferably 5- to 10-membered) aromatic heterocycle containing, as a ring-constituting atom besides carbon atom, 1 to 4 hetero atoms selected from nitrogen, sulfur and oxygen atoms. Preferable examples of the "aromatic heterocycle" include 5- or 6-membered monocyclic aromatic heterocycles such as thiophene, furan, pyrrole, imidazole, pyrazole, thiazole, isothiazole, oxazole, isoxazole, pyridine, pyrazine, pyrimidine, pyridazine, 1,2,4-oxadiazole, 1,3,4-oxadiazole, 1,2,4-thiadiazole, 1,3,4-thiadiazole, triazole, tetrazole, triazine and the like; and
8- to 14-membered fused polycyclic (preferably bi or tricyclic) aromatic heterocycles such as benzothiophene, benzofuran, benzimidazole, benzoxazole, benzisoxazole, benzothiazole, benzisothiazole, benzotriazole, imidazopyridine, thienopyridine, furopyridine, pyrrolopyridine, pyrazolopyridine, oxazolopyridine, thiazolopyridine, imidazopyrazine, imidazopyrimidine, thienopyrimidine, furopyrimidine, pyrrolopyrimidine, pyrazolopyrimidine, oxazolopyrimidine, thiazolopyrimidine, pyrazolopyrimidine, pyrazolotriazine, naphtho[2,3-b]thiophene, phenoxathiin, indole, isoindole, 1H-indazole, purine, isoquinoline, quinoline, phthalazine, naphthyridine, quinoxaline, quinazoline, cinnoline, carbazole, β-carboline, phenanthridine, acridine, phenazine, phenothiazine, phenoxazine and the like.

In the present specification, examples of the "non-aromatic heterocycle" include a 3- to 14-membered (preferably 4- to 10-membered) non-aromatic heterocycle containing, as a ring-constituting atom besides carbon atom, 1 to 4 hetero atoms selected from nitrogen, sulfur and oxygen atoms. Preferable examples of the "non-aromatic heterocycle" include 3- to 8-membered monocyclic non-aromatic heterocycles such as aziridine, oxirane, thiirane, azetidine, oxetane, thietane, tetrahydrothiophene, tetrahydrofuran, pyrroline, pyrrolidine, imidazoline, imidazolidine, oxazoline, oxazolidine, pyrazoline, pyrazolidine, thiazoline, thiazolidine, tetrahydroisothiazole, tetrahydrooxazole, tetrahydroisoxazole, piperidine, piperazine, tetrahydropyridine, dihydropyridine, dihydrothiopyran, tetrahydropyrimidine, tetrahydropyridazine, dihydropyran, tetrahydropyran, tetrahydrothiopyran, morpholine, thiomorpholine, azepanine, diazepane, azepine, azocane, diazocane, oxepane and the like; and 9- to 14-membered fused polycyclic (preferably bi or tricyclic) non-aromatic heterocycles such as dihydrobenzofuran, dihydrobenzimidazole, dihydrobenzoxazole, dihydrobenzothiazole, dihydrobenzisothiazole, dihydronaphtho[2,3-b]thiophene, tetrahydroisoquinoline, tetrahydroquinoline, 4H-quinolizine, indoline, isoindoline, tetrahydrothieno[2,3-c]pyridine, tetrahydrobenzazepine, tetrahydroquinoxaline, tetrahydrophenanthridine, hexahydrophenothiazine, hexahydrophenoxazine, tetrahydrophthalazine, tetrahydronaphthyridine, tetrahydroquinazoline, tetrahydrocinnoline, tetrahydrocarbazole, tetrahydro-β-carboline, tetrahydroacridine, tetrahydrophenazine, tetrahydrothioxanthene, octahydroisoquinoline and the like.

In the present specification, examples of the "nitrogen-containing heterocycle" include a "heterocycle" containing at least one nitrogen atom as a ring-constituting atom.

In the present specification, the "9- to 14-membered fused polycyclic non-aromatic heterocyclic group" also includes dihydroisoindolyl.

In the present specification, the "7- to 10-membered bridged heterocyclic group" also includes 8-oxa-3-azabicyclo[3.2.1]octanyl, 2-oxa-5-azabicyclo[2.2.1]heptanyl, 3-oxa-6-azabicyclo[3.1.1]heptanyl, 3-oxa-8-azabicyclo[3.2.1]octanyl, 2-oxa-5-azabicyclo[2.2.1]heptanyl, 2,5-diazabicyclo[2.2.1]heptanyl, 6-oxa-3-azabicyclo[3.1.1]heptanyl, 2-oxa-7-azaspiro[3.5]nonyl, and 2-oxa-6-azaspiro[3.3]heptanyl.

In the present specification, examples of the "nitrogen-containing aromatic heterocyclic group" further include N-oxido-pyridine.

Preferred examples of $R^1$, $R^2$, $R^3$, $R^4$, $R^{5a}$, $R^{5b}$, $R^{6a}$, $R^{6b}$, $R^7$, and $R^8$ in the formula (I) are shown in the following.

$R^1$ is preferably a hydrogen atom.

$R^2$ is preferably a hydrogen atom, a halogen atom (particularly, a chlorine atom), an amino group or a hydroxy group; more preferably a hydrogen atom.

$R^3$ is preferably a hydrogen atom or a halogen atom (particularly, fluorine atom).

The "aromatic heterocyclic group" in the "optionally substituted aromatic heterocyclic group" represented by $R^4$ is preferably a 5- or 6-membered monocyclic aromatic heterocyclic group (particularly, thienyl, furyl, pyrrolyl, imidazolyl, pyrazolyl, triazolyl, thiazolyl, isothiazolyl, pyridyl or pyrimidinyl) or an 8- to 14-membered fused polycyclic (particularly, bicyclic) aromatic heterocyclic group (benzimidazolyl, pyrazolopyridinyl, imidazopyridinyl, indolyl, pyrrolopyridinyl or indazolyl). Among these, pyrazolyl (particularly, 4-pyrazolyl) is more preferred.

R⁴ is preferably a 5- or 6-membered monocyclic aromatic heterocyclic group (particularly, thienyl, furyl, pyrrolyl, imidazolyl, pyrazolyl, triazolyl, thiazolyl, isothiazolyl, pyridyl or pyrimidinyl) or an 8- to 14-membered fused polycyclic (preferably bicyclic) aromatic heterocyclic group (particularly, benzimidazolyl, pyrazolopyridinyl, imidazopyridinyl, indolyl, pyrrolopyridinyl or indazolyl), optionally substituted by 1 to 3 (particularly, 1 or 2) substituents selected from the following substituents (1) to (11):

(1) a $C_{1-6}$ alkyl group optionally having 1 to 7, preferably 1 to 5 halogen atoms (particularly, fluorine atom) (particularly, optionally halogenated methyl, ethyl, propyl, isopropyl, tert-butyl or isobutyl), (2) a $C_{1-6}$ alkyl group (particularly, methyl or ethyl) substituted by 1 to 7, preferably 1 to 5, more preferably 1 substituent selected from (i) a hydroxy group, (ii) an amino group, (iii) a $C_{1-6}$ alkoxy group (particularly, methoxy), (iv) an optionally halogenated $C_{3-10}$ cycloalkyl group (particularly, cyclopropyl), (v) a 5- to 14-membered aromatic heterocyclic group (particularly, a 5- or 6-membered monocyclic aromatic heterocyclic group, preferably pyridyl), (vi) a 3- to 14-membered non-aromatic heterocyclic group (particularly, a 3- to 8-membered monocyclic non-aromatic heterocyclic group, preferably morpholinyl or oxetanyl), (vii) a $C_{1-6}$ alkoxy-carbonyl group (particularly, ethoxycarbonyl), and (viii) a carbamoyl group, (3) a $C_{3-10}$ cycloalkyl group (particularly, cyclopropyl or cyclobutyl), (4) a $C_{7-16}$ aralkyl group (particularly, benzyl or phenethyl) optionally substituted by 1 to 7, preferably 1 to 5 substituents selected from the following (i) to (iii):

(i) a halogen atom (particularly, fluorine atom), (ii) an optionally halogenated $C_{1-6}$ alkyl group (particularly, methyl), and (iii) a cyano group, (5) a 3- to 14-membered non-aromatic heterocyclic group (particularly, a 3- to 8-membered monocyclic non-aromatic heterocyclic group, preferably oxetanyl, tetrahydropyranyl or piperidinyl), (6) a $C_{1-6}$ alkyl-carbonyl group (particularly, acetyl), (7) a $C_{1-6}$ alkoxy group (particularly, methoxy), (8) a $C_{1-6}$ alkoxy-carbonyl group (particularly, ethoxycarbonyl), (9) a carbamoyl group,

(10) a cyano group, and

(11) a halogen atom (particularly, fluorine atom).

R⁴ is more preferably a 5- or 6-membered monocyclic aromatic heterocyclic group (particularly, pyrazolyl or thiazolyl) or an 8- to 14-membered fused bicyclic aromatic heterocyclic group (particularly, benzimidazolyl), optionally substituted by 1 to 3 substituents selected from the following substituents (1) to (4):

(1) a $C_{1-6}$ alkyl group (particularly, methyl) optionally having 1 to 3 halogen atoms (particularly, fluorine atom), (2) a $C_{1-6}$ alkyl group (particularly, methyl) substituted by 1 to 3 optionally halogenated $C_{3-10}$ cycloalkyl groups (particularly, cyclopropyl or fluorocyclopropyl), (3) a $C_{3-10}$ cycloalkyl group (particularly, cyclopropyl), and (4) a $C_{1-6}$ alkoxy group (particularly, methoxy).

R⁴ is further preferably pyrazolyl (preferably 4-pyrazolyl) optionally substituted by 1 to 3 substituents selected from the following substituents (1) to (3):

(1) a $C_{1-6}$ alkyl group (particularly, methyl) optionally having 1 to 3 halogen atoms (particularly, fluorine atom), (2) a $C_{1-6}$ alkyl group (particularly, methyl) substituted by 1 to 3 halogenated $C_{3-10}$ cycloalkyl groups (particularly, cyclopropyl), and (3) a $C_{3-10}$ cycloalkyl group (particularly, cyclopropyl).

R⁴ is still further preferably pyrazolyl (preferably 4-pyrazolyl) optionally substituted by 1 to 3 substituents selected from the following substituents (1) and (2):

(1) a $C_{1-6}$ alkyl group (particularly, methyl), and (2) a $C_{3-10}$ cycloalkyl group (particularly, cyclopropyl).

$R^{5a}$ and $R^{6a}$ are, preferably, each independently a hydrogen atom or a $C_{1-6}$ alkyl group (particularly, methyl).

More preferably, $R^{5a}$ and $R^{6a}$ are both hydrogen atoms.

Preferably, both of $R^{5b}$ and $R^{6b}$ are hydrogen atoms, or $R^{5b}$ and $R^{6b}$ together (i) form a double bond or (ii) form a $C_{3-4}$ cycloalkyl (particularly, cyclopropyl) including the carbon atom to which they are mutually bound.

More preferably $R^{5b}$ and $R^{6b}$ together form a double bond.

As for R⁷ and R⁸, preferably either R⁷ or R⁸ is a hydrogen atom, and the other is a substituent, wherein the substituent is (I) a $C_{6-14}$ aryl group (particularly, phenyl) optionally having 1 to 3 substituents selected from the following (i) to (xvii):

(i) a halogen atom (particularly, a fluorine, chlorine or bromine atom), (ii) a cyano group, (iii) a hydroxy group, (iv) a $C_{1-6}$ alkoxy group (particularly, methoxy or ethoxy) optionally having 1 to 3 substituents selected from a halogen atom (particularly, fluorine atom), a $C_{1-6}$ alkoxy group (particularly, methoxy), a mono- or di-$C_{1-6}$ alkyl-amino group (particularly, dimethylamino) and a $C_{3-10}$ cycloalkyl group (particularly, cyclopropyl), (v) a 5- to 14-membered aromatic heterocyclyloxy group (particularly, pyridyloxy), (vi) a 3- to 14-membered non-aromatic heterocyclic group (particularly, oxetanyl, azetidinyl, pyrrolidinyl, piperidinyl or morpholinyl) optionally having 1 to 5 halogen atoms (particularly, fluorine atom), (vii) a 5- to 14-membered aromatic heterocyclic group (particularly, pyrazolyl, pyridyl, oxadiazolyl or isoxazolyl) optionally having 1 to 3 optionally halogenated $C_{1-6}$ alkyl groups (particularly, methyl), (viii) a 3- to 14-membered non-aromatic heterocyclylcarbonyl group (particularly, morpholinylcarbonyl), (ix) a $C_{1-6}$ alkoxy-carbonyl group (particularly, methoxycarbonyl), (x) a carbamoyl group, (xi) a $C_{1-6}$ alkylsulfonyl group (particularly, methylsulfonyl), (xii) a $C_{1-6}$ alkyl-carbonylamino group (particularly, acetylamino), (xiii) a ($C_{1-6}$ alkyl)($C_{1-6}$ alkyl-carbonyl)amino group (particularly, N-acetyl-N-methylamino), (xiv) a $C_{1-6}$ alkylsulfonylamino group (particularly, methylsulfonylamino), (xv) a sulfamoyl group, (xvi) a $C_{3-10}$ cycloalkyl group (particularly, cyclopropyl), and (xvii) a $C_{1-6}$ alkyl group (particularly, methyl, ethyl, propyl, isopropyl or isobutyl) optionally having 1 to 7 (preferably 1 to 3) substituents selected from the following (1) to (10):
(1) a halogen atom (particularly, fluorine atom),
(2) a cyano group,
(3) a hydroxy group,
(4) a 3- to 14-membered non-aromatic heterocyclic group (particularly, azetidinyl, pyrrolidinyl, thiazolidinyl, oxazolidinyl, morpholinyl, 1,1-dioxidothiomorpholinyl, piperazinyl, piperidinyl or hexahydropyrrolo[1,2-a]pyrazinyl) optionally having 1 to 5 substituents selected from an optionally hydroxy group-substituted $C_{1-6}$ alkyl group (particularly, methyl or ethyl), a halogen atom (particularly, fluorine atom), a hydroxy group, a carboxy group, a carbamoyl group, a $C_{1-6}$ alkoxy group (particularly, methoxy) and an oxo group,
(5) an optionally halogenated $C_{1-6}$ alkoxy group (particularly, methoxy or ethoxy),
(6) a $C_{1-6}$ alkylsulfonyl group (particularly, methylsulfonyl),
(7) 2-oxa-7-azaspiro[3.5]nonyl or 2-oxa-6-azaspiro[3.3]heptanyl,
(8) a 5- to 14-membered aromatic heterocyclic group (particularly, oxadiazolyl, pyrazolyl or imidazolyl) optionally having 1 to 3 substituents selected from an amino group and a $C_{1-6}$ alkyl group (particularly, methyl),
(9) a 7- to 10-membered bridged heterocyclic group (particularly, 8-oxa-3-azabicyclo[3.2.1]octanyl, 2-oxa-5-azabicyclo[2.2.1]heptanyl, 3-oxa-6-azabicyclo[3.1.1]heptanyl, 3-oxa-8-azabicyclo[3.2.1]octanyl, 2-oxa-5-azabicyclo[2.2.1]heptanyl, 2,5-diazabicyclo[2.2.1]heptanyl or 6-oxa-3-azabicyclo[3.1.1]heptanyl) optionally having 1 to 3 $C_{1-6}$ alkyl groups (particularly, methyl), and
(10) an amino group optionally mono- or di-substituted by a substituent selected from the following (a) to (0:
(a) a $C_{1-6}$ alkyl-carbonyl group (particularly, acetyl),
(b) a $C_{1-6}$ alkoxy-carbonyl group (particularly, tert-butoxycarbonyl),
(c) a $C_{1-6}$ alkyl group (particularly, methyl, ethyl or propyl) optionally having 1 to 5 substituents selected from a halogen atom (particularly, fluorine atom), a cyano group, a hydroxy group, a $C_{1-6}$ alkoxy group (particularly, methoxy), a carboxy group, a $C_{1-6}$ alkylsulfonyl group (particularly, methylsulfonyl), a $C_{1-6}$ alkyl-carbonylamino group (particularly, acetylamino), a $C_{1-6}$ alkyl-sulfamoyl group (particularly, methylsulfamoyl) and a 3- to 14-membered non-aromatic heterocyclic group (particularly, oxetanyl),
(d) an optionally halogenated $C_{3-10}$ cycloalkyl group (particularly, cyclopropyl or cyclobutyl),
(e) a 5- to 14-membered aromatic heterocyclic group (particularly, pyrazolyl), and
(f) a 3- to 14-membered non-aromatic heterocyclic group (particularly, oxetanyl, tetrahydrofuranyl, piperidinyl or 1,1-dioxidotetrahydrothiopyranyl) optionally having 1 to 3 substituents selected from a $C_{1-6}$ alkyl group (particularly, methyl) and an oxo group; (II) a 5- to 14-membered aromatic heterocyclic group (particularly, thienyl, pyrazolyl, pyridyl, benzothienyl, 1,1-dioxido-1-benzothienyl, benzimidazolyl, benzoxazolyl, benzothiazolyl, indolyl, 1H-indazolyl, 2H-indazolyl or isoquinolyl) optionally having 1 to 3 substituents selected from the following (i) to (iv):
(i) a carbamoyl group,
(ii) an optionally halogenated $C_{1-6}$ alkyl group (particularly, methyl or ethyl),
(iii) a $C_{3-10}$ cycloalkyl-$C_{1-6}$ alkyl group (particularly, cyclopropylmethyl), and
(iv) a 3- to 14-membered non-aromatic heterocyclyl-$C_{1-6}$ alkyl group (particularly, morpholinylmethyl);
(III) a 3- to 14-membered non-aromatic heterocyclic group (particularly, dihydrobenzofuranyl, dihydrobenzimidazolyl, tetrahydroquinolyl, tetrahydroisoquinolyl, benzodioxolyl, benzodioxinyl, dihydrobenzodioxinyl, dihydroindolyl or dihydroisoindolyl) optionally having 1 to 3 substituents selected from the following (i) to (viii):
(i) a halogen atom (particularly, fluorine atom),
(ii) an oxo group,
(iii) a $C_{1-6}$ alkyl group (particularly, methyl, ethyl or propyl) optionally having 1 to 5 substituents selected from a halogen atom (particularly, fluorine atom), a hydroxy group and a $C_{1-6}$ alkoxy group (particularly, methoxy),
(iv) a $C_{3-10}$ cycloalkyl-$C_{1-6}$ alkyl group (particularly, cyclopropylmethyl) optionally having 1 to 5 halogen atoms (particularly, fluorine atom),
(v) an optionally halogenated $C_{1-6}$ alkyl-carbonyl group (particularly, acetyl),
(vi) a $C_{1-6}$ alkoxy-carbonyl group (particularly, tert-butoxycarbonyl),
(vii) a $C_{3-10}$ cycloalkyl-carbonyl group (particularly, cyclopropylcarbonyl), and
(viii) a 3- to 14-membered non-aromatic heterocyclyl-carbonyl group (particularly, oxetanylcarbonyl) optionally having 1 to 3 $C_{1-6}$ alkyl groups (particularly, methyl);
(IV) a $C_{6-14}$ aryl-$C_{3-10}$ cycloalkyl group (particularly, phenylcyclopropyl);
(V) a $C_{7-16}$ aralkyl group (particularly, benzyl) optionally having 1 to 3 substituents selected from the following (i) to (iii):
(i) a cyano group,
(ii) an optionally hydroxy group-substituted $C_{1-6}$ alkyl group (particularly, methyl), and
(iii) an optionally halogenated $C_{1-6}$ alkoxy group (particularly, methoxy);
(VI) a 5- to 14-membered aromatic heterocyclyl-$C_{1-6}$ alkyl group (particularly, benzofuranmethyl);
(VII) a 3- to 14-membered non-aromatic heterocyclyl-$C_{1-6}$ alkyl group (particularly, pyrrolidinemethyl or benzodioxolylmethyl) optionally having 1 to 3 $C_{1-6}$ alkyl groups (particularly, methyl); or
(VIII) dihydroindenyl or tetrahydronaphthalenyl optionally having a substituent selected from a $C_{1-6}$ alkyl group (particularly, methyl) and an oxo group.
More preferably, either $R^7$ or $R^8$ is a hydrogen atom, and the other is
(I) a $C_{6-14}$ aryl group (preferably phenyl) optionally having 1 to 3 substituents selected from the following (i) and (ii):
(i) a halogen atom (particularly, fluorine atom), and
(ii) a $C_{1-6}$ alkyl group (particularly, methyl, ethyl or 2-methylpropyl) optionally having 1 to 3 substituents selected from the following (1) to (4):
(1) a halogen atom (particularly, fluorine atom),
(2) a 3- to 14-membered non-aromatic heterocyclic group (particularly, azetidinyl or morpholinyl) optionally having 1 to 3 substituents selected from a halogen atom (particularly, fluorine atom) and a $C_{1-6}$ alkoxy group (particularly, methoxy),
(3) a 5- to 14-membered aromatic heterocyclic group (particularly, imidazolyl), and
(4) a 7- to 10-membered bridged heterocyclic group (particularly, 6-oxa-3-azabicyclo[3.1.1]heptanyl);

(II) a 5- to 14-membered aromatic heterocyclic group (preferably indolyl) optionally having 1 to 3 substituents of the following (i):
(i) an optionally halogenated $C_{1-6}$ alkyl group (particularly, methyl or ethyl); or (III) a 3- to 14-membered non-aromatic heterocyclic group (particularly, tetrahydroisoquinolinyl or dihydroisoindolyl) optionally having 1 to 3 substituents of the following (i):
(i) a $C_{1-6}$ alkyl group (particularly, ethyl) optionally having 1 to 3 halogen atoms (particularly, fluorine atom).
More preferably, either $R^7$ or $R^8$ is a hydrogen atom, and the other is
(I) a $C_{6-14}$ aryl group (particularly, phenyl) optionally having 1 to 3 substituents selected from the following (i) and (ii):
(i) a halogen atom (particularly, fluorine atom), and
(ii) a $C_{1-6}$ alkyl group (particularly, methyl) optionally having 1 to 3 substituents of the following (1):
(1) a 3- to 14-membered non-aromatic heterocyclic group (particularly, azetidinyl or morpholinyl) optionally substituted by 1 to 3 substituents selected from
(A) a halogen atom (particularly, fluorine atom), and
(B) a $C_{1-6}$ alkoxy group (particularly, methoxy); or
(II) a 9- to 14-membered fused polycyclic (particularly, di- or tri-cyclic) non-aromatic heterocyclic group (particularly, dihydroisoindolyl) optionally having 1 to 3 substituents of the following (i):
(i) a $C_{1-6}$ alkyl group (particularly, ethyl) optionally having 1 to 3 halogen atoms (particularly, fluorine atom).
Preferred specific examples of compound (I) include the following:
Compound (A):
compound (I) wherein
$R^1$ is a hydrogen atom;
$R^2$ is a hydrogen atom, a halogen atom (particularly, a chlorine atom), an amino group or a hydroxy group;
$R^3$ is a hydrogen atom or a halogen atom (particularly, fluorine atom);
$R^4$ is a 5- or 6-membered monocyclic aromatic heterocyclic group (particularly, thienyl, furyl, pyrrolyl, imidazolyl, pyrazolyl, triazolyl, thiazolyl, isothiazolyl, pyridyl or pyrimidinyl) or an 8- to 14-membered fused polycyclic (preferably bicyclic) aromatic heterocyclic group (particularly, benzimidazolyl, pyrazolopyridinyl, imidazopyridinyl, indolyl, pyrrolopyridinyl or indazolyl), optionally substituted by 1 to 3 (particularly, 1 or 2) substituents selected from the following substituents (1) to (11):
(1) a $C_{1-6}$ alkyl group optionally having 1 to 7, preferably 1 to 5 halogen atoms (particularly, fluorine atom) (particularly, optionally halogenated methyl, ethyl, propyl, isopropyl, tert-butyl or isobutyl),
(2) a $C_{1-6}$ alkyl group (particularly, methyl or ethyl) substituted by 1 to 7, preferably 1 to 5, more preferably 1 substituent selected from
(i) a hydroxy group,
(ii) an amino group,
(iii) a $C_{1-6}$ alkoxy group (particularly, methoxy),
(iv) an optionally halogenated $C_{3-10}$ cycloalkyl group (particularly, cyclopropyl),
(v) a 5- to 14-membered aromatic heterocyclic group (particularly, a 5- or 6-membered monocyclic aromatic heterocyclic group, preferably pyridyl),
(vi) a 3- to 14-membered non-aromatic heterocyclic group (particularly, a 3- to 8-membered monocyclic non-aromatic heterocyclic group, preferably morpholinyl or oxetanyl),
(vii) a $C_{1-6}$ alkoxy-carbonyl group (particularly, ethoxycarbonyl), and
(viii) a carbamoyl group,
(3) a $C_{3-10}$ cycloalkyl group (particularly, cyclopropyl or cyclobutyl),
(4) a $C_{7-16}$ aralkyl group (particularly, benzyl or phenethyl) optionally substituted by 1 to 7, preferably 1 to 5 substituents selected from the following (i) to (iii):
(i) a halogen atom (particularly, fluorine atom),
(ii) an optionally halogenated $C_{1-6}$ alkyl group (particularly, methyl), and
(iii) a cyano group,
(5) a 3- to 14-membered non-aromatic heterocyclic group (particularly, a 3- to 8-membered monocyclic non-aromatic heterocyclic group, preferably oxetanyl, tetrahydropyranyl or piperidinyl),
(6) a $C_{1-6}$ alkyl-carbonyl group (particularly, acetyl),
(7) a $C_{1-6}$ alkoxy group (particularly, methoxy),
(8) a $C_{1-6}$ alkoxy-carbonyl group (particularly, ethoxycarbonyl),
(9) a carbamoyl group,
(10) a cyano group, and
(11) a halogen atom (particularly, fluorine atom);
$R^{5a}$ and $R^{6a}$ are each independently a hydrogen atom or a $C_{1-6}$ alkyl group (particularly, methyl);
both of $R^{5b}$ and $R^{6b}$ are hydrogen atoms, or $R^{5b}$ and $R^{6b}$ together (i) form a double bond or (ii) form a $C_{3-4}$ cycloalkyl (particularly, cyclopropyl) including the carbon atom to which they are mutually bound; and
either $R^7$ or $R^8$ is a hydrogen atom, and the other is a substituent, wherein the substituent is
(I) a $C_{6-14}$ aryl group (particularly, phenyl) optionally having 1 to 3 substituents selected from the following (i) to (xvii):
(i) a halogen atom (particularly, a fluorine, a chlorine or bromine atom),
(ii) a cyano group,
(iii) a hydroxy group,
(iv) a $C_{1-6}$ alkoxy group (particularly, methoxy or ethoxy) optionally having 1 to 3 substituents selected from a halogen atom (particularly, fluorine atom), a $C_{1-6}$ alkoxy group (particularly, methoxy), a mono- or di-$C_{1-6}$ alkyl-amino group (particularly, dimethylamino) and a $C_{3-10}$ cycloalkyl group (particularly, cyclopropyl),
(v) a 5- to 14-membered aromatic heterocyclyloxy group (particularly, pyridyloxy),
(vi) a 3- to 14-membered non-aromatic heterocyclic group (particularly, oxetanyl, azetidinyl, pyrrolidinyl, piperidinyl or morpholinyl) optionally having 1 to 5 halogen atoms (particularly, fluorine atom),
(vii) a 5- to 14-membered aromatic heterocyclic group (particularly, pyrazolyl, pyridyl, oxadiazolyl or isoxazolyl) optionally having 1 to 3 optionally halogenated $C_{1-6}$ alkyl groups (particularly, methyl),
(viii) a 3- to 14-membered non-aromatic heterocyclylcarbonyl group (particularly, morpholinylcarbonyl),
(ix) a $C_{1-6}$ alkoxy-carbonyl group (particularly, methoxycarbonyl),
(x) a carbamoyl group,
(xi) a $C_{1-6}$ alkylsulfonyl group (particularly, methylsulfonyl),
(xii) a $C_{1-6}$ alkyl-carbonylamino group (particularly, acetylamino),
(xiii) a ($C_{1-6}$ alkyl)($C_{1-6}$ alkyl-carbonyl)amino group (particularly, N-acetyl-N-methylamino),
(xiv) a $C_{1-6}$ alkylsulfonylamino group (particularly, methylsulfonylamino),
(xv) a sulfamoyl group,
(xvi) a $C_{3-10}$ cycloalkyl group (particularly, cyclopropyl), and (xvii) a $C_{1-6}$ alkyl group (particularly, methyl, ethyl, propyl, isopropyl or isobutyl) optionally having 1 to 7 (preferably 1 to 3) substituents selected from the following (1) to (10):

(1) a halogen atom (particularly, fluorine atom), (2) a cyano group, (3) a hydroxy group, (4) a 3- to 14-membered non-aromatic heterocyclic group (particularly, azetidinyl, pyrrolidinyl, thiazolidinyl, oxazolidinyl, morpholinyl, 1,1-dioxidothiomorpholinyl, piperazinyl, piperidinyl or hexahydropyrrolo[1,2-a]pyrazinyl) optionally having 1 to 5 substituents selected from an optionally hydroxy group-substituted $C_{1-6}$ alkyl group (particularly, methyl or ethyl), a halogen atom (particularly, fluorine atom), a hydroxy group, a carboxy group, a carbamoyl group, a $C_{1-6}$ alkoxy group (particularly, methoxy) and an oxo group, (5) an optionally halogenated $C_{1-6}$ alkoxy group (particularly, methoxy or ethoxy), (6) a $C_{1-6}$ alkylsulfonyl group (particularly, methylsulfonyl), (7) 2-oxa-7-azaspiro[3.5]nonyl or 2-oxa-6-azaspiro[3.3]heptanyl, (8) a 5- to 14-membered aromatic heterocyclic group (particularly, oxadiazolyl, pyrazolyl or imidazolyl) optionally having 1 to 3 substituents selected from an amino group and a $C_{1-6}$ alkyl group (particularly, methyl), (9) a 7- to 10-membered bridged heterocyclic group (particularly, 8-oxa-3-azabicyclo[3.2.1]octanyl, 2-oxa-5-azabicyclo[2.2.1]heptanyl, 3-oxa-6-azabicyclo[3.1.1]heptanyl, 3-oxa-8-azabicyclo[3.2.1]octanyl, 2-oxa-5-azabicyclo[2.2.1]heptanyl, 2,5-diazabicyclo[2.2.1]heptanyl or 6-oxa-3-azabicyclo[3.1.1]heptanyl) optionally having 1 to 3 $C_{1-6}$ alkyl groups (particularly, methyl), and

(10) an amino group optionally mono- or di-substituted by a substituent selected from the following (a) to (f):

(a) a $C_{1-6}$ alkyl-carbonyl group (particularly, acetyl), (b) a $C_{1-6}$ alkoxy-carbonyl group (particularly, tert-butoxycarbonyl), (c) a $C_{1-6}$ alkyl group (particularly, methyl, ethyl or propyl) optionally having 1 to 5 substituents selected from a halogen atom (particularly, fluorine atom), a cyano group, a hydroxy group, a $C_{1-6}$ alkoxy group (particularly, methoxy), a carboxy group, a $C_{1-6}$ alkylsulfonyl group (particularly, methylsulfonyl), a $C_{1-6}$ alkyl-carbonylamino group (particularly, acetylamino), a $C_{1-6}$ alkyl-sulfamoyl group (particularly, methylsulfamoyl) and a 3- to 14-membered non-aromatic heterocyclic group (particularly, oxetanyl), (d) an optionally halogenated $C_{3-10}$ cycloalkyl group (particularly, cyclopropyl or cyclobutyl), (e) a 5- to 14-membered aromatic heterocyclic group (particularly, pyrazolyl), and (f) a 3- to 14-membered non-aromatic heterocyclic group (particularly, oxetanyl, tetrahydrofuranyl, piperidinyl or 1,1-dioxidotetrahydrothiopyranyl) optionally having 1 to 3 substituents selected from a $C_{1-6}$ alkyl group (particularly, methyl) and an oxo group; (II) a 5- to 14-membered aromatic heterocyclic group (particularly, thienyl, pyrazolyl, pyridyl, benzothienyl, 1,1-dioxido-1-benzothienyl, benzimidazolyl, benzoxazolyl, benzothiazolyl, indolyl, 1H-indazolyl, 2H-indazolyl or isoquinolyl) optionally having 1 to 3 substituents selected from the following (i) to (iv):

(i) a carbamoyl group, (ii) an optionally halogenated $C_{1-6}$ alkyl group (particularly, methyl or ethyl), (iii) a $C_{3-10}$ cycloalkyl-$C_{1-6}$ alkyl group (particularly, cyclopropylmethyl), and (iv) a 3- to 14-membered non-aromatic heterocyclyl-$C_{1-6}$ alkyl group (particularly, morpholinylmethyl);

(III) a 3- to 14-membered non-aromatic heterocyclic group (particularly, dihydrobenzofuranyl, dihydrobenzimidazolyl, tetrahydroquinolyl, tetrahydroisoquinolyl, benzodioxolyl, benzodioxinyl, dihydrobenzodioxinyl, dihydroindolyl or dihydroisoindolyl) optionally having 1 to 3 substituents selected from the following (i) to (viii):

(i) a halogen atom (particularly, fluorine atom), (ii) an oxo group, (iii) a $C_{1-6}$ alkyl group (particularly, methyl, ethyl or propyl) optionally having 1 to 5 substituents selected from a halogen atom (particularly, fluorine atom), a hydroxy group and a $C_{1-6}$ alkoxy group (particularly, methoxy), (iv) a $C_{3-10}$ cycloalkyl-$C_{1-6}$ alkyl group (particularly, cyclopropylmethyl) optionally having 1 to 5 halogen atoms (particularly, fluorine atom), (v) an optionally halogenated $C_{1-6}$ alkyl-carbonyl group (particularly, acetyl), (vi) a $C_{1-6}$ alkoxy-carbonyl group (particularly, tert-butoxycarbonyl), (vii) a $C_{3-10}$ cycloalkyl-carbonyl group (particularly, cyclopropylcarbonyl), and (viii) a 3- to 14-membered non-aromatic heterocyclyl-carbonyl group (particularly, oxetanylcarbonyl) optionally having 1 to 3 $C_{1-6}$ alkyl groups (particularly, methyl);

(IV) a $C_{6-14}$ aryl-$C_{3-10}$ cycloalkyl group (particularly, phenylcyclopropyl);

(V) a $C_{7-16}$ aralkyl group (particularly, benzyl) optionally having 1 to 3 substituents selected from the following (i) to (iii):

(i) a cyano group, (ii) an optionally hydroxy group-substituted $C_{1-6}$ alkyl group (particularly, methyl), and (iii) an optionally halogenated $C_{1-6}$ alkoxy group (particularly, methoxy);

(VI) a 5- to 14-membered aromatic heterocyclyl-$C_{1-6}$ alkyl group (particularly, benzofuranmethyl);

(VII) a 3- to 14-membered non-aromatic heterocyclyl-$C_{1-6}$ alkyl group (particularly, pyrrolidinemethyl or benzodioxolylmethyl) optionally having 1 to 3 $C_{1-6}$ alkyl groups (particularly, methyl); or (VIII) dihydroindenyl or tetrahydronaphthalenyl optionally having a substituent selected from a $C_{1-6}$ alkyl group (particularly, methyl) and an oxo group.

Compound (B-p):

compound (A) wherein $R^2$ is a hydrogen atom;

$R^4$ is a 5- or 6-membered monocyclic aromatic heterocyclic group (particularly, pyrazolyl or thiazolyl) or an 8- to 14-membered fused bicyclic aromatic heterocyclic group (particularly, benzimidazolyl), optionally substituted by 1 to 3 substituents selected from the following substituents (1) to (4):

(1) a $C_{1-6}$ alkyl group (particularly, methyl) optionally having 1 to 3 halogen atoms (particularly, fluorine atom), (2) a $C_{1-6}$ alkyl group (particularly, methyl) substituted by 1 to 3 optionally halogenated $C_{3-10}$ cycloalkyl groups (particularly, cyclopropyl or fluorocyclopropyl), (3) a $C_{3-10}$ cycloalkyl group (particularly, cyclopropyl), and (4) a $C_{1-6}$ alkoxy group (particularly, methoxy);
$R^{5a}$ and $R^{6a}$ are each a hydrogen atom;
$R^{5b}$ and $R^{6b}$ together form a double bond; and
either $R^7$ or $R^8$ is a hydrogen atom, and the other is
(I) a $C_{6-14}$ aryl group (preferably phenyl) optionally having 1 to 3 substituents selected from the following (i) and (ii):
  (i) a halogen atom (particularly, fluorine atom), and
  (ii) a $C_{1-6}$ alkyl group (particularly, methyl, ethyl or 2-methylpropyl) optionally having 1 to 3 substituents selected from the following (1) to (4):
    (1) a halogen atom (particularly, fluorine atom),
    (2) a 3- to 14-membered non-aromatic heterocyclic group (particularly, azetidinyl or morpholinyl) optionally having 1 to 3 substituents selected from a halogen atom (particularly, fluorine atom) and a $C_{1-6}$ alkoxy group (particularly, methoxy),
    (3) a 5- to 14-membered aromatic heterocyclic group (particularly, imidazolyl), and
    (4) a 7- to 10-membered bridged heterocyclic group (particularly, 6-oxa-3-azabicyclo[3.1.1]heptanyl);
(II) a 5- to 14-membered aromatic heterocyclic group (preferably indolyl) optionally having 1 to 3 substituents of the following (i):
  (i) an optionally halogenated $C_{1-6}$ alkyl group (particularly, methyl or ethyl); or
(III) a 3- to 14-membered non-aromatic heterocyclic group (particularly, tetrahydroisoquinolinyl or dihydroisoindolyl) optionally having 1 to 3 substituents of the following (i):
  (i) a $C_{1-6}$ alkyl group (particularly, ethyl) optionally having 1 to 3 halogen atoms (particularly, fluorine atom).

Compound (B):
compound (A) wherein
$R^2$ is a hydrogen atom;
$R^4$ is pyrazolyl (preferably 4-pyrazolyl) optionally substituted by 1 to 3 substituents selected from the following substituents (1) to (3):
  (1) a $C_{1-6}$ alkyl group (particularly, methyl) optionally having 1 to 3 halogen atoms (particularly, fluorine atom),
  (2) a $C_{1-6}$ alkyl group (particularly, methyl) substituted by 1 to 3 halogenated $C_{3-10}$ cycloalkyl groups (particularly, cyclopropyl), and
  (3) a $C_{3-10}$ cycloalkyl group (particularly, cyclopropyl);
each of $R^{5a}$ and $R^{6a}$ is a hydrogen atom;
$R^{5b}$ and $R^{6b}$ together form a double bond; and
either $R^7$ or $R^8$ is a hydrogen atom, and the other is
(I) a $C_{6-14}$ aryl group (preferably phenyl) optionally having 1 to 3 substituents selected from the following (i) and (ii):
  (i) a halogen atom (particularly, fluorine atom), and
  (ii) a $C_{1-6}$ alkyl group (particularly, methyl, ethyl or 2-methylpropyl) optionally having 1 to 3 substituents selected from the following (1) to (4):
    (1) a halogen atom (particularly, fluorine atom),
    (2) a 3- to 14-membered non-aromatic heterocyclic group (particularly, azetidinyl or morpholinyl) optionally having 1 to 3 substituents selected from a halogen atom (particularly, fluorine atom) and a $C_{1-6}$ alkoxy group (particularly, methoxy),
    (3) a 5- to 14-membered aromatic heterocyclic group (particularly, imidazolyl), and
    (4) a 7- to 10-membered bridged heterocyclic group (particularly, 6-oxa-3-azabicyclo[3.1.1]heptanyl);
(II) a 5- to 14-membered aromatic heterocyclic group (preferably indolyl) optionally having 1 to 3 substituents of the following (i):
  (i) an optionally halogenated $C_{1-6}$ alkyl group (particularly, methyl or ethyl); or
(III) a 3- to 14-membered non-aromatic heterocyclic group (particularly, tetrahydroisoquinolinyl or dihydroisoindolyl) optionally having 1 to 3 substituents of the following (i):
  (i) a $C_{1-6}$ alkyl group (particularly, ethyl) optionally having 1 to 3 halogen atoms (particularly, fluorine atom).

Compound (C):
compound (B) wherein
$R^4$ is pyrazolyl (preferably 4-pyrazolyl) optionally substituted by 1 to 3 substituents selected from the following substituents (1) and (2):
  (1) a $C_{1-6}$ alkyl group (particularly, methyl), and
  (2) a $C_{3-10}$ cycloalkyl group (particularly, cyclopropyl); and
either $R^7$ or $R^8$ is a hydrogen atom, and the other is
(I) a $C_{6-14}$ aryl group (particularly, phenyl) optionally having 1 to 3 substituents selected from the following (i) and (ii):
  (i) a halogen atom (particularly, fluorine atom), and
  (ii) a $C_{1-6}$ alkyl group (particularly, methyl) optionally having 1 to 3 substituents of the following (1):
    (1) a 3- to 14-membered non-aromatic heterocyclic group (particularly, azetidinyl or morpholinyl) optionally substituted by 1 to 3 substituents selected from
    (A) a halogen atom (particularly, fluorine atom), and
    (B) a $C_{1-6}$ alkoxy group (particularly, methoxy); or
(II) a 9- to 14-membered fused polycyclic (particularly, di- or tri-cyclic) non-aromatic heterocyclic group (particularly, dihydroisoindolyl) optionally having 1 to 3 substituents of the following (i):
  (i) a $C_{1-6}$ alkyl group (particularly, ethyl) optionally having 1 to 3 halogen atoms (particularly, fluorine atom).

The following compounds also have inhibitory activity against CDK8 and/or CDK19, as with the compound of the present invention, and are useful as a medicament for the prevention or treatment of diseases associated with CDK8 and/or CDK19, including cancer, etc.

[Formula 1]

wherein each symbol is as defined above.

The salt of compound (I) is preferably a pharmacologically acceptable salt. Examples thereof include salts with inorganic bases, salts with organic bases, salts with inorganic acids, salts with organic acids and salts with basic or acidic amino acids.

Preferred examples of salts with inorganic bases include: alkali metal salts such as sodium salt and potassium salt; alkaline earth metal salts such as calcium salt and magnesium salt; and aluminum salt and ammonium salt.

Preferred examples of salts with organic bases include salts with trimethylamine, triethylamine, pyridine, picoline, ethanolamine, diethanolamine, triethanolamine, tromethamine [tris(hydroxymethyl)methylamine], tert-butylamine, cyclohexylamine, benzylamine, dicyclohexylamine or N,N-dibenzylethylenediamine.

Preferred examples of salts with inorganic acids include salts with hydrochloric acid, hydrobromic acid, nitric acid, sulfuric acid or phosphoric acid.

Preferred examples of salts with organic acids include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid or p-toluenesulfonic acid.

Preferred examples of salts with basic amino acids include salts with arginine, lysine or ornithine.

Preferred examples of salts with acidic amino acids include salts with aspartic acid or glutamic acid.

The method for producing the compound of the present invention is described below.

A starting material or a reagent used in each step in the production method given below, as well as the obtained compound, may each form a salt. Such salts are regarded as equivalent to the given compounds, such as described above for the aforementioned salt of the compound of the present invention.

When the compound obtained in each step is a free compound, this compound can be converted to a salt of interest by a method known per se in the art. On the contrary, when the compound obtained in each step is a salt, this salt can be converted to a free form or another type of salt of interest by a method known per se in the art.

The compound obtained in each step may be used in the next reaction in the form of its reaction solution or after being obtained as a crude product. Alternatively, the compound obtained in each step can be isolated and/or purified from the reaction mixture by a separation approach such as concentration, crystallization, recrystallization, distillation, solvent extraction, fractionation, or chromatography according to a routine method.

If a starting material or a reagent compound for each step is commercially available, the commercially available product can be used directly.

In the reaction of each step, the reaction time can differ depending on the reagent or the solvent used and is usually 1 minute to 48 hours, preferably 10 minutes to 8 hours, unless otherwise specified.

In the reaction of each step, the reaction temperature can differ depending on the reagent or the solvent used and is usually −78° C. to 300° C., preferably −78° C. to 150° C., unless otherwise specified.

In the reaction of each step, the pressure can differ depending on the reagent or the solvent used and is usually 1 atm to 20 atm, preferably 1 atm to 3 atm, unless otherwise specified.

In the reaction of each step, for example, a microwave synthesis apparatus such as a Biotage Initiator may be used. The reaction temperature can differ depending on the reagent or the solvent used and is usually room temperature to 300° C., preferably 50° C. to 250° C., unless otherwise specified. The reaction time can differ depending on the reagent or the solvent used and is usually 1 minute to 48 hours, preferably 1 minute to 8 hours, unless otherwise specified.

In the reaction of each step, the reagent is used at 0.5 equivalents to 20 equivalents, preferably 0.8 equivalents to 5 equivalents, with respect to the substrate, unless otherwise specified. In the case of using the reagent as a catalyst, the reagent is used at 0.001 equivalents to 1 equivalent, preferably 0.01 equivalents to 0.2 equivalents, with respect to the substrate. When the reagent also serves as a reaction solvent, the reagent is used in the amount of the solvent.

In each step of a reaction, the reaction is carried out without a solvent or by dissolution or suspension in an appropriate solvent, unless otherwise specified. Specific examples of solvents that may be used include solvents described in the Examples and those given below:

alcohols such as methanol, ethanol, tert-butyl alcohol and 2-methoxyethanol;

ethers such as diethyl ether, diphenyl ether, tetrahydrofuran and 1,2-dimethoxyethane;

aromatic hydrocarbons such as chlorobenzene, toluene and xylene;

saturated hydrocarbons such as cyclohexane and hexane;

amides such as N,N-dimethylformamide and N-methylpyrrolidone;

halogenated hydrocarbons such as dichloromethane and carbon tetrachloride;

nitriles such as acetonitrile;

sulfoxides such as dimethyl sulfoxide;

aromatic organic bases such as pyridine;

acid anhydrides such as acetic anhydride;

organic acids such as formic acid, acetic acid and trifluoroacetic acid;

inorganic acids such as hydrochloric acid and sulfuric acid;

esters such as ethyl acetate;

ketones such as acetone and methyl ethyl ketone; and water.

Two or more of these solvents may be used as a mixture at an appropriate ratio.

In each reaction step making use of a base, examples of bases that may be used are those given in the Examples or listed below:

inorganic bases such as sodium hydroxide and magnesium hydroxide;

basic salts such as sodium carbonate, potassium carbonate and sodium bicarbonate;

organic bases such as triethylamine, diethylamine, pyridine, 4-dimethylaminopyridine, N,N-dimethylaniline, 1,4-diazabicyclo[2.2.2]octane, 1,8-diazabicyclo[5.4.0]-7-undecene, imidazole and piperidine;

metal alkoxides such as sodium ethoxide and potassium tert-butoxide;

alkali metal hydrides such as sodium hydride;

metal amides such as sodium amide, lithium diisopropylamide and lithium hexamethyldisilazide; and organolithium reagents such as n-butyllithium.

In each reaction step making use of an acid or acid catalyst, examples of acids or acid catalysts that may be used are those given in the Examples or listed below:

inorganic acids such as hydrochloric acid, sulfuric acid, nitric acid, hydrobromic acid and phosphoric acid;

organic acids such as acetic acid, trifluoroacetic acid, citric acid, p-toluenesulfonic acid and 10-camphorsulfonic acid; and Lewis acids such as boron trifluoride-diethyl ether complex, zinc iodide, anhydrous aluminum chloride, anhydrous zinc chloride and anhydrous iron chloride.

Unless stated otherwise, each reaction step may be carried out according to a method given in the Examples or a standard method known per se in the art, such as those described in Jikken Kagaku Koza (Encyclopedia of Experimental Chemistry in English), 5th Ed., Vol. 13 to Vol. 19 (edited by the Chemical Society of Japan); Shin Jikken Kagaku Koza (New Encyclopedia of Experimental Chemistry in English), Vol. 14 to Vol. 15 (edited by the Chemical Society of Japan); Reactions and Syntheses: In the Organic Chemistry Laboratory, 2th Ed. Revised (L. F. Tietze, Th. Eicher, Nankodo); Organic Name Reactions; The Reaction Mechanism and Essence, Revised (Hideo Togo, Kodansha); Organic Syntheses Collective Volume I-VII (John Wiley & Sons, Inc.); Modern Organic Synthesis in the Laboratory: A Collection of Standard Experimental Procedures (Jie Jack Li, Oxford University Press); Comprehensive Heterocyclic Chemistry III, Vol. 1 to Vol. 14 (Elsevier Japan KK); Strategic Applications of Named Reactions in Organic Synthesis (translated by Kiyoshi Tomioka, Kagaku-Dojin Publishing); Comprehensive Organic Transformations (VCH Publishers, Inc.), 1989; etc.

In each step, the protection or deprotection reaction of a functional group may be carried out according to a method described in the Examples or a method known per se in the art, for example, a method described in "Protective Groups in Organic Synthesis, 4th Ed." (Theodora W. Greene, Peter G. M. Wuts), Wiley-Interscience, 2007; "Protecting Groups, 3rd Ed." (P. J. Kocienski) Thieme, 2004); etc.

Examples of a protective group for a hydroxy group or a phenolic hydroxy group in alcohols or the like include: ether-type protective groups such as methoxymethyl ether, benzyl ether, t-butyldimethylsilyl ether and tetrahydropyranyl ether; carboxylic acid ester-type protective groups such as acetic acid ester; sulfonic acid ester-type protective groups such as methanesulfonic acid ester; and carbonic acid ester-type protective groups such as t-butyl carbonate.

Examples of a protective group for a carbonyl group in aldehydes include: acetal-type protective groups such as dimethylacetal; and cyclic acetal-type protective groups such as cyclic 1,3-dioxane.

Examples of a protective group for a carbonyl group in ketones include: ketal-type protective groups such as dimethylketal; cyclic ketal-type protective groups such as cyclic 1,3-dioxane; oxime-type protective groups such as O-methyloxime; and hydrazone-type protective groups such as N,N-dimethylhydrazone.

Examples of a protective group for a carboxyl group include: ester-type protective groups such as methyl ester; and amide-type protective groups such as N,N-dimethylamide.

Examples of a protective group for thiol include: ether-type protective groups such as benzyl thioether; and ester-type protective groups such as thioacetic acid ester, thiocarbonate and thiocarbamate.

Examples of a protective group for an amino group or aromatic heterocycle such as imidazole, pyrrole or indole include: carbamate-type protective groups such as benzyl carbamate; amide-type protective groups such as acetamide; alkylamine-type protective groups such as N-triphenylmethylamine; and sulfonamide-type protective groups such as methanesulfonamide.

These protective groups can be removed by use of a method known per se in the art, for example, a method using an acid, a base, ultraviolet light, hydrazine, phenylhydrazine, sodium N-methyldithiocarbamate, tetrabutylammonium fluoride, palladium acetate or trialkylsilyl halide (for example, trimethylsilyl iodide or trimethylsilyl bromide), or a reduction method.

In each step making use of a reduction reaction, examples of reducing agents that may be used include: metal hydrides such as lithium aluminum hydride, sodium triacetoxyborohydride, sodium cyanoborohydride, diisobutyl aluminum hydride (DIBAL-H), sodium borohydride and tetramethylammonium triacetoxyborohydride; boranes such as borane-tetrahydrofuran complex; Raney nickel; Raney cobalt; hydrogen; and formic acid. In the case of reducing a carbon-carbon double bond or triple bond, a method using a catalyst such as palladium-carbon or Lindlar's catalyst may be used.

In each step making use of an oxidation reaction, examples of oxidizing agents that may be used include: peracids such as m-chloroperbenzoic acid (MCPBA), hydrogen peroxide and t-butyl hydroperoxide; perchlorates such as tetrabutylammonium perchlorate; chlorates such as sodium chlorate; chlorites such as sodium chlorite; periodates such as sodium periodate; high-valent iodine reagents such as iodosylbenzene; manganese reagents, such as manganese dioxide and potassium permanganate; lead reagents such as lead tetraacetate; chromium reagents, such as pyridinium chlorochromate (PCC), pyridinium dichromate (PDC) and Jones' reagent; halogen reagents such as N-bromosuccinimide (NBS); oxygen; ozone; sulfur trioxide-pyridine complex; osmium tetraoxide; selenium dioxide; and 2,3-dichloro-5,6-dicyano-1,4-benzoquinone (DDQ).

In each step making use of a radical cyclization reaction, examples of radical initiators that may be used include: azo compounds such as azobisisobutyronitrile (AIBN); water-soluble radical initiators such as 4-4'-azobis-4-cyanopentanoic acid (ACPA); triethylboron in the presence of air or oxygen; and benzoyl peroxide. Examples of radical initiators that may be used include tributylstannane, tristrimethylsilylsilane, 1,1,2,2-tetraphenyldisilane, diphenylsilane and samarium iodide.

In each step making use of a Wittig reaction, examples of Wittig reagents that may be used include alkylidenephosphoranes. The alkylidenephosphoranes can be prepared by a method known per se in the art, for example, the reaction between a phosphonium salt and a strong base.

In each step making use of a Horner-Emmons reaction, examples of reagents that may be used include: phosphonoacetic acid esters such as methyl dimethylphosphonoacetate and ethyl diethylphosphonoacetate, and bases such as alkali metal hydrides and organic lithiums.

In each step making use of a Friedel-Crafts reaction, examples of reagents that may be used include a Lewis acid and an acid chloride or alkylating agent (e.g., alkyl halides, alcohols and olefins). Alternatively, an organic or inorganic acid may be used instead of the Lewis acid, and acid anhydrides such as acetic anhydride may be used instead of the acid chloride.

In each step making use of an aromatic nucleophilic substitution reaction, a nucleophile (e.g., amine or imidazole) and a base (e.g., basic salt or organic base) may be used as reagents.

In each step making use of a nucleophilic addition reaction using a carbanion, nucleophilic 1,4-addition reaction (Michael addition reaction) using a carbanion, or nucleophilic substitution reaction using a carbanion, examples of bases that may be used for generating the carbanion include organolithium reagents, metal alkoxides, inorganic bases and organic bases.

In each step making use of a Grignard reaction, examples of Grignard reagents that may be used include aryl magnesium halides such as phenyl magnesium bromide, and alkyl magnesium halides such as methyl magnesium bromide. The Grignard reagent can be prepared by a method known per se in the art, for example, the reaction between an alkyl halide or aryl halide and magnesium metal in ether or tetrahydrofuran as a solvent.

In each step making use of a Knoevenagel condensation reaction, an active methylene compound flanked by two electron-attracting groups (e.g., malonic acid, diethyl malonate or malononitrile) and a base (e.g., organic bases, metal alkoxides or inorganic bases) may be used as reagents.

In each step making use of a Vilsmeier-Haack reaction, phosphoryl chloride and an amide derivative (e.g., N,N-dimethylformamide) may be used as reagents.

In each step making use of an azidation reaction of alcohols, alkyl halides or sulfonic acid esters, examples of azidating agents that may be used include diphenylphosphorylazide (DPPA), trimethylsilylazide and sodium azide. In the case of azidating, for example, alcohols, a method using diphenylphosphorylazide and 1,8-diazabicyclo[5,4,0]undec-7-ene (DBU), a method using trimethylsilylazide and Lewis acid, or the like can be used.

In each step making use of a reductive amination reaction, examples of reducing agents that may be used include sodium triacetoxyborohydride, sodium cyanoborohydride, hydrogen and formic acid. When the substrate is an amine compound, examples of carbonyl compounds that may be used include p-formaldehyde as well as aldehydes such as acetaldehyde and ketones such as cyclohexanone. When the substrate is a carbonyl compound, examples of amines that may be used include primary amines such as ammonia and methylamine, and secondary amines such as dimethylamine.

In each step making use of a Mitsunobu reaction, azodicarboxylic acid esters (e.g., diethyl azodicarboxylate (DEAD) and diisopropyl azodicarboxylate (DIAD)) and triphenylphosphine may be used as reagents.

In each step making use of an esterification, amidation or ureation reaction, examples of reagents that may be used include acyl halides such as acid chlorides or acid bromides, and activated carboxylic acids such as acid anhydrides, active esters or sulfate esters. Examples of the activating agents for carboxylic acids include: carbodiimide condensing agents such as 1-ethyl-3-(3-dimethylaminopropyl)carbodiimide hydrochloride (WSCD); triazine condensing agents such as 4-(4,6-dimethoxy-1,3,5-triazin-2-yl)-4-methylmorpholinium chloride-n-hydrate (DMT-MM); carbonic acid ester condensing agents such as 1,1-carbonyldiimidazole (CDI); diphenylphosphorylazide (DPPA); benzotriazol-1-yloxy-trisdimethylaminophosphonium salt (BOP reagent); 2-chloro-1-methyl-pyridinium iodide (Mukaiyama reagent); thionyl chloride; lower alkyl haloformate such as ethyl chloroformate; O-(7-azabenzotriazol-1-yl)-N,N,N',N'-tetramethyluronium hexafluorophosphate (HATU); sulfuric acid; and combinations thereof. In the case of using a carbodiimide condensing agent, the addition of an additive such as 1-hydroxybenzotriazole (HOBt), N-hydroxysuccinimide (HOSu) or dimethylaminopyridine (DMAP) to the reaction may be beneficial.

In each step making use of a coupling reaction, examples of metal catalysts that may be used include palladium compounds such as palladium(II) acetate, tetrakis(triphenylphosphine)palladium(0), dichlorobis(triphenylphosphine)palladium(II), dichlorobis(triethylphosphine)palladium(II), tris(dibenzylideneacetone)dipalladium(0), 1,1'-bis(diphenylphosphino)ferrocene palladium(II) chloride and palladium(II) acetate; nickel compounds such as tetrakis(triphenylphosphine)nickel(0); rhodium compounds such as tris(triphenylphosphine)rhodium(III) chloride; cobalt compounds; copper compounds such as copper oxide and copper(I) iodide; and platinum compounds. Addition of a base to the reaction may also be beneficial. Examples of such bases include inorganic bases and basic salts.

In each step making use of a thiocarbonylation reaction, diphosphorus pentasulfide is typically used as a thiocarbonylating agent. A reagent having a 1,3,2,4-dithiadiphosphetane-2,4-disulfide structure such as 2,4-bis(4-methoxyphenyl-1,3,2,4-dithiadiphosphetane-2,4-disulfide (Lawesson reagent) may be used instead of diphosphorus pentasulfide.

In each step making use of a Wohl-Ziegler reaction, examples of halogenating agents that may be used include N-iodosuccinimide, N-bromosuccinimide (NBS), N-chlorosuccinimide (NCS), bromine and sulfuryl chloride. The reaction can be accelerated by the further addition of a radical initiator such as heat, light, benzoyl peroxide or azobisisobutyronitrile.

In each step making use of a halogenation reaction of a hydroxy group, examples of halogenating agents that may be used include a hydrohalic acid or the acid halide of an inorganic acid; examples include hydrochloric acid, thionyl chloride, and phosphorus oxychloride for chlorination and 48% hydrobromic acid for bromination. In addition, a method for obtaining an alkyl halide from an alcohol by the action of triphenylphosphine and carbon tetrachloride or carbon tetrabromide, etc., may also be used. Alternatively, a method for synthesizing an alkyl halide through a 2-step reaction involving the conversion of an alcohol to a sulfonic acid ester and subsequent reaction with lithium bromide, lithium chloride or sodium iodide may also be used.

In each step making use of an Arbuzov reaction, examples of reagents that may be used include alkyl halides such as bromoethyl acetate, and phosphites such as triethylphosphite and tri(isopropyl)phosphite.

In each step making use of a sulfone-esterification reaction, examples of the sulfonylating agent used include methanesulfonyl chloride, p-toluenesulfonyl chloride, methanesulfonic anhydride and p-toluenesulfonic anhydride.

In each step making use of a hydrolysis reaction, an acid or a base may be used as a reagent. In the case of carrying out the acid hydrolysis reaction of a t-butyl ester, reagents such as formic acid, triethylsilane or the like may be added to reductively trap the by-product t-butyl cation.

In each step making use of a dehydration reaction, examples of dehydrating agents that may be used include sulfuric acid, diphosphorus pentaoxide, phosphorus oxychloride, N,N'-dicyclohexylcarbodiimide, alumina and polyphosphoric acid.

In each step making use of an alkylation reaction of alcohols, amines, or aromatic heterocycles having a NH group in the ring (e.g., imidazole and pyrazole), examples of the alkylating agent include optionally substituted alkyl halides (e.g., iodomethane), optionally substituted alkyls having an optionally substituted $C_{1-6}$ alkylsulfonyloxy group as a leaving group, optionally substituted alkyls having a $C_{6-14}$ arylsulfonyloxy group optionally substituted by a $C_{1-6}$ alkyl group, sodium 2-chloro-2,2-difluoroacetate and 2,2-difluoro-2-(fluorosulfonyl)acetic acid. Examples of the base used include organolithiums, metal alkoxides, inorganic bases and organic bases.

In each step making use of a fluorination reaction in, examples of the fluorinating agent used include DAST (diethylaminosulfur trifluoride) and bis(2-methoxyethyl)aminosulfur trifluoride.

In each step making use of a coupling reaction, examples of the coupling reaction include Suzuki coupling, Still coupling, Buchwald coupling, Negishi coupling, Heck reaction, and cyanation reaction using copper cyanide or zinc cyanide. The reagents used in such coupling reactions, such as metal catalyst, phosphine ligand and base, can be the aforementioned reagents or those used in methods known per se in the art [for example, a method described in J. F. Hartwig, S. Shekhar, Q. Shen, F. Barrios-Landeros, in The Chemistry of Anilines, Z. Rappoport, Ed., Wiley-Interscience, New York (2007); L. Jiang, S. L. Buchwald, in Metal-Catalyzed Cross-Coupling Reactions, $2^{nd}$ Ed., A. de Meijere, F. Diederich, Eds., Wiley-VCH, Weinheim, Germany (2004); J. F. Hartwig, in Handbook of Organopalladium Chemistry for Organic Synthesis, A. de Meijere, F. Diederich, Eds., Wiley, New York (2002); and J. F. Hartwig, in Modern Amination Methods, A. Ricci, Ed., Wiley-VCH, Weinheim, (2000)] or a method equivalent thereto.

Examples of leaving groups that may be used in each step include halogen atoms (e.g., fluorine, chlorine, bromine or iodine atoms), $C_{1-6}$ alkoxy groups (e.g., methoxy), $C_{6-14}$ aryloxy groups (e.g., phenoxy), optionally substituted acyloxy groups (e.g., acetyloxy and benzoyloxy), optionally substituted $C_{1-6}$ alkoxysulfonyloxy groups (e.g., methoxysulfonyloxy), optionally halogenated $C_{1-6}$ alkylsulfonyl-oxy groups (e.g., methanesulfonyloxy, ethanesulfonyloxy, trichloromethanesulfonyloxy and trifluoromethanesulfonyloxy (triflate)) and optionally substituted $C_{6-14}$ aryl-sulfonyloxy groups [examples thereof include $C_{6-14}$ aryl-sulfonyloxy groups each optionally having 1 to 3 substituents selected from $C_{1-6}$ alkyl groups (e.g., methyl, ethyl, propyl, isopropyl, butyl, isobutyl, sec-butyl, tert-butyl, pentyl and hexyl), $C_{1-6}$ alkoxy groups (e.g., methoxy, ethoxy, propoxy, isopropoxy, butoxy, isobutoxy, sec-butoxy, pentyloxy and hexyloxy) and a nitro group, and specifically include benzenesulfonyloxy, m-nitrobenzenesulfonyloxy, p-toluenesulfonyloxy and naphthylsulfonyloxy].

The method for producing compound (I) is described in the following.

Each symbol in the reaction schemes given below represents the same meaning as that described above, unless otherwise specified. Each starting compound (specifically, compounds (2a), (4a), (3), (6), (7a), (8a), (9), (10), (11), (13), (14) and (15) described below) can be readily obtained as a commercially available product or can be produced by a method known per se in the art or a method equivalent thereto, unless a specific production method thereof is given.

[Production Method 1]

Compound (I) can be produced, for example, from compound (2a) or (4a) by a method shown in the following Reaction Scheme 1 or a method equivalent thereto.

Reaction Scheme 1

[Formula 2]

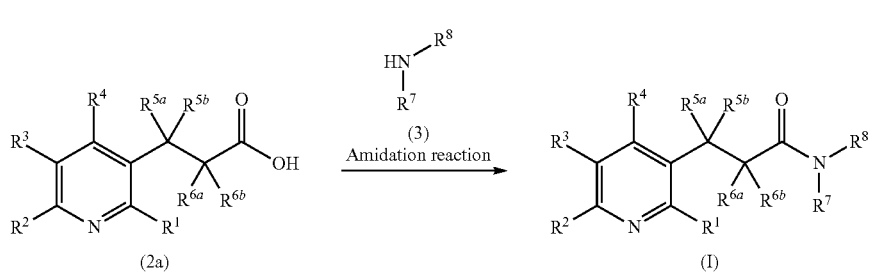

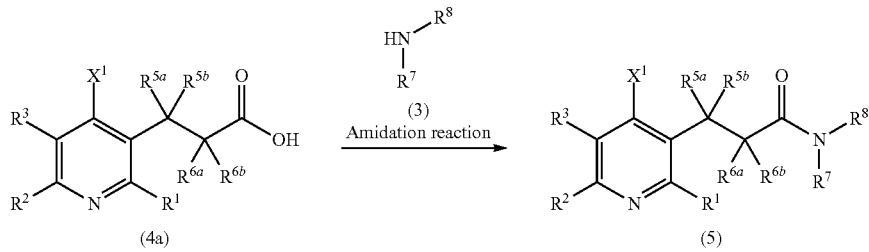

In the reaction scheme, $X^1$ represents the aforementioned leaving group.

In the reaction scheme, compound (6) represents a boronic acid derivative, a stannyl derivative or a nucleophile such as imidazole.

The other symbols are as defined above.

When compound (6) is a boronic acid derivative or a stannyl derivative, examples of $X^2$ include a boryl group

[Formula 3]

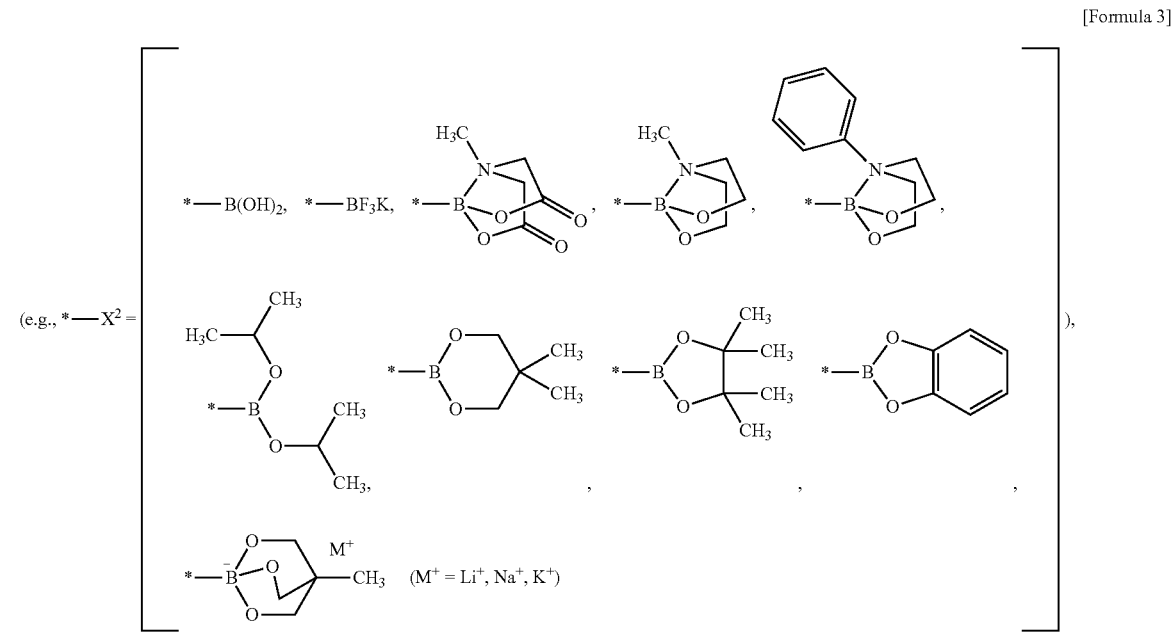

an optionally substituted $C_{1-6}$ alkylstannyl group (e.g., trimethylstannyl or n-tributylstannyl) and an optionally substituted $C_{2-6}$ alkenylstannyl group.

In this case, the compound (I) can be produced by subjecting compound (6) to coupling reaction with compound (5).

When compound (6) is a nucleophile such as imidazole, compound (I) can be produced by subjecting compound (6) to aromatic nucleophilic substitution reaction with compound (5).

In the reaction scheme, compounds (2a) and (4a) can be produced, for example, from compound (7a) or (8a) by a method shown in the following Reaction Scheme 2 or a method equivalent thereto.

Reaction Scheme 2

[Formula 4]

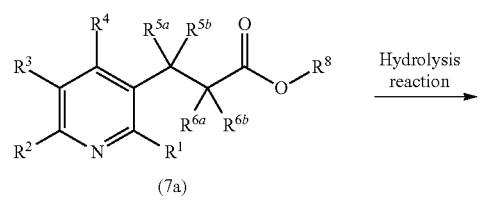

-continued

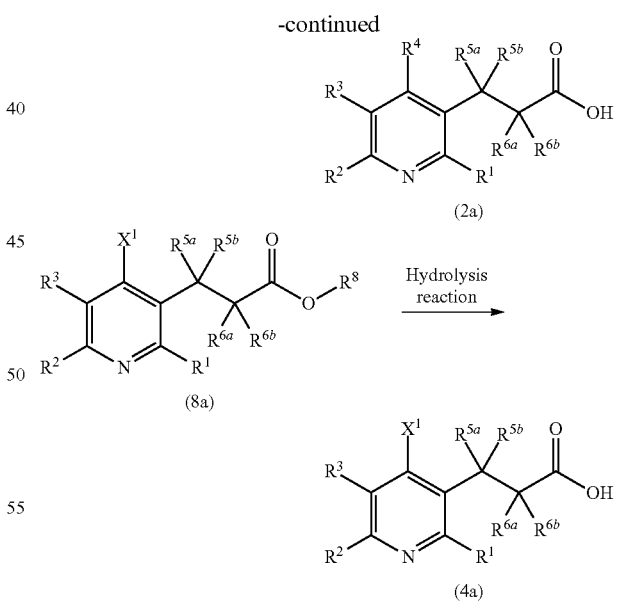

In the reaction scheme, $R^9$ represents an optionally substituted $C_{1-6}$ alkyl group.

Other symbols are as defined above.

Compound (7b) or (8b), compound (7a) or (8a) wherein $R^{5b}$ and $R^{6b}$ together form a double bond; compound (7c) or (8c), compound (7a) or (8a) wherein $R^{5b}$ and $R^{6b}$ are each a hydrogen atom; or compound (7d) or (8d), compound (7a)

or (8a) wherein $R^{5b}$ and $R^{6b}$ together form a cyclopropyl including the carbon atom to which they are mutually bound, can also be produced from compound (9) by a method shown in the following Reaction Scheme 3 or a method equivalent thereto.

Reaction Scheme 3

[Formula 5]

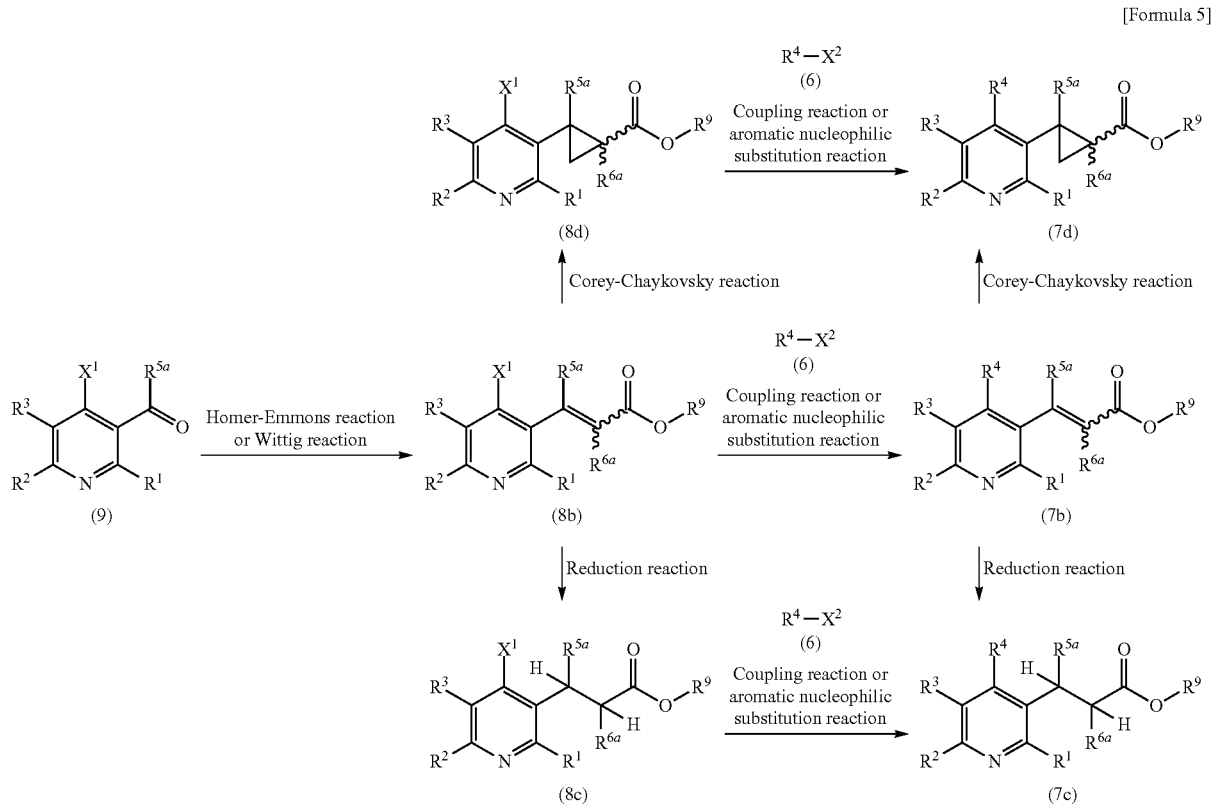

Examples of reagents used in the reduction reaction in the reaction scheme include the aforementioned reagents as well as benzenesulfonohydrazide.

Compound (7d) or (8d) can be produced by subjecting compound (7b) or (8b) to Corey-Chaykovsky conditions in the presence of an ylide.

Examples of the ylide include dimethylsulfonium methylide and dimethylsulfoxonium methylide.

The ylide can be produced by a method known per se in the art [for example, a method described in Journal of the American Chemical Society, 87, 1353, (1965)] or a method equivalent thereto.

Compound (7b) can also be produced, for example, from compound (8b), (10) or (14) by a method shown in the following Reaction Scheme 4 or a method equivalent thereto.

Reaction Scheme 4

[Formula 6]

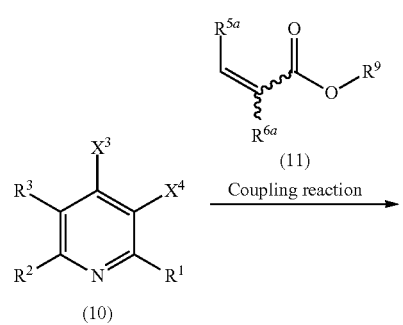

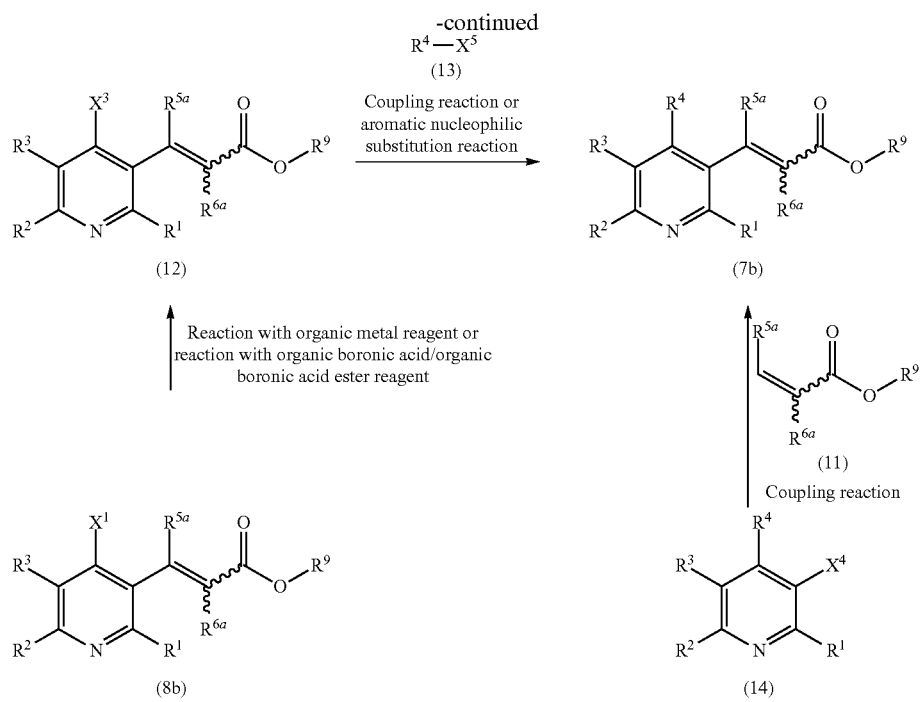

In the reaction scheme, X³ represents a boryl group

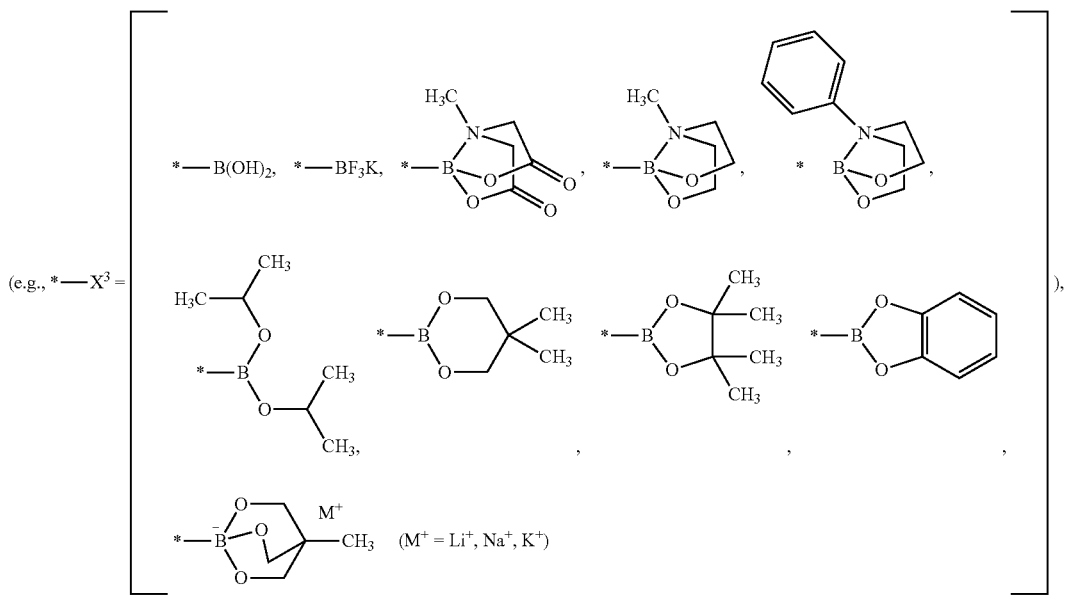

an optionally substituted $C_{1-6}$ alkylstannyl group (e.g., trimethylstannyl or n-tributylstannyl), an optionally substituted $C_{2-6}$ alkenylstannyl group, or the like.

In the reaction scheme, $X^4$ and $X^5$ each represent the aforementioned leaving group.

Other symbols are as defined above.

Compound (12) can be produced by coupling reaction using compound (10).

Furthermore, compound (12) can be produced by reacting compound (8b), wherein $X^1$ is a leaving group (e.g., a chlorine atom), with an organometallic reagent (e.g., hexabutyldistannane) or an organic boronic acid/organic boronic acid ester reagent (e.g., bis(pinacolato)diboron).

The reaction can be carried out in the presence of a base or an inorganic salt such as a lithium salt.

In addition, the reaction can be carried out in the presence of a metal complex (e.g., [1,1-bis(diphenylphosphino)ferrocene]palladium(II) dichloride dichloromethane complex, tris(dibenzylideneacetone)dipalladium(0), palladium(II) acetate, tetrakis(triphenylphosphine)palladium(0) and dichlorobis(triphenylphosphine)palladium(II)).

Compound (12) can also be produced by other methods known per se in the art.

[Production Method 2]

Compound (Ib), a compound of formula (I) wherein $R^8$ is an optionally substituted $C_{6-14}$ aryl group or an optionally substituted 5- to 14-membered aromatic heterocyclic group, can also be produced by a method shown in the following Reaction Scheme 5 or a method equivalent thereto.

Reaction Scheme 5

[Formula 8]

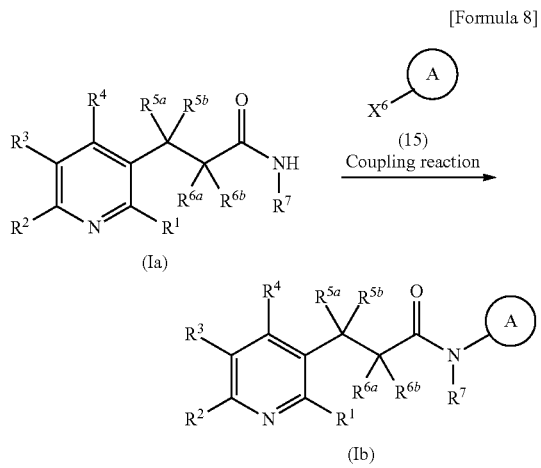

In the reaction scheme, ring A represents an optionally substituted $C_{6-14}$ aromatic hydrocarbon ring or an optionally substituted 5- to 14-membered aromatic heterocycle.

In the reaction scheme, $X^6$ represents the aforementioned leaving group.

Other symbols are as defined above.

In Reaction Scheme 5, compound (Ia) can be produced by the aforementioned method shown in Reaction Scheme 1.

Other compounds related to compound (I), wherein $R^7$ is an optionally substituted $C_{6-14}$ aryl group or an optionally substituted 5- to 14-membered aromatic heterocyclic group, can also be produced according to Reaction Scheme 5.

A compound included within the scope of the present invention can also be produced by further subjecting a compound of formula (I) (e.g., compound (I), (Ia) or (Ib) obtained by a method described above) to the introduction of substituents or functional group conversion by the application of an approach known per se in the art.

In addition, depending on the type of substituents in the starting compound, a compound produced by the production method described above can be used as a starting material in an approach known per se in the art to produce a starting compound with differing substituents.

The resulting product of these reactions, compound (I), may be produced as a single compound or as a mixture.

When the compound (I) consists of isomers such as optical isomers, stereoisomers, positional isomers or rotational isomers, either of the isomers and a mixture thereof are both included in the definition of compound (I).

For example, when compound (I) consists of optical isomers, the optical isomers resolved from a racemate are also included in the definition of compound (I). These isomers can each be obtained as a single product by synthesis or separation methods (e.g., concentration, solvent extraction, column chromatography and recrystallization) known per se in the art.

In addition, when the compound (I) consists of stereoisomers, each of these individual isomers or mixtures thereof are both included in the present invention.

When isomer formation occurs, the stereoisomers (E and Z forms) of compound (I) can be isolated and purified by common separation approaches, for example, extraction, recrystallization, distillation or chromatography. In this manner, pure compound can be produced. Alternatively, isomerization of the double bond may be promoted by use of heating, an acid catalyst, a transition metal complex, a metal catalyst, a radical initiator, light irradiation, or a strong base catalyst, etc., according to a method described in Shin Jikken Kagaku Koza (New Experimental Chemistry in English), Vol. 14, (edited by The Chemical Society of Japan), p. 251-253 or The Fourth Series of Experimental Chemistry, Vol. 19 (edited by The Chemical Society of Japan), p. 273-274, or a method equivalent thereto to obtain the corresponding pure isomers.

Compound (I) may be crystalline, and both the single crystal form and a mixture of crystal forms are included in the definition of compound (I). The crystals can be produced by crystallization by the application of a crystallization method known per se in the art.

In addition, the compound (I) may be a pharmaceutically acceptable cocrystal or cocrystal salt. In this context, a cocrystal or a cocrystal salt refers to a crystalline substance constituted by two or more unique substances at room temperature, each having distinctive physical properties (for example, structure, melting point, heat of melting, hygroscopicity and stability). The cocrystal and the cocrystal salt can be produced according to a cocrystallization method known per se in the art.

Examples of counter molecules in the cocrystal or cocrystal salt of compound (I) may include acids (for example, carboxylic acids, phosphoric acid, sugar acids and sulfonic acids), amides, ureas, bases, maltols and amino acids.

Preferred examples of the above-mentioned carboxylic acids include fumaric acid, citric acid, glutaric acid, malonic acid, succinic acid, maleic acid, malic acid, tartaric acid, mandelic acid, lactic acid, gluconic acid, acetic acid, benzoic acid, gentisic acid, salicylic acid and hippuric acid.

Preferred examples of the above-mentioned sugar acids include ascorbic acid.

Preferred examples of the above-mentioned sulfonic acids include 2-naphthalenesulfonic acid, 10-camphorsulfonic acid and methanesulfonic acid.

Preferred examples of the above-mentioned amides include nicotinamide, benzamide, lactamide, glycol amide and saccharin.

Preferred examples of the above-mentioned bases include tromethamine and meglumine.

Preferred examples of the above-mentioned maltols include ethyl maltol.

Preferred examples of the above-mentioned amino acids include tyrosine, alanine, serine, threonine, isoleucine, leucine, arginine, lysine, proline, tryptophan, valine, glutamic acid, aspartic acid, glycine, asparagine, methionine, cysteine, phenylalanine, glutamine and histidine.

Compound (I) may be a hydrate, a non-hydrate, a solvate or a non-solvate.

Compound (I) may be labeled with an isotope (e.g., $^2H$, $^3H$, $^{11}C$, $^{14}C$, $^{35}S$, $^{125}I$) or the like. A compound of formula (I) labeled or substituted with an isotope can be used as, for example, as a tracer (PET tracer), in positron emission tomography (PET) and is useful in fields of medical diagnosis and the like.

Compound (I) may be a prodrug.

A prodrug of compound (I) is a compound that is converted to compound (I) under physiological conditions in vivo, such as through a reaction caused by an enzyme, gastric acid or the like, i.e., a compound that is converted to compound (I) by enzymatic oxidation, reduction, hydrolysis, etc., or a compound that is converted to compound (I) by hydrolysis, etc., caused by gastric acid or the like. Examples of the prodrug of compound (I) include: a compound in which amino group of compound (I) is acylated, alkylated or phosphorylated (e.g., a compound in which the amino group of compound (I) is eicosanoylated, alanylated, pentylaminocarbonylated, (5-methyl-2-oxo-1,3-dioxolen-4-yl)methoxycarbonylated, tetrahydrofuranylated, pyrrolidylmethylated, pivaloyloxymethylated or tert-butylated); a compound in which the hydroxy group of compound (I) is acylated, alkylated, phosphorylated or boronated (e.g., a compound in which hydroxy of the compound (I) is acetylated, palmitoylated, propanoylated, pivaloylated, succinylated, fumarylated, alanylated or dimethylaminomethylcarbonylated); and a compound in which the carboxy group of compound (I) is esterified or amidated (e.g., a compound in which carboxy of the compound (I) is ethyl-esterified, phenyl-esterified, carboxymethyl-esterified, dimethylaminomethyl-esterified, pivaloyloxymethyl-esterified, ethoxycarbonyloxyethyl-esterified, phthalidyl-esterified, (5-methyl-2-oxo-1,3-dioxolen-4-yl)methyl-esterified, cyclohexyloxycarbonylethyl-esterified or methylamidated). These compounds can be produced from compound (I) by a method known per se in the art.

The prodrug of compound (I) may be converted to compound (I) under physiological conditions as described in IYAKUHIN no KAIHATSU (Development of Pharmaceuticals in English), Vol. 7, Molecular Design, p. 163-198, Hirokawa Shoten Ltd. (1990).

Compound (I) or the prodrug thereof (in the present specification, sometimes abbreviated as the "compound of the present invention") has CDK8 and/or CDK19 inhibitory activity and is useful as a clinically useful preventive or therapeutic agent for cancer, a cancer growth inhibitor, a cancer metastasis inhibitor, an apoptosis promoter and the like.

The compound of the present invention can be used in the prevention or treatment of diseases associated with CDK8 and/or CDK19 in mammals (e.g., mice, rats, hamsters, rabbits, cats, dogs, cattle, sheep, monkeys and humans).

The compound of the present invention possesses excellent membrane permeability and may provide efficacy at lose dose, thus making it a superior preventive or therapeutic agent for cancer or the like with reduced adverse reactions. The compound of the present invention demonstrates superior properties in terms of efficacy, pharmacokinetics (e.g., absorbability, distribution, metabolism and excretion), solubility (e.g., water solubility), interaction with other medicaments (e.g., drug-metabolizing enzyme inhibitory action), safety (e.g., acute toxicity, chronic toxicity, genotoxicity, reproductive toxicity, cardiotoxicity, carcinogenicity and central toxicity) and stability (e.g., chemical stability and stability against enzymes) and is therefore useful as a medicament.

Examples of the cancer to which the compound of the present invention is applied include colorectal cancer (e.g., colon cancer, rectal cancer, anal cancer, familial colorectal cancer, hereditary non-polyposis colorectal cancer and gastrointestinal stromal tumors), lung cancer (e.g., non-small cell lung cancer, small-cell lung cancer and malignant mesothelioma), mesothelioma, pancreatic cancer (e.g., ductal pancreatic cancer and pancreatic endocrine tumor), throat cancer, cancer of larynx, esophageal cancer, stomach cancer (e.g., papillary adenocarcinoma, mucinous adenocarcinoma and adenosquamous carcinoma), duodenal cancer, small intestine cancer, breast cancer (e.g., invasive ductal breast cancer, noninvasive ductal breast cancer and inflammatory breast cancer), ovarian cancer (e.g., epithelial ovarian cancer, extragonadal germ cell tumors, ovarian germ cell tumors and ovarian low malignant potential tumors), testicular tumors, prostate cancer (e.g., hormone-dependent prostate cancer, hormone-independent prostate cancer and castration-resistant prostate cancer), liver cancer (e.g., hepatocellular cancer, primary liver cancer and extrahepatic bile duct cancer), thyroid cancer (e.g., medullary thyroid cancer), kidney cancer (e.g., renal cell cancer and transitional cell cancer of the renal pelvis and ureter), uterine cancer (e.g., endometrial cancer, uterine cervical cancer, uterine body cancer and uterine sarcoma), gestational choriocarcinoma, brain tumors (e.g., medulloblastoma, glioma, pineal astrocytoma, pilocytic astrocytoma, diffuse astrocytoma, anaplastic astrocytoma and pituitary adenoma), retinoblastoma, skin cancer (e.g., basalioma and malignant melanoma), sarcoma (e.g., rhabdomyosarcoma, leiomyosarcoma, soft tissue sarcoma and spindle cell sarcoma), malignant bone tumor, bladder cancer, blood cancer (e.g., multiple myeloma, leukemia (e.g., acute myeloid leukemia), malignant lymphoma, Hodgkin disease and chronic myeloproliferative disease) and cancer of unknown primary.

Among these cancers, the compound of the present invention is particularly efficacious against colorectal cancer, pancreatic cancer, prostate cancer, sarcoma and blood cancer (e.g., multiple myeloma and leukemia (e.g., acute myeloid leukemia)).

The compound of the present invention can be orally or parenterally administered as a medicament to mammals (preferably, humans), either alone or as a mixture with a pharmacologically acceptable carrier.

The medicament comprising the compound of the present invention (also referred to as the "medicament of the present invention") is described in detail in the following. Examples of the dosage form of the medicament of the present invention include oral preparations such as tablets (including sugar-coated tablets, film-coated tablets, sublingual tablets, buccal tablets and orally disintegrating tablets), pills, granules, powders, capsules (including soft capsules and microcapsules), syrups, emulsions, suspensions and films (e.g., orally disintegrating films and patch films for application to the oral mucosa). Other examples of the dosage form of the medicament of the present invention include parenteral preparations such as injections, transfusions, transdermal preparations (e.g., iontophoresis dermal preparations), suppositories, ointments, transnasal preparations, transpulmonary preparations and eye drops. Alternatively, the medicament of the present invention may be a controlled-release preparation such as a rapid-release preparation or a sustained-release preparation (including a sustained-release microcapsule).

The medicament of the present invention can be produced by a production method known in the art (e.g., a method described in Japanese Pharmacopoeia) generally used in the field of pharmaceutical technology. If necessary, the medicament of the present invention can contain appropriate amounts of additives commonly used in the pharmaceutical field, such as excipients, binders, disintegrants, lubricants, sweeteners, surfactants, suspending agents, emulsifiers, colorants, preservatives, fragrances, corrigents, stabilizers and viscosity modifiers.

Examples of the pharmacologically acceptable carriers described above include these additives.

For example, tablets can be produced using excipients, binders, disintegrants, lubricants and the like. Pills and granules can be produced using excipients, binder and disintegrants. Powders and capsules can be produced using excipients and the like. Syrups can be produced using sweeteners and the like. Emulsions or suspensions can be produced using suspending agents, surfactants, emulsifiers and the like.

Examples of excipients include lactose, saccharose, glucose, starch, sucrose, microcrystalline cellulose, licorice powder, mannitol, sodium bicarbonate, calcium phosphate and calcium sulfate.

Examples of binders include solutions containing 5 to 10 wt % (% by weight) starch paste, 10 to 20 wt % gum arabic or gelatin, 1 to 5 wt % tragacanth, carboxymethylcellulose, sodium alginate solutions or glycerin.

Examples of disintegrants include starch and calcium carbonate.

Examples of lubricants include magnesium stearate, stearic acid, calcium stearate and purified talc.

Examples of sweeteners include glucose, fructose, invert sugar, sorbitol, xylitol, glycerin and simple syrup.

Examples of surfactants include sodium lauryl sulfate, polysorbate 80, sorbitan monofatty acid ester and polyoxyl 40 stearate.

Examples of suspending agents include gum arabic, sodium alginate, carboxymethylcellulose sodium, methylcellulose and bentonite.

Examples of emulsifiers include gum arabic, tragacanth, gelatin and polysorbate 80.

When the medicament of the present invention is, for example, in tablet form, the tablets can be produced according to a method known per se in the art by adding, for example, excipients (e.g., lactose, saccharose, starch), disintegrants (e.g., starch, calcium carbonate), binders (e.g., starch, gum arabic, carboxymethylcellulose, polyvinylpyrrolidone, hydroxypropylcellulose) or lubricants (e.g., talc, magnesium stearate, polyethylene glycol 6000) to the compound of the present invention and molding the mixture by compression, followed by coating, if necessary, by a method known per se in the art for the purpose of taste masking, enteric properties or durability. For example, hydroxypropylmethylcellulose, ethylcellulose, hydroxymethylcellulose, hydroxypropylcellulose, polyoxyethylene glycol, Tween 80, Pluronic F68, cellulose acetate phthalate, hydroxypropylmethylcellulose phthalate, hydroxymethylcellulose acetate succinate, Eudragit (manufactured by Rohm GmbH, Germany, a methacrylic acid-acrylic acid copolymer) and dyes (e.g., red iron oxide, titanium dioxide) are used as coating agents for the coating.

The injectable formulations mentioned above include intravenous injections as well as subcutaneous injections, intracutaneous injections, intramuscular injections, intraperitoneal injections, drip injections and the like.

Such injections may be prepared by a method known per se in the art, i.e., by dissolving, suspending or emulsifying the compound of the present invention in a sterile aqueous solution or oily liquid. Examples of the aqueous solution include saline and isotonic solutions containing glucose or additional adjuvants (e.g., D-sorbitol, D-mannitol, sodium chloride). The aqueous solution may contain appropriate solubilizing agents, for example, alcohols (e.g., ethanol), polyalcohols (e.g., propylene glycol, polyethylene glycol), or nonionic surfactants (e.g., polysorbate 80, HCO-50). Examples of the oily liquid include sesame oil and soybean oil. The oily liquid may contain appropriate solubilizing agents. Examples of solubilizing agents include benzyl benzoate and benzyl alcohol. The injections may be further supplemented with buffering agents (e.g., phosphate buffer solutions, sodium acetate buffer solutions), soothing agents (e.g., benzalkonium chloride, procaine hydrochloride), stabilizers (e.g., human serum albumin, polyethylene glycol), preservatives (e.g., benzyl alcohol, phenol) or the like. Prepared injectable solutions are usually filled in ampules.

The content of the compound of the present invention in the medicament of the present invention differs depending on the form of the preparation and is usually approximately 0.01 to approximately 100 wt %, preferably approximately 2 to approximately 85 wt %, more preferably approximately 5 to approximately 70 wt %, with respect to the whole preparation.

The content of additives in the medicament of the present invention differs depending on the form of the preparation and is usually approximately 1 to approximately 99.9 wt %, preferably approximately 10 to approximately 90 wt %, with respect to the whole preparation.

The compound of the present invention is stable and possesses low toxicity, and thus can be used safely. The daily dose of the compound of the present invention differs depending on the condition and body weight of the patient, the type of the compound, the administration route, etc. In the case of, for example, oral administration to a patient for the purpose of treating cancer, the daily dose in adults (body weight: approximately 60 kg) is approximately 1 to approximately 1000 mg, preferably approximately 3 to approximately 300 mg, more preferably approximately 10 to approximately 200 mg, of the compound of the present invention, which can be administered in one portion or in two or three portions.

In the case of parenteral administration, the compound of the present invention is usually administered in the form of a solution (e.g., an injection). A single dose of the compound of the present invention differs depending on the recipient, target organ, indication, administration method, etc. For example, usually approximately 0.01 to approximately 100 mg, preferably approximately 0.01 to approximately 50 mg, more preferably approximately 0.01 to approximately 20 mg, of the compound of the present invention per kg of body weight is preferably administered by intravenous injection.

The compound of the present invention can be used in combination with other drugs. Specifically, the compound of the present invention can be used in combination with drugs such as hormone therapeutics, chemotherapeutics, immunotherapeutics or agents inhibiting the effects of cell growth factors and their receptors. Hereinafter, drugs that may be used in combination with the compound of the present invention are referred to as concomitant drugs.

Examples of "hormone therapeutics" that may be used include fosfestrol, diethylstilbestrol, chlorotrianisene, medroxyprogesterone acetate, megestrol acetate, chlormadinone acetate, cyproterone acetate, danazol, allylestrenol, gestrinone, mepartricin, raloxifene, ormeloxifene, levormeloxifene, anti-estrogens (e.g., tamoxifen citrate, toremifene citrate), contraceptive pills, mepitiostane, testololactone, aminoglutethimide, LH-RH agonists (e.g., goserelin acetate, buserelin, leuprorelin acetate), droloxifene, epitiostanol, ethinyl estradiol sulfonate, aromatase inhibitors (e.g., fadrozole hydrochloride, anastrozole, letrozole, exemestane, vorozole, formestane), anti-androgens (e.g., flutamide, bicalutamide, nilutamide), 5α-reductase inhibitors (e.g., finasteride, epristeride), adrenal corticosteroid agents (e.g., dexamethasone, prednisolone, betamethasone, triamcinolone), androgen synthesis inhibitors (e.g., abiraterone), retinoids and agents delaying retinoid metabolism (e.g., liarozole), thyroid hormones and DDS (drug delivery system) preparations thereof.

Examples of "chemotherapeutics" that may be used include alkylating agents, antimetabolites, anticancer antibiotics, and plant-derived anticancer agents.

Examples of "alkylating agents" that may be used include nitrogen mustards, nitrogen mustard-N-oxide hydrochloride, chlorambucil, cyclophosphamide, ifosfamide, thiotepa, carboquone, improsulfan tosilate, busulfan, nimustine hydrochloride, mitobronitol, melphalan, dacarbazine, ranimustine, estramustine sodium phosphate, triethylenemelamine, carmustine, lomustine, streptozocin, pipobroman, etoglucid, carboplatin, cisplatin, miboplatin, nedaplatin, oxaliplatin, altretamine, ambamustine, dibrospidium hydrochloride, fotemustine, prednimustine, pumitepa, Ribomustin, temozolomide, treosulfan, trofosfamide, zinostatin stimalamer, adozelesin, cystemustine, bizelesin and DDS preparations thereof.

Examples of "antimetabolites" that may be used include mercaptopurine, 6-mercaptopurine riboside, thioinosine, methotrexate, pemetrexed, enocitabine, cytarabine, cytarabine ocfosfate, ancitabine hydrochloride, 5-FU related drugs (e.g., fluorouracil, tegafur, UFT, doxifluridine, carmofur, galocitabine, emitefur, capecitabine), aminopterin, nelarabine, leucovorin calcium, Tabloid, butocine, calcium folinate, calcium levofolinate, cladribine, emitefur, fludarabine, gemcitabine, hydroxycarbamide, pentostatin, piritrexim, idoxuridine, mitoguazone, tiazofurin, ambamustine, bendamustine and DDS preparations thereof.

Examples of "anticancer antibiotics" that may be used include actinomycin D, actinomycin C, mitomycin C, chromomycin A3, bleomycin hydrochloride, bleomycin sulfate, peplomycin sulfate, daunorubicin hydrochloride, doxorubicin hydrochloride, aclarubicin hydrochloride, pirarubicin hydrochloride, epirubicin hydrochloride, neocarzinostatin, mithramycin, sarkomycin, carzinophilin, mitotane, zorubicin hydrochloride, mitoxantrone hydrochloride, idarubicin hydrochloride and DDS preparations thereof.

Examples of "plant-derived anticancer agents" that may be used include etoposide, etoposide phosphate, vinblastine sulfate, vincristine sulfate, vindesine sulfate, teniposide, paclitaxel, docetaxel, vinorelbine and DDS preparations thereof.

Examples of "immunotherapeutics" that may be used include picibanil, Krestin, schizophyllan, lentinan, ubenimex, interferon, interleukins, macrophage colony-stimulating factor, granulocyte colony-stimulating factor, erythropoietin, lymphotoxin, BCG vaccines, *Corynebacterium parvum*, levamisole, polysaccharide K, procodazol and anti-CTLA4 antibodies.

The "cell growth factors" referred to in "agents inhibiting the effects of cell growth factors and their receptors" can be any substance that promotes the growth of cells. Typical examples of such factors include peptides with molecular weights less than or equal to 20,000 that exert effects at a low concentrations through binding to their receptors. Specific examples of such cell growth factors that may be used include (1) EGF (epidermal growth factor) or a substance having activity substantially identical thereto [e.g., TGFα], (2) insulin or a substance having activity substantially identical thereto [e.g., insulin, IGF (insulin-like growth factor)-1 and IGF-2], (3) FGF (fibroblast growth factor) or a substance having activity substantially identical thereto [e.g., acidic FGF, basic FGF, KGF (keratinocyte growth factor) and FGF-10], and (4) other cell growth factors [e.g., CSF (colony stimulating factor), EPO (erythropoietin), IL-2 (interleukin-2), NGF (nerve growth factor), PDGF (platelet-derived growth factor), TGFβ (transforming growth factor β), HGF (hepatocyte growth factor), VEGF (vascular endothelial growth factor), heregulin and angiopoietin].

The "receptor of cell growth factors" can be any receptor having the ability to bind to any of the aforementioned cell growth factors. Specific examples of the receptor that may be used include EGF receptor, heregulin receptor (e.g., HER3), insulin receptor, IGF receptor-1, IGF receptor-2, FGF receptor-1 or FGF receptor-2, VEGF receptor, angiopoietin receptor (e.g., Tie2) and PDGF receptor.

Examples of the "agents inhibiting the effects of cell growth factors and their receptors" that may be used include EGF inhibitors, TGFα inhibitors, heregulin inhibitors, insulin inhibitors, IGF inhibitors, FGF inhibitors, KGF inhibitors, CSF inhibitors, EPO inhibitors, IL-2 inhibitors, NGF inhibitors, PDGF inhibitors, TGFβ inhibitors, HGF inhibitors, VEGF inhibitors, angiopoietin inhibitors, EGF receptor inhibitors, HER2 inhibitors, HER4 inhibitors, insulin receptor inhibitors, IGF-1 receptor inhibitors, IGF-2 receptor inhibitors, FGF receptor-1 inhibitors, FGF receptor-2 inhibitors, FGF receptor-3 inhibitors, FGF receptor-4 inhibitors, VEGF receptor inhibitors, Tie-2 inhibitors, PDGF receptor inhibitors, Abl inhibitors, Raf inhibitors, FLT3 inhibitors, c-Kit inhibitors, Src inhibitors, PKC inhibitors, Trk inhibitors, Ret inhibitors, mTOR inhibitors, Aurora inhibitors, PLK inhibitors, MEK (MEK1/2) inhibitors, MET inhibitors, CDK inhibitors, Akt inhibitors and ERK inhibitors. More specific examples of agents that may be used include anti-VEGF antibodies (e.g., bevacizumab), anti-HER2 antibodies (e.g., trastuzumab and pertuzumab), anti-EGFR antibodies (e.g., cetuximab, panitumumab, matuzumab and nimotuzumab), anti-VEGFR antibodies, anti-HGF antibodies, imatinib mesylate, erlotinib, gefitinib, sorafenib, sunitinib, dasatinib, lapatinib, vatalanib, 4-(4-fluoro-2-methyl-1H-indol-5-yloxy)-6-methoxy-7-[3-(1-pyrrolidinyl)propoxy]quinazoline (AZD-2171), lestaurtinib, pazopanib, canertinib, tandutinib, 3-(4-bromo-2,6-difluorobenzyloxy)-5-[3-[4-(1-pyrrolidinyl)butyl]ureido]isothiazole-4-carboxamide (CP-547632), axitinib, N-(3,3-dimethyl-2,3-dihydro-1H-indol-6-yl)-2-(pyridin-4-ylmethylamino)pyridine-3-carboxamide (AMG-706), nilotinib, 6-[4-(4-ethylpiperazin-1-ylmethyl)phenyl]-N-[1(R)-phenylethyl]-7H-pyrrolo[2,3-d]pyrimidin-4-amine (AEE-788), vandetanib, temsirolimus, everolimus, enzastaurin, N-[4-[4-(4-methylpiperazin-1-yl)-6-(3-methyl-1H-pyrazol-5-ylamino)pyrimidin-2-ylsulfanyl]phenyl]cyclopropanecarboxamide (VX-680), phosphoric acid 2-[N-[3-[4-[5-[N-(3-fluorophenyl)carbamoylmethyl]-1H-pyrazol-3-ylamino]quinazolin-7-yloxy]propyl]-N-ethylamino]ethyl ester (AZD-1152), 4-[9-chloro-7-(2,6-difluorophenyl)-5H-pyrimido[5,4-d][2]benzazepin-2-ylamino]benzoic acid, N-[2-methoxy-5-[(E)-2-(2,4,6-trimethoxyphenyl)vinylsulfonylmethyl]phenyl]glycine sodium salt (ON-1910Na), 4-[8-cyclopentyl-7(R)-ethyl-5-methyl-6-oxo-5,6,7,8-tetrahydropteridin-2-ylamino]-3-methoxy-N-(1-methylpiperidin-4-yl)benzamide (BI-2536), 5-(4-bromo-2-chlorophenylamino)-4-fluoro-1-methyl-1H-benzimidazole-6-carbohydroximic acid 2-hydroxyethyl ester (AZD-6244), N-[2(R),3-dihydroxypropoxy]-3,4-difluoro-2-(2-fluoro-4-iodophenylamino)benzamide (PD-0325901) and everolimus (RAD001).

In addition to the drugs described above, L-asparaginase, aceglatone, procarbazine hydrochloride, protoporphyrin-cobalt complex salt, mercury hematoporphyrin-sodium, topoisomerase I inhibitors (e.g., irinotecan, topotecan), topoisomerase II inhibitors (e.g., sobuzoxane), differentiation inducers (e.g., retinoids and vitamin D related compounds), other angiogenesis inhibitors (e.g., fumagillin, shark extracts, COX-2 inhibitors), α-blockers (e.g., tamsulosin hydrochloride), bisphosphonic acids (e.g., pamidronate, zoledronate), thalidomide, 5-azacytidine, decitabine, proteasome inhibitors (e.g., bortezomib), antitumor antibodies such as anti-CD20 antibodies, toxin-labeled antibodies or the like can also be used as concomitant drugs.

Combination of the compound of the present invention and concomitant drugs can produce significant advantages, such as: (1) the dose can be reduced compared to administration of either the compound of the present invention or the concomitant drug alone, (2) the compound of the present invention and the concomitant drug can be selected according to the patient conditions (mild disease, serious disease, etc.), (3) the period of treatment can be made longer, (4) a sustained therapeutic effect can be achieved, and (5) a synergistic effects can be obtained by combined use of the compound of the present invention and the concomitant drug.

Hereinafter, the combined use of the compound of the present invention and the concomitant drug is referred to as the "combination drug of the present invention".

For use of the combination drug of the present invention, the time of administration for the compound of the present invention and the time of administration of the concomitant drug are not limited, and the compound of the present invention and the concomitant drug may be administered simultaneously or in a staggered manner. In the case of staggered administration, the time lag between doses differs depending on the active ingredients to be administered, the dosage forms and the administration methods. For example, when administering the concomitant drug first, the compound of the present invention can then be administered within 1 minute to 3 days, preferably within 10 minutes to 1 day, more preferably within 15 minutes to 1 hour, after administration of the concomitant drug. In the case of first administering the compound of the present invention, the concomitant drug can then be administered within 1 minute to 1 day, preferably within 10 minutes to 6 hours, more preferably within 15 minutes to 1 hour, after administration of the compound of the present invention. The dose of the concomitant drug can be in accordance with the clinically used dose, or can be selected appropriately according to recipient, administration route, indication, combination, etc.

Examples of the administration mode of the compound of the present invention and the concomitant drug used in combination include: (1) administration of a single preparation obtained by simultaneously formulating the compound of the present invention and the concomitant drug, (2) simultaneous administration through the same administration route of two preparations obtained by separately formulating the compound of the present invention and the concomitant drug, (3) administration at different times through the same administration route of two preparations obtained by separately formulating the compound of the present invention and the concomitant drug, (4) simultaneous administration through different administration routes of two preparations obtained by separately formulating the compound of the present invention and the concomitant drug, and (5) administration at different times through different administration routes of two preparations obtained by separately formulating the compound of the present invention and the concomitant drug (e.g., administration of the compound of the present invention followed by the concomitant drug, or in the reverse order).

The dose of the concomitant drug can be selected appropriately according to the clinically used dose. In addition, the ratio between the compound of the present invention and the concomitant drug used can be selected appropriately according to recipient, administration route, target disease, indication, combination, etc. For example, when the recipient is a human, 0.01 to 100 parts by weight of the concomitant drug can be used with respect to 1 part by weight of the compound of the present invention.

The compound of the present invention or the combination drug of the present invention can be further used in combination with a non-drug therapies.

Specifically, the compound of the present invention or the combination drug of the present invention may be combined with a non-drug therapies such as (1) surgery, (2) induced hypertension chemotherapy using angiotensin II or the like, (3) gene therapy, (4) thermotherapy, (5) cryotherapy, (6) laser cauterization or (7) radiation therapy.

The compound of the present invention or the combination drug of the present invention can be used, for example, before or after the surgery, etc. described above, or before or after treatment involving a combination of two or three of these therapies to produce effects such as preventing the development of resistance, prolonged disease-free survival, inhibition of cancer metastasis or recurrence, and prolonged survival.

In addition, treatment with the compound of the present invention or the combination drug of the present invention may be combined with supportive care [e.g., (i) the administration of antibiotics (for example, β-lactam antibiotics such as Pansporin or macrolide antibiotics such as clarithromycin) against various types of intercurrent infection, (ii) the administration of a high-calorie infusions, an amino acid preparations or multivitamins for the treatment of malnutrition, (iii) the administration of morphine for pain relief, (iv) the administration of drugs for treatment adverse reactions such as nausea, vomiting, anorexia, diarrhea, leukopenia, thrombocytopenia, decreased hemoglobin concentration, alopecia, liver damage, kidney damage, DIC or fever and (v) the administration of drugs for the prevention of cancer multidrug resistance].

The present invention is described in further in further detail in the Examples, Formulation Examples and Test Examples below. However, the present invention is not intended to be limited by them, and various changes or modifications may be made therein without departing from the scope of the present invention.

EXAMPLES

In the Examples below, the term "room temperature" usually means approximately 10° C. to approximately 35° C. A ratio used for a mixed solvent represents a volume ratio unless otherwise specified. Unless otherwise specified, % represents wt %.

The term "NH" in silica gel column chromatography represents that an aminopropylsilane-bound silica gel was used. The term "C18" in HPLC (high-performance liquid chromatography) represents that an octadecyl-bound silica gel was used. A ratio used for elution solvents represents a volume ratio unless otherwise specified.

In the Examples, Preparation Examples and Test Examples below, the following abbreviations are used:
mp: melting point
MS: mass spectrum
M: molar concentration
$CDCl_3$: deuterated chloroform DMSO-d$_6$: deuterated dimethyl sulfoxide
$^1$H NMR: proton nuclear magnetic resonance
LC/MS: liquid chromatograph-mass spectrometer
ESI: electrospray ionization
APCI: atmospheric pressure chemical ionization
DME: 1,2-dimethoxyethane
DMA: N,N-dimethylacetamide
THF: tetrahydrofuran
HATU: 2-(7-azabenzotriazol-1-yl)-1,1,3,3-tetramethyluronium hexafluorophosphate
HOBt: 1-hydroxybenzotriazole
Pd$_2$(dba)$_3$: tris(dibenzylideneacetone)dipalladium(0)
Pd(OAc)$_2$: palladium(II) acetate
Pd(PPh$_3$)$_4$: tetrakis(triphenylphosphine)palladium(0)
PdCl$_2$(dppf) CH$_2$Cl$_2$ adduct: [1,1'-bis(diphenylphosphino)ferrocene]palladium(II) dichloride dichloromethane adduct
MTBE: methyl tert-butyl ether
EDCI: 1-ethyl-3-(3-dimethylaminopropyl)carbodiimide hydrochloride
NaBH$_4$: sodium borohydride
LAH: lithium aluminum hydride
NaBH(OAc)$_3$: sodium triacetoxyborohydride
Sphos: 2-dicyclohexylphosphino-2',6'-dimethoxybiphenyl
Ruphos: dicyclohexyl(2',6'-diisopropoxybiphenyl-2-yl)phosphine
Xphos: 2-dicyclohexylphosphino-2',4',6'-triisopropylbiphenyl
BINAP: 2,2'-bis(diphenylphosphino)-1,1'-binaphthyl
Xantphos: 4,5-bis(diphenylphosphino)-9,9-dimethylxanthene
IPE: isopropyl ether
CPME: cyclopentyl methyl ether
DAST: N,N-diethylaminosulfur trifluoride
Boc$_2$O: di-tert-butyl dicarbonate
DMAP: N,N-dimethyl-4-aminopyridine
DIAD: diisopropyl azodicarboxylate
PPh$_3$: triphenylphosphine
TFA: trifluoroacetic acid
DIEA: diisopropylethylamine
ADDP: 1,1'-(azodicarbonyl)dipiperidine
DEAD: diethyl azodicarboxylate $^1$H NMR spectra were measured by Fourier transform NMR. ACD/SpecManager (trade name) or the like was used in the analysis. No mention is made of very broad peaks for protons of hydroxy groups, amino groups and the like.

MS was measured using an LC/MS. ESI or APCI were used as ionization methods. Data presented are the experimentally measured values (found). In general, molecular ion peaks ([M+H]$^+$, [M–H]$^-$ etc.) are observed. In the case of, for example, a compound having a tert-butoxycarbonyl group, a fragment ion peak derived from the elimination of the tert-butoxycarbonyl group or the tert-butyl group may be observed. In the case of a compound having a hydroxy group, a fragment ion peak derived from the elimination of H$_2$O may be observed. In the case of a salt, a molecular ion peak or fragment ion peak of the free form is usually observed.

The units for sample concentration (c) in optical rotation ([α]$_D$) measurements are g/100 mL.

Elemental analysis values (Anal.) shown the calculated values (Calcd) and experimentally measured values (Found).

Example 1

(2E)-N-(4-(2-(1,3,4-Oxadiazol-2-yl)ethyl)phenyl)-3-(4-(2-thienyl)pyridin-3-yl)acrylamide (A) (2E)-N-(4-(2-(1,3,4-Oxadiazol-2-yl)ethyl)phenyl)-3-(4-chloropyridin-3-yl)acrylamide To a solution of (2E)-3-(4-chloropyridin-3-yl)acrylic acid (700 mg) in DMF (15 mL), 4-(2-(1,3,4-oxadiazol-2-yl)ethyl)aniline (794 mg), HATU (1740 mg) and DIEA (1.971 mL) were added at room temperature, and the mixture was stirred at the same temperature for 24 hours. The reaction mixture was diluted with ethyl acetate (50 mL) and water (50 mL), and the aqueous layer was extracted with ethyl acetate. The extract was washed with water and brine and then dried over anhydrous sodium sulfate, and the solvent was distilled off under reduced pressure. The residue was purified by silica gel column chromatography (ethyl acetate/hexane and subsequently methanol/ethyl acetate) to obtain the title compound (586 mg).
MS: [M+H]$^+$ 354.9.

(B) (2E)-N-(4-(2-(1,3,4-Oxadiazol-2-yl)ethyl)phenyl)-3-(4-(2-thienyl)pyridin-3-yl)acrylamide To a solution of (2E)-N-(4-(2-(1,3,4-oxadiazol-2-yl)ethyl)phenyl)-3-(4-chloropyridin-3-yl)acrylamide (21.29 mg) in DME (900 uL), thiophen-2-ylboronic acid (15.35 mg), bis(di-tert-butyl(4-dimethylaminophenyl)phosphine)dichloropalladium(II) (4.25 mg) and a 1.2 M aqueous cesium carbonate solution (100 uL) were added, and the mixture was heated at 130° C. for 2 hours under microwave irradiation. Water (1 mL) and ethyl acetate (3 mL) were added to the reaction mixture, and the mixture was stirred. Then, the organic layer was passed through a phase separation filter, and the solvent was evaporated from the separated solution by blowing dry with a stream of air. The residue was purified by HPLC (C18, mobile phase: acetonitrile/10 mM aqueous ammonium bicarbonate solution), and the solvent was evaporated by blowing dry with a stream of air to obtain the title compound (11.4 mg).

Example 3

(2E)-N-(4-(2-(1,3,4-Oxadiazol-2-yl)ethyl)phenyl)-3-(4-(1H-pyrrol-2-yl)pyridin-3-yl)acrylamide To a solution of (2E)-N-(4-(2-(1,3,4-oxadiazol-2-yl)ethyl)phenyl)-3-(4-chloropyridin-3-yl)acrylamide (21.29 mg) in DME (900 uL), (1-(tert-butoxycarbonyl)-1H-pyrrol-2-yl)boronic acid (25.3 mg), bis(di-tert-butyl(4-dimethylaminophenyl)phosphine)dichloropalladium(II) (4.25 mg) and a 1.2 M aqueous cesium carbonate solution (100 uL) were added, and the mixture was heated at 130° C. for 2 hours under microwave irradiation. Then, (1-(tert-butoxycarbonyl)-1H-pyrrol-2-yl)boronic acid (25.3 mg) and bis(di-tert-butyl(4-dimethylaminophenyl)phosphine)dichloropalladium(II) (4.25 mg) were added thereto, and the mixture was heated at 130° C. for 2 hours under microwave irradiation. Water (1 mL) and ethyl acetate (3 mL) were added to the reaction mixture, and the mixture was stirred. Then, the organic layer was passed through a phase separation filter, and the solvent was evaporated from the separated solution by blowing dry with a stream of air. The residue was purified by HPLC (C18, mobile phase: acetonitrile/10 mM aqueous ammonium bicarbonate solution), and the solvent was evaporated by blowing dry with a stream of air to obtain the title compound (16.5 mg).

Example 5

(2E)-3-(4-(5-Cyano-2-thienyl)pyridin-3-yl)-N-(4-(2-(1,3,4-oxadiazol-2-yl)ethyl)phenyl)acrylamide To a solution of (2E)-N-(4-(2-(1,3,4-oxadiazol-2-yl)ethyl) phenyl)-3-(4-chloropyridin-3-yl)acrylamide (21.29 mg) in 2-methyl-2-butanol (900 uL), (5-cyanothiophen-2-yl)boronic acid (18.36 mg), SPhos (2.4 mg), chloro(2-dicyclohexylphosphino-2',6'-dimethoxy-1,1'-biphenyl)[2-(2-aminoethylphenyl)]palladium(II) methyl-tert-butyl ether adduct (4.5 mg) and a 1.2 M aqueous cesium carbonate solution (100 uL) were added, and the mixture was heated at 130° C. for 30 minutes under microwave irradiation. Water (1 mL) and ethyl acetate (3 mL) were added to the reaction mixture, and the mixture was stirred. Then, the organic layer was passed through a phase separation filter, and the solvent was evaporated from the separated solution by blowing dry with a stream of air. The residue was purified by HPLC (C18, mobile phase: acetonitrile/10 mM aqueous ammonium bicarbonate solution), and the solvent was evaporated by blowing dry with a stream of air to obtain the title compound (21.9 mg).

Example 31

(2E)-3-(4-(1-Methyl-1H-pyrazol-4-yl)pyridin-3-yl)-N-(4-(morpholin-4-ylmethyl)phenyl)acrylamide (A) 4-(4-Nitrobenzyl)morpholine To a solution of 1-(bromomethyl)-4-nitrobenzene (10 g) in anhydrous THF (200 mL), morpholine (8 mL) and triethylamine (9.7 mL) were added at room temperature, and the mixture was stirred at 60° C. for 2 hours. The solvent was distilled off under reduced pressure, ethyl acetate (100 mL) and saturated aqueous sodium bicarbonate solution (100 mL) were added to the residue at room temperature, and the aqueous layer was extracted with ethyl acetate. The extract was washed with water and brine and then dried over anhydrous sodium sulfate, and the solvent was distilled off under reduced pressure to obtain the title compound as a crude product (10.12 g). This compound was used in the next step without being further purified.
$^1$H NMR (300 MHz, CDCl$_3$) δ 2.40-2.49 (4H, m), 3.59 (2H, s), 3.69-3.76 (4H, m), 7.53 (2H, d, J=8.9 Hz), 8.15-8.22 (2H, m).

(B) 4-(Morpholinomethyl)aniline

To a solution of 4-(4-nitrobenzyl)morpholine (510.8 mg) in THF (4 mL) and methanol (4 mL), activated carbon (50 mg), iron trichloride hexahydrate (31.1 mg) and hydrazine hydrate (0.669 mL) were added at room temperature, and the mixture was heated at reflux at 70° C. for 13 hours. The insoluble matter was removed by filtration through Celite, and the filtrate was concentrated under reduced pressure. Then, ethyl acetate (30 mL) and saturated aqueous sodium bicarbonate solution (30 mL) were added to the residue at room temperature, and the aqueous layer was extracted with ethyl acetate. The extract was washed with brine and then dried over anhydrous magnesium sulfate, and the solvent was distilled off under reduced pressure to obtain the title compound as a crude product (428 mg). This compound was used in the next step without being further purified.
$^1$H NMR (300 MHz, CDCl$_3$) δ 2.37-2.45 (4H, m), 3.38 (2H, s), 3.62 (2H, brs), 3.66-3.73 (4H, m), 6.61-6.67 (2H, m), 7.06-7.12 (2H, m).

(C) (2E)-Ethyl 3-(4-chloropyridin-3-yl)acrylate

To a mixture of 60% sodium hydride (1.836 g) and THF (40 mL), a solution of ethyl 2-(diethoxyphosphoryl)acetate (10 mL) in THF (10 mL) was added with ice cooling under nitrogen atmosphere, and the resulting mixture was stirred at the same temperature for 1 hour. A mixture of 4-chloronicotinaldehyde (5.056 g) and DMF (35 mL) was added dropwise to the reaction mixture under ice cooling, and the resulting mixture was stirred at room temperature for 4 hours. The reaction mixture was concentrated under reduced pressure, then water (50 mL) and ethyl acetate (50 mL) were added to the residue at room temperature, and the aqueous layer was extracted with ethyl acetate. The extract was washed with water and brine and then dried over anhydrous magnesium sulfate, and the solvent was distilled off under reduced pressure. The residue was purified by silica gel column chromatography (ethyl acetate/hexane) to obtain the title compound (6.47 g).
MS: [M+H]$^+$ 211.9.

(C') (2E)-Ethyl 3-(4-chloropyridin-3-yl)acrylate

To a mixture of 4-chloronicotinaldehyde hydrochloride (25 g), ethyl 2-(diethoxyphosphoryl)acetate (32.2 mL), lithium chloride (7.14 g) and acetonitrile (500 mL), 2,3,4,6,7,8,9,10-octahydropyrimido[1,2-a]azepine (46.6 mL) was added at 0° C., and the reaction mixture was stirred at room temperature for 2 hours. Ethyl acetate and water were added to the reaction mixture at 0° C., and the aqueous layer was extracted with ethyl acetate. The extract was washed with water and brine, and then dried over anhydrous magnesium sulfate, and the solvent was distilled off under reduced pressure. The residue was purified by silica gel column chromatography (ethyl acetate/hexane) to obtain the title compound (23.78 g).
MS: [M+H]$^+$ 212.1.

(D) (2E)-3-(4-Chloropyridin-3-yl)acrylic acid

To a solution of (2E)-ethyl 3-(4-chloropyridin-3-yl)acrylate (7.91 g) in THF (50 mL) and ethanol (50 mL), a 2 N aqueous sodium hydroxide solution (56.1 mL) was added at room temperature, and the mixture was stirred at the same temperature for 6 hours. The solvent was distilled off under reduced pressure, and 2 N hydrochloric acid was added to the residue under ice cooling to adjust the pH to 3. The precipitate was collected by filtration and washed with water to obtain the title compound (6.62 g).
MS: [M+H]$^+$ 184.1.

(E) (2E)-3-(4-Chloropyridin-3-yl)-N-(4-(morpholinomethyl)phenyl)acrylamide

To a suspension of (2E)-3-(4-chloropyridin-3-yl)acrylic acid (51 mg) in anhydrous THF (3 mL), DMF (one drop) and oxalyl dichloride (0.072 mL) were added at room temperature, and the mixture was stirred at the same temperature for 40 minutes. Oxalyl dichloride (0.072 ml) was added to the reaction mixture at room temperature, and the mixture was further stirred at the same temperature for 20 minutes. The solvent was distilled off under reduced pressure to obtain a solid. To a solution of 4-(morpholinomethyl)aniline (58.7 mg) in DMA (2 mL), a solution of the solid thus obtained (whole amount) in DMA (1 mL) was added at room temperature, and the mixture was stirred at the same temperature for 2 hours to obtain a reaction mixture containing the title compound. Likewise, to a suspension of (2E)-3-(4-chloropyridin-3-yl)acrylic acid (601 mg) in anhydrous THF (40 mL), DMF (5 drops) and oxalyl dichloride (1.4 mL) were added at room temperature, and the mixture was stirred at the same temperature for 1 hour. The solvent was distilled off under reduced pressure to obtain a solid. To a solution of 4-(morpholinomethyl)aniline (692 mg) in DMA (10 mL), a solution of the solid thus obtained (whole amount) in DMA (10 mL) was added at room temperature, and the mixture was stirred at the same temperature for 2.5 hours to obtain a reaction mixture containing the title compound. The reaction mixtures containing the title compounds were combined and added to saturated aqueous sodium bicarbonate solution/water (1/5, 300 mL), and the precipitate was then collected by filtration, washed with water, and then dried under reduced pressure at 80° C. to obtain the title compound (1132 mg).

MS: $[M+H]^+$ 358.0.

(F) (2E)-3-(4-(1-Methyl-1H-pyrazol-4-yl)pyridin-3-yl)-N-(4-(morpholin-4-ylmethyl)phenyl)acrylamide A mixture of (2E)-3-(4-chloropyridin-3-yl)-N-(4-(morpholinomethyl)phenyl)acrylamide (500 mg), 1-methyl-4-(4,4,5,5-tetramethyl-1,3,2-dioxaborolan-2-yl)-1H-pyrazole (581 mg), 2-(dicyclohexylphosphino)biphenyl (61.2 mg), $Pd_2(dba)_3$ (64 mg), a 2 M aqueous cesium carbonate solution (1.75 mL) and DME (8 mL) was stirred overnight under nitrogen atmosphere at 80° C. The reaction mixture was concentrated under reduced pressure, and the residue was purified by silica gel column chromatography (NH, methanol/ethyl acetate) to obtain the title compound (418 mg).

$^1$H NMR (300 MHz, DMSO-$d_6$) δ 2.30-2.38 (4H, m), 3.42 (2H, s), 3.52-3.59 (4H, m), 3.93 (3H, s), 6.85 (1H, d, J=15.6 Hz), 7.27 (2H, d, J=8.5 Hz), 7.49 (1H, d, J=5.7 Hz), 7.61-7.77 (4H, m), 8.08 (1H, s), 8.53 (1H, d, J=5.3 Hz), 8.77 (1H, s), 10.28 (1H, s).

Example 32

(2E)-N-(4-((2,4-Dioxo-1,3-thiazolidin-5-yl)methyl)phenyl)-3-(4-(1H-pyrazol-4-yl)pyridin-3-yl)acrylamide (A) (2E)-Ethyl 3-(4-(1H-pyrazol-4-yl)pyridin-3-yl)acrylate A mixture of (2E)-ethyl 3-(4-chloropyridin-3-yl)acrylate (995 mg), tert-butyl 4-(4,4,5,5-tetramethyl-1,3,2-dioxaborolan-2-yl)-1H-pyrazole-1-carboxylate (2655 mg), Sphos (185 mg), chloro(2-dicyclohexylphosphino-2',6'-dimethoxy-1,1'-biphenyl)[2-(2-aminoethylphenyl)]palladium(II) methyl-tert-butyl ether complex (343 mg), cesium carbonate (4411 mg), DME (15 mL) and water (3 mL) was stirred at 130° C. for 1.5 hours. The reaction mixture was filtered through Celite, and the filtrate was extracted with ethyl acetate. The organic layer was washed with brine and then dried over anhydrous magnesium sulfate, and the solvent was distilled off under reduced pressure. The residue was purified by silica gel column chromatography (ethyl acetate/hexane) to obtain the title compound (750 mg).

MS: $[M+H]^+$ 243.9.

(B) (2E)-tert-Butyl 4-(3-(3-ethoxy-3-oxoprop-1-en-1-yl)pyridin-4-yl)-1H-pyrazole-1-carboxylate $Boc_2O$ (0.79 mL) was added to a mixture of (2E)-ethyl 3-(4-(1H-pyrazol-4-yl)pyridin-3-yl)acrylate (750 mg), DMAP (38 mg) and THF (20 mL) at room temperature, and the resulting mixture was stirred at the same temperature for 2 hours. $Boc_2O$ (0.36 mL) and DMAP (19 mg) were added thereto at room temperature, and the mixture was further stirred at the same temperature for 16 hours. Water was added to the reaction mixture, followed by extraction with ethyl acetate. The organic layer was dried over anhydrous magnesium sulfate, and the solvent was distilled off under reduced pressure to obtain the title compound (1055 mg).

MS: $[M+H]^+$ 344.0.

(C) (2E)-3-(4-(1H-Pyrazol-4-yl)pyridin-3-yl)acrylic acid

To a solution of (2E)-tert-butyl 4-(3-(3-ethoxy-3-oxoprop-1-en-1-yl)pyridin-4-yl)-1H-pyrazole-1-carboxylate (1.06 g) in ethanol (10 mL) and THF (10 mL), a 2 N aqueous sodium hydroxide solution (6.2 mL) was added at room temperature, and the mixture was stirred at the same temperature for 2 hours. The reaction mixture was concentrated under reduced pressure, the residue was neutralized by the addition of 1 N hydrochloric acid under ice cooling, and the mixture was stirred for 1 hour under ice cooling. The precipitated solid was recovered and washed with water to obtain the title compound (172 mg).

MS: $[M+H]^+$ 215.9.

(D) (2E)-N-(4-((2,4-Dioxo-1,3-thiazolidin-5-yl)methyl)phenyl)-3-(4-(1H-pyrazol-4-yl)pyridin-3-yl)acrylamide EDCI (107 mg) was added to a mixture of (2E)-3-(4-(1H-pyrazol-4-yl)pyridin-3-yl)acrylic acid (80 mg), 5-(4-aminobenzyl)thiazolidine-2,4-dione (99 mg), HOBt (75 mg) and DMF (2 mL) at room temperature, and the resulting mixture was stirred at the same temperature for 16 hours. Water was added to the reaction mixture, followed by extraction with ethyl acetate. The organic layer was washed with brine and then dried over anhydrous magnesium sulfate, and the solvent was distilled off under reduced pressure. The residue was purified by silica gel column chromatography (ethyl acetate/hexane) and then recrystallized from ethyl acetate to obtain the title compound (48 mg).

$^1$H NMR (300 MHz, DMSO-$d_6$) δ 3.09 (1H, dd, J=14.2, 9.1 Hz), 3.35-3.40 (1H, m), 4.90 (1H, dd, J=9.1, 4.4 Hz), 6.84 (1H, d, J=15.6 Hz), 7.22 (2H, d, J=8.7 Hz), 7.54 (1H, d, J=5.1 Hz), 7.65 (2H, d, J=8.5 Hz), 7.75 (1H, d, J=15.6 Hz), 7.82 (1H, s), 8.12 (1H, s), 8.53 (1H, d, J=5.1 Hz), 8.78 (1H, s), 10.31 (1H, s), 12.04 (1H, brs), 13.35 (1H, brs).

Example 37

(2E)-N-(4-((2,2-Dimethylmorpholin-4-yl)methyl)phenyl)-3-(4-(1-methyl-1H-pyrazol-4-yl)pyridin-3-yl)acrylamide (A) (2E)-N-(4-(Hydroxymethyl)phenyl)-3-(4-(1-methyl-1H-pyrazol-4-yl)pyridin-3-yl)acrylamide EDCI (836 mg) was added to a mixture of (2E)-3-(4-(1-methyl-1H-pyrazol-4-yl)pyridin-3-yl)acrylic acid (500 mg), (4-aminophenyl)methanol (322 mg), HOBt (442 mg) and DMF (10 mL) at room temperature, and the resulting mixture was stirred at the same temperature for 16 hours. The reaction mixture was concentrated under reduced pressure, and the residue was purified by silica gel column chromatography (NH, ethyl acetate/hexane and subsequently methanol/ethyl acetate) to obtain the title compound (638 mg).
MS: [M+H]$^+$ 335.2.

(B) (2E)-N-(4-Formylphenyl)-3-(4-(1-methyl-1H-pyrazol-4-yl)pyridin-3-yl)acrylamide Manganese dioxide (6.2 g) was added to a mixture of (2E)-N-(4-(hydroxymethyl)phenyl)-3-(4-(1-methyl-1H-pyrazol-4-yl)pyridin-3-yl)acrylamide (2.4 g) and ethyl acetate (400 mL) at room temperature, and the resulting mixture was stirred at 65° C. for 5 hours. The reaction mixture was filtered through Celite. Then, THF (500 mL) was added to the recovered solid, and the mixture was stirred at 70° C. for 1 hour and then filtered through Celite. The filtrates were combined and concentrated under reduced pressure to obtain the title compound (2.2 g).
$^1$H NMR (300 MHz, DMSO-d$_6$) δ 3.94 (3H, s), 6.89 (1H, d, J=15.1 Hz), 7.51 (1H, d, J=4.5 Hz), 7.72-7.97 (6H, m), 8.10 (1H, s), 8.55 (1H, d, J=4.9 Hz), 8.80 (1H, s), 9.90 (1H, s), 10.73 (1H, s).

(C) (2E)-N-(4-((2,2-Dimethylmorpholin-4-yl)methyl)phenyl)-3-(4-(1-methyl-1H-pyrazol-4-yl)pyridin-3-yl)acrylamide To a mixture of 2,2-dimethylmorpholine (42 mg), (2E)-N-(4-formylphenyl)-3-(4-(1-methyl-1H-pyrazol-4-yl)pyridin-3-yl)acrylamide (60 mg), methanol (2 mL) and acetic acid (0.2 mL), 2-picoline-boron complex (29 mg) was added at room temperature, and the resulting mixture was stirred at the same temperature for 16 hours. Water was added to the reaction mixture, the mixture was concentrated under reduced pressure, and the residue was then extracted with ethyl acetate. The organic layer was washed with brine and then dried over anhydrous magnesium sulfate, and the solvent was distilled off under reduced pressure. The residue was purified by silica gel column chromatography (NH, ethyl acetate/hexane) to obtain the title compound (57 mg).
$^1$H NMR (300 MHz, DMSO-d$_6$) δ 1.09-1.17 (6H, m), 2.11 (2H, s), 2.29 (2H, d, J=4.7 Hz), 3.38 (2H, s), 3.61 (2H, t, J=4.6 Hz), 3.93 (3H, s), 6.85 (1H, d, J=15.6 Hz), 7.27 (2H, d, J=8.3 Hz), 7.49 (1H, d, J=5.1 Hz), 7.62-7.77 (4H, m), 8.09 (1H, s), 8.53 (1H, d, J=5.3 Hz), 8.78 (1H, s), 10.28 (1H, s).

Example 40

(2E)-3-(4-(1-Methyl-1H-pyrazol-4-yl)pyridin-3-yl)-N-(5-(morpholin-4-ylmethyl)pyridin-2-yl)acrylamide

(A) 5-(Morpholinomethyl)pyridin-2-amine

To a mixture of 6-aminonicotinaldehyde (710 mg), methanol (5 mL) and THF (5 mL), NaBH(OAc)$_3$ (3080 mg) was added at room temperature, and the resulting mixture was stirred at the same temperature for 16 hours. Saturated aqueous ammonium chloride solution was added to the reaction mixture, and the mixture was concentrated under reduced pressure. Ethyl acetate was added to the residue, and the mixture was filtered through Celite. The filtrate was concentrated under reduced pressure, and the residue was purified by silica gel column chromatography (NH, ethyl acetate) and then recrystallized from ethyl acetate to obtain the title compound (440 mg).
MS: [M+H]$^+$ 194.0.

(B) (2E)-3-(4-(1-Methyl-1H-pyrazol-4-yl)pyridin-3-yl)-N-(5-(morpholin-4-ylmethyl)pyridin-2-yl)acrylamide EDCI (100 mg) was added to a mixture of (2E)-3-(4-(1-methyl-1H-pyrazol-4-yl)pyridin-3-yl)acrylic acid (60 mg), 5-(morpholinomethyl)pyridin-2-amine (76 mg), HOBt (71 mg) and DMF (2 mL) at room temperature, and the resulting mixture was stirred at the same temperature for 2 hours and then stirred at 50° C. for 2 hours. Brine was added to the reaction mixture, followed by extraction with a mixed ethyl acetate/THF solution. The organic layer was dried over anhydrous magnesium sulfate, and the solvent was distilled off under reduced pressure. The residue was purified by silica gel column chromatography (NH, ethyl acetate/hexane) and then recrystallized from ethyl acetate to obtain the title compound (7 mg).
$^1$H NMR (300 MHz, DMSO-d$_6$) δ 2.31-2.39 (4H, m), 3.45-3.54 (2H, m), 3.54-3.62 (4H, m), 3.89-4.03 (3H, m), 6.93-7.15 (1H, m), 7.39-7.60 (1H, m), 7.75 (3H, s), 8.04-8.16 (1H, m), 8.17-8.34 (2H, m), 8.42-8.61 (1H, m), 8.69-8.80 (1H, m), 10.71-10.88 (1H, m).

Example 41

(2E)-N-(2-Fluoro-4-(morpholin-4-ylmethyl)phenyl)-3-(4-(1-methyl-1H-pyrazol-4-yl)pyridin-3-yl)acrylamide

(A) 4-(3-Fluoro-4-nitrobenzyl)morpholine

3-Fluoro-4-nitrobenzoic acid (7.61 g) was added dropwise to a mixture of NaBH$_4$ (3.11 g) and THF (150 mL) under ice cooling. The reaction mixture was stirred for 30 minutes, then boron trifluoride-diethyl ether complex (13.7 mL) was added dropwise thereto under ice cooling, and the reaction mixture was stirred at room temperature for 16 hours. A 1 N hydrochloric acid solution was added to the reaction mixture under ice cooling, followed by extraction with ethyl acetate. The organic layer was washed with brine and then dried over anhydrous magnesium sulfate, and the solvent was distilled off under reduced pressure. Methanesulfonyl chloride (5.4 mL) and triethylamine (9.8 mL) were added to the reaction mixture of the residue (5.96 g) and THF (100 mL) under ice cooling, and the mixture was stirred at room temperature for 2 hours. Methanesulfonyl chloride (10.9 mL) and triethylamine (19.5 mL) were added to the reaction mixture under ice cooling, and the mixture was stirred at room temperature for 4 hours. Then, methanesulfonyl chloride (5.4 mL) and triethylamine (9.8 mL) were added thereto under ice cooling, and the mixture was stirred at room temperature for 2 hours. Water was added to the reaction mixture, followed by extraction with ethyl acetate. The organic layer was washed with brine and then dried over anhydrous magnesium sulfate, and the solvent was distilled off under reduced pressure. Toluene (30 mL) was added to the residue, and the solvent was distilled off under reduced pressure. Acetonitrile (100 mL) and morpholine (6.0 mL) were added to the residue, and the reaction mixture was stirred at room temperature for 5 hours. Then, morpholine (6.0 mL) was added thereto, and the reaction mixture was stirred at room temperature for 16 hours. Water was added to the reaction mixture, followed by extraction with ethyl acetate. The organic layer was washed with brine and then dried over anhydrous magnesium sulfate, and the solvent was distilled off under reduced pressure. The residue was purified by silica gel column chromatography (ethyl acetate/hexane) to obtain the title compound as a crude product (7.17 g). This compound was used in the next step without being further purified.

MS: [M+H]$^+$ 241.1.

(B) 2-Fluoro-4-(morpholinomethyl)aniline

To a mixture of crude 4-(3-fluoro-4-nitrobenzyl)morpholine (7.17 g), calcium chloride (3.57 g), ethanol (100 mL) and water (20 mL), reduced iron (6.56 g) was added at 90° C., and the resulting mixture was stirred at the same temperature for 1.5 hours. The reaction mixture was filtered through Celite, and the filtrate was concentrated under reduced pressure. Water was added to the residue, followed by extraction with ethyl acetate. The extract was washed with brine and then dried over anhydrous magnesium sulfate, and the solvent was distilled off under reduced pressure. The residue was purified by silica gel column chromatography (ethyl acetate/hexane) and silica gel column chromatography (NH, ethyl acetate/hexane) to obtain the title compound (2.80 g).

MS: [M+H]$^+$ 211.3.

(C) (2E)-N-(2-Fluoro-4-(morpholin-4-ylmethyl) phenyl)-3-(4-(1-methyl-1H-pyrazol-4-yl)pyridin-3-yl)acrylamide EDCI (246 mg) was added to a mixture of (2E)-3-(4-(1-methyl-1H-pyrazol-4-yl)pyridin-3-yl)acrylic acid (147 mg), 2-fluoro-4-(morpholinomethyl)aniline (270 mg), HOBt (174 mg) and DMF (3 mL) at room temperature, and the resulting mixture was stirred at the same temperature for 16 hours. Water was added to the reaction mixture, followed by extraction with a mixed ethyl acetate/THF solution. The organic layer was dried over anhydrous magnesium sulfate, and the solvent was distilled off under reduced pressure. The residue was purified by silica gel column chromatography (ethyl acetate/hexane) and then crystallized from ethyl acetate to obtain the title compound (107 mg).

$^1$H NMR (300 MHz, DMSO-d$_6$) δ 2.28-2.39 (4H, m), 3.45 (2H, s), 3.54-3.62 (4H, m), 3.93 (3H, s), 7.12 (2H, s), 7.17-7.29 (1H, m), 7.49 (1H, d, J=5.3 Hz), 7.69-7.79 (2H, m), 8.09 (2H, s), 8.53 (1H, d, J=5.3 Hz), 8.78 (1H, s), 10.03 (1H, s).

Example 42

(2E)-N-(3-Chloro-4-(morpholin-4-ylmethyl)phenyl)-3-(4-(1-methyl-1H-pyrazol-4-yl)pyridin-3-yl)acrylamide (A) 4-(2-Chloro-4-nitrobenzyl)morpholine To a mixture of 2-chloro-4-nitrobenzaldehyde (1.0 g), morpholine (0.94 g), methanol (20 mL) and acetic acid (2 mL) was added 2-picoline-boron complex (0.87 g) at room temperature, and the resulting mixture was stirred at room temperature for 3 hours. Saturated aqueous sodium bicarbonate solution was added to the reaction mixture, followed by extraction with ethyl acetate. The extract was washed with brine. Then, the organic layer was dried over anhydrous magnesium sulfate, and the solvent was distilled off under reduced pressure. The residue was purified by silica gel column chromatography (ethyl acetate/hexane) to obtain the title compound (0.56 g).

MS: [M+H]$^+$ 257.2.

(B) 3-Chloro-4-(morpholinomethyl)aniline

To a reaction mixture of 4-(2-chloro-4-nitrobenzyl)morpholine (560 mg), calcium chloride (117 mg), ethanol (10 mL) and water (10 mL), reduced iron (487 mg) was added at room temperature, and the mixture was stirred at 90° C. for 2 hours. The reaction mixture was filtered through Celite, and water was added to the filtrate, followed by extraction with ethyl acetate. The extract was washed with brine and then dried over anhydrous magnesium sulfate, and the solvent was distilled off under reduced pressure. The residue was purified by silica gel column chromatography (ethyl acetate/hexane) to obtain the title compound (270 mg).

$^1$H NMR (300 MHz, CDCl$_3$) δ 2.36-2.59 (4H, m), 3.50 (2H, s), 3.60-3.79 (6H, m), 6.55 (1H, dd, J=8.2, 2.4 Hz), 6.69 (1H, d, J=2.3 Hz), 7.18 (1H, d, J=8.1 Hz).

(C) (2E)-N-(3-Chloro-4-(morpholin-4-ylmethyl) phenyl)-3-(4-(1-methyl-1H-pyrazol-4-yl)pyridin-3-yl)acrylamide EDCI (139 mg) was added to a mixture of (2E)-3-(4-(1-methyl-1H-pyrazol-4-yl)pyridin-3-yl)acrylic acid (83 mg), 3-chloro-4-(morpholinomethyl)aniline (107 mg), HOBt (98 mg) and DMF (2 mL) at room temperature, and the resulting mixture was stirred at the same temperature for 6 hours. Water was added to the reaction mixture, followed by extraction with a mixed ethyl acetate/THF solution. The organic layer was washed with brine and then dried over anhydrous magnesium sulfate, and the solvent was distilled off under reduced pressure. The residue was purified by silica gel column chromatography (ethyl acetate/hexane) and then solidified from ethyl acetate to obtain the title compound (42 mg).

$^1$H NMR (300 MHz, DMSO-d$_6$) δ 2.41 (4H, brs), 3.52 (2H, s), 3.57 (4H, d, J=4.5 Hz), 3.94 (3H, s), 6.75-6.90 (1H, m), 7.51 (3H, s), 7.75 (2H, d, J=0.66 Hz), 7.95-7.99 (1H, m), 8.08 (1H, s), 8.53 (1H, d, J=5.2 Hz), 8.78 (1H, s), 10.42-10.51 (1H, m).

Example 44

(2E)-N-(4-(Morpholin-4-ylmethyl)phenyl)-3-(4-(1-(2,2,3,3,3-pentafluoropropyl)-1H-pyrazol-4-yl)pyridin-3-yl)acrylamide To a mixture of (2E)-N-(4-(morpholin-4-ylmethyl)phenyl)-3-(4-(1H-pyrazol-4-yl)pyridin-3-yl)acrylamide (47 mg), triethylamine (0.082 mL) and THF (5 mL), 2,2,3,3,3-pentafluoropropyl trifluoromethanesulfonate (102 mg) was added at room temperature, and the resulting mixture was stirred at 70° C. for 3 hours. Cesium carbonate (587 mg) was added to the reaction mixture, and the mixture was stirred at 80° C. for 1.5 hours. Water was added to the reaction mixture, followed by extraction with ethyl acetate. The organic layer was washed with brine and then dried over anhydrous magnesium sulfate, and the solvent was distilled off under reduced pressure. The residue was separated by HPLC (C18, mobile phase: water/acetonitrile (containing 0.1% TFA)), and saturated aqueous sodium bicarbonate solution was added to the collected fractions, followed by extraction with ethyl acetate. The extract was dried over anhydrous magnesium sulfate and then concentrated under reduced pressure to obtain the title compound (12 mg).

$^1$H NMR (300 MHz, DMSO-d6) δ 2.34 (4H, brs), 3.42 (2H, s), 3.50-3.64 (4H, m), 5.32 (2H, t, J=15.3 Hz), 6.88 (1H, d, J=15.7 Hz), 7.27 (2H, d, J=8.6 Hz), 7.53 (1H, d, J=5.3 Hz), 7.59-7.77 (3H, m), 7.96 (1H, s), 8.24 (1H, s), 8.56 (1H, d, J=5.1 Hz), 8.81 (1H, s), 10.28 (1H, s).

Example 45

(2E)-3-(4-(1-(Cyclopropylmethyl)-1H-pyrazol-4-yl) pyridin-3-yl)-N-(4-(morpholin-4-ylmethyl)phenyl) acrylamide (A) (2E)-Ethyl 3-(4-(1-(cyclopropylmethyl)-1H-pyrazol-4-yl)pyridin-3-yl)acrylate A mixture of (2E)-ethyl 3-(4-chloropyridin-3-yl)acrylate (300 mg), 1-(cyclopropylmethyl)-4-(4,4,5,5-tetramethyl-1,3,2-dioxaborolan-2-yl)-1H-pyrazole (703 mg), Sphos (58 mg), chloro(2-dicyclohexylphosphino-2',6'-dimethoxy-1,1'-biphenyl)[2-(2'-amino-1,1'-biphenyl)]palladium(II) (102 mg), cesium carbonate (1155 mg), DME (4 mL) and water (0.8 mL) was stirred at 130° C. for 2 hours under microwave irradiation. The reaction mixture was filtered through Celite, and water was added to the filtrate, followed by extraction with ethyl acetate. The organic layer was washed with brine and then dried over anhydrous magnesium sulfate, and the solvent was distilled off under reduced pressure. The residue was purified by silica gel column chromatography (ethyl acetate/hexane) to obtain the title compound (235 mg).

MS: [M+H]$^+$ 298.0.

(B) (2E)-3-(4-(1-(Cyclopropylmethyl)-1H-pyrazol-4-yl)pyridin-3-yl)acrylic acid

To a mixture of (2E)-ethyl 3-(4-(1-(cyclopropylmethyl)-1H-pyrazol-4-yl)pyridin-3-yl)acrylate (235 mg), ethanol (3 mL) and THF (3 mL), a 2 N aqueous sodium hydroxide solution (1.6 mL) was added at room temperature, and the resulting mixture was stirred at the same temperature for 2 hours and at 50° C. for 30 minutes. The reaction mixture was neutralized by the addition of 1 N hydrochloric acid under ice cooling and stirred at 0° C. for 30 minutes. The precipitate was collected by filtration and washed with water to obtain the title compound (148 mg).

MS: [M+H]$^+$ 270.2.

(C) (2E)-3-(4-(1-(Cyclopropylmethyl)-1H-pyrazol-4-yl)pyridin-3-yl)-N-(4-(morpholin-4-ylmethyl)phenyl)acrylamide EDCI (211 mg) was added to a mixture of (2E)-3-(4-(1-(cyclopropylmethyl)-1H-pyrazol-4-yl)pyridin-3-yl)acrylic acid (148 mg), 4-(morpholinomethyl)aniline (137 mg), HOBt (111 mg) and DMF (2 mL) at room temperature, and the resulting mixture was stirred at the same temperature for 5 hours. Water and saturated aqueous potassium carbonate solution were added to the reaction mixture, followed by extraction with a mixed ethyl acetate/THF solution. The organic layer was washed with brine and then dried over anhydrous magnesium sulfate, and the solvent was distilled off under reduced pressure. The residue was purified by silica gel column chromatography (ethyl acetate/hexane) and then crystallized from ethyl acetate to obtain the title compound (216 mg).

$^1$H NMR (300 MHz, DMSO-d$_6$) δ 0.41 (2H, q, J=4.9 Hz), 0.49-0.59 (2H, m), 1.22-1.37 (1H, m), 2.34 (4H, d, J=4.3 Hz), 3.42 (2H, s), 3.50-3.61 (4H, m), 4.00-4.08 (2H, m), 6.85 (1H, d, J=15.7 Hz), 7.27 (2H, d, J=8.5 Hz), 7.52 (1H, d, J=5.2 Hz), 7.66 (2H, d, J=8.4 Hz), 7.70-7.80 (2H, m), 8.16 (1H, s), 8.53 (1H, d, J=5.2 Hz), 8.78 (1H, s), 10.27 (1H, s).

Example 49

(2E)-N-(4-((Cyclopropylamino)methyl)phenyl)-3-(4-(1-methyl-1H-pyrazol-4-yl)pyridin-3-yl)acrylamide A mixture of cyclopropylamine (7 mg), (2E)-N-(4-formylphenyl)-3-(4-(1-methyl-1H-pyrazol-4-yl)pyridin-3-yl) acrylamide (20 mg), methanol (0.5 mL), THF (0.2 mL) and acetic acid (0.1 mL) was stirred at room temperature for 30 minutes, then a mixture of 2-picoline-boron complex (13 mg) and methanol (0.3 mL) was added thereto at room temperature, and the resulting mixture was stirred overnight at the same temperature. Ethyl acetate and saturated aqueous ammonium chloride solution were added to the reaction mixture, and the mixture was stirred for 5 minutes. The organic layer was separated, and the aqueous layer was extracted with ethyl acetate. The organic layers were combined, and the solvent was distilled off at 60° C. by blowing dry with a stream of air. The residue was separated by HPLC (C18, mobile phase: acetonitrile/10 mM aqueous ammonium bicarbonate solution) to obtain the title compound (6 mg).

$^1$H NMR (400 MHz, DMSO-d$_6$) δ 0.22-0.31 (2H, m), 0.31-0.41 (2H, m), 2.03-2.11 (1H, m), 3.71 (2H, s), 3.94 (3H, s), 6.86 (1H, d, J=15.7 Hz), 7.29 (2H, m, J=8.6 Hz), 7.47-7.53 (1H, m), 7.65 (2H, m, J=8.6 Hz), 7.69-7.78 (2H, m), 8.09 (1H, s), 8.53 (1H, d, J=5.1 Hz), 8.77 (1H, s), 10.28 (1H, s).

Example 59

(2E)-3-(4-(1-Methyl-1H-pyrazol-4-yl)pyridin-3-yl)-N-(4-(piperazin-1-ylmethyl)phenyl)acrylamide A mixture of 1-Boc-piperazine (22 mg), (2E)-N-(4-formylphenyl)-3-(4-(1-methyl-1H-pyrazol-4-yl)pyridin-3-yl) acrylamide (20 mg), methanol (0.5 mL), THF (0.2 mL) and acetic acid (0.1 mL) was stirred at room temperature for 30 minutes, then a mixture of 2-picoline-boron complex (13 mg) and methanol (0.3 mL) was added thereto at room temperature, and the resulting mixture was stirred overnight at the same temperature. Ethyl acetate and saturated aqueous ammonium chloride solution were added to the reaction mixture, and the mixture was stirred for 5 minutes. The organic layer was separated, and the aqueous layer was extracted with ethyl acetate. The organic layers were combined, and the solvent was distilled off at 60° C. by blowing dry with a stream of air. The residue was separated by HPLC (C18, mobile phase: acetonitrile/10 mM aqueous ammonium bicarbonate solution). The obtained compound was dissolved in TFA (0.5 ml), and the reaction mixture was stirred at room temperature for 1 hour. The solvent was distilled off at 60° C., and the residue was separated by HPLC (C18, mobile phase: acetonitrile/10 mM aqueous ammonium bicarbonate solution) to obtain the title compound (9 mg).

$^1$H NMR (400 MHz, DMSO-d$_6$) δ 2.27 (4H, brs), 2.68 (4H, t, J=4.6 Hz), 3.37 (2H, s), 3.94 (3H, s), 6.85 (1H, d, J=15.7 Hz), 7.25 (2H, m, J=8.6 Hz), 7.49 (1H, d, J=5.1 Hz), 7.65 (2H, m, J=8.6 Hz), 7.69-7.77 (2H, m), 8.08 (1H, s), 8.53 (1H, d, J=5.1 Hz), 8.78 (1H, s), 10.28 (1H, s).

Example 91

(2E)-3-(4-(1-Methyl-1H-pyrazol-4-yl)pyridin-3-yl)-N-(4-(2-(morpholin-4-yl)ethyl)phenyl)acrylamide (A) 2-(4-Nitrophenyl)acetaldehyde To a solution of 2-(4-nitrophenyl)ethanol (990 mg) in acetonitrile (15 mL), 1,1,1-triacetoxy-1,1-dihydro-1,2-benziodoxol-3(1H)-one (3000 mg) was added at room temperature, and the mixture was stirred at the same temperature for 1 hour. The insoluble matter was removed by filtration. Then, the filtrate was concentrated under reduced pressure, and the residue was purified by silica gel column chromatography (ethyl acetate/hexane) to obtain the title compound (752 mg).
$^1$H NMR (300 MHz, CDCl$_3$) δ 3.87 (2H, d, J=1.6 Hz), 7.37-7.43 (2H, m), 8.21-8.26 (2H, m), 9.82 (1H, t, J=1.7 Hz).

(B) 4-(4-Nitrophenethyl)morpholine

Morpholine (0.490 mL) was added to a mixture of 2-(4-nitrophenyl)acetaldehyde (464 mg), methanol (6.36 mL) and acetic acid (0.64 mL), subsequently 2-picoline-boron complex (451 mg) was added to the reaction mixture at room temperature, and the mixture was stirred at the same temperature for 23 hours. The reaction mixture was concentrated under reduced pressure, water (20 mL) and ethyl acetate (20 mL) were added to the residue at room temperature, and the aqueous layer was extracted with ethyl acetate. The extract was washed with saturated aqueous sodium bicarbonate solution and brine and then dried over anhydrous sodium sulfate, and the solvent was distilled off under reduced pressure. The residue was purified by silica gel column chromatography (methanol/ethyl acetate) to obtain the title compound (495 mg).
MS: [M+H]$^+$ 236.9.

(C) 4-(2-Morpholinoethyl)aniline

A mixture of 4-(4-nitrophenethyl)morpholine (495 mg), 10% palladium-carbon (50 mg) and methanol (4 mL) was stirred under hydrogen atmosphere (1 atm) at room temperature for 2.5 hours. The reaction mixture was filtered, and the solvent in the filtrate was distilled off under reduced pressure to obtain the title compound (387 mg).
$^1$H NMR (300 MHz, CDCl$_3$) δ 2.45-2.57 (6H, m), 2.65-2.74 (2H, m), 3.57 (2H, brs), 3.70-3.77 (4H, m), 6.59-6.65 (2H, m), 6.99 (2H, d, J=8.3 Hz).

(D) (2E)-Ethyl 3-(4-(1-methyl-1H-pyrazol-4-yl)pyridin-3-yl)acrylate

A mixture of (2E)-ethyl 3-(4-chloropyridin-3-yl)acrylate (5.79 g), 1-methyl-4-(4,4,5,5-tetramethyl-1,3,2-dioxaborolan-2-yl)-1H-pyrazole (6.278 g), 2-(dicyclohexylphosphino) biphenyl (0.294 g), Pd$_2$(dba)$_3$ (0.377 g), potassium carbonate (9.405 g), DME (100 mL) and water (33 mL) was stirred under nitrogen atmosphere at 75° C. for 16 hours. The reaction mixture was diluted with ethyl acetate (100 mL) and water (50 mL). Then, the insoluble matter was removed by filtration through Celite, and the aqueous layer of the filtrate was extracted with ethyl acetate. The extract was washed with saturated aqueous sodium bicarbonate solution and brine, and the insoluble matter was then removed by filtration. The filtrate was dried over anhydrous magnesium sulfate, and the solvent was distilled off under reduced pressure. The obtained solid was washed with MTBE and then collected by filtration to obtain the title compound (4.479 g). The filtrate was concentrated under reduced pressure, and the residue was then purified by silica gel column chromatography (ethyl acetate/hexane). The obtained solid was washed with MTBE and then collected by filtration to obtain the title compound (0.921 g).
MS: [M+H]$^+$ 257.9.

(E) (2E)-3-(4-(1-Methyl-1H-pyrazol-4-yl)pyridin-3-yl)acrylic acid

To a solution of (2E)-ethyl 3-(4-(1-methyl-1H-pyrazol-4-yl)pyridin-3-yl)acrylate (5.40 g) in ethanol (50 mL) and THF (50 mL), a 2 N aqueous sodium hydroxide solution (21 mL) was added at room temperature, and the mixture was stirred at the same temperature for 15 hours. The solvent was distilled off under reduced pressure, and acetic acid (3 mL) and water (40 mL) were added to the residue at room temperature. The precipitate was collected by filtration, washed with water, and then dried under reduced pressure at 50° C. The obtained solid was washed with MTBE and then collected by filtration to obtain the title compound (3.43 g).
MS: [M+H]$^+$ 229.9.

(F) (2E)-3-(4-(1-Methyl-1H-pyrazol-4-yl)pyridin-3-yl)-N-(4-(2-(morpholin-4-yl)ethyl)phenyl)acrylamide To a solution of (2E)-3-(4-(1-methyl-1H-pyrazol-4-yl)pyridin-3-yl)acrylic acid (61.7 mg) in DMF (4 mL), 4-(2-morpholinoethyl)aniline (61.1 mg), HATU (123 mg) and DIEA (0.139 mL) were added at room temperature, and the mixture was stirred at the same temperature for 6 hours. The solvent was distilled off under reduced pressure, and the residue was purified by silica gel column chromatography (NH, ethyl acetate/hexane). The obtained solid was washed with ethyl acetate/hexane (1/1) and then collected by filtration to obtain the title compound (77 mg).
$^1$H NMR (300 MHz, DMSO-d$_6$) δ 2.36-2.49 (6H, m), 2.66-2.75 (2H, m), 3.53-3.61 (4H, m), 3.93 (3H, s), 6.84 (1H, d, J=15.7 Hz), 7.19 (1H, d, J=8.5 Hz), 7.49 (1H, d, J=5.2 Hz), 7.61 (2H, d, J=8.4 Hz), 7.69-7.76 (2H, m), 8.08 (1H, s), 8.52 (1H, d, J=5.2 Hz), 8.77 (1H, s), 10.22 (1H, s).

Example 92

(2E)-3-(4-(1-Ethyl-1H-pyrazol-4-yl)pyridin-3-yl)-N-(4-(morpholin-4-ylmethyl)phenyl)acrylamide (A) (2E)-3-(4-(1-Ethyl-1H-pyrazol-4-yl)pyridin-3-yl)acrylic acid A mixture of (2E)-ethyl 3-(4-chloropyridin-3-yl)acrylate (305.2 mg), 1-ethyl-4-(4,4,5,5-tetramethyl-1,3,2-dioxaborolan-2-yl)-1H-pyrazole (641 mg), SPhos (59.2 mg), chloro (2-dicyclohexylphosphino-2',6'-dimethoxy-1,1'-biphenyl) [2-(2'-amino-1,1'-biphenyl)]palladium(II) (104 mg), a 2 M aqueous cesium carbonate solution (1.80 mL) and DME (9 mL) was stirred at 130° C. for 2 hours under microwave irradiation. The reaction mixture was diluted with ethyl acetate (20 mL) and brine (15 mL), and the aqueous layer was extracted with ethyl acetate. The extract was washed with brine and then dried over anhydrous sodium sulfate, and the solvent was distilled off under reduced pressure. The residue was purified by silica gel column chromatography (NH, ethyl acetate/hexane) to obtain an oil (481 mg). To a solution of the obtained oil (481 mg) in THF (2 mL) and ethanol (2 mL), a 2 N aqueous sodium hydroxide solution (2 mL) was added at room temperature, and the mixture was stirred at the same temperature for 3 hours. The solvent was distilled off under reduced pressure, and 2 N hydrochloric acid (2.5 mL) was added to the residue. The precipitate was collected by filtration, washed with water, and then dried under reduced pressure to obtain the title compound (85 mg).

MS: [M+H]$^+$ 243.9.

(B) (2E)-3-(4-(1-Ethyl-1H-pyrazol-4-yl)pyridin-3-yl)-N-(4-(morpholin-4-ylmethyl)phenyl)acrylamide To a solution of (2E)-3-(4-(1-ethyl-1H-pyrazol-4-yl)pyridin-3-yl)acrylic acid (84 mg) in DMF (3 mL), 4-(morpholinomethyl)aniline (76 mg), HATU (158 mg) and DIEA (0.179 mL) were added at room temperature, and the mixture was stirred at the same temperature for 20 hours. The solvent was distilled off under reduced pressure, and the residue was purified by silica gel column chromatography (NH, ethyl acetate/hexane). The obtained solid was washed with ethyl acetate/hexane (1/1) and then collected by filtration to obtain the title compound (118 mg).

$^1$H NMR (300 MHz, DMSO-d$_6$) δ 1.43 (3H, t, J=7.3 Hz), 2.25-2.40 (4H, m), 3.42 (2H, s), 3.53-3.61 (4H, m), 4.23 (2H, q, J=7.3 Hz), 6.85 (1H, d, J=15.7 Hz), 7.27 (2H, d, J=8.5 Hz), 7.50 (1H, d, J=5.2 Hz), 7.66 (2H, d, J=8.4 Hz), 7.71-7.79 (2H, m), 8.14 (1H, s), 8.53 (1H, d, J=5.2 Hz), 8.78 (1H, s), 10.28 (1H, s).

Example 97

(2E)-3-(4-(1-Cyclopropyl-1H-pyrazol-4-yl)pyridin-3-yl)-N-(4-(morpholin-4-ylmethyl)phenyl)acrylamide (A) (2E)-Ethyl 3-(4-(1-cyclopropyl-1H-pyrazol-4-yl)pyridin-3-yl)acrylate A mixture of (2E)-ethyl 3-(4-chloropyridin-3-yl)acrylate (2.22 g), 1-cyclopropyl-4-(4,4,5,5-tetramethyl-1,3,2-dioxaborolan-2-yl)-1H-pyrazole (2.89 g), 2-(dicyclohexylphosphino)biphenyl (0.19 g), Pd$_2$(dba)$_3$ (0.24 g), potassium carbonate (3.64 g), DME (50 mL) and water (13 mL) was stirred under nitrogen atmosphere at 75° C. for 9 hours. Water (50 mL) and ethyl acetate (100 mL) were added to the reaction mixture, and the aqueous layer was extracted with ethyl acetate (50 mL). The organic layers were combined, washed with saturated aqueous sodium bicarbonate solution and brine, and then dried over anhydrous magnesium sulfate, and the solvent was distilled off under reduced pressure. The residue was purified by silica gel column chromatography (ethyl acetate/hexane) to obtain the title compound (2.73 g).

MS: [M+H]$^+$ 284.0.

(A') (2E)-Ethyl 3-(4-(1-cyclopropyl-1H-pyrazol-4-yl)pyridin-3-yl)acrylate hydrochloride A mixture of (2E)-ethyl 3-(4-chloropyridin-3-yl)acrylate (16.63 g), 1-cyclopropyl-4-(4,4,5,5-tetramethyl-1,3,2-dioxaborolan-2-yl)-1H-pyrazole (22.99 g), 2-(dicyclohexylphosphino)biphenyl (1.377 g), Pd$_2$(dba)$_3$ (1.799 g), 2 M aqueous potassium carbonate solution (98 mL) and DME (400 mL) was stirred overnight under nitrogen atmosphere at 75° C. Water (200 mL) and ethyl acetate (400 mL) were added to the reaction mixture, and the mixture was stirred at room temperature for 5 minutes. The insoluble matter was removed by filtration. The organic layer of the filtrate was washed with water (200 mL), a 3% aqueous ammonia solution (100 mL) and brine (200 mL) and then dried over anhydrous magnesium sulfate, and the solvent was distilled off under reduced pressure. Ethyl acetate (800 mL) and NH silica gel (350 g) were added to the residue at room temperature, and the mixture was stirred overnight at the same temperature. NH silica gel was removed by filtration and washed with ethyl acetate (1500 mL), and the solvent in the combined filtrate and washings was distilled off under reduced pressure. Ethyl acetate (800 mL) and NH silica gel (350 g) were added to the residue at room temperature, and the mixture was stirred overnight at the same temperature. NH silica gel was removed by filtration and washed with ethyl acetate (1500 mL), and the solvent in the combined filtrate and washings was distilled off under reduced pressure. Ethyl acetate (800 mL) and NH silica gel (350 g) were added to the residue at room temperature, and the mixture was stirred overnight at the same temperature. NH silica gel was removed by filtration and washed with ethyl acetate (1500 mL), and was the solvent in the combined filtrate and washings was distilled off under reduced pressure. Ethyl acetate (750 mL) and a 4 N solution of hydrogen chloride in ethyl acetate (58.9 mL) were added to the residue at 0° C., and the solvent was distilled off under reduced pressure. Ethyl acetate (150 mL) was added to the residue, and the mixture was stirred at 0° C. for 1 hour. The precipitate was collected by filtration and washed with ethyl acetate to obtain the title compound (19.76 g).

MS: [M+H]$^+$ 284.2.

(B) (2E)-3-(4-(1-Cyclopropyl-1H-pyrazol-4-yl)pyridin-3-yl)acrylic acid

To a solution of (2E)-ethyl 3-(4-(1-cyclopropyl-1H-pyrazol-4-yl)pyridin-3-yl)acrylate (2.67 g) in ethanol (20 mL) and THF (20 mL), a 2 N aqueous sodium hydroxide solution (10.0 mL) was added at room temperature, and the mixture was stirred at the same temperature for 16 hours. The solvent was distilled off under reduced pressure, and acetic acid and water were added to the residue at room temperature. The precipitate was collected by filtration and dried under reduced pressure to obtain the title compound (2.00 g).

MS: [M+H]$^+$ 256.0.

(B') (2E)-3-(4-(1-Cyclopropyl-1H-pyrazol-4-yl)pyridin-3-yl)acrylic acid

To a solution of (2E)-ethyl 3-(4-(1-cyclopropyl-1H-pyrazol-4-yl)pyridin-3-yl)acrylate hydrochloride (100 g) in ethanol (470 mL) and THF (470 mL), a 2 N aqueous sodium hydroxide solution (469 mL) was added at 0° C., and the mixture was stirred at room temperature for 1.5 hours. The organic solvent was distilled off under reduced pressure, water (750 mL) was added to the residue at room temperature, and the mixture was washed with isopropyl acetate (1000 mL). The aqueous layer was filtered through Celite using water (350 mL). Water (100 mL) and 2 N hydrochloric acid (255 mL) were added to the filtrate at 0° C., and the mixture was stirred overnight at room temperature. The reaction mixture was ice-cooled, and the precipitate was then collected by filtration, washed with water (50 mL), and then dried under reduced pressure at 50° C. to obtain the title compound (74.1 g).

MS: [M+H]$^+$ 256.2.

(C) (2E)-3-(4-(1-Cyclopropyl-1H-pyrazol-4-yl)pyridin-3-yl)-N-(4-(morpholin-4-ylmethyl)phenyl)acrylamide EDCI (1.65 g) was added to a mixture of (2E)-3-(4-(1-cyclopropyl-1H-pyrazol-4-yl)pyridin-3-yl)acrylic acid (1.1 g), 4-(morpholinomethyl)aniline (0.99 g), HOBt (0.87 g) and DMF (20 mL) at room temperature, and the resulting mixture was stirred at the same temperature for 3 hours. The reaction mixture was poured into ice water, and saturated aqueous potassium carbonate solution was added to the mixture, followed by extraction with a mixed ethyl acetate/THF solution. The organic layer was washed with brine and then dried over anhydrous magnesium sulfate, and the solvent was distilled off under reduced pressure. The residue was purified by silica gel column chromatography (NH, ethyl acetate/hexane) to obtain the title compound as a crude crystalline solid (1.5 g). Likewise, EDCI (3.11 g) was added to a mixture of (2E)-3-(4-(1-cyclopropyl-1H-pyrazol-4-yl)pyridin-3-yl)acrylic acid (2.07 g), 4-(morpholinomethyl)aniline (1.56 g), HOBt (1.64 g) and DMF (20 mL) at room temperature, and the resulting mixture was stirred at the same temperature for 16 hours. The reaction mixture was poured into water, and saturated aqueous potassium carbonate solution was added to the mixture, followed by extraction with a mixed ethyl acetate/THF solution. The organic layer was washed with brine and then dried over anhydrous magnesium sulfate, and the solvent was distilled off under reduced pressure. The residue was purified by silica gel column chromatography (NH, ethyl acetate/hexane) to obtain the title compound as a crude crystalline solid (1.7 g). Both batches of the title compound thus obtained were combined and recrystallized from ethanol/hexane to obtain the title compound (2.23 g).

$^1$H NMR (300 MHz, DMSO-d$_6$) δ 0.94-1.19 (4H, m), 2.30-2.40 (4H, m), 3.42 (2H, s), 3.51-3.61 (4H, m), 3.85 (1H, dt, J=7.5, 3.5 Hz), 6.85 (1H, d, J=15.7 Hz), 7.27 (2H, d, J=8.5 Hz), 7.51 (1H, d, J=5.2 Hz), 7.66 (2H, d, J=8.5 Hz), 7.69-7.80 (2H, m), 8.18 (1H, s), 8.52 (1H, d, J=5.2 Hz), 8.77 (1H, s), 10.28 (1H, s).

Example 98

(2E)-3-(4-(1-(Difluoromethyl)-1H-pyrazol-4-yl)pyridin-3-yl)-N-(4-(morpholin-4-ylmethyl)phenyl)acrylamide (A) 1-(Difluoromethyl)-4-(4,4,5,5-tetramethyl-1,3,2-dioxaborolan-2-yl)-1H-pyrazole Sodium 2-chloro-2,2-difluoroacetate (471 mg) was added to a mixture of 4-(4,4,5,5-tetramethyl-1,3,2-dioxaborolan-2-yl)-1H-pyrazole (500 mg), 18-crown-6 (136 mg) and acetonitrile (10 mL), and the reaction mixture was heated at reflux for 16 hours. Water was added to the reaction mixture, followed by extraction with ethyl acetate. The organic layer was washed with brine and then dried over anhydrous magnesium sulfate, and the solvent was distilled off under reduced pressure to obtain the title compound as a crude product (466 mg). This compound was used in the next step without being further purified.

$^1$H NMR (300 MHz, CDCl$_3$) δ 1.33 (12H, s), 7.01-7.43 (1H, m), 7.88 (1H, s), 8.12 (1H, s).

(B) (2E)-3-(4-(1-(Difluoromethyl)-1H-pyrazol-4-yl)pyridin-3-yl)-N-(4-(morpholin-4-ylmethyl)phenyl)acrylamide A mixture of (2E)-3-(4-chloropyridin-3-yl)-N-(4-(morpholinomethyl)phenyl)acrylamide (154 mg), crude 1-(difluoromethyl)-4-(4,4,5,5-tetramethyl-1,3,2-dioxaborolan-2-yl)-1H-pyrazole (210 mg), Sphos (18 mg), chloro(2-dicyclohexylphosphino-2',6'-dimethoxy-1,1'-biphenyl)[2-(2'-amino-1,1'-biphenyl)]palladium(II) (31 mg), cesium carbonate (350 mg), DME (4 mL) and water (1 mL) was stirred at 130° C. for 2 hours under microwave irradiation. The reaction mixture was filtered through Celite, and water was added to the filtrate, followed by extraction with ethyl acetate. The organic layer was washed with brine and then dried over anhydrous magnesium sulfate, and the solvent was distilled off under reduced pressure. The residue was purified by silica gel column chromatography (ethyl acetate/hexane) and then crystallized from ethyl acetate/hexane to obtain the title compound (119 mg).

$^1$H NMR (300 MHz, DMSO-d$_6$) δ 2.29-2.39 (4H, m), 3.42 (2H, s), 3.51-3.61 (4H, m), 6.89 (1H, d, J=15.7 Hz), 7.27 (2H, d, J=8.5 Hz), 7.58 (1H, d, J=5.1 Hz), 7.61-7.72 (3H, m), 7.72-8.17 (2H, m), 8.58-8.66 (2H, m), 8.85 (1H, s), 10.30 (1H, s).

Example 99

3-(4-(1-Ethyl-1H-pyrazol-4-yl)pyridin-3-yl)-N-(4-(morpholin-4-ylmethyl)phenyl)propanamide To a mixture of (2E)-3-(4-(1-ethyl-1H-pyrazol-4-yl)pyridin-3-yl)-N-(4-(morpholin-4-ylmethyl)phenyl)acrylamide (50.6 mg) and toluene (2 mL), benzenesulfonohydrazide (104 mg) was added at room temperature, and the resulting mixture was heated up to 100° C. and stirred at the same temperature for 16 hours. The reaction mixture was diluted with ethyl acetate (15 mL) and water (15 mL), and the aqueous layer was then extracted with ethyl acetate. The extract was washed with brine and then dried over anhydrous sodium sulfate, and the solvent was distilled off under reduced pressure. The residue was purified by silica gel column chromatography (NH, ethyl acetate/hexane and subsequently methanol/ethyl acetate), and the obtained solid was washed with ethyl acetate/hexane (1/10) and then collected by filtration to obtain the title compound (4 mg).

$^1$H NMR (300 MHz, DMSO-d$_6$) δ 1.42 (3H, t, J=7.3 Hz), 2.24-2.37 (4H, m), 2.61 (2H, t, J=7.6 Hz), 3.09 (2H, t, J=7.5 Hz), 3.38 (2H, s), 3.52-3.59 (4H, m), 4.20 (2H, q, J=7.3 Hz), 7.21 (2H, d, J=8.2 Hz), 7.41 (1H, d, J=5.2 Hz), 7.51 (2H, d, J=8.4 Hz), 7.88 (1H, s), 8.24 (1H, s), 8.35 (1H, d, J=5.2 Hz), 8.45 (1H, s), 9.91 (1H, s).

Example 102

(2E)-3-(4-(1-(4-Fluorobenzyl)-1H-pyrazol-4-yl)pyridin-3-yl)-N-(4-(morpholin-4-ylmethyl)phenyl)acrylamide (A) 1-(4-Fluorobenzyl)-4-(4,4,5,5-tetramethyl-1,3,2-dioxaborolan-2-yl)-1H-pyrazole To a solution of 4-(4,4,5,5-tetramethyl-1,3,2-dioxaborolan-2-yl)-1H-pyrazole (520 mg) in acetonitrile (15 mL), 1-(bromomethyl)-4-fluorobenzene (667 mg) and potassium carbonate (741 mg) were added at room temperature, and the mixture was heated up to 75° C. and stirred under nitrogen atmosphere at the same temperature for 14 hours. The insoluble matter was removed by filtration. Then, the filtrate was concentrated under reduced pressure, and the residue was purified by silica gel column chromatography (ethyl acetate/hexane) to obtain the title compound (660 mg).

MS: [M+H]$^+$ 302.9.

(B) (2E)-3-(4-(1-(4-Fluorobenzyl)-1H-pyrazol-4-yl)pyridin-3-yl)-N-(4-(morpholin-4-ylmethyl)phenyl)acrylamide A mixture of (2E)-3-(4-chloropyridin-3-yl)-N-(4-(morpholinomethyl)phenyl)acrylamide (66 mg), 1-(4-fluorobenzyl)-4-(4,4,5,5-tetramethyl-1,3,2-dioxaborolan-2-yl)-1H-pyrazole (111 mg), SPhos (7.57 mg), chloro(2-dicyclohexylphosphino-2',6'-dimethoxy-1,1'-biphenyl)[2-(2'-amino-1,1'-biphenyl)]palladium(II) (13.29 mg), a 2 M cesium carbonate aqueous solution (0.231 mL) and DME (2 mL) was stirred at 130° C. for 2 hours under microwave irradiation. The reaction mixture was diluted with ethyl acetate (20 mL) and brine (15 mL), and the aqueous layer was extracted with ethyl acetate. The extract was washed with brine and then dried over anhydrous sodium sulfate, and the solvent was distilled off under reduced pressure. The residue was purified by silica gel column chromatography (NH, ethyl acetate/hexane), and the obtained solid was washed with ethyl acetate/hexane (1/2) and then collected by filtration to obtain the title compound (52 mg).

$^1$H NMR (300 MHz, DMSO-d$_6$) δ 2.34 (4H, brs), 3.42 (2H, s), 3.51-3.61 (4H, m), 5.42 (2H, s), 6.85 (1H, d, J=15.7 Hz), 7.14-7.23 (2H, m), 7.27 (2H, d, J=8.4 Hz), 7.35-7.42 (2H, m), 7.51 (1H, d, J=5.2 Hz), 7.66 (2H, d, J=8.4 Hz), 7.73 (1H, d, J=15.8 Hz), 7.80 (1H, s), 8.26 (1H, d, J=5.2 Hz), 8.53 (1H, s), 8.78 (1H, s), 10.27 (1H, s).

Example 109

(2E)-N-(3-Methyl-4-(morpholin-4-ylmethyl)phenyl)-3-(4-(1-methyl-1H-pyrazol-4-yl)pyridin-3-yl)acrylamide

(A) (2-Methyl-4-nitrophenyl)methanol

A 1.0 M solution of borane-THF complex in THF (110 mL) was added dropwise to a mixture of 2-methyl-4-nitrobenzoic acid (10 g) and THF (200 mL) at room temperature, and the resulting mixture was stirred at 80° C. for 5.5 hours. The reaction mixture was cooled to room temperature, then methanol (50 mL) was added thereto, and the mixture was stirred at room temperature 10 minutes and then stirred at 80° C. for 1 hour. The solvent was distilled off under reduced pressure, and ethyl acetate was added to the residue. The reaction mixture was washed with 0.5 N hydrochloric acid, saturated aqueous sodium bicarbonate solution and brine and dried over anhydrous sodium sulfate, and the solvent was then distilled off under reduced pressure to obtain the title compound (9.0 g).

$^1$H NMR (300 MHz, CDCl$_3$) δ 1.81 (1H, t, J=5.6 Hz), 2.40 (3H, s), 4.80 (2H, d, J=5.6 Hz), 7.62 (1H, d, J=8.4 Hz), 8.00-8.11 (2H, m).

(B) 4-(2-Methyl-4-nitrobenzyl)morpholine

To a reaction mixture of (2-methyl-4-nitrophenyl)methanol (9.0 g), triethylamine (14.8 mL) and THF (100 mL), methanesulfonyl chloride (6.3 mL) was added under ice cooling, and the mixture was stirred at the same temperature for 1 hour. Water was added to the reaction mixture under ice cooling, followed by extraction with ethyl acetate. The organic layer was washed with brine and then dried over anhydrous sodium sulfate, and the solvent was distilled off under reduced pressure. Acetonitrile (100 mL) and morpholine (23.6 mL) were added to the residue, and the reaction mixture was stirred at room temperature for 21 hours. The reaction mixture was concentrated into half the amount under reduced pressure, and water was added thereto, followed by extraction with ethyl acetate. The organic layer was washed with brine and then dried over anhydrous magnesium sulfate, and the solvent was distilled off under reduced pressure. The residue was purified by silica gel column chromatography (ethyl acetate/hexane) to obtain the title compound (11.8 g).

MS: [M+H]$^+$ 236.9.

(C) 3-Methyl-4-(morpholinomethyl)aniline

To a solution of 4-(2-methyl-4-nitrobenzyl)morpholine (10.8 g) in THF (150 mL) and methanol (150 mL), activated carbon (1.1 g), iron trichloride hexahydrate (0.6 g) and hydrazine hydrate (11.1 mL) were added at 70° C., and the mixture was stirred at the same temperature for 3 hours. The insoluble matter was removed by filtration through Celite, and the filtrate was concentrated under reduced pressure. Then, saturated aqueous sodium bicarbonate solution was added to the residue, followed by extraction with ethyl acetate. The organic layer was washed with brine and then dried over anhydrous magnesium sulfate, and the solvent was distilled off under reduced pressure. The residue was purified by silica gel column chromatography (ethyl acetate/hexane) to obtain the title compound (9.8 g).

$^1$H NMR (300 MHz, CDCl$_3$) δ 2.29 (3H, s), 2.33-2.47 (4H, m), 3.34 (2H, s), 3.49-3.72 (6H, m), 6.37-6.58 (2H, m), 6.99 (1H, d, J=7.9 Hz).

(D) (2E)-3-(4-Chloropyridin-3-yl)-N-(3-methyl-4-(morpholinomethyl)phenyl)acrylamide To a suspension of (2E)-3-(4-chloropyridin-3-yl)acrylic acid (4.2 g) in THF (80 mL), DMF (0.4 mL) and oxalyl dichloride (9.7 mL) were added at room temperature, and the mixture was stirred at the same temperature for 1 hour. The solvent was distilled off under reduced pressure, and toluene was added to the residue. The solvent was distilled off under reduced pressure, and DMA (20 mL) was then added to the residue. The obtained mixture was added to a mixture of 3-methyl-4-(morpholinomethyl)aniline and DMA (20 mL) at room temperature, and the resulting mixture was stirred at the same temperature for 2 hours. The reaction mixture was poured into a mixed solution of saturated aqueous sodium bicarbonate solution (50 mL) and water (300 mL) under ice cooling, followed by extraction with a mixed ethyl acetate/THF solution. The organic layer was washed with brine and then dried over anhydrous magnesium sulfate, and the solvent was distilled off under reduced pressure. The residue was purified by silica gel column chromatography (NH, ethyl acetate/hexane) to obtain the title compound (8.3 g).

MS: [M+H]$^+$ 372.0.

(E) (2E)-N-(3-Methyl-4-(morpholin-4-ylmethyl)phenyl)-3-(4-(1-methyl-1H-pyrazol-4-yl)pyridin-3-yl)acrylamide A mixture of (2E)-3-(4-chloropyridin-3-yl)-N-(3-methyl-4-(morpholinomethyl)phenyl)acrylamide (4.0 g), 1-methyl- 4-(4,4,5,5-tetramethyl-1,3,2-dioxaborolan-2-yl)-1H-pyrazole (4.5 g), Ruphos (0.5 g), chloro(2-dicyclohexylphosphino-2',6'-di-i-propoxy-1,1'-biphenyl)[2-(2-aminoethylphenyl)]palladium(II) methyl-tert-butyl ether complex (0.9 g), cesium carbonate (10.5 g), DME (120 mL) and water (24 mL) was stirred under nitrogen atmosphere at 90° C. for 18 hours. The reaction mixture was filtered through Celite, and water was added to the filtrate. The organic layer was separated and washed with a 5% aqueous ammonia solution. The aqueous layers were combined, followed by extraction with a mixed ethyl acetate/THF solution. The organic layers were combined and washed with brine, and the solvent was then distilled off under reduced pressure. The residue was purified by silica gel column chromatography (NH, ethyl acetate/hexane) and then recrystallized from ethanol/heptane to obtain the title compound (2.1 g).

$^1$H NMR (300 MHz, DMSO-d$_6$) δ 2.25-2.39 (7H, m), 3.38 (2H, s), 3.50-3.61 (4H, m), 3.94 (3H, s), 6.85 (1H, d, J=15.6 Hz), 7.17 (1H, d, J=8.1 Hz), 7.41-7.57 (3H, m), 7.68-7.79 (2H, m), 8.08 (1H, s), 8.52 (1H, d, J=5.2 Hz), 8.77 (1H, s), 10.20 (1H, s).

Example 145

(2E)-N-(4-(Morpholin-4-ylmethyl)phenyl)-3-(4-(1,2-thiazol-4-yl)pyridin-3-yl)acrylamide (A) (2E)-Ethyl 3-(4-(tributylstannyl)pyridin-3-yl)acrylate To a solution of (2E)-ethyl 3-(4-chloropyridin-3-yl)acrylate (1500 mg) in toluene (100 mL), 1,1,1,2,2,2-hexabutyldistannane (9.85 mL), lithium chloride (1502 mg) and Pd(Ph$_3$P)$_4$ (819 mg) were added at room temperature, and the mixture was heated at reflux under nitrogen atmosphere at 120° C. for 30 hours. The insoluble matter was removed by filtration. Then, the filtrate was concentrated under reduced pressure, and the residue was purified by silica gel column chromatography (ethyl acetate/hexane) to obtain the title compound (631 mg).

MS: [M+H]$^+$ 468.0.

(B) (2E)-Ethyl 3-(4-(isothiazol-4-yl)pyridin-3-yl)acrylate

A mixture of (2E)-ethyl 3-(4-(tributylstannyl)pyridin-3-yl)acrylate (33 mg), 4-bromoisothiazole (17.41 mg), Pd(Ph$_3$P)$_4$ (8.18 mg), copper(I) iodide (2.70 mg), cesium fluoride (21.50 mg) and DMF (1.5 mL) was stirred under nitrogen atmosphere at 100° C. for 13 hours. Likewise, a mixture of (2E)-ethyl 3-(4-(tributylstannyl)pyridin-3-yl)acrylate (497 mg), 4-bromoisothiazole (262 mg), Pd(Ph$_3$P)$_4$ (123 mg), copper(I) iodide (40.6 mg), cesium fluoride (324 mg) and DMF (10 mL) was stirred under nitrogen atmosphere at 100° C. for 13 hours. The reaction mixtures were combined, and the insoluble matter was then filtered. The filtrate was diluted with ethyl acetate (20 mL), water (10 mL) and saturated aqueous sodium bicarbonate solution (10 mL), and the aqueous layer was extracted with ethyl acetate. The extract was washed with water and brine and then dried over anhydrous sodium sulfate, and the solvent was distilled off under reduced pressure. The residue was purified by silica gel column chromatography (ethyl acetate/hexane) to obtain the title compound (222 mg).

MS: [M+H]$^+$ 260.9.

(C) (2E)-3-(4-(Isothiazol-4-yl)pyridin-3-yl)acrylic acid

To a mixture of (2E)-ethyl 3-(4-(isothiazol-4-yl)pyridin-3-yl)acrylate (213 mg), THF (0.3 mL) and ethanol (0.3 mL), a 2 N aqueous sodium hydroxide solution (2 mL) was added at room temperature, and the resulting mixture was stirred at the same temperature for 3 hours. A 2 N hydrochloric acid solution (2.2 mL) was added to the reaction mixture at room temperature, and the solvent was then distilled off under reduced pressure. The residue was diluted with ethyl acetate (15 mL) and water (15 mL), and the aqueous layer was extracted with ethyl acetate. The extract was washed with brine and then dried over anhydrous sodium sulfate, and the solvent was distilled off under reduced pressure. The precipitate was washed with ethyl acetate/hexane (1/1) and then collected by filtration to obtain the title compound (156 mg).

MS: [M+H]$^+$ 233.1.

(D) (2E)-N-(4-(Morpholin-4-ylmethyl)phenyl)-3-(4-(1,2-thiazol-4-yl)pyridin-3-yl)acrylamide To a solution of (2E)-3-(4-(isothiazol-4-yl)pyridin-3-yl)acrylic acid (69.6 mg) in DMF (4 mL), 4-(morpholinomethyl)aniline (63.4 mg), HATU (137 mg) and DIEA (0.155 mL) were added at room temperature, and the mixture was stirred at the same temperature for 22 hours. The reaction mixture was diluted with ethyl acetate (20 mL) and water (20 mL), and the aqueous layer was extracted with ethyl acetate. The extract was washed with water and brine and then dried over anhydrous sodium sulfate, and the solvent was distilled off under reduced pressure. The residue was purified by silica gel column chromatography (NH, ethyl acetate/hexane), and the obtained solid was washed with ethyl acetate/hexane (1/5) and then collected by filtration to obtain the title compound (101 mg).

$^1$H NMR (300 MHz, DMSO-d$_6$) δ 2.29-2.37 (4H, m), 3.41 (2H, s), 3.52-3.61 (4H, m), 6.90 (1H, d, J=15.7 Hz), 7.26 (2H, d, J=8.5 Hz), 7.50-7.67 (4H, m), 8.65 (1H, d, J=5.1 Hz), 8.79 (1H, s), 8.92 (1H, s), 9.28 (1H, s), 10.29 (1H, s).

Example 148

(2E)-N-(3-Hydroxy-4-(morpholin-4-ylmethyl)phenyl)-3-(4-(1-methyl-1H-pyrazol-4-yl)pyridin-3-yl)acrylamide (A) N-(3-Hydroxy-4-(morpholinomethyl)phenyl)acetamide A 37% aqueous formaldehyde solution (2.68 g) was added to a mixture of N-(3-hydroxyphenyl)acetamide (5.00 g), morpholine (2.88 mL) and ethanol (25 mL) at room temperature, and the resulting mixture was stirred at 90° C. for 24 hours. The reaction mixture was concentrated under reduced pressure, and the residue was purified by silica gel column chromatography (ethyl acetate/hexane) to obtain the title compound (7.50 g).

MS: [M+H]$^+$ 251.2.

(B) 5-Amino-2-(morpholinomethyl)phenol

A 6 N hydrochloric acid solution (49.9 mL) was added to a mixture of N-(3-hydroxy-4-(morpholinomethyl)phenyl)acetamide (7.50 g) and ethanol (50 mL) at room temperature, and the resulting mixture was stirred at 90° C. for 2.5 hours. The reaction mixture was neutralized by the addition of a 6 N aqueous sodium hydroxide solution and concentrated under reduced pressure. The residue was purified by silica gel column chromatography (NH, ethyl acetate/hexane) to obtain the title compound (600 mg).

MS: [M+H]$^+$ 209.2.

(C) (2E)-N-(3-Hydroxy-4-(morpholin-4-ylmethyl)phenyl)-3-(4-(1-methyl-1H-pyrazol-4-yl)pyridin-3-yl)acrylamide EDCI (1105 mg) was added to a mixture of (2E)-3-(4-(1-methyl-1H-pyrazol-4-yl)pyridin-3-yl)acrylic acid (660 mg), HOBt (684 mg), 5-amino-2-(morpholinomethyl)phenol (600 mg) and DMF (10 mL) at room temperature, and the resulting mixture was stirred at the same temperature for 2 hours. Water and saturated aqueous potassium carbonate solution were added to the reaction mixture, followed by extraction with a mixed ethyl acetate/THF solution. The organic layer was separated and dried over anhydrous magnesium sulfate, and the solvent was distilled off under reduced pressure. The residue was purified by silica gel column chromatography (NH, ethyl acetate/hexane) to obtain the title compound (159 mg).

$^1$H NMR (300 MHz, DMSO-d$_6$) δ 2.42 (4H, brs), 3.54 (2H, s), 3.55-3.63 (4H, m), 3.93 (3H, s), 6.86 (1H, s), 7.06 (2H, d, J=0.94 Hz), 7.29 (1H, s), 7.50 (1H, s), 7.74 (2H, d, J=0.66 Hz), 8.08 (1H, s), 8.52 (1H, d, J=5.2 Hz), 8.76 (1H, s), 10.15 (2H, s).

Example 149

(2E)-N-(3-(2-Methoxyethoxy)-4-(morpholin-4-ylmethyl)phenyl)-3-(4-(1-methyl-1H-pyrazol-4-yl)pyridin-3-yl)acrylamide A 40% solution of DIAD in toluene (0.16 mL) was added to a mixture of (2E)-N-(3-hydroxy-4-(morpholinomethyl)phenyl)-3-(4-(1-methyl-1H-pyrazol-4-yl)pyridin-3-yl)acrylamide (67 mg), PPh$_3$ (84 mg), 2-methoxyethanol (0.03 mL) and THF (5 mL) at room temperature, and the resulting mixture was stirred at the same temperature for 2 hours. A 40% solution of DIAD in toluene (194 mg), PPh$_3$ (251 mg) and 2-methoxyethanol (24 mg) were added to the reaction mixture, and the mixture was stirred at 60° C. for 16 hours. Water was added to the reaction mixture, followed by extraction with ethyl acetate. The organic layer was washed with brine and then dried over anhydrous magnesium sulfate, and the solvent was distilled off under reduced pressure. The residue was purified by silica gel column chromatography (NH, ethyl acetate/hexane) to obtain the title compound (11 mg).

$^1$H NMR (300 MHz, DMSO-d$_6$) δ 2.38 (4H, d, J=4.5 Hz), 3.34 (3H, s), 3.44 (2H, s), 3.55 (4H, brs), 3.65-3.73 (2H, m), 3.94 (3H, s), 4.02-4.10 (2H, m), 6.85 (1H, d, J=15.7 Hz), 7.22 (2H, q, J=8.3 Hz), 7.44-7.56 (2H, m), 7.66-7.80 (2H, m), 8.09 (1H, s), 8.53 (1H, d, J=5.1 Hz), 8.77 (1H, s), 10.29 (1H, s).

Example 150

(2E)-N-(3-Cyano-4-(morpholin-4-ylmethyl)phenyl)-3-(4-(1-methyl-1H-pyrazol-4-yl)pyridin-3-yl)acrylamide

(A) 5-(((2E)-3-(4-(1-Methyl-1H-pyrazol-4-yl)pyridin-3-yl)prop-2-enoyl)amino)-2-(morpholin-4-ylmethyl)phenyl trifluoromethanesulfonate 1,1,1-Trifluoro-N-phenyl-N-((trifluoromethyl)sulfonyl)methanesulfonamide (240 mg) was added to a mixture of (2E)-N-(3-hydroxy-4-(morpholinomethyl)phenyl)-3-(4-(1-methyl-1H-pyrazol-4-yl)pyridin-3-yl)acrylamide (94 mg), DIEA (0.13 mL) and THF (5 mL) at room temperature, and the resulting mixture was stirred at 70° C. for 3 hours. 1,1,1-Trifluoro-N-phenyl-N-((trifluoromethyl)sulfonyl)methanesulfonamide (240 mg) and DIEA (0.13 mL) were added to the reaction mixture, and the mixture was stirred at 70° C. for 16 hours. Water was added to the reaction mixture, followed by extraction with ethyl acetate. The organic layer was washed with brine and then dried over anhydrous magnesium sulfate, and the solvent was distilled off under reduced pressure. The residue was purified by silica gel column chromatography (ethyl acetate/hexane) to obtain the title compound (56 mg).

MS: [M+H]$^+$ 552.1.

(B) (2E)-N-(3-Cyano-4-(morpholin-4-ylmethyl)phenyl)-3-(4-(1-methyl-1H-pyrazol-4-yl)pyridin-3-yl)acrylamide A mixture of 5-(((2E)-3-(4-(1-methyl-1H-pyrazol-4-yl)pyridin-3-yl)prop-2-enoyl)amino)-2-(morpholin-4-ylmethyl)phenyl trifluoromethanesulfonate (54 mg), Pd(PPh$_3$)$_4$ (23 mg), dicyanozinc (17 mg) and DMF (2 mL) was stirred at 130° C. for 1 hour under microwave irradiation. The reaction mixture was filtered through Celite, and water was added to the filtrate, followed by extraction with ethyl acetate. The organic layer was washed with brine and then dried over anhydrous magnesium sulfate, and the solvent was distilled off under reduced pressure. The residue was purified by silica gel column chromatography (NH, ethyl acetate/hexane) to obtain the title compound (18 mg).

$^1$H NMR (300 MHz, DMSO-d$_6$) δ 2.40 (4H, brs), 3.49-3.61 (6H, m), 3.94 (3H, s), 6.83 (1H, d, J=15.6 Hz), 7.46-7.64 (2H, m), 7.67-7.89 (3H, m), 8.09 (1H, s), 8.22 (1H, d, J=1.9 Hz), 8.54 (1H, d, J=5.2 Hz), 8.79 (1H, s), 10.62 (1H, s).

Example 175

(2E)-N-(1-Methyl-1H-indol-5-yl)-3-(4-(1-methyl-1H-pyrazol-4-yl)pyridin-3-yl)acrylamide HATU (474 mg) was added to a mixture of (2E)-3-(4-(1-methyl-1H-pyrazol-4-yl)pyridin-3-yl)acrylic acid (200 mg), 1-methyl-1H-indol-5-amine (121 mg), DIEA (0.435 mL) and DMF (4 mL) at room temperature, and the resulting mixture was stirred under nitrogen atmosphere at the same temperature for 2 hours. The solvent was distilled off under reduced pressure, and the residue was purified by silica gel column chromatography (NH, ethyl acetate/hexane) and recrystallized from ethanol/hexane to obtain the title compound (209 mg).

$^1$H NMR (300 MHz, DMSO-d$_6$) δ 3.78 (3H, s), 3.94 (3H, s), 6.39 (1H, d, J=3.0 Hz), 6.88 (1H, d, J=15.6 Hz), 7.31 (1H, d, J=2.8 Hz), 7.39 (2H, s), 7.49 (1H, d, J=5.3 Hz), 7.66-7.79 (2H, m), 8.07 (2H, d, J=13.2 Hz), 8.52 (1H, d, J=5.1 Hz), 8.78 (1H, s), 10.15 (1H, s).

Example 194

(2E)-3-(4-(1-Cyclopropyl-1H-pyrazol-4-yl)pyridin-3-yl)-N-(2-fluoro-4-(morpholin-4-ylmethyl)phenyl)acrylamide HATU (1811 mg) was added to a mixture of (2E)-3-(4-(1-cyclopropyl-1H-pyrazol-4-yl)pyridin-3-yl)acrylic acid (806 mg), 2-fluoro-4-(morpholinomethyl)aniline (738 mg), DIEA (1.7 mL) and DMF (15 mL) at room temperature, and the resulting mixture was stirred at the same temperature for 2 hours. Water and saturated aqueous potassium carbonate solution were added to the reaction mixture, followed by extraction with a mixed ethyl acetate/THF solution. The organic layer was washed with brine and then dried over anhydrous magnesium sulfate, and the solvent was distilled off under reduced pressure. The residue was purified by silica gel column chromatography (NH, ethyl acetate/hexane) and then recrystallized from ethanol/heptane to obtain the title compound (603 mg).

$^1$H NMR (300 MHz, DMSO-$d_6$) δ 0.97-1.20 (4H, m), 2.37 (4H, d, J=4.5 Hz), 3.45 (2H, s), 3.54-3.63 (4H, m), 3.76-3.90 (1H, m), 7.12 (3H, s), 7.48-7.55 (1H, m), 7.71 (2H, d, J=0.8 Hz), 8.01-8.09 (1H, m), 8.18 (1H, s), 8.53 (1H, d, J=5.2 Hz), 8.78 (1H, s), 9.99-10.06 (1H, m).

Example 203

(2E)-N-(4-(2-Hydroxypropan-2-yl)phenyl)-3-(4-(1-methyl-1H-pyrazol-4-yl)pyridin-3-yl)acrylamide Example 204

(2E)-3-(4-(1-Methyl-1H-pyrazol-4-yl)pyridin-3-yl)-N-phenylacrylamide (A) (2E)-3-(4-(1-Methyl-1H-pyrazol-4-yl)pyridin-3-yl)acrylamide A 28% aqueous ammonia solution (318 mg) was added to a mixture of (2E)-3-(4-(1-methyl-1H-pyrazol-4-yl)pyridin-3-yl)acrylic acid (300 mg), HOBt (265 mg), EDCI (502 mg) and DMF (5 mL) at room temperature, and the resulting mixture was stirred at the same temperature for 16 hours. Water was added to the reaction mixture, the mixture was concentrated under reduced pressure, and the residue was purified by silica gel column chromatography (NH, methanol/ethyl acetate) and then solidified from heptane to obtain the title compound (266 mg).

MS: [M+H]$^+$ 229.1.

(B) (2E)-N-(4-(2-Hydroxypropan-2-yl)phenyl)-3-(4-(1-methyl-1H-pyrazol-4-yl)pyridin-3-yl)acrylamide (2E)-3-(4-(1-Methyl-1H-pyrazol-4-yl)pyridin-3-yl)-N-phenylacrylamide A mixture of (2E)-3-(4-(1-methyl-1H-pyrazol-4-yl)pyridin-3-yl)acrylamide (266 mg), 2-(4-bromophenyl)propan-2-ol (276 mg), Xantphos (67 mg), Pd$_2$(dba)$_3$ (53 mg), sodium tert-butoxide (157 mg) and toluene (5 mL) was stirred at 120° C. for 45 minutes under microwave irradiation. The reaction mixture was filtered through Celite, and water was added to the filtrate, followed by extraction with ethyl acetate. The organic layer was washed with brine and then dried over anhydrous magnesium sulfate, and the solvent was distilled off under reduced pressure. The residue was purified by silica gel column chromatography (NH, ethyl acetate/hexane) to obtain (2E)-N-(4-(2-hydroxypropan-2-yl)phenyl)-3-(4-(1-methyl-1H-pyrazol-4-yl)pyridin-3-yl)acrylamide (101 mg) and (2E)-3-(4-(1-methyl-1H-pyrazol-4-yl)pyridin-3-yl)-N-phenylacrylamide (6 mg).

$^1$H NMR (300 MHz, DMSO-$d_6$) δ 1.41 (6H, s), 3.94 (3H, s), 4.94 (1H, s), 6.85 (1H, d, J=15.6 Hz), 7.42 (2H, d, J=8.7 Hz), 7.49 (1H, d, J=5.2 Hz), 7.62 (2H, d, J=8.7 Hz), 7.64-7.80 (2H, m), 8.08 (1H, s), 8.53 (1H, d, J=5.2 Hz), 8.77 (1H, s), 10.23 (1H, s).

$^1$H NMR (300 MHz, DMSO-$d_6$) δ 3.94 (3H, s), 6.86 (1H, d, J=15.7 Hz), 7.02-7.15 (1H, m), 7.35 (2H, t, J=7.9 Hz), 7.49 (1H, d, J=4.8 Hz), 7.66-7.80 (4H, m), 8.09 (1H, s), 8.53 (1H, d, J=5.2 Hz), 8.78 (1H, s), 10.29 (1H, s).

Example 205

(2E)-3-(4-(1-Methyl-1H-pyrazol-4-yl)pyridin-3-yl)-N-(4-((2-oxopyridin-1(2H)-yl)methyl)phenyl)acrylamide To a reaction mixture of (2E)-N-(4-(hydroxymethyl)phenyl)-3-(4-(1-methyl-1H-pyrazol-4-yl)pyridin-3-yl)acrylamide (205 mg), triethylamine (0.17 mL), THF (3 mL), acetonitrile (3 mL) and DMF (2 mL), methanesulfonyl chloride (0.10 mL) was added under ice cooling, and the mixture was stirred at room temperature for 16 hours. Water was added to the reaction mixture, followed by extraction with a mixed ethyl acetate/THF solution. The organic layer was washed with brine and then dried over anhydrous magnesium sulfate, and the solvent was distilled off under reduced pressure. THF (3 mL) was added to the residue, then a mixture of 60% sodium hydride (23 mg), pyridin-2-ol (58 mg) and THF (3 mL) was added to the mixture, and the reaction mixture was stirred at room temperature for 2 hours. Water was added to the reaction mixture, followed by extraction with ethyl acetate. The organic layer was washed with brine and then dried over anhydrous magnesium sulfate, and the solvent was distilled off under reduced pressure. The residue was purified by silica gel column chromatography (NH, ethyl acetate/hexane and subsequently methanol/ethyl acetate) and then recrystallized from ethanol/heptane to obtain the title compound (12 mg).

$^1$H NMR (300 MHz, DMSO-$d_6$) δ 3.93 (3H, s), 5.05 (2H, s), 6.24 (1H, td, J=6.7, 1.3 Hz), 6.41 (1H, d, J=9.3 Hz), 6.84 (1H, d, J=15.7 Hz), 7.29 (2H, d, J=8.5 Hz), 7.42 (1H, ddd, J=9.0, 6.7, 2.0 Hz), 7.49 (1H, d, J=5.3 Hz), 7.60-7.85 (5H, m), 8.08 (1H, s), 8.52 (1H, d, J=5.2 Hz), 8.77 (1H, s), 10.32 (1H, s).

Example 209

(2E)-N-(2-(Cyclopropylcarbonyl)-1,2,3,4-tetrahydroisoquinolin-7-yl)-3-(4-(1-methyl-1H-pyrazol-4-yl)pyridin-3-yl)acrylamide HATU (141 mg) was added to a mixture of (2E)-3-(4-(1-methyl-1H-pyrazol-4-yl)pyridin-3-yl)-N-(1,2,3,4-tetrahydroisoquinolin-7-yl)acrylamide dihydrochloride (80 mg), cyclopropanecarboxylic acid (21 mg), DIEA (0.13 mL) and DMF (2 mL) at room temperature, and the resulting mixture was stirred at the same temperature for 1.5 hours. The reaction mixture was concentrated under reduced pressure, and the residue was purified by silica gel column chromatography (NH, ethyl acetate/hexane) and then recrystallized from ethanol/heptane to obtain the title compound (8 mg).

$^1$H NMR (300 MHz, DMSO-$d_6$) δ 0.67-0.79 (4H, m), 2.09 (1H, brs), 2.73 (1H, brs), 2.86 (1H, brs), 3.68 (1H, brs), 3.87-3.98 (4H, m), 4.59 (1H, brs), 4.88 (1H, brs), 6.85 (1H, d, J=15.6 Hz), 7.15 (1H, d, J=7.7 Hz), 7.43-7.81 (5H, m), 8.08 (1H, s), 8.53 (1H, d, J=5.2 Hz), 8.77 (1H, s), 10.26 (1H, brs).

Example 214 tert-Butyl 7-(((2E)-3-(4-(1-methyl-1H-pyrazol-4-yl) pyridin-3-yl)prop-2-enoyl)amino)-3,4-dihydroisoquinoline-2(1H)-carboxylate HATU (1483 mg) was added to a mixture of (2E)-3-(4-(1-methyl-1H-pyrazol-4-yl)pyridin-3-yl)acrylic acid (656 mg), tert-butyl 7-amino-3,4-dihydroisoquinoline-2(1H)-carboxylate (646 mg), DIEA (1.363 mL) and DMF (13 mL) at room temperature, and the resulting mixture was stirred overnight under nitrogen atmosphere at the same temperature. The solvent was distilled off under reduced pressure, and the residue was purified by silica gel column chromatography (NH, ethyl acetate/hexane) to obtain the title compound (1.13 g).

$^1$H NMR (300 MHz, DMSO-d$_6$) δ 1.43 (9H, s), 2.65-2.82 (2H, m), 3.55 (2H, t, J=5.8 Hz), 3.94 (3H, s), 4.48 (2H, s), 6.84 (1H, d, J=15.6 Hz), 7.13 (1H, d, J=8.3 Hz), 7.28-7.66 (3H, m), 7.67-7.82 (2H, m), 8.08 (1H, s), 8.53 (1H, d, J=5.3 Hz), 8.77 (1H, s), 10.25 (1H, s).

Example 215

(2E)-3-(4-(1-Methyl-1H-pyrazol-4-yl)pyridin-3-yl)-N-(1,2,3,4-tetrahydroisoquinolin-7-yl)acrylamide dihydrochloride To a mixture of tert-butyl 7-(((2E)-3-(4-(1-methyl-1H-pyrazol-4-yl)pyridin-3-yl)prop-2-enoyl)amino)-3,4-dihydroisoquinoline-2(1H)-carboxylate (50 mg), ethyl acetate (0.5 mL), and methanol (0.5 mL) was added a 4 M solution of hydrogen chloride in CPME (1 mL) at room temperature, and the resulting mixture was stirred overnight under nitrogen atmosphere at the same temperature. The solvent was distilled off under reduced pressure, and the residue was suspended in ethyl acetate. The precipitate was collected by filtration under nitrogen stream and washed with ethyl acetate to obtain the title compound (44 mg).

$^1$H NMR (300 MHz, DMSO-d$_6$) δ 2.97 (2H, t, J=5.9 Hz), 3.35 (2H, d, J=6.0 Hz), 3.98 (3H, s), 4.26 (2H, brs), 4.39-5.80 (1H, m), 7.05 (1H, d, J=15.6 Hz), 7.21 (1H, d, J=8.5 Hz), 7.58 (1H, dd, J=8.4, 2.0 Hz), 7.66-7.78 (2H, m), 8.01 (1H, s), 8.08 (1H, d, J=6.2 Hz), 8.39 (1H, s), 8.78 (1H, d, J=6.0 Hz), 8.93 (1H, s), 9.49 (2H, brs), 10.77 (1H, s).

Example 216

(2E)-3-(4-(1-Methyl-1H-pyrazol-4-yl)pyridin-3-yl)-N-(2-(2,2,2-trifluoroethyl)-1,2,3,4-tetrahydroisoquinolin-7-yl)acrylamide To a mixture of (2E)-3-(4-(1-methyl-1H-pyrazol-4-yl)pyridin-3-yl)-N-(1,2,3,4-tetrahydroisoquinolin-7-yl)acrylamide dihydrochloride (61 mg) and acetonitrile (1 mL), triethylamine (0.197 mL) and 2,2,2-trifluoroethyl trifluoromethanesulfonate (0.101 mL) were added at room temperature, and the resulting mixture was stirred overnight under nitrogen atmosphere at the same temperature. Water was added to the reaction mixture, and the aqueous layer was extracted with ethyl acetate. The extract was washed with water and brine and then dried over anhydrous magnesium sulfate, and the solvent was distilled off under reduced pressure. The residue was purified by silica gel column chromatography (NH, ethyl acetate/hexane) to obtain the title compound (46.4 mg).

$^1$H NMR (300 MHz, DMSO-d$_6$) δ 2.72-2.84 (2H, m), 2.86-2.97 (2H, m), 3.23-3.45 (2H, m), 3.80 (2H, s), 3.94 (3H, s), 6.84 (1H, d, J=15.6 Hz), 7.08 (1H, d, J=8.1 Hz), 7.36-7.53 (3H, m), 7.61-7.78 (2H, m), 8.08 (1H, s), 8.52 (1H, d, J=5.1 Hz), 8.77 (1H, s), 10.21 (1H, s).

Example 217

(2E)-N-(4-(Morpholin-4-ylmethyl)phenyl)-3-(4-(1-(oxetan-3-yl)-1H-pyrazol-4-yl)pyridin-3-yl)acrylamide To a mixture of oxetan-3-ol (92 mg), DIEA (0.59 mL) and THF (3 mL), methanesulfonyl chloride (0.24 mL) was added under ice cooling, and the resulting mixture was stirred at the same temperature for 2 hours. Water was added to the reaction mixture, followed by extraction with ethyl acetate. The organic layer was washed with brine and then dried over anhydrous magnesium sulfate, and the solvent was distilled off under reduced pressure. DMF (3 mL) was added to the residue, then (2E)-N-(4-(morpholin-4-ylmethyl)phenyl)-3-(4-(1H-pyrazol-4-yl)pyridin-3-yl)acrylamide (227 mg) and cesium carbonate (607 mg) were added to the mixture, and the reaction mixture was stirred at 100° C. for 1.5 hours. Water was added to the reaction mixture, followed by extraction with ethyl acetate. The organic layer was washed with brine and then dried over anhydrous magnesium sulfate, and the solvent was distilled off under reduced pressure. The residue was purified by silica gel column chromatography (NH, ethyl acetate/hexane) to obtain the title compound (25 mg).

$^1$H NMR (300 MHz, DMSO-d$_6$) δ 2.35 (4H, brs), 3.42 (2H, s), 3.52-3.61 (4H, m), 4.96 (4H, d, J=7.0 Hz), 5.64-5.76 (1H, m), 6.86 (1H, d, J=15.7 Hz), 7.27 (2H, d, J=8.5 Hz), 7.53 (1H, d, J=5.3 Hz), 7.61-7.76 (3H, m), 7.91 (1H, s), 8.29 (1H, s), 8.55 (1H, d, J=5.2 Hz), 8.79 (1H, s), 10.28 (1H, s).

Example 218

(2E)-3-(4-(1-Acetyl-1H-pyrazol-4-yl)pyridin-3-yl)-N-(4-(morpholin-4-ylmethyl)phenyl)acrylamide To a reaction mixture of (2E)-N-(4-(morpholin-4-ylmethyl)phenyl)-3-(4-(1H-pyrazol-4-yl)pyridin-3-yl)acrylamide (80 mg), triethylamine (0.09 mL), DMAP (1 piece) and THF (5 mL), acetic anhydride (42 mg) was added, and the mixture was stirred at the same temperature for 1.5 hours. The reaction mixture was concentrated under reduced pressure, and the residue was then crystallized from ethyl acetate to obtain the title compound (46 mg).

$^1$H NMR (300 MHz, DMSO-d$_6$) δ 2.29-2.36 (4H, m), 2.71 (3H, s), 3.42 (2H, s), 3.53-3.62 (4H, m), 6.88 (1H, d, J=15.7 Hz), 7.27 (2H, d, J=8.5 Hz), 7.61-7.76 (4H, m), 8.20 (1H, d, J=0.66 Hz), 8.61 (1H, d, J=5.1 Hz), 8.70 (1H, d, J=0.7 Hz), 8.86 (1H, s), 10.30 (1H, s).

Example 219

(2E)-3-(6-Amino-4-(1-methyl-1H-pyrazol-4-yl)pyridin-3-yl)-N-(4-(morpholin-4-ylmethyl)phenyl)acrylamide (A) (2E)-Ethyl 3-(4,6-dichloropyridin-3-yl)acrylate To a mixture of 60% sodium hydride (0.46 g) and THF (40 mL), a solution of ethyl diethylphosphonoacetate (2.3 mL) in THF (10 mL) was added dropwise under ice cooling, and the resulting mixture was stirred at the same temperature for 2 hours. A mixture of 4,6-dichloronicotinaldehyde (1.54 g) and DMF (10 mL) was added to the reaction mixture under ice cooling, and the resulting mixture was stirred for 2 hours while being heated up to room temperature. Saturated aqueous ammonium chloride solution was added to the reaction mixture under ice cooling, and the mixture was then concentrated into half the amount under reduced pressure. The residue was extracted with ethyl acetate. The extract was washed with brine and then dried over anhydrous magnesium sulfate, and the solvent was distilled off under reduced pressure. The residue was purified by silica gel column chromatography (ethyl acetate/hexane) to obtain the title compound (2.12 g).

MS: [M+H]$^+$ 245.8.

(B) (2E)-Ethyl 3-(6-chloro-4-(1-methyl-1H-pyrazol-4-yl)pyridin-3-yl)acrylate A mixture of (2E)-ethyl 3-(4,6-dichloropyridin-3-yl)acrylate (1.45 g), 1-methyl-4-(4,4,5,5-tetramethyl-1,3,2-dioxaborolan-2-yl)-1H-pyrazole (1.26 g), 2-(dicyclohexylphosphino)biphenyl (258 mg), Pd$_2$(dba)$_3$ (270 mg), cesium carbonate (4.80 g), DME (35 mL) and water (5 mL) was stirred under nitrogen atmosphere at 80° C. for 18 hours. The reaction mixture was filtered through Celite, and water was added to the filtrate, followed by extraction with ethyl acetate. The extract was washed with brine and then dried over anhydrous magnesium sulfate, and the solvent was distilled off under reduced pressure. The residue was purified by silica gel column chromatography (ethyl acetate/hexane) to obtain the title compound (1.08 g).

MS: [M+H]$^+$ 291.9.

(C) (2E)-Ethyl 3-(6-((tert-butoxycarbonyl)amino)-4-(1-methyl-1H-pyrazol-4-yl)pyridin-3-yl)acrylate A mixture of (2E)-ethyl 3-(6-chloro-4-(1-methyl-1H-pyrazol-4-yl)pyridin-3-yl)acrylate (500 mg), tert-butyl carbamate (241 mg), Xphos (16 mg), Pd$_2$(dba)$_3$ (16 mg), cesium carbonate (2234 mg) and THF (20 mL) was stirred under nitrogen atmosphere at 70° C. for 7 hours. The reaction mixture was filtered through Celite, and water was added to the filtrate, followed by extraction with ethyl acetate. The organic layer was washed with brine and then dried over anhydrous magnesium sulfate, and the solvent was distilled off under reduced pressure. The residue was purified by silica gel column chromatography (NH, ethyl acetate/hexane) to obtain the title compound as a crude product (558 mg).

MS: [M+H]$^+$ 373.0.

(D) (2E)-3-(6-((tert-Butoxycarbonyl)amino)-4-(1-methyl-1H-pyrazol-4-yl)pyridin-3-yl)acrylic acid To a solution of crude (2E)-ethyl 3-(6-((tert-butoxycarbonyl)amino)-4-(1-methyl-1H-pyrazol-4-yl)pyridin-3-yl)acrylate (588 mg) in ethanol (5 mL) and THF (5 mL), a 2 N aqueous sodium hydroxide solution (3.2 mL) was added at room temperature, and the mixture was stirred at the same temperature for 3 hours. A 2 N hydrochloric acid solution was added to the reaction mixture under ice cooling to adjust the pH to 3. The precipitated solid was recovered and washed with water to obtain the title compound as a crude product (289 mg).

MS: [M+H]$^+$ 344.9.

(E) (2E)-tert-Butyl (4-(1-methyl-1H-pyrazol-4-yl)-5-(3-((4-(morpholinomethyl)phenyl)amino)-3-oxo-prop-1-en-1-yl)pyridin-2-yl)carbamate HATU (439 mg) was added to a mixture of crude (2E)-3-(6-((tert-butoxycarbonyl)amino)-4-(1-methyl-1H-pyrazol-4-yl)pyridin-3-yl)acrylic acid (265 mg), 4-(morpholinomethyl)aniline (152 mg), DIEA (0.55 mL) and DMF (5 mL) at room temperature, and the resulting mixture was stirred at the same temperature for 6 hours. Water was added to the reaction mixture, followed by extraction with ethyl acetate. The organic layer was washed with brine and then dried over anhydrous magnesium sulfate, and the solvent was distilled off under reduced pressure. The residue was purified by silica gel column chromatography (NH, ethyl acetate/hexane) to obtain the title compound as a crude product (382 mg).

MS: [M+H]$^+$ 519.3.

(F) (2E)-3-(6-Amino-4-(1-methyl-1H-pyrazol-4-yl)pyridin-3-yl)-N-(4-(morpholin-4-ylmethyl)phenyl)acrylamide A 2 N solution of hydrogen chloride in methanol (6 mL) was added to crude (2E)-tert-butyl(4-(1-methyl-1H-pyrazol-4-yl)-5-(3-((4-(morpholinomethyl)phenyl)amino)-3-oxo-prop-1-en-1-yl)pyridin-2-yl)carbamate (278 mg) at room temperature, and the mixture was stirred at 45° C. for 16 hours. The reaction mixture was concentrated under reduced pressure, toluene was added to the residue, and the mixture was concentrated under reduced pressure. The residue was purified by silica gel column chromatography (NH, ethyl acetate/hexane and subsequently methanol/ethyl acetate) and then recrystallized from ethyl acetate/heptane to obtain the title compound (56 mg).

$^1$H NMR (300 MHz, DMSO-d$_6$) δ 2.33 (4H, brs), 3.40 (2H, s), 3.51-3.61 (4H, m), 3.92 (3H, s), 6.34 (2H, s), 6.42 (1H, s), 6.61 (1H, d, J=15.5 Hz), 7.23 (2H, d, J=8.5 Hz), 7.51-7.67 (4H, m), 7.91 (1H, s), 8.30 (1H, s), 10.03 (1H, s).

Example 221

(2E)-3-(4-(2-Methoxy-1,3-thiazol-5-yl)pyridin-3-yl)-N-(4-(morpholin-4-ylmethyl)phenyl)acrylamide

(A) (2E)-tert-Butyl 3-(4-(4,4,5,5-tetramethyl-1,3,2-dioxaborolan-2-yl)pyridin-3-yl)acrylate A mixture of 3-bromo-4-(4,4,5,5-tetramethyl-1,3,2-dioxaborolan-2-yl)pyridine (4718 mg), tert-butyl acrylate (3.64 mL), triethylamine (6.95 mL), tri-o-tolylphosphine (1011 mg), Pd(OAc)$_2$ (373 mg) and DMF (50 mL) was stirred under nitrogen atmosphere at 130° C. for 3 hours. The reaction mixture was cooled to 0° C. Then, the insoluble matter was collected by filtration, and the filtrate was concentrated under reduced pressure. Ethyl acetate was added to the residue. The precipitate was collected by filtration, and the filtrate was concentrated under reduced pressure. Ethyl acetate/hexane (1/5) was added to the residue. The precipitate was collected by filtration, and the filtrate was concentrated under reduced pressure. The residue was cooled to 0° C., and the precipitate was washed with hexane and then collected by filtration to obtain the title compound (1657 mg).

MS: [M+H]$^+$ 332.3.

(B) (2E)-3-(4-(2-Methoxythiazol-5-yl)pyridin-3-yl) acrylic acid trifluoroacetate A mixture of (2E)-tert-butyl 3-(4-(4,4,5,5-tetramethyl-1,3,2-dioxaborolan-2-yl)pyridin-3-yl)acrylate (512 mg), 5-bromo-2-methoxythiazole (200 mg), SPhos (21.16 mg), chloro(2-dicyclohexylphosphino-2',6'-dimethoxy-1,1'-biphenyl)[2-(2'-amino-1,1'-biphenyl)]palladium(II) (37.1 mg), a 2 M aqueous cesium carbonate solution (1.29 mL) and DME (8 mL) was stirred at 130° C. for 2 hours under microwave irradiation. The reaction mixture was diluted with ethyl acetate (10 mL), anhydrous magnesium sulfate was added thereto, and the insoluble matter was removed by filtration. The filtrate was concentrated under reduced pressure, and the residue was purified by silica gel column chromatography (NH, ethyl acetate/hexane) to obtain a solid (196 mg). A mixture of the obtained solid (196 mg) and TFA (10 mL) was stirred at room temperature for 45 minutes. The reaction mixture was concentrated under reduced pressure, the residue was diluted with ethyl acetate (10 mL), and the precipitate was collected by filtration to obtain the title compound (132 mg).

$^1$H NMR (300 MHz, DMSO-d$_6$) δ 4.11 (3H, s), 6.62 (1H, d, J=16.0 Hz), 7.45 (1H, s), 7.51 (1H, d, J=5.2 Hz), 7.75 (1H, d, J=16.1 Hz), 8.59 (1H, d, J=5.2 Hz), 8.93 (1H, s), 12.67 (1H, brs).

(C) (2E)-3-(4-(2-Methoxy-1,3-thiazol-5-yl)pyridin-3-yl)-N-(4-(morpholin-4-ylmethyl)phenyl)acrylamide To a solution of (2E)-3-(4-(2-methoxythiazol-5-yl)pyridin-3-yl)acrylic acid trifluoroacetate (79.4 mg) in DMF (4 mL), 4-(morpholinomethyl)aniline (52.7 mg), HATU (104 mg) and DIEA (0.127 mL) were added at room temperature, and the mixture was stirred at the same temperature for 1.5 hours. The solvent was distilled off under reduced pressure, and the residue was purified by silica gel column chromatography (NH, ethyl acetate/hexane). The obtained solid was washed with ethyl acetate/hexane (1/5) and then collected by filtration to obtain the title compound (92 mg).

$^1$H NMR (300 MHz, DMSO-d$_6$) δ 2.30-2.38 (4H, m), 3.42 (2H, s), 3.53-3.60 (4H, m), 4.11 (3H, s), 6.86 (1H, d, J=15.6 Hz), 7.27 (2H, d, J=8.5 Hz), 7.49 (1H, s), 7.53 (1H, d, J=5.6 Hz), 7.65 (2H, d, J=8.5 Hz), 7.76 (1H, d, J=15.7 Hz), 8.59 (1H, d, J=5.2 Hz), 8.83 (1H, s), 10.31 (1H, s).

Example 223

(2E)-N-(4-Bromo-3-((methylsulfonyl)methyl)phenyl)-3-(4-(1-methyl-1H-pyrazol-4-yl)pyridin-3-yl) acrylamide (A) Methyl 5-amino-2-bromobenzoate To a mixture of methyl 2-bromo-5-nitrobenzoate (5.0 g) and acetic acid (100 mL), a zinc powder (12.57 g) was added at room temperature, and the resulting mixture was stirred at the same temperature for 10 minutes. The reaction mixture was filtered, and the solvent in the filtrate was distilled off under reduced pressure. Saturated aqueous sodium bicarbonate solution was added to the residue, and the aqueous layer was extracted with ethyl acetate. The extract was washed with water and brine and then dried over anhydrous magnesium sulfate, and the solvent was distilled off under reduced pressure to obtain the title compound (4.92 g).

$^1$H NMR (300 MHz, DMSO-d$_6$) δ 3.80 (3H, s), 5.54 (2H, s), 6.63 (1H, dd, J=8.7, 2.8 Hz), 6.94 (1H, d, J=2.8 Hz), 7.29 (1H, d, J=8.7 Hz).

(B) (5-Amino-2-bromophenyl)methanol

To a mixture of calcium chloride (1.259 g) and THF (10 mL), sodium tetrahydroborate (0.858 g) was added at 0° C., and the resulting mixture was stirred under nitrogen atmosphere at the same temperature for 5 minutes. Methyl 5-amino-2-bromobenzoate (1.5 g) was added to the reaction mixture at 0° C., and the mixture was stirred overnight at room temperature. A 1 N hydrochloric acid solution was added to the reaction mixture at room temperature, and the mixture was neutralized by the addition of aqueous potassium carbonate solution. Then, the aqueous layer was extracted with ethyl acetate. The extract was washed with water and brine and then dried over anhydrous magnesium sulfate, and the solvent was distilled off under reduced pressure to obtain the title compound (775 mg).

$^1$H NMR (300 MHz, DMSO-d$_6$) δ 4.36 (2H, d, J=5.7 Hz), 5.18-5.27 (3H, m), 6.37 (1H, dd, J=8.5, 2.8 Hz), 6.79 (1H, d, J=2.8 Hz), 7.10 (1H, d, J=8.5 Hz).

(C) (2E)-N-(4-Bromo-3-(hydroxymethyl)phenyl)-3-(4-(1-methyl-1H-pyrazol-4-yl)pyridin-3-yl)acrylamide HATU (1283 mg) was added to a mixture of (2E)-3-(4-(1-methyl-1H-pyrazol-4-yl)pyridin-3-yl)acrylic acid (516 mg), (5-amino-2-bromophenyl)methanol (500 mg), DIEA (1.179 mL) and DMF (10 mL) under nitrogen atmosphere at room temperature, and the resulting mixture was stirred overnight at the same temperature. The solvent was distilled off under reduced pressure, and the residue was purified by silica gel column chromatography (NH, methanol/ethyl acetate) to obtain the title compound (221 mg).

$^1$H NMR (300 MHz, DMSO-d$_6$) δ 3.94 (3H, s), 4.49 (2H, d, J=5.5 Hz), 5.51 (1H, t, J=5.4 Hz), 6.85 (1H, d, J=15.6 Hz), 7.45-7.56 (2H, m), 7.64-7.81 (3H, m), 7.87 (1H, s), 8.09 (1H, s), 8.53 (1H, d, J=5.3 Hz), 8.77 (1H, s), 10.45 (1H, s).

(D) (2E)-N-(4-Bromo-3-((methylthio)methyl)phenyl)-3-(4-(1-methyl-1H-pyrazol-4-yl)pyridin-3-yl) acrylamide To a mixture of (2E)-N-(4-bromo-3-(hydroxymethyl)phenyl)-3-(4-(1-methyl-1H-pyrazol-4-yl)pyridin-3-yl)acrylamide (137 mg), triethylamine (0.231 mL) and THF (5 mL), methanesulfonyl chloride (0.103 mL) was added at 0° C., and the resulting mixture was stirred under nitrogen atmosphere at room temperature for 1 hour. Water was added to the reaction mixture at room temperature, and the aqueous layer was extracted with ethyl acetate and THF. The extract was washed with water/brine (1/1) and brine and then dried over anhydrous magnesium sulfate, and the solvent was distilled off under reduced pressure. The residue was dissolved in DMF (2 mL). To the solution, sodium methanethiolate (116 mg) was added at room temperature, and the mixture was stirred under nitrogen atmosphere at the same temperature for 5 minutes. Water was added to the reaction mixture at room temperature, and the aqueous layer was extracted with ethyl acetate. The extract was washed with water and brine and then dried over anhydrous magnesium sulfate, and the solvent was distilled off under reduced pressure, and the residue was purified by silica gel column chromatography (NH, ethyl acetate/hexane) to obtain the title compound (60.1 mg).

$^1$H NMR (300 MHz, DMSO-$d_6$) δ 2.05 (3H, s), 3.77 (2H, s), 3.94 (3H, s), 6.84 (1H, d, J=15.4 Hz), 7.50 (1H, d, J=4.9 Hz), 7.57 (2H, s), 7.70-7.86 (3H, m), 8.09 (1H, s), 8.53 (1H, d, J=5.1 Hz), 8.78 (1H, s), 10.45 (1H, s).

(E) (2E)-N-(4-Bromo-3-((methylsulfonyl)methyl) phenyl)-3-(4-(1-methyl-1H-pyrazol-4-yl)pyridin-3-yl)acrylamide To a mixture of (2E)-N-(4-bromo-3-((methylthio)methyl) phenyl)-3-(4-(1-methyl-1H-pyrazol-4-yl)pyridin-3-yl)acrylamide (60.1 mg) and methanol (10 mL), a solution of oxone (500 mg) in water (2 mL) was added at room temperature, and the mixture was stirred at the same temperature for 10 minutes. Water was added to the reaction mixture, and the precipitate was collected by filtration and washed with water and IPE to obtain the title compound (58.1 mg).

$^1$H NMR (300 MHz, DMSO-$d_6$) δ 3.05 (3H, s), 3.95 (3H, s), 4.67 (2H, s), 6.87 (1H, d, J=15.6 Hz), 7.63-7.95 (6H, m), 8.18 (1H, s), 8.61 (1H, d, J=5.5 Hz), 8.83 (1H, s), 10.60 (1H, s).

Example 224

(2E)-3-(4-(1H-Imidazol-1-yl)pyridin-3-yl)-N-(4-(morpholin-4-ylmethyl)phenyl)acrylamide A mixture of (2E)-3-(4-chloropyridin-3-yl)-N-(4-(morpholinomethyl)phenyl)acrylamide (100 mg), imidazole (38 mg), DMF (2 mL) and cesium carbonate (182 mg) was stirred overnight under nitrogen atmosphere at 100° C. The reaction mixture was filtered, and the solvent in the filtrate was distilled off under reduced pressure. The residue was dissolved in ethyl acetate, and the solution was filtered using NH silica gel. The solvent in the filtrate was distilled off under reduced pressure, and the residue was dissolved in ethyl acetate and THF. The reaction mixture was washed with water and brine and then dried over anhydrous magnesium sulfate, and the solvent was distilled off under reduced pressure to obtain the title compound (7.6 mg).

$^1$H NMR (300 MHz, DMF) δ 2.69-2.78 (4H, m), 3.82 (2H, s), 3.94-4.00 (4H, m), 7.33 (1H, d, J=15.6 Hz), 7.58-7.71 (3H, m), 7.78 (1H, d, J=15.8 Hz), 7.94-8.08 (4H, m), 8.42 (1H, s), 9.13 (1H, d, J=5.3 Hz), 9.41 (1H, s), 10.73 (1H, s).

Example 228

(2E)-N-(4-(1,1-Difluoro-2-hydroxy-2-methylpropyl) phenyl)-3-(4-(1-methyl-1H-pyrazol-4-yl)pyridin-3-yl)acrylamide (A) 1-(4-Bromophenyl)-1,1-difluoro-2-methylpropan-2-ol A 1.13 M solution of methyllithium in diethyl ether (2.2 mL) was added dropwise to a mixture of ethyl 2-(4-bromophenyl)-2,2-difluoroacetate (140 mg) and diethyl ether (5 mL) under ice cooling, and the resulting mixture was stirred at room temperature for 19 hours. Saturated aqueous ammonium chloride solution was added to the reaction mixture, followed by extraction with ethyl acetate. The organic layer was washed with brine and then dried over anhydrous magnesium sulfate, and the solvent was distilled off under reduced pressure to obtain the title compound as a crude product (133 mg). This compound was used in the next step without being further purified.

$^1$H NMR (300 MHz, CDCl$_3$) δ 1.29 (6H, t, J=1.3 Hz), 1.87 (1H, brs), 7.39 (2H, d, J=8.7 Hz), 7.55 (2H, d, J=8.7 Hz).

(B) (2E)-N-(4-(1,1-Difluoro-2-hydroxy-2-methylpropyl)phenyl)-3-(4-(1-methyl-1H-pyrazol-4-yl) pyridin-3-yl)acrylamide A mixture of (2E)-3-(4-(1-methyl-1H-pyrazol-4-yl)pyridin-3-yl)acrylamide (96 mg), 1-(4-bromophenyl)-1,1-difluoro-2-methylpropan-2-ol (133 mg), Xantphos (26 mg), Pd$_2$(dba)$_3$ (21 mg), sodium tert-butoxide (61 mg) and toluene (2 mL) was stirred at 120° C. for 45 minutes under microwave irradiation. The reaction mixture was filtered through Celite, and water was added to the filtrate, followed by extraction with ethyl acetate. The organic layer was washed with brine and then dried over anhydrous magnesium sulfate, and the solvent was distilled off under reduced pressure. The residue was purified by silica gel column chromatography (NH, ethyl acetate/hexane) to obtain the title compound (29 mg).

$^1$H NMR (300 MHz, DMSO-$d_6$) δ 1.17 (6H, s), 3.94 (3H, s), 5.24 (1H, s), 6.87 (1H, d, J=15.7 Hz), 7.41-7.53 (3H, m), 7.70-7.83 (4H, m), 8.09 (1H, s), 8.53 (1H, d, J=5.1 Hz), 8.79 (1H, s), 10.46 (1H, s).

Example 229

(2E)-N-(4-Cyclopropyl-3-((2,2,2-trifluoroethoxy) methyl)phenyl)-3-(4-(1-methyl-1H-pyrazol-4-yl) pyridin-3-yl)acrylamide (A) tert-Butyl (4-bromo-3-(((tert-butoxycarbonyl) oxy)methyl)phenyl)carbamate and tert-butyl (4-bromo-3-(hydroxymethyl)phenyl)carbamate A mixture of (5-amino-2-bromophenyl)methanol (2.65 g), di-tert-butyl dicarbonate (13.25 mL), a 1 N aqueous sodium hydroxide solution (95 mL) and THF (65 mL) was stirred overnight at room temperature. Water was added to the reaction mixture at room temperature, and the aqueous layer was extracted with ethyl acetate. The extract was washed with water and brine and then dried over anhydrous magnesium sulfate, and the solvent was distilled off under reduced pressure. The residue was purified by silica gel column chromatography (ethyl acetate/hexane) to obtain crude tert-butyl (4-bromo-3-(((tert-butoxycarbonyl)oxy)methyl)phenyl)carbamate (1.39 g) and tert-butyl (4-bromo-3-(hydroxymethyl)phenyl)carbamate (2.56 g).

$^1$H NMR (300 MHz, DMSO-$d_6$) δ 1.44 (9H, s), 1.47 (9H, s), 5.05 (2H, s), 7.34 (1H, dd, J=8.8, 2.5 Hz), 7.51 (1H, d, J=8.7 Hz), 7.63 (1H, d, J=2.6 Hz), 9.57 (1H, s).

$^1$H NMR (300 MHz, DMSO-$d_6$) δ 1.47 (9H, s), 4.43 (2H, d, J=5.7 Hz), 5.39 (1H, t, J=5.7 Hz), 7.26 (1H, dd, J=8.7, 2.6 Hz), 7.40 (1H, d, J=8.7 Hz), 7.74 (1H, d, J=2.6 Hz), 9.47 (1H, s).

(B) tert-Butyl (3-(((tert-butoxycarbonyl)oxy) methyl)-4-cyclopropylphenyl)carbamate A mixture of crude tert-butyl (4-bromo-3-(((tert-butoxycarbonyl)oxy)methyl)phenyl)carbamate (1.39 g), cyclopropylboronic acid (261 mg), palladium acetate (34 mg), tricyclohexylphosphine (128 mg), potassium phosphate (968 mg), toluene (9 mL) and water (3 mL) was stirred overnight under nitrogen atmosphere at 100° C. Water was added to the reaction mixture at room temperature, and the aqueous layer was extracted with ethyl acetate. The extract was washed with water and brine and then dried over anhydrous magnesium sulfate, and the solvent was distilled off under reduced pressure. The residue was purified by silica gel column chromatography (ethyl acetate/hexane) to obtain the title compound (767.2 mg).

$^1$H NMR (300 MHz, DMSO-$d_6$) δ 0.48-0.66 (2H, m), 0.79-0.94 (2H, m), 1.44 (9H, s), 1.46 (9H, s), 1.77-1.94 (1H, m), 5.20 (2H, s), 6.92 (1H, d, J=8.3 Hz), 7.27 (1H, dd, J=8.4, 2.2 Hz), 7.45 (1H, d, J=2.3 Hz), 9.29 (1H, s).

(C) tert-Butyl (4-cyclopropyl-3-(hydroxymethyl)phenyl)carbamate

To a mixture of tert-butyl (3-(((tert-butoxycarbonyl)oxy)methyl)-4-cyclopropylphenyl)carbamate (762 mg), THF (8 mL) and ethanol (4 mL), a 1 N aqueous sodium hydroxide solution (8 mL) was added at room temperature, and the resulting mixture was stirred overnight at 80° C. Water was added to the reaction mixture at room temperature, and the aqueous layer was extracted with ethyl acetate. The extract was washed with water and brine and then dried over anhydrous magnesium sulfate, and the solvent was distilled off under reduced pressure to obtain the title compound (518 mg).

$^1$H NMR (300 MHz, DMSO-$d_6$) δ 0.46-0.60 (2H, m), 0.74-0.89 (2H, m), 1.46 (9H, s), 1.73-1.90 (1H, m), 4.61 (2H, d, J=5.3 Hz), 5.06 (1H, t, J=5.4 Hz), 6.81 (1H, d, J=8.3 Hz), 7.18 (1H, d, J=8.1 Hz), 7.52 (1H, s), 9.18 (1H, s).

(D) tert-Butyl (4-cyclopropyl-3-((2,2,2-trifluoroethoxy)methyl)phenyl)carbamate

To a mixture of tert-butyl (4-cyclopropyl-3-(hydroxymethyl)phenyl)carbamate (145 mg), 2,2,2-trifluoroethanol (0.395 mL) and toluene (8 mL), ADDP (222 mg) and tributylphosphine (0.217 mL) were added at room temperature, and the resulting mixture was stirred under nitrogen atmosphere at the same temperature for 20 minutes. Ethyl acetate/hexane (1/1) was added to the reaction mixture, and the insoluble matter was removed by filtration. The solvent in the filtrate was distilled off under reduced pressure, and the residue was purified by silica gel column chromatography (ethyl acetate/hexane) to obtain the title compound (165.8 mg).

$^1$H NMR (300 MHz, DMSO-$d_6$) δ 0.48-0.60 (2H, m), 0.80-0.91 (2H, m), 1.46 (9H, s), 1.81-1.96 (1H, m), 4.13 (2H, q, J=9.5 Hz), 4.76 (2H, s), 6.89 (1H, d, J=8.5 Hz), 7.28 (1H, d, J=8.7 Hz), 7.45 (1H, s), 9.26 (1H, s).

(E) (2E)-N-(4-Cyclopropyl-3-((2,2,2-trifluoroethoxy)methyl)phenyl)-3-(4-(1-methyl-1H-pyrazol-4-yl)pyridin-3-yl)acrylamide A 4 M solution of hydrogen chloride in CPME (2 mL) was added to tert-butyl (4-cyclopropyl-3-((2,2,2-trifluoroethoxy)methyl)phenyl)carbamate (85.8 mg) at room temperature, and the mixture was stirred at the same temperature for 20 minutes. The solvent was distilled off under reduced pressure. A mixture of the obtained residue, HATU (142 mg), (2E)-3-(4-(1-methyl-1H-pyrazol-4-yl)pyridin-3-yl)acrylic acid (57 mg), DIEA (0.130 mL) and DMF (2 mL) was stirred under nitrogen atmosphere at room temperature for 30 minutes. Water was added to the reaction mixture, and the precipitate was collected by filtration and washed with water. The obtained solid was purified by silica gel column chromatography (methanol/ethyl acetate) to obtain the title compound (66.1 mg).

$^1$H NMR (300 MHz, DMSO-$d_6$) δ 0.53-0.68 (2H, m), 0.82-0.96 (2H, m), 1.92 (1H, s), 3.93 (3H, s), 4.18 (2H, q, J=9.3 Hz), 4.83 (2H, s), 6.85 (1H, d, J=15.4 Hz), 6.99 (1H, d, J=8.3 Hz), 7.49 (1H, d, J=5.1 Hz), 7.57-7.79 (4H, m), 8.08 (1H, s), 8.53 (1H, d, J=5.5 Hz), 8.77 (1H, s), 10.28 (1H, s).

Example 230

(2E)-N-(3-((Acetyl(methyl)amino)methyl)-4-bromophenyl)-3-(4-(1-methyl-1H-pyrazol-4-yl)pyridin-3-yl)acrylamide (A) tert-Butyl (4-bromo-3-((N-methylacetamido)methyl)phenyl)carbamate To a mixture of tert-butyl (4-bromo-3-(hydroxymethyl)phenyl)carbamate (150 mg), triethylamine (0.208 mL) and THF (3 mL), methanesulfonyl chloride (0.077 mL) was added at 0° C., and the resulting mixture was stirred under nitrogen atmosphere at room temperature for 20 minutes. Water was added to the reaction mixture at room temperature, and the aqueous layer was extracted with ethyl acetate. The extract was washed with water and brine and then dried over anhydrous magnesium sulfate, and the solvent was distilled off under reduced pressure. To a mixture of the obtained residue, N-methylacetamide (181 mg) and DMF (2 mL), was added 60% sodium hydride (59.6 mg) at 0° C., and the resulting mixture was stirred under nitrogen atmosphere at room temperature for 10 minutes. Water was added to the reaction mixture at room temperature, and the aqueous layer was extracted with ethyl acetate. The extract was washed with water and brine and then dried over anhydrous magnesium sulfate, and the solvent was distilled off under reduced pressure to obtain the title compound as a crude product (179 mg). This compound was used in the next step without being further purified.

$^1$H NMR (300 MHz, DMSO-$d_6$) δ 1.46 (9H, s), 1.92-2.16 (3H, m), 2.69-3.05 (3H, m), 4.36-4.54 (2H, m), 7.04-7.27 (1H, m), 7.37-7.59 (2H, m), 9.33-9.57 (1H, m).

(B) (2E)-N-(3-((Acetyl(methyl)amino)methyl)-4-bromophenyl)-3-(4-(1-methyl-1H-pyrazol-4-yl)pyridin-3-yl)acrylamide A 4 M solution of hydrogen chloride in CPME (3 mL) was added to crude tert-butyl (4-bromo-3-((N-methylacetamido)methyl)phenyl)carbamate (179 mg) at room temperature, and the mixture was stirred at the same temperature for 1 hour. The solvent was distilled off under reduced pressure. A mixture of the obtained residue, HATU (285 mg), (2E)-3-(4-(1-methyl-1H-pyrazol-4-yl)pyridin-3-yl)acrylic acid (115 mg), DIEA (0.262 mL) and DMF (3 mL) was stirred under nitrogen atmosphere at room temperature for 1 hour. Water was added to the reaction mixture, and the precipitate was collected by filtration and washed with water. The obtained solid was purified by silica gel column chromatography (methanol/ethyl acetate) to obtain the title compound (115 mg).

$^1$H NMR (300 MHz, DMSO-$d_6$) δ 1.96-2.18 (3H, m), 2.85-3.06 (3H, m), 3.93 (3H, s), 4.47-4.62 (2H, m), 6.70-

6.87 (1H, m), 7.41 (1H, s), 7.49 (1H, d, J=5.3 Hz), 7.53-7.84 (4H, m), 8.09 (1H, s), 8.53 (1H, d, J=5.1 Hz), 8.77 (1H, s), 10.25-10.64 (1H, m).

Example 233

(2E)-N-(4-Cyclopropyl-3-((methylsulfonyl)methyl) phenyl)-3-(4-(1-methyl-1H-pyrazol-4-yl)pyridin-3-yl)acrylamide A mixture of (2E)-N-(4-bromo-3-((methylsulfonyl)methyl)phenyl)-3-(4-(1-methyl-1H-pyrazol-4-yl)pyridin-3-yl)acrylamide (55.1 mg), cyclopropylboronic acid (19.91 mg), palladium acetate (2.6 mg), tricyclohexylphosphine (9.75 mg), potassium phosphate (73.8 mg), toluene (1.5 mL), DME (0.5 mL) and water (0.5 mL) was stirred overnight under nitrogen atmosphere at 100° C. The solvent in the reaction mixture was distilled off under reduced pressure, and the residue was purified by silica gel column chromatography (methanol/ethyl acetate). The residue was suspended in ethanol, and the suspension was then washed with IPE to obtain the title compound (10.3 mg).

$^1$H NMR (300 MHz, DMSO-$d_6$) δ 0.63 (2H, d, J=5.1 Hz), 0.93 (2H, d, J=8.5 Hz), 2.05-2.21 (1H, m), 3.05 (3H, s), 3.93 (3H, s), 4.69 (2H, s), 6.86 (1H, d, J=15.6 Hz), 7.03 (1H, d, J=8.3 Hz), 7.49 (1H, d, J=4.9 Hz), 7.59-7.79 (4H, m), 8.08 (1H, s), 8.53 (1H, d, J=5.1 Hz), 8.77 (1H, s), 10.34 (1H, s).

Example 244

(2E)-3-(6-Hydroxy-4-(1-methyl-1H-pyrazol-4-yl) pyridin-3-yl)-N-(4-(morpholin-4-ylmethyl)phenyl) acrylamide To a mixture of (2E)-3-(4-(1-methyl-1H-pyrazol-4-yl) pyridin-3-yl)-N-(4-(morpholin-4-ylmethyl)phenyl)acrylamide (100 mg) and ethyl acetate (2 mL), 70% m-chloroperbenzoic acid (122 mg) was added at room temperature, and the resulting mixture was stirred at the same temperature for 10 minutes. The precipitate was collected by filtration and washed with ethyl acetate and IPE. A mixture of the obtained solid and acetic anhydride (2 mL) was heated at reflux overnight, and the solvent was distilled off under reduced pressure. Ethyl acetate and THF were added to the residue, and the insoluble matter was removed by filtration. The solvent in the filtrate was distilled off under reduced pressure, and the residue was purified by silica gel column chromatography (NH, methanol/ethyl acetate). To a mixture of the obtained solid and methanol (0.5 mL), 1 N aqueous sodium hydroxide solution (0.248 mL) was added at room temperature, and the resulting mixture was stirred at the same temperature for 5 minutes. A 1 N hydrochloric acid solution (2.248 mL) was added to the reaction mixture. The solvent was distilled off under reduced pressure, and the residue was purified by silica gel column chromatography (methanol/ethyl acetate) to obtain the title compound (3.7 mg).

$^1$H NMR (300 MHz, CDCl$_3$) δ 2.15-2.30 (3H, m), 3.24-4.06 (8H, m), 4.53-4.67 (2H, m), 6.64 (1H, d, J=15.4 Hz), 7.15-7.25 (2H, m), 7.37 (1H, d, J=4.9 Hz), 7.51-7.72 (2H, m), 7.60 (1H, s), 7.75 (1H, s), 7.93-8.15 (2H, m), 8.55 (1H, brs), 8.80 (1H, brs).

Example 247

(2E)-3-(4-(1-Cyclopropyl-1H-pyrazol-4-yl)pyridin-3-yl)-N-(2-(2,2,2-trifluoroethyl)-1,2,3,4-tetrahydroisoquinolin-7-yl)acrylamide Example 248

(2E)-3-(4-(1-Cyclopropyl-1H-pyrazol-4-yl)pyridin-3-yl)-N-(2-(trifluoroacetyl)-1,2,3,4-tetrahydroisoquinolin-7-yl)acrylamide (A) (2E)-tert-Butyl 7-(3-(4-(1-cyclopropyl-1H-pyrazol-4-yl)pyridin-3-yl)acrylamido)-3,4-dihydroisoquinoline-2(1H)-carboxylate HATU (670 mg) was added to a mixture of (2E)-3-(4-(1-cyclopropyl-1H-pyrazol-4-yl)pyridin-3-yl)acrylic acid (300 mg), tert-butyl 7-amino-3,4-dihydroisoquinoline-2(1H)-carboxylate (292 mg), DIEA (0.616 mL) and DMF (5 mL) at room temperature, and the resulting mixture was stirred overnight under nitrogen atmosphere at the same temperature. The solvent was distilled off under reduced pressure, and the residue was purified by silica gel column chromatography (NH, ethyl acetate/hexane). The obtained solid was washed with IPE to obtain the title compound (436.5 mg).

$^1$H NMR (300 MHz, DMSO-$d_6$) δ 0.96-1.19 (4H, m), 1.43 (9H, s), 2.65-2.81 (2H, m), 3.55 (2H, t, J=5.9 Hz), 3.76-3.91 (1H, m), 4.48 (2H, s), 6.84 (1H, d, J=15.8 Hz), 7.13 (1H, d, J=8.5 Hz), 7.29-7.79 (5H, m), 8.19 (1H, s), 8.53 (1H, d, J=5.1 Hz), 8.77 (1H, s), 10.26 (1H, s).

(B) (2E)-3-(4-(1-Cyclopropyl-1H-pyrazol-4-yl)pyridin-3-yl)-N-(2-(2,2,2-trifluoroethyl)-1,2,3,4-tetrahydroisoquinolin-7-yl)acrylamide (2E)-3-(4-(1-Cyclopropyl-1H-pyrazol-4-yl)pyridin-3-yl)-N-(2-(trifluoroacetyl)-1,2,3,4-tetrahydroisoquinolin-7-yl)acrylamide Trifluoroacetic acid (3 mL) was added to (2E)-tert-butyl 7-(3-(4-(1-cyclopropyl-1H-pyrazol-4-yl)pyridin-3-yl)acrylamido)-3,4-dihydroisoquinoline-2(1H)-carboxylate (86.3 mg) at room temperature, and the mixture was stirred at the same temperature for 10 minutes. The reaction mixture was concentrated under reduced pressure. To a mixture of the residue and acetonitrile (2 mL), triethylamine (0.248 mL) and 2,2,2-trifluoroethyl trifluoromethanesulfonate (0.128 mL) were added at room temperature, and the resulting mixture was stirred under nitrogen atmosphere at 50° C. for 1 hour. Water was added to the reaction mixture, and the aqueous layer was extracted with ethyl acetate. The extract was washed with water and brine and then dried over anhydrous magnesium sulfate, and the solvent was distilled off under reduced pressure. The residue was purified by silica gel column chromatography (ethyl acetate/hexane) to obtain (2E)-3-(4-(1-cyclopropyl-1H-pyrazol-4-yl)pyridin-3-yl)-N-(2-(2,2,2-trifluoroethyl)-1,2,3,4-tetrahydroisoquinolin-7-yl)acrylamide (48.9 mg) and (2E)-3-(4-(1-cyclopropyl-1H-pyrazol-4-yl)pyridin-3-yl)-N-(2-(trifluoroacetyl)-1,2,3,4-tetrahydroisoquinolin-7-yl)acrylamide (1.2 mg).

$^1$H NMR (300 MHz, DMSO-$d_6$) δ 0.94-1.07 (2H, m), 1.07-1.18 (2H, m), 2.73-2.83 (2H, m), 2.87-2.98 (2H, m), 3.28-3.44 (2H, m), 3.73-3.91 (3H, m), 6.83 (1H, d, J=15.6 Hz), 7.08 (1H, d, J=8.3 Hz), 7.34-7.55 (3H, m), 7.72 (2H, t, J=7.7 Hz), 8.18 (1H, s), 8.52 (1H, d, J=5.3 Hz), 8.77 (1H, s), 10.21 (1H, s).

¹H NMR (300 MHz, DMSO-d₆) δ 0.93-1.08 (2H, m), 1.11 (2H, brs), 2.82-2.94 (2H, m), 3.73-3.92 (3H, m), 4.74 (2H, s), 6.85 (1H, d, J=15.3 Hz), 7.18 (1H, d, J=7.5 Hz), 7.45-7.56 (2H, m), 7.59-7.78 (3H, m), 8.19 (1H, s), 8.53 (1H, d, J=5.3 Hz), 8.78 (1H, s), 10.31 (1H, s).

Example 250

(2E)-N-(2-Fluoro-4-(morpholin-4-ylmethyl)phenyl)-3-(4-(2-methoxy-1,3-thiazol-5-yl)pyridin-3-yl)acrylamide HATU (133 mg) was added to a mixture of (2E)-3-(4-(2-methoxythiazol-5-yl)pyridin-3-yl)acrylic acid (52 mg), 2-fluoro-4-(morpholinomethyl)aniline (53 mg), DIEA (0.106 mL) and DMF (2 mL) at room temperature, and the resulting mixture was stirred at the same temperature for 2 hours. Water and saturated aqueous potassium carbonate solution were added to the reaction mixture, followed by extraction with ethyl acetate. The organic layer was washed with brine and then dried over anhydrous magnesium sulfate, and the solvent was distilled off under reduced pressure. The residue was purified by silica gel column chromatography (NH, ethyl acetate/hexane) and then solidified from ethyl acetate/heptane to obtain the title compound (33 mg).
¹H NMR (300 MHz, DMSO-d₆) δ 2.32-2.40 (4H, m), 3.45 (2H, s), 3.54-3.62 (4H, m), 4.11 (3H, s), 7.04-7.17 (2H, m), 7.22 (1H, d, J=11.9 Hz), 7.48 (1H, s), 7.53 (1H, d, J=5.3 Hz), 7.77 (1H, d, J=15.4 Hz), 8.04 (1H, t, J=8.4 Hz), 8.59 (1H, d, J=5.3 Hz), 8.83 (1H, s), 10.06 (1H, s).

Example 251

(2E)-3-(4-(1-Cyclopropyl-1H-pyrazol-4-yl)pyridin-3-yl)-N-(1-methyl-1H-indol-5-yl)acrylamide HATU (213 mg) was added to a mixture of (2E)-3-(4-(1-cyclopropyl-1H-pyrazol-4-yl)pyridin-3-yl)acrylic acid (100 mg), 1-methyl-1H-indol-5-amine (54.5 mg), DIEA (0.195 mL) and DMF (4 mL) at room temperature, and the resulting mixture was stirred under nitrogen atmosphere at the same temperature for 1 hour. The solvent was distilled off under reduced pressure, and the residue was purified by silica gel column chromatography (NH, ethyl acetate/hexane) and recrystallized from ethanol/hexane to obtain the title compound (102 mg).
¹H NMR (300 MHz, DMSO-d₆) δ 0.97-1.18 (4H, m), 3.78 (3H, s), 3.80-3.92 (1H, m), 6.39 (1H, d, J=3.0 Hz), 6.88 (1H, d, J=15.6 Hz), 7.31 (1H, d, J=3.0 Hz), 7.39 (2H, s), 7.51 (1H, d, J=5.1 Hz), 7.66-7.78 (2H, m), 8.05 (1H, s), 8.19 (1H, s), 8.52 (1H, d, J=5.3 Hz), 8.78 (1H, s), 10.15 (1H, s).

Example 260

(2E)-3-(5-Fluoro-4-(1-methyl-1H-pyrazol-4-yl)pyridin-3-yl)-N-(2-fluoro-4-(morpholin-4-ylmethyl)phenyl)acrylamide (A) (2E)-Ethyl 3-(4-chloro-5-fluoropyridin-3-yl)acrylate To a mixture of 60% sodium hydride (0.29 g) and THF (4 mL), a mixture of ethyl 2-(diethoxyphosphoryl)acetate (1.4 mL) and THF (4 mL) was added under ice cooling, and the resulting mixture was stirred at the same temperature for 25 minutes. A mixture of 4-chloro-5-fluoronicotinaldehyde (1.0 g) and DMF (4 mL) was added to the reaction mixture under ice cooling, and the resulting mixture was stirred for 16 hours while being heated up to room temperature. Saturated aqueous ammonium chloride solution was added to the reaction mixture under ice cooling, followed by extraction with ethyl acetate. The extract was washed with brine and then dried over anhydrous magnesium sulfate, and the solvent was distilled off under reduced pressure. The residue was purified by silica gel column chromatography (ethyl acetate/hexane) to obtain the title compound (1.3 g).
MS: [M+H]⁺ 230.2.

(B) (2E)-Ethyl 3-(5-fluoro-4-(1-methyl-1H-pyrazol-4-yl)pyridin-3-yl)acrylate

A mixture of (2E)-ethyl 3-(4-chloro-5-fluoropyridin-3-yl)acrylate (500 mg), 1-methyl-4-(4,4,5,5-tetramethyl-1,3,2-dioxaborolan-2-yl)-1H-pyrazole (498 mg), 2-(dicyclohexylphosphino)biphenyl (95 mg), Pd₂(dba)₃ (100 mg), cesium carbonate (1774 mg), DME (14 mL) and water (2 mL) was stirred under nitrogen atmosphere at 85° C. for 16 hours. Water was added to the reaction mixture, followed by extraction with ethyl acetate. The extract was washed with brine and then dried over anhydrous magnesium sulfate, and the solvent was distilled off under reduced pressure. The residue was purified by silica gel column chromatography (ethyl acetate/hexane) to obtain the title compound (450 mg).
MS: [M+H]⁺ 276.2.

(C) (2E)-3-(5-Fluoro-4-(1-methyl-1H-pyrazol-4-yl)pyridin-3-yl)acrylic acid

To a mixture of (2E)-ethyl 3-(5-fluoro-4-(1-methyl-1H-pyrazol-4-yl)pyridin-3-yl)acrylate (450 mg), ethanol (4 mL) and THF (4 mL), a 2 N aqueous sodium hydroxide solution (3.3 mL) was added under ice cooling, and the resulting mixture was stirred at room temperature for 2 hours. The reaction mixture was concentrated under reduced pressure, and 1 N hydrochloric acid was added to the residue under ice cooling to adjust the pH to 3. The precipitated solid was collected by filtration and washed with water to obtain the title compound (243 mg).
MS: [M+H]⁺ 248.2.

(D) (2E)-3-(5-Fluoro-4-(1-methyl-1H-pyrazol-4-yl)pyridin-3-yl)-N-(2-fluoro-4-(morpholin-4-ylmethyl)phenyl)acrylamide HATU (189 mg) was added to a mixture of (2E)-3-(5-fluoro-4-(1-methyl-1H-pyrazol-4-yl)pyridin-3-yl)acrylic acid (82 mg), 2-fluoro-4-(morpholinomethyl)aniline (77 mg), DIEA (0.12 mL) and DMF (2 mL) at room temperature, and the resulting mixture was stirred at the same temperature for 3 hours. Water was added to the reaction mixture, followed by extraction with ethyl acetate. The organic layer was washed with brine and then dried over anhydrous magnesium sulfate, and the solvent was distilled off under reduced pressure. The residue was purified by silica gel column chromatography (NH, ethyl acetate/hexane) and then solidified from ethyl acetate/heptane to obtain the title compound (75 mg).
¹H NMR (300 MHz, DMSO-d₆) δ 2.30-2.40 (4H, m), 3.45 (2H, s), 3.51-3.62 (4H, m), 3.96 (3H, s), 7.07-7.28 (3H, m), 7.52-7.71 (2H, m), 8.04 (1H, s), 8.11 (1H, s), 8.62 (1H, d, J=1.7 Hz), 8.69 (1H, s), 10.06 (1H, s).

Example 265

(2E)-3-(6-Methoxy-3,4'-bipyridin-3'-yl)-N-(4-(morpholin-4-ylmethyl)phenyl)acrylamide A mixture of (2E)-3-(4-chloropyridin-3-yl)-N-(4-(morpholinomethyl)phenyl)acrylamide (200 mg), 2-methoxy-5-(4,4,5,5-tetramethyl-1,3,2-dioxaborolan-2-yl)pyridine (263 mg), 2-(dicyclohexylphosphino)biphenyl (24.49 mg), $Pd_2(dba)_3$ (25.6 mg), a 2 M aqueous cesium carbonate solution (0.699 mL) and DME (3.5 mL) was stirred under nitrogen atmosphere at 80° C. for 8 hours. The solvent was distilled off under reduced pressure, and the residue was purified by silica gel column chromatography (NH, ethyl acetate/hexane). The obtained solid was washed with IPE to obtain the title compound (115 mg).

$^1$H NMR (300 MHz, DMSO-$d_6$) δ 2.34 (4H, d, J=4.3 Hz), 3.41 (2H, s), 3.51-3.62 (4H, m), 3.94 (3H, s), 6.90 (1H, d, J=15.8 Hz), 7.01 (1H, d, J=8.7 Hz), 7.25 (2H, d, J=8.5 Hz), 7.47 (2H, dd, J=10.4, 5.3 Hz), 7.62 (2H, d, J=8.5 Hz), 7.81 (1H, dd, J=8.7, 2.4 Hz), 8.24 (1H, d, J=2.4 Hz), 8.64 (1H, d, J=5.1 Hz), 8.92 (1H, s), 10.28 (1H, s).

Example 266

(2E)-3-(4-(1-Cyclopropyl-1H-pyrazol-4-yl)pyridin-3-yl)-N-(1-(2,2,2-trifluoroethyl)-1H-indol-5-yl)acrylamide (A) 5-Nitro-1-(2,2,2-trifluoroethyl)-1H-indole To a mixture of 5-nitro-1H-indole (500 mg), 2,2,2-trifluoroethyl trifluoromethanesulfonate (0.798 mL) and DMF (5 mL), 60% sodium hydride (148 mg) was added at 0° C., and the resulting mixture was stirred under nitrogen atmosphere at room temperature for 1 hour. Water was added to the reaction mixture at room temperature, and the precipitate was collected by filtration and washed with water. The obtained solid was dissolved in ethyl acetate, and the solvent was distilled off under reduced pressure to obtain the title compound as a crude product (752 mg). This compound was used in the next step without being further purified.

$^1$H NMR (300 MHz, DMSO-d6) δ 5.36 (2H, q, J=9.2 Hz), 6.87 (1H, d, J=3.4 Hz), 7.67 (1H, d, J=3.2 Hz), 7.85 (1H, d, J=9.0 Hz), 8.11 (1H, dd, J=9.1, 2.4 Hz), 8.61 (1H, d, J=2.3 Hz).

(B) 1-(2,2,2-Trifluoroethyl)-1H-indol-5-amine

To a mixture of 5-nitro-1-(2,2,2-trifluoroethyl)-1H-indole (752 mg) and acetic acid (15 mL), a zinc powder (2.014 g) was added under ice cooling, and the resulting mixture was stirred at room temperature for 20 minutes. The reaction mixture was filtered, and the solvent in the filtrate was distilled off under reduced pressure. An aqueous potassium carbonate solution was added to the residue, and the aqueous layer was extracted with ethyl acetate. The extract was washed with water and brine and then dried over anhydrous magnesium sulfate, and the solvent was distilled off under reduced pressure. The residue was purified by silica gel column chromatography (ethyl acetate/hexane) to obtain the title compound (184 mg).

$^1$H NMR (300 MHz, DMSO-$d_6$) δ 4.33 (2H, brs), 5.02 (2H, q, J=9.4 Hz), 6.24 (1H, dd, J=3.2, 0.8 Hz), 6.56 (1H, dd, J=8.7, 2.1 Hz), 6.68 (1H, d, J=1.9 Hz), 7.17 (1H, d, J=3.2 Hz), 7.24 (1H, d, J=8.5 Hz).

(C) (2E)-3-(4-(1-Cyclopropyl-1H-pyrazol-4-yl)pyridin-3-yl)-N-(1-(2,2,2-trifluoroethyl)-1H-indol-5-yl)acrylamide HATU (112 mg) was added to a mixture of (2E)-3-(4-(1-cyclopropyl-1H-pyrazol-4-yl)pyridin-3-yl)acrylic acid (50 mg), 1-(2,2,2-trifluoroethyl)-1H-indol-5-amine (42 mg), DIEA (0.103 mL) and DMF (1 mL) at room temperature, and the resulting mixture was stirred under nitrogen atmosphere at the same temperature for 2 hours. The solvent was distilled off under reduced pressure, and the residue was purified by silica gel column chromatography (NH, ethyl acetate/hexane) and recrystallized from ethanol/hexane to obtain the title compound (46.9 mg).

$^1$H NMR (300 MHz, DMSO-$d_6$) δ 0.94-1.09 (2H, m), 1.09-1.17 (2H, m), 3.73-3.95 (1H, m), 5.01-5.31 (2H, m), 6.54 (1H, d, J=2.8 Hz), 6.88 (1H, d, J=15.6 Hz), 7.34-7.46 (2H, m), 7.51 (1H, d, J=5.3 Hz), 7.57 (1H, d, J=8.7 Hz), 7.74 (2H, t, J=7.8 Hz), 8.08 (1H, s), 8.19 (1H, s), 8.52 (1H, d, J=5.3 Hz), 8.79 (1H, s), 10.21 (1H, s).

Example 269

(2E)-N-(4-(Morpholin-4-ylmethyl)phenyl)-3-(6-oxo-1,6-dihydro-3,4'-bipyridin-3'-yl)acrylamide To a mixture of (2E)-3-(6-methoxy-3,4'-bipyridin-3'-yl)-N-(4-(morpholin-4-ylmethyl)phenyl)acrylamide (100 mg) and DMF (0.3 mL), pyridinium chloride (268 mg) was added at room temperature, and the resulting mixture was stirred under nitrogen atmosphere at 130° C. for 2 hours. The reaction mixture was diluted with methanol and filtered. The solvent in the filtrate was distilled off under reduced pressure, and the residue was purified by silica gel column chromatography (methanol/ethyl acetate) to obtain the title compound (32.5 mg).

$^1$H NMR (300 MHz, DMSO-$d_6$) δ 2.95-3.30 (4H, m), 3.67-3.97 (4H, m), 4.29 (2H, d, J=4.1 Hz), 6.49 (1H, d, J=10.2 Hz), 6.95 (1H, d, J=15.6 Hz), 7.46-7.64 (6H, m), 7.79 (2H, d, J=8.7 Hz), 8.66 (1H, d, J=5.3 Hz), 8.90 (1H, s), 10.63 (2H, s).

Example 273

(2E)-3-(4-(1-Cyclopropyl-1H-pyrazol-4-yl)-5-fluoropyridin-3-yl)-N-(2-fluoro-4-(morpholin-4-ylmethyl)phenyl)acrylamide HATU (943 mg) was added to a mixture of (2E)-3-(4-(1-cyclopropyl-1H-pyrazol-4-yl)-5-fluoropyridin-3-yl)acrylic acid (450 mg), 2-fluoro-4-(morpholinomethyl)aniline (380 mg), DIEA (0.90 mL) and DMF (7 mL) at room temperature, and the resulting mixture was stirred at the same temperature for 16 hours. Water was added to the reaction mixture under ice cooling, followed by extraction with a mixed ethyl acetate/THF solution. The organic layer was washed with brine and then dried over anhydrous magnesium sulfate, and the solvent was distilled off under reduced pressure. The residue was purified by silica gel column chromatography (NH, ethyl acetate/hexane) and then recrystallized from ethyl acetate/IPE to obtain the title compound (362 mg).

$^1$H NMR (300 MHz, DMSO-d6) δ 0.96-1.05 (2H, m), 1.09-1.17 (2H, m), 2.30-2.39 (4H, m), 3.45 (2H, s), 3.52-3.62 (4H, m), 3.89 (1H, tt, J=7.4, 3.8 Hz), 7.08-7.28 (3H, m), 7.55-7.72 (2H, m), 8.03 (1H, t, J=8.3 Hz), 8.18 (1H, d, J=1.1 Hz), 8.63 (1H, d, J=1.7 Hz), 8.70 (1H, s), 10.06 (1H, s).

Example 275

(2E)-N-(4-(1H-Imidazol-1-ylmethyl)phenyl)-3-(4-(1-methyl-1H-pyrazol-4-yl)pyridin-3-yl)acrylamide HATU (118 mg) was added to a mixture of (2E)-3-(4-(1-methyl-1H-pyrazol-4-yl)pyridin-3-yl)acrylic acid (50 mg), 4-((1H-imidazol-1-yl)methyl)aniline (36 mg), DIEA (0.109 mL) and DMF (1 mL) at room temperature, and the resulting mixture was stirred overnight under nitrogen atmosphere at the same temperature. The solvent was distilled off under reduced pressure, and the residue was purified by silica gel column chromatography (NH, ethyl acetate/hexane). The obtained solid was washed with IPE to obtain the title compound (38.9 mg).
$^1$H NMR (300 MHz, DMSO-$d_6$) δ 3.93 (3H, s), 5.29 (2H, s), 6.27 (1H, t, J=2.0 Hz), 6.84 (1H, d, J=15.6 Hz), 7.21 (2H, d, J=8.7 Hz), 7.43-7.52 (2H, m), 7.62-7.82 (5H, m), 8.08 (1H, s), 8.52 (1H, d, J=5.1 Hz), 8.77 (1H, s), 10.32 (1H, s).

Example 283

(2E)-3-(4-(1-(Cyclopropylmethyl)-1H-benzimidazol-6-yl)pyridin-3-yl)-N-(4-(morpholin-4-ylmethyl)phenyl)acrylamide (A) 2-(3-Fluoro-4-nitrophenyl)-4,4,5,5-tetramethyl-1,3,2-dioxaborolane A mixture of 4-bromo-2-fluoro-1-nitrobenzene (5011 mg), bis(pinacolato)diboron (8676 mg), potassium acetate (6706 mg), PdCl$_2$(dppf) CH$_2$Cl$_2$ adduct (930 mg) and DME (50 mL) was stirred under nitrogen atmosphere at 100° C. for 14 hours. The reaction mixture was diluted with ethyl acetate (50 mL), and the insoluble matter was removed by filtration. The filtrate was concentrated under reduced pressure, and the residue was purified by silica gel column chromatography (ethyl acetate/hexane) to obtain the title compound (4224 mg).
$^1$H NMR (300 MHz, CDCl$_3$) δ 1.36 (12H, s), 7.64-7.73 (2H, m), 7.97-8.04 (1H, m).

(B) (2E)-3-(4-(3-Fluoro-4-nitrophenyl)pyridin-3-yl)-N-(4-(morpholinomethyl)phenyl)acrylamide A mixture of (2E)-3-(4-chloropyridin-3-yl)-N-(4-(morpholinomethyl)phenyl)acrylamide (609 mg), 2-(3-fluoro-4-nitrophenyl)-4,4,5,5-tetramethyl-1,3,2-dioxaborolane (685 mg), 2-(dicyclohexylphosphino)biphenyl (74.6 mg), Pd$_2$(dba)$_3$ (104 mg), 2 M aqueous cesium carbonate solution (2.55 mL) and DME (15 mL) was stirred under nitrogen atmosphere at 80° C. for 14 hours. The reaction mixture was diluted with ethyl acetate (30 mL), then anhydrous magnesium sulfate was added thereto, and the insoluble matter was removed by filtration. The filtrate was concentrated under reduced pressure, and the residue was purified by silica gel column chromatography (NH, ethyl acetate/hexane) to obtain the title compound (432 mg).
MS: [M+H]$^+$ 463.1.

(C) (2E)-3-(4-(1-(Cyclopropylmethyl)-1H-benzimidazol-6-yl)pyridin-3-yl)-N-(4-(morpholin-4-ylmethyl)phenyl)acrylamide To a mixture of (2E)-3-(4-(3-fluoro-4-nitrophenyl)pyridin-3-yl)-N-(4-(morpholinomethyl)phenyl)acrylamide (48.7 mg) and ethanol (2 mL), cyclopropylmethanamine (0.091 mL) was added at room temperature, and the resulting mixture was heated up to 70° C. and stirred at the same temperature for 15 hours. The reaction mixture was concentrated under reduced pressure, formic acid (2 mL) and reduced iron (77 mg) were added to the residue at room temperature, and the mixture was heated up to 100° C. and stirred at the same temperature for 4 hours. The insoluble matter was removed by filtration, and the filtrate was concentrated under reduced pressure. The residue was diluted with ethyl acetate (20 mL) and saturated aqueous sodium bicarbonate solution (20 mL), and the aqueous layer was extracted with ethyl acetate. The extract was washed with brine and then dried over anhydrous sodium sulfate, and the solvent was distilled off under reduced pressure. The residue was purified by silica gel column chromatography (NH, ethyl acetate/hexane), and the obtained solid was washed with ethyl acetate/hexane (1/1) and then collected by filtration to obtain the title compound (19 mg).
$^1$H NMR (300 MHz, DMSO-$d_6$) δ 0.33-0.53 (4H, m), 1.28-1.41 (1H, m), 2.27-2.38 (4H, m), 3.39 (2H, s), 3.51-3.61 (4H, m), 4.14 (2H, d, J=7.2 Hz), 6.92 (1H, d, J=15.7 Hz), 7.19-7.30 (3H, m), 7.49-7.63 (4H, m), 7.73 (1H, d, J=1.1 Hz), 7.80 (1H, d, J=8.4 Hz), 8.39 (1H, s), 8.64 (1H, d, J=5.0 Hz), 8.93 (1H, s), 10.27 (1H, s).

Example 288

(2E)-3-(4-(1-((1-Fluorocyclopropyl)methyl)-1H-pyrazol-4-yl)pyridin-3-yl)-N-(4-(morpholin-4-ylmethyl)phenyl)acrylamide (A) 1-((1-Fluorocyclopropyl)methyl)-4-(4,4,5,5-tetramethyl-1,3,2-dioxaborolan-2-yl)-1H-pyrazole To a mixture of 4-(4,4,5,5-tetramethyl-1,3,2-dioxaborolan-2-yl)-1H-pyrazole (400 mg), 65% (1-fluorocyclopropyl)methanol (170.5 mg), PPh$_3$ (811 mg) and THF (4 mL), a 2.2 M solution of DEAD in toluene (1.406 mL) was added at room temperature, and the resulting mixture was stirred overnight under nitrogen atmosphere at the same temperature. The solvent was distilled off under reduced pressure, and the residue was purified by silica gel column chromatography (ethyl acetate/hexane) to obtain the title compound (222.9 mg).
$^1$H NMR (300 MHz, CDCl$_3$) δ 0.78-0.91 (2H, m), 1.07-1.22 (2H, m), 1.32 (12H, s), 4.47 (2H, d, J=20.8 Hz), 7.81 (1H, s), 7.86 (1H, s).

(B) (2E)-3-(4-(1-((1-Fluorocyclopropyl)methyl)-1H-pyrazol-4-yl)pyridin-3-yl)-N-(4-(morpholin-4-ylmethyl)phenyl)acrylamide A mixture of (2E)-3-(4-chloropyridin-3-yl)-N-(4-(morpholinomethyl)phenyl)acrylamide (100 mg), 1-((1-fluorocyclopropyl)methyl)-4-(4,4,5,5-tetramethyl-1,3,2-dioxaborolan-2-yl)-1H-pyrazole (89 mg), 2-(dicyclohexylphosphino)biphenyl (12.24 mg), Pd$_2$(dba)$_3$ (17.06 mg), 2 M aqueous cesium carbonate solution (0.349 mL) and DME (2 mL) was stirred under nitrogen atmosphere at 80° C. for 8 hours. The solvent was distilled off under reduced pressure, and the residue was purified by silica gel column chromatography (NH, ethyl acetate/hexane). The obtained solid was washed with IPE to obtain the title compound (48.3 mg).
$^1$H NMR (300 MHz, DMSO-$d_6$) δ 0.92-1.21 (4H, m), 2.29-2.38 (4H, m), 3.42 (2H, s), 3.56 (4H, d, J=4.3 Hz), 4.63

(2H, d, J=22.6 Hz), 6.86 (1H, d, J=15.8 Hz), 7.27 (2H, d, J=8.1 Hz), 7.54 (1H, d, J=5.1 Hz), 7.66 (2H, d, J=8.1 Hz), 7.76 (1H, d, J=15.4 Hz), 7.83 (1H, s), 8.18 (1H, s), 8.54 (1H, d, J=5.1 Hz), 8.79 (1H, s), 10.29 (1H, s).

Example 289

(2E)-3-(4-(1-Methyl-1H-pyrazol-4-yl)pyridin-3-yl)-N-(2-(2,2,2-trifluoroethyl)-2,3-dihydro-1H-isoindol-5-yl)acrylamide HATU (644.1 mg) was added to a mixture of (2E)-3-(4-(1-methyl-1H-pyrazol-4-yl)pyridin-3-yl)acrylic acid (252.9 mg), 2-(2,2,2-trifluoroethyl)isoindolin-5-amine (236.1 mg), DIEA (0.867 mL) and DMF (3 mL) at room temperature, and the resulting mixture was stirred under nitrogen atmosphere at the same temperature for 3 hours. Water was added to the reaction mixture, and the aqueous layer was extracted with a mixed ethyl acetate/THF solution. The extract was washed with water and brine and then dried over anhydrous magnesium sulfate, and the solvent was distilled off under reduced pressure. The residue was purified by silica gel column chromatography (NH, ethyl acetate/hexane) to obtain the title compound as a crude product (364.6 mg). The obtained crude product (whole amount) was dissolved in ethyl acetate (56 mL) at 85° C. To the solution, hexane (28 mL) was added dropwise at the same temperature. The mixture was stirred at the same temperature for 30 minutes and at room temperature for 1 hour, and the precipitate was then collected by filtration and washed with ethyl acetate/hexane (2/1) to obtain the title compound (268.7 mg).
$^1$H NMR (300 MHz, DMSO-$d_6$) δ 3.54 (2H, q, J=10.2 Hz), 3.94 (3H, s), 4.06 (2H, s), 4.09 (2H, s), 6.85 (1H, d, J=15.6 Hz), 7.22 (1H, d, J=8.1 Hz), 7.50 (2H, d, J=5.3 Hz), 7.68-7.82 (3H, m), 8.09 (1H, s), 8.53 (1H, d, J=5.3 Hz), 8.77 (1H, s), 10.31 (1H, s).

Example 291

(2E)-3-(4-(1-Cyclopropyl-1H-pyrazol-4-yl)pyridin-3-yl)-N-(4-(1,1-difluoro-2-methoxyethyl)phenyl)acrylamide (A) 2,2-Difluoro-2-(4-nitrophenyl)ethanol NaBH$_4$ (1.5 g) was added to a mixture of ethyl 2,2-difluoro-2-(4-nitrophenyl)acetate (5 g) and ethanol (50 mL) at room temperature. The reaction mixture was stirred at the same temperature for 20 minutes. Then, 1 N hydrochloric acid was added to the reaction mixture, followed by extraction with ethyl acetate. The organic layer was washed with 1 N hydrochloric acid, saturated aqueous sodium bicarbonate solution and brine and then dried over anhydrous magnesium sulfate, and the solvent was distilled off under reduced pressure. The residue was washed with hexane to obtain the title compound (3.9 g).
$^1$H NMR (300 MHz, DMSO-$d_6$) δ 3.91 (2H, td, J=13.7, 6.3 Hz), 5.74 (1H, t, J=6.3 Hz), 7.82 (2H, d, J=9.0 Hz), 8.34 (2H, d, J=9.1 Hz).

(B) 1-(1,1-Difluoro-2-methoxyethyl)-4-nitrobenzene

To a mixture of 2,2-difluoro-2-(4-nitrophenyl)ethanol (1.00 g) and THF (20 mL), 60% sodium hydride (0.45 g) was added at 50° C., and the resulting mixture was stirred at the same temperature for 15 minutes. Iodomethane (0.74 mL) was added to the reaction mixture, and the mixture was stirred at room temperature for 2 days. Saturated aqueous ammonium chloride solution was added to the reaction mixture, followed by extraction with ethyl acetate. The extract was washed with brine and then dried over anhydrous magnesium sulfate, and the solvent was distilled off under reduced pressure. The residue was purified by silica gel column chromatography (ethyl acetate/hexane) to obtain the title compound (943 mg).
$^1$H NMR (300 MHz, CDCl$_3$) δ 3.42 (3H, s), 3.84 (2H, t, J=12.3 Hz), 7.72 (2H, d, J=8.9 Hz), 8.30 (2H, d, J=8.9 Hz).

(C) 1-(4-Aminophenyl)-2-methoxyethanone

To a reaction mixture of 1-(1,1-difluoro-2-methoxyethyl)-4-nitrobenzene (943 mg), calcium chloride (482 mg), ethanol (25 mL) and water (8 mL), reduced iron (970 mg) was added at 80° C., and the mixture was stirred at the same temperature for 16 hours. The reaction mixture was filtered through Celite, and water was added to the filtrate, followed by extraction with ethyl acetate. The extract was washed with brine and then dried over anhydrous magnesium sulfate, and the solvent was distilled off under reduced pressure. The residue was purified by silica gel column chromatography (ethyl acetate/hexane) to obtain the title compound (440 mg).
MS: [M+H]$^+$ 166.1.

(D) 4-(1,1-Difluoro-2-methoxyethyl)aniline

DAST (0.7 mL) was added to a mixture of 1-(4-aminophenyl)-2-methoxyethanone (362 mg) and toluene (10 mL) at room temperature, and the resulting mixture was stirred under nitrogen atmosphere at the same temperature for 16 hours. Saturated aqueous sodium bicarbonate solution was added to the reaction mixture under ice cooling, followed by extraction with ethyl acetate. The organic layer was washed with brine and then dried over anhydrous magnesium sulfate, and the solvent was distilled off under reduced pressure. The residue was purified by silica gel column chromatography (ethyl acetate/hexane) to obtain the title compound as a crude product (78 mg).
$^1$H NMR (300 MHz, CDCl$_3$) δ 3.51 (3H, s), 3.78-3.82 (2H, m), 4.67 (2H, s), 7.34 (2H, d, J=7.5 Hz), 7.89 (2H, d, J=7.9 Hz).

(E) (2E)-3-(4-(1-Cyclopropyl-1H-pyrazol-4-yl)pyridin-3-yl)-N-(4-(1,1-difluoro-2-methoxyethyl)phenyl)acrylamide HATU (158 mg) was added to a mixture of (2E)-3-(4-(1-cyclopropyl-1H-pyrazol-4-yl)pyridin-3-yl)acrylic acid (64 mg), crude 4-(1,1-difluoro-2-methoxyethyl)aniline (78 mg), DIEA (0.07 mL) and DMF (2 mL) at room temperature, and the resulting mixture was stirred at the same temperature for 16 hours. Water was added to the reaction mixture, followed by extraction with ethyl acetate. The organic layer was washed with brine and then dried over anhydrous magnesium sulfate, and the solvent was distilled off under reduced pressure. The residue was purified by silica gel column chromatography (NH, ethyl acetate/hexane) and then solidified from ethyl acetate/hexane to obtain the title compound (26 mg).
$^1$H NMR (300 MHz, CDCl$_3$) δ 1.09 (2H, dt, J=7.4, 1.8 Hz), 1.18-1.24 (2H, m), 3.45 (3H, s), 3.69 (1H, dt, J=7.3, 3.5 Hz), 3.82 (2H, t, J=12.9 Hz), 6.64 (1H, d, J=15.4 Hz), 7.37

(1H, d, J=5.2 Hz), 7.53 (2H, d, J=8.8 Hz), 7.66-7.79 (4H, m), 7.86 (1H, s), 8.00 (1H, d, J=15.6 Hz), 8.55 (1H, d, J=5.2 Hz), 8.83 (1H, s).

Example 292

(2E)-3-(4-(1-Cyclopropyl-1H-pyrazol-4-yl)pyridin-3-yl)-N-(4-((difluoromethoxy)methyl)phenyl)acrylamide (A) 1-Bromo-4-((difluoromethoxy)methyl)benzene 2,2-Difluoro-2-(fluorosulfonyl)acetic acid (476 mg) was added to a mixture of (4-bromophenyl)methanol (1.00 g), sodium sulfate (76 mg) and acetonitrile (20 mL) at 45° C., and the resulting mixture was stirred at the same temperature for 3 hours and subsequently stirred at room temperature for 2 days. Water was added to the reaction mixture, followed by extraction with ethyl acetate. The organic layer was washed with brine and then dried over anhydrous magnesium sulfate, and the solvent was distilled off under reduced pressure. The residue was purified by silica gel column chromatography (ethyl acetate/hexane) to obtain the title compound as a crude product (195 mg).
$^1$H NMR (300 MHz, CDCl$_3$) δ 4.85 (2H, s), 6.01-6.57 (1H, m), 7.22-7.25 (2H, m), 7.50-7.53 (2H, m).

(B) (2E)-3-(4-(1-Cyclopropyl-1H-pyrazol-4-yl)pyridin-3-yl)-N-(4-((difluoromethoxy)methyl)phenyl)acrylamide A mixture of (2E)-3-(4-(1-cyclopropyl-1H-pyrazol-4-yl)pyridin-3-yl)acrylamide (211 mg), 1-bromo-4-((difluoromethoxy)methyl)benzene (195 mg), Xantphos (116 mg), Pd$_2$(dba)$_3$ (106 mg), sodium tert-butoxide (106 mg) and toluene (2 mL) was stirred at 140° C. for 1 hour under microwave irradiation. The reaction mixture was filtered through Celite, and water was added to the filtrate, followed by extraction with ethyl acetate. The organic layer was washed with brine and then dried over anhydrous magnesium sulfate, and the solvent was distilled off under reduced pressure. The residue was purified by silica gel column chromatography (NH, ethyl acetate/hexane) and then separated by HPLC (C18, mobile phase: water/acetonitrile (containing 0.1% TFA)), and saturated aqueous potassium carbonate solution were added to the collected fractions, followed by extraction with ethyl acetate. The extract was dried over anhydrous magnesium sulfate and then concentrated under reduced pressure to obtain the title compound (6 mg).
$^1$H NMR (300 MHz, CDCl$_3$) δ 1.11-1.19 (2H, m), 1.26-1.31 (2H, m), 3.69-3.80 (1H, m), 4.87 (2H, s), 5.97-6.60 (1H, m), 6.93-7.07 (1H, m), 7.31-7.39 (2H, m), 7.64-7.80 (3H, m), 7.87-8.06 (3H, m), 8.42-8.54 (1H, m), 8.54-8.63 (1H, m), 9.17-9.33 (1H, m).

Example 302

(2E)-N-(2-(Cyclopropylmethyl)-1,2,3,4-tetrahydroisoquinolin-7-yl)-3-(4-(1-cyclopropyl-1H-pyrazol-4-yl)pyridin-3-yl)acrylamide (A) (2E)-3-(4-(1-Cyclopropyl-1H-pyrazol-4-yl)pyridin-3-yl)-N-(1,2,3,4-tetrahydroisoquinolin-7-yl)acrylamide trihydrochloride To a mixture of (2E)-tert-butyl 7-(3-(4-(1-cyclopropyl-1H-pyrazol-4-yl)pyridin-3-yl)acrylamido)-3,4-dihydroisoquinoline-2(1H)-carboxylate (350 mg) and methanol (3.5 mL), a 2 N solution of hydrogen chloride in methanol (5 mL) was added at room temperature under nitrogen atmosphere, and the resulting mixture was stirred overnight. The solvent was distilled off under reduced pressure, ethyl acetate was added to the residue, and the precipitate was collected by filtration and washed with ethyl acetate to obtain the title compound (360.4 mg).
$^1$H NMR (300 MHz, DMSO-d$_6$) δ 0.97-1.17 (4H, m), 2.90-3.02 (2H, m), 3.29-3.44 (2H, m), 3.55-3.64 (1H, m), 3.69-4.10 (2H, m), 4.22-4.34 (2H, m), 6.94 (1H, d, J=15.7 Hz), 7.21 (1H, d, J=8.1 Hz), 7.53 (1H, d, J=8.7 Hz), 7.67-7.92 (4H, m), 8.39 (1H, s), 8.69 (1H, d, J=5.7 Hz), 8.88 (1H, s), 9.21 (2H, brs), 10.55 (1H, s).

(B) (2E)-N-(2-(Cyclopropylmethyl)-1,2,3,4-tetrahydroisoquinolin-7-yl)-3-(4-(1-cyclopropyl-1H-pyrazol-4-yl)pyridin-3-yl)acrylamide To a mixture of (2E)-3-(4-(1-cyclopropyl-1H-pyrazol-4-yl)pyridin-3-yl)-N-(1,2,3,4-tetrahydroisoquinolin-7-yl)acrylamide trihydrochloride (60 mg), cyclopropanecarbaldehyde (0.036 mL) and DMA (1 mL), NaBH(OAc)$_3$ (128 mg) was added at room temperature, and the resulting mixture was stirred at the same temperature for 20 minutes. The solvent was distilled off under reduced pressure, and the residue was purified by silica gel column chromatography (NH, methanol/ethyl acetate) to obtain the title compound (26.8 mg).
$^1$H NMR (300 MHz, DMSO-d$_6$) δ 0.09-0.21 (2H, m), 0.45-0.57 (2H, m), 0.87-0.98 (1H, m), 0.98-1.22 (4H, m), 2.35 (2H, d, J=6.4 Hz), 2.65-2.83 (4H, m), 3.60 (2H, s), 3.77-3.92 (1H, m), 6.83 (1H, d, J=15.6 Hz), 7.06 (1H, d, J=8.7 Hz), 7.38 (1H, d, J=9.2 Hz), 7.51 (2H, d, J=4.5 Hz), 7.66-7.77 (2H, m), 8.19 (1H, s), 8.52 (1H, d, J=5.1 Hz), 8.77 (1H, s), 10.19 (1H, s).

Example 306

(2E)-3-(4-(1-Cyclopropyl-1H-pyrazol-4-yl)pyridin-3-yl)-N-(2-fluoro-4-(1-methyl-1H-pyrazol-5-yl)phenyl)acrylamide (A) (2E)-3-(4-(1-Cyclopropyl-1H-pyrazol-4-yl)pyridin-3-yl)-N-(2-fluoro-4-iodophenyl)acrylamide HATU (1.41 g) was added to a mixture of (2E)-3-(4-(1-cyclopropyl-1H-pyrazol-4-yl)pyridin-3-yl)acrylic acid (600 mg), 2-fluoro-4-iodoaniline (650 mg), DIEA (1.75 mL) and DMF (10 mL) at room temperature, and the resulting mixture was stirred at the same temperature for 16 hours. Water was added to the reaction mixture, and the precipitated solid was collected by filtration to obtain the title compound as a crude product (1.11 g).
MS: [M+H]$^+$ 475.1.

(B) (2E)-3-(4-(1-Cyclopropyl-1H-pyrazol-4-yl)pyridin-3-yl)-N-(2-fluoro-4-(1-methyl-1H-pyrazol-5-yl)phenyl)acrylamide A mixture of crude (2E)-3-(4-(1-cyclopropyl-1H-pyrazol-4-yl)pyridin-3-yl)-N-(2-fluoro-4-iodophenyl)acrylamide (150 mg), 1-methyl-5-(4,4,5,5-tetramethyl-1,3,2-dioxaborolan-2-yl)-1H-pyrazole (82 mg), PdCl$_2$(dppf) CH$_2$Cl$_2$ adduct (40 mg), potassium carbonate (100 mg), DME (4 mL) and water (0.8 mL) was stirred at 130° C. for 45 minutes under microwave irradiation. The reaction mixture was filtered through Celite, and water was added to the filtrate, followed by extraction with ethyl acetate. The organic layer was washed with brine and then dried over anhydrous magnesium sulfate, and the solvent was distilled off under reduced pressure. The residue was purified by silica gel column chromatography (ethyl acetate/hexane) and then solidified from ethyl acetate to obtain the title compound (50 mg).

$^1$H NMR (300 MHz, DMSO-$d_6$) δ 0.98-1.07 (2H, m), 1.08-1.17 (2H, m), 3.77-3.94 (4H, m), 6.47 (1H, d, J=1.9 Hz), 7.13 (1H, s), 7.39 (1H, dd, J=8.4, 1.8 Hz), 7.45-7.59 (3H, m), 7.69-7.86 (2H, m), 8.20 (1H, s), 8.30 (1H, t, J=8.5 Hz), 8.54 (1H, d, J=5.2 Hz), 8.80 (1H, s), 10.22 (1H, s).

Example 309

(2E)-3-(4-(1-Cyclopropyl-1H-pyrazol-4-yl)pyridin-3-yl)-N-(4-((3,3-difluoroazetidin-1-yl)methyl)phenyl)acrylamide (A) 3,3-Difluoro-1-(4-nitrobenzyl)azetidine To a mixture of 1-(bromomethyl)-4-nitrobenzene (16.7 g), 3,3-difluoroazetidine hydrochloride (10.0 g) and acetonitrile (100 mL), DIEA (48 mL) was added at room temperature, and the resulting mixture was stirred at the same temperature for 2 days. The reaction mixture was concentrated under reduced pressure, and water was added to the residue, followed by extraction with ethyl acetate. The extract was washed with brine and then dried over anhydrous magnesium sulfate, and the solvent was distilled off under reduced pressure. The residue was purified by silica gel column chromatography (ethyl acetate/hexane) to obtain the title compound (16.65 g).

MS: [M+H]$^+$ 229.1.

(A') 3,3-Difluoro-1-(4-nitrobenzyl)azetidine

To a mixture of 1-(bromomethyl)-4-nitrobenzene (41.7 g), 3,3-difluoroazetidine hydrochloride (25 g) and acetonitrile (250 mL), DIEA (118 mL) was added at room temperature, and the resulting mixture was stirred at the same temperature for 2 days. The reaction mixture was concentrated under reduced pressure, and water was added to the residue, followed by extraction with ethyl acetate. The extract was washed with brine and then dried over anhydrous magnesium sulfate, and the solvent was distilled off under reduced pressure to obtain the title compound (44 g).

MS: [M+H]$^+$ 229.1.

(B) 4-((3,3-Difluoroazetidin-1-yl)methyl)aniline

To a mixture of 3,3-difluoro-1-(4-nitrobenzyl)azetidine (15.1 g), activated carbon (1.96 g), iron trichloride hexahydrate (4.47 g), THF (100 mL) and methanol (100 mL), hydrazine hydrate (25.0 mL) was added at room temperature, and the resulting mixture was stirred at 75° C. for 7 hours. The reaction mixture was filtered through Celite, and the filtrate was concentrated under reduced pressure. Water and brine were added to the residue, followed by extraction with a mixed ethyl acetate/THF solution. The extract was washed with brine and then dried over anhydrous magnesium sulfate, and the solvent was distilled off under reduced pressure to obtain the title compound (13.7 g).

$^1$H NMR (300 MHz, CDCl$_3$) δ 3.48-3.70 (8H, m), 6.64 (2H, d, J=8.3 Hz), 7.04-7.11 (2H, m).

(B'-1) 4-((3,3-Difluoroazetidin-1-yl)methyl)aniline

To a mixture of 3,3-difluoro-1-(4-nitrobenzyl)azetidine (44 g), activated carbon (4.4 g), iron trichloride hexahydrate (14 g), THF (250 mL) and methanol (250 mL), hydrazine hydrate (70 mL) was gradually added at room temperature, and the reaction mixture was stirred at 75° C. for 4 hours. The reaction mixture was filtered through Celite, and the filtrate was concentrated under reduced pressure. Water and brine were added to the residue, followed by extraction with a mixed ethyl acetate/THF solution. The extract was washed with brine and then dried over anhydrous magnesium sulfate, and the solvent was distilled off under reduced pressure to obtain the title compound (36.9 g).

(B'-2) 4-((3,3-Difluoroazetidin-1-yl)methyl)aniline dihydrochloride

To a solution of 4-((3,3-difluoroazetidin-1-yl)methyl)aniline (39 g) in ethyl acetate (200 mL), a 4 N solution of hydrogen chloride in ethyl acetate (197 mL) was added at 0° C., and the mixture was stirred at the same temperature for 1 hour. The solvent was distilled off under reduced pressure, toluene was added to the residue at room temperature, and the solvent was distilled off under reduced pressure. Methanol (250 mL) and IPE (200 mL) were added to the residue, and the precipitate was collected by filtration and washed with IPE to obtain the title compound (51.5 g).

$^1$H NMR (300 MHz, DMSO-$d_6$) δ 4.43 (2H, s), 4.63 (4H, s), 7.17 (2H, d, J=8.2 Hz), 7.56 (2H, d, J=8.4 Hz).

(C) (2E)-3-(4-(1-Cyclopropyl-1H-pyrazol-4-yl)pyridin-3-yl)-N-(4-((3,3-difluoroazetidin-1-yl)methyl)phenyl)acrylamide DIEA (2.0 mL) was added to a mixture of (2E)-3-(4-(1-cyclopropyl-1H-pyrazol-4-yl)pyridin-3-yl)acrylic acid (731 mg), 4-((3,3-difluoroazetidin-1-yl)methyl)aniline (604 mg), HATU (1.75 g) and DMF (5 mL) at room temperature, and the resulting mixture was stirred at the same temperature for 15 hours. Water was added to the reaction mixture, followed by extraction with ethyl acetate. The organic layer was washed with brine and then dried over anhydrous magnesium sulfate, and the solvent was distilled off under reduced pressure. The residue was purified by silica gel column chromatography (methanol/ethyl acetate) and silica gel column chromatography (NH, ethyl acetate/hexane) and then recrystallized from ethyl acetate/ethanol/heptane to obtain the title compound (606 mg).

$^1$H NMR (300 MHz, DMSO-$d_6$) δ 0.96-1.08 (2H, m), 1.08-1.18 (2H, m), 3.57 (4H, t, J=12.5 Hz), 3.67 (2H, s), 3.77-3.92 (1H, m), 6.85 (1H, d, J=15.7 Hz), 7.27 (2H, d, J=8.5 Hz), 7.51 (1H, d, J=5.2 Hz), 7.58-7.80 (4H, m), 8.16 (1H, s), 8.53 (1H, d, J=5.2 Hz), 8.76 (1H, s), 10.29 (1H, s).

(C') (2E)-3-(4-(1-Cyclopropyl-1H-pyrazol-4-yl)pyridin-3-yl)-N-(4-((3,3-difluoroazetidin-1-yl)methyl)phenyl)acrylamide DIEA (317 mL) was gradually added to a mixture of (2E)-3-(4-(1-cyclopropyl-1H-pyrazol-4-yl)pyridin-3-yl)acrylic acid (151.1 g), 4-((3,3-difluoroazetidin-1-yl)methyl)aniline dihydrochloride (177 g), EDCI (136 g), 1-hydroxybenzotriazole monohydrate and DMF (1500 mL) at 0° C., and the resulting mixture was stirred overnight at room temperature. Ethyl acetate (1500 mL), saturated aqueous sodium bicarbonate solution (1130 mL) and water (1900 mL) were added to the reaction mixture. The organic layer was separated, and the aqueous layer was then extracted with ethyl acetate (1500 mL and subsequently 800 mL). The combined organic layers were washed with a 28% aqueous ammonia solution (380 mL) and brine (1130 mL). Then, the organic layer was purified by silica gel column chromatography (NH, 10% THF/ethyl acetate), and fractions containing the target compound were concentrated under reduced pressure. Toluene (2000 mL) was added to the residue, and the solvent was distilled off under reduced pressure. MTBE (2270 mL) was added to the residue, and the mixture was stirred overnight at room temperature. The precipitate was collected by filtration, washed with MTBE (810 mL), and then dried under reduced pressure at room temperature to obtain the title compound (227 g).

$^1$H NMR (300 MHz, DMSO-$d_6$) δ 0.98-1.07 (2H, m), 1.07-1.16 (2H, m), 3.57 (4H, t, J=12.5 Hz), 3.67 (2H, s), 3.80-3.90 (1H, m), 6.85 (1H, d, J=15.9 Hz), 7.27 (2H, d, J=5.2 Hz), 7.51 (1H, d, J=5.3 Hz), 7.63-7.76 (4H, m), 8.19 (1H, s), 8.53 (1H, d, J=4.9 Hz), 8.78 (1H, s), 10.30 (1H, s).

Example 316

(2E)-3-(4-(1-Cyclopropyl-1H-pyrazol-4-yl)pyridin-3-yl)-N-(2-(2,2,2-trifluoroethyl)-1,2,3,4-tetrahydroisoquinolin-6-yl)acrylamide (A) 2,2,2-Trichloroethyl (1,2,3,4-tetrahydroisoquinolin-6-yl)carbamate hydrochloride To a mixture of tert-butyl 6-amino-3,4-dihydroisoquinoline-2(1H)-carboxylate (500 mg), triethylamine (0.337 mL) and THF (10 mL), 2,2,2-trichloroethyl chloroformate (0.333 mL) was added at room temperature, and the resulting mixture was stirred under nitrogen atmosphere at the same temperature for 10 minutes. Water was added to the reaction mixture at room temperature, and the aqueous layer was extracted with ethyl acetate. The extract was washed with water and brine and then dried over anhydrous magnesium sulfate, and the solvent was distilled off under reduced pressure. To a mixture of the residue and ethyl acetate (5 mL), a 4 M solution of hydrogen chloride in ethyl acetate (5 mL) was added at room temperature, and the resulting mixture was stirred under nitrogen atmosphere at the same temperature for 3 days. The precipitate was collected by filtration and washed with ethyl acetate to obtain the title compound (652 mg).

$^1$H NMR (300 MHz, DMSO-$d_6$) δ 2.97 (2H, t, J=5.8 Hz), 3.29-3.41 (2H, m), 4.20 (2H, brs), 4.94 (2H, s), 7.16 (1H, d, J=8.1 Hz), 7.34 (1H, d, J=7.9 Hz), 7.40 (1H, s), 9.14 (2H, brs), 10.19 (1H, brs).

(B) 2-(2,2,2-Trifluoroethyl)-1,2,3,4-tetrahydroisoquinolin-6-amine

To a mixture of 2,2,2-trichloroethyl (1,2,3,4-tetrahydroisoquinolin-6-yl)carbamate hydrochloride (308 mg) and DMF (10 mL), triethylamine (0.358 mL) and 2,2,2-trifluoroethyl trifluoromethanesulfonate (0.184 mL) were added at room temperature, and the resulting mixture was stirred overnight under nitrogen atmosphere at the same temperature. Water was added to the reaction mixture at room temperature, and the aqueous layer was extracted with ethyl acetate. The extract was washed with water and brine and then dried over anhydrous magnesium sulfate, and the solvent was distilled off under reduced pressure. To a mixture of the residue and acetic acid (5 mL), a zinc powder (559 mg) was added at room temperature, and the mixture was stirred at the same temperature for 30 minutes. The reaction mixture was filtered, and the solvent in the filtrate was distilled off under reduced pressure. Aqueous potassium carbonate solution was added to the residue, and the aqueous layer was extracted with ethyl acetate. The extract was washed with water and brine and then dried over anhydrous magnesium sulfate, and the solvent was distilled off under reduced pressure. The residue was purified by silica gel column chromatography (ethyl acetate/hexane) to obtain the title compound (135.6 mg).

MS: [M+H]$^+$ 230.9.

(C) (2E)-3-(4-(1-Cyclopropyl-1H-pyrazol-4-yl)pyridin-3-yl)-N-(2-(2,2,2-trifluoroethyl)-1,2,3,4-tetrahydroisoquinolin-6-yl)acrylamide HATU (100 mg) was added to a mixture of (2E)-3-(4-(1-cyclopropyl-1H-pyrazol-4-yl)pyridin-3-yl)acrylic acid (48.3 mg), 2-(2,2,2-trifluoroethyl)-1,2,3,4-tetrahydroisoquinolin-6-amine (40.2 mg), DIEA (0.091 mL) and DMF (1 mL) at room temperature, and the resulting mixture was stirred under nitrogen atmosphere at the same temperature for 24 hours. The solvent was distilled off under reduced pressure, and the residue was purified by silica gel column chromatography (NH, ethyl acetate/hexane). The obtained solid was collected by filtration and washed with ethyl acetate and IPE to obtain the title compound (53.3 mg).

$^1$H NMR (300 MHz, DMSO-$d_6$) δ 0.93-1.19 (4H, m), 2.77-2.85 (2H, m), 2.87-2.98 (2H, m), 3.24-3.42 (2H, m), 3.77 (2H, s), 3.80-3.90 (1H, m), 6.84 (1H, d, J=15.4 Hz), 7.02 (1H, d, J=8.7 Hz), 7.42 (1H, d, J=7.3 Hz), 7.48-7.58 (2H, m), 7.72 (2H, t, J=8.0 Hz), 8.19 (1H, s), 8.52 (1H, d, J=5.1 Hz), 8.77 (1H, s), 10.21 (1H, s).

Example 319

(2E)-3-(4-(1-Cyclopropyl-1H-pyrazol-4-yl)pyridin-3-yl)-N-(2-(2,2,2-trifluoroethyl)-2,3-dihydro-1H-isoindol-5-yl)acrylamide HATU (107.7 mg) was added to a mixture of (2E)-3-(4-(1-cyclopropyl-1H-pyrazol-4-yl)pyridin-3-yl)acrylic acid (47.4 mg), 2-(2,2,2-trifluoroethyl)isoindolin-5-amine (40.6 mg), DIEA (0.098 mL) and DMF (1 mL) at room temperature, and the resulting mixture was stirred under nitrogen atmosphere at the same temperature for 3 days. The solvent was distilled off under reduced pressure, and the residue was purified by silica gel column chromatography (NH, ethyl acetate/hexane). The obtained solid was washed with ethyl acetate/hexane (1/1) to obtain the title compound (34 mg).

$^1$H NMR (300 MHz, DMSO-$d_6$) δ 0.99-1.20 (4H, m), 3.45-3.69 (2H, m), 3.77-3.93 (1H, m), 4.06 (2H, s), 4.09 (2H, brs), 6.85 (1H, d, J=15.6 Hz), 7.22 (1H, d, J=8.1 Hz), 7.43-7.55 (2H, m), 7.66-7.82 (3H, m), 8.19 (1H, s), 8.53 (1H, d, J=5.3 Hz), 8.77 (1H, s), 10.30 (1H, s).

Example 324

(2E)-3-(4-(1-Cyclopropyl-1H-pyrazol-4-yl)-5-fluoropyridin-3-yl)-N-(2-(2,2,2-trifluoroethyl)-2,3-dihydro-1H-isoindol-5-yl)acrylamide (A) (2E)-Ethyl 3-(4-(1-cyclopropyl-1H-pyrazol-4-yl)-5-fluoropyridin-3-yl)acrylate A mixture of (2E)-ethyl 3-(4-chloro-5-fluoropyridin-3-yl)acrylate (800 mg), 1-cyclopropyl-4-(4,4,5,5-tetramethyl-1,3,2-dioxaborolan-2-yl)-1H-pyrazole (923 mg), 2-(dicyclohexylphosphino)biphenyl (160 mg), Pd$_2$(dba)$_3$ (163 mg), cesium carbonate (2.76 g), DME (21 mL) and water (3 mL) was stirred under nitrogen atmosphere at 85° C. for 24 hours. The reaction mixture was filtered through Celite. Water was added to the reaction mixture, and the aqueous layer was extracted with ethyl acetate. The extract was washed with brine and then dried over anhydrous magnesium sulfate, and the solvent was distilled off under reduced pressure. The residue was purified by silica gel column chromatography (ethyl acetate/hexane) to obtain the title compound (495 mg).
MS: [M+H]$^+$ 302.2.

(B) (2E)-3-(4-(1-Cyclopropyl-1H-pyrazol-4-yl)-5-fluoropyridin-3-yl)acrylic acid To a solution of (2E)-ethyl 3-(4-(1-cyclopropyl-1H-pyrazol-4-yl)-5-fluoropyridin-3-yl)acrylate (495 mg) in ethanol (5 mL) and THF (5 mL), 2 N aqueous sodium hydroxide solution (3.29 mL) was added at room temperature, and the mixture was stirred at the same temperature for 2.5 hours. The solvent was distilled off under reduced pressure, and acetic acid was added to the residue at room temperature to adjust the pH to 4. The reaction mixture was concentrated under reduced pressure, and water was added to the residue. The precipitate was collected by filtration and washed with water to obtain the title compound (223 mg).
MS: [M+H]$^+$ 273.9.

(C) 5-Nitro-2-(2,2,2-trifluoroethyl)isoindoline-1,3-dione

A mixture of 5-nitroisobenzofuran-1,3-dione (10.16 g), 2,2,2-trifluoroethanamine (10.42 g) and acetic acid (100 mL) was stirred overnight at 100° C. Water was added to the reaction mixture at 0° C. The precipitate was collected by filtration and dissolved in acetonitrile, and the solvent was distilled off under reduced pressure to obtain the title compound (13.62 g).
$^1$H NMR (300 MHz, DMSO-d$_6$) δ 4.49 (2H, q, J=9.4 Hz), 8.22 (1H, d, J=8.1 Hz), 8.59 (1H, d, J=2.1 Hz), 8.68 (1H, dd, J=8.1, 2.1 Hz).

(D) 2-(2,2,2-Trifluoroethyl)isoindolin-5-amine

A 1.0 M solution of THF-boron complex in THF (190 mL) was added to a solution of 5-nitro-2-(2,2,2-trifluoroethyl)isoindoline-1,3-dione (5.21 g) in THF (50 mL) at room temperature, and the mixture was heated at reflux overnight under nitrogen atmosphere. A 1 N hydrochloric acid solution was added to the reaction mixture at 0° C., and the mixture was stirred at room temperature for 1 hour and extracted with ethyl acetate. The extract was washed with water and brine and then dried over anhydrous magnesium sulfate, and the solvent was distilled off under reduced pressure to obtain an oil. A mixture of the obtained oil (whole amount), 10% palladium-carbon (2.03 g) and methanol (100 mL) was stirred under hydrogen atmosphere (1 atm) at room temperature for 30 minutes. The reaction mixture was filtered, and the solvent in the filtrate was distilled off under reduced pressure. The residue was purified by silica gel column chromatography (ethyl acetate/hexane) to obtain the title compound (2.74 g).
MS: [M+H]$^+$ 216.9.

(E) (2E)-3-(4-(1-Cyclopropyl-1H-pyrazol-4-yl)-5-fluoropyridin-3-yl)-N-(2-(2,2,2-trifluoroethyl)-2,3-dihydro-1H-isoindol-5-yl)acrylamide HATU (529.3 mg) was added to a mixture of (2E)-3-(4-(1-cyclopropyl-1H-pyrazol-4-yl)-5-fluoropyridin-3-yl) acrylic acid (250.5 mg), 2-(2,2,2-trifluoroethyl)isoindolin-5-amine (198.3 mg), DIEA (0.480 mL) and DMF (3 mL) at room temperature, and the resulting mixture was stirred under nitrogen atmosphere at the same temperature for 3 hours. The solvent was distilled off under reduced pressure, and the residue was purified by silica gel column chromatography (NH, ethyl acetate/hexane), washed with IPE, and then collected by filtration to obtain the title compound as a crude product (350.2 mg). The obtained crude product (whole amount) was dissolved in isopropyl acetate (22 mL) at 80° C. To the solution, hexane (22 mL) was added dropwise at the same temperature. The mixture was stirred at room temperature for 2 hours, and the precipitate was then collected by filtration and washed with isopropyl acetate/hexane (1/2) to obtain the title compound (317.8 mg).
$^1$H NMR (300 MHz, DMSO-d$_6$) δ 0.97-1.08 (2H, m), 1.09-1.20 (2H, m), 3.54 (2H, q, J=10.2 Hz), 3.89 (1H, tt, J=7.4, 3.8 Hz), 4.06 (2H, s), 4.09 (2H, s), 6.90 (1H, d, J=15.6 Hz), 7.22 (1H, d, J=8.3 Hz), 7.48 (1H, dd, J=8.2, 1.6 Hz), 7.59 (1H, d, J=15.6 Hz), 7.65-7.73 (2H, m), 8.18 (1H, d, J=1.3 Hz), 8.63 (1H, d, J=1.7 Hz), 8.70 (1H, s), 10.33 (1H, s).

Example 327

(2E)-3-(5-Fluoro-4-(1-methyl-1H-pyrazol-4-yl)pyridin-3-yl)-N-(2-(2,2,2-trifluoroethyl)-2,3-dihydro-1H-isoindol-5-yl)acrylamide DIEA (0.6 mL) was added to a mixture of (2E)-3-(5-fluoro-4-(1-methyl-1H-pyrazol-4-yl)pyridin-3-yl)acrylic acid dihydrochloride (230 mg), 2-(2,2,2-trifluoroethyl)isoindolin-5-amine (186 mg), HATU (293 mg) and DMF (3 mL) at room temperature, and the resulting mixture was stirred at the same temperature for 16 hours. Water was added to the reaction mixture, and the aqueous layer was extracted with ethyl acetate. The extract was washed with brine and then dried over anhydrous magnesium sulfate, and the solvent was distilled off under reduced pressure. The residue was purified by silica gel column chromatography (ethyl acetate/hexane) and recrystallized from ethyl acetate/hexane and subsequently ethanol to obtain the title compound (205 mg).
$^1$H NMR (300 MHz, DMSO-d$_6$) δ ppm 3.47-3.61 (2H, m), 3.96 (3H, s), 3.99-4.17 (4H, m), 6.84-6.96 (1H, m), 7.16-7.27 (1H, m), 7.42-7.52 (1H, m), 7.52-7.65 (1H, m), 7.65-7.72 (2H, m), 8.04-8.14 (1H, m), 8.57-8.66 (1H, m), 8.66-8.74 (1H, m), 10.24-10.39 (1H, m).

Example 328

(2E)-3-(4-(7-Fluoro-1-methyl-1H-benzimidazol-6-yl)pyridin-3-yl)-N-(2-(2,2,2-trifluoroethyl)-2,3-dihydro-1H-isoindol-5-yl)acrylamide

(A) 6-Bromo-7-fluoro-1-methyl-1H-benz[d]imidazole

To a mixture of 1-bromo-2,3-difluoro-4-nitrobenzene (760.5 mg) and methanol (11 mL), a 40% solution of methylamine in methanol (3.216 mL) was added at room temperature, and the resulting mixture was stirred at 60° C. for 2 hours. The solvent was distilled off under reduced pressure, and the residue was dissolved in ethanol (30 mL). To the solution, 90% reduced iron (926 mg) and 88% formic acid (0.640 mL) were added at room temperature, and the mixture was stirred at 100° C. for 2 hours. The reaction mixture was filtered, saturated aqueous sodium bicarbonate solution was added thereto, and the aqueous layer was extracted with ethyl acetate. The extract was washed with brine and then dried over anhydrous sodium sulfate, and the solvent was distilled off under reduced pressure. To a mixture of the residue and THF (20 mL), triethyl orthoformate (1.24 mL) and p-toluenesulfonic acid hydrate (55 mg) were added at room temperature, and the resulting mixture was heated at reflux for 1.5 hours. Saturated aqueous sodium bicarbonate solution was added to the reaction mixture, and the aqueous layer was extracted with ethyl acetate. The extract was washed with brine and then dried over anhydrous sodium sulfate, and the solvent was distilled off under reduced pressure. The obtained solid was suspended in hexane, collected by filtration, and washed with hexane to obtain the title compound (573.1 mg).

MS: [M+H]$^+$ 228.8.

(B) (2E)-tert-Butyl 3-(4-(7-fluoro-1-methyl-1H-benz[d]imidazol-6-yl)pyridin-3-yl)acrylate A mixture of (2E)-tert-butyl 3-(4-(4,4,5,5-tetramethyl-1,3,2-dioxaborolan-2-yl)pyridin-3-yl)acrylate (434 mg), 6-bromo-7-fluoro-1-methyl-1H-benz[d]imidazole (200 mg), chloro(2-dicyclohexylphosphino-2',6'-dimethoxy-1,1'-biphenyl)[2-(2'-amino-1,1'-biphenyl)]palladium(II) (62.9 mg), SPhos (35.8 mg), 2 M cesium carbonate (0.873 mL) and DME (5 mL) was stirred at 130° C. for 2 hours under microwave irradiation. The solvent was distilled off under reduced pressure, and the residue was purified by silica gel column chromatography (NH, ethyl acetate/hexane) to obtain the title compound (303.7 mg).

MS: [M+H]$^+$ 354.0.

(C) (2E)-3-(4-(7-Fluoro-1-methyl-1H-benz[d]imidazol-6-yl)pyridin-3-yl)acrylic acid ditrifluoroacetate To (2E)-tert-butyl 3-(4-(7-fluoro-1-methyl-1H-benz[d]imidazol-6-yl)pyridin-3-yl)acrylate (303.7 mg), trifluoroacetic acid (10 mL) was added at room temperature, and the mixture was stirred at the same temperature for 1 hour. The solvent was distilled off under reduced pressure, and the obtained solid was washed with IPE to obtain the title compound (410.2 mg).

MS: [M+H]$^+$ 297.9.

(D) (2E)-3-(4-(7-Fluoro-1-methyl-1H-benzimidazol-6-yl)pyridin-3-yl)-N-(2-(2,2,2-trifluoroethyl)-2,3-dihydro-1H-isoindol-5-yl)acrylamide HATU (146.1 mg) was added to a mixture of (2E)-3-(4-(7-fluoro-1-methyl-1H-benz[d]imidazol-6-yl)pyridin-3-yl) acrylic acid ditrifluoroacetate (119.4 mg), 2-(2,2,2-trifluoroethyl)isoindolin-5-amine (51.1 mg), DIEA (0.165 mL) and DMF (1 mL) at room temperature, and the resulting mixture was stirred under nitrogen atmosphere at the same temperature for 3 days. Water was added to the reaction mixture at 0° C., and the precipitate was collected by filtration, washed with water, and dissolved in methanol. The solvent was distilled off under reduced pressure, and the residue was purified by silica gel column chromatography (NH, ethyl acetate/hexane) to obtain the title compound (67.1 mg).

$^1$H NMR (300 MHz, DMSO-d$_6$) δ 3.52 (2H, q, J=10.2 Hz), 3.94-4.11 (7H, m), 6.93 (1H, d, J=15.8 Hz), 7.05-7.22 (2H, m), 7.30-7.45 (2H, m), 7.48 (1H, d, J=4.9 Hz), 7.54-7.68 (2H, m), 8.32 (1H, s), 8.66 (1H, d, J=4.7 Hz), 9.02 (1H, s), 10.27 (1H, s).

Example 330

(2E)-3-(4-(1-Cyclopropyl-1H-pyrazol-4-yl)pyridin-3-yl)-N-(2-fluoro-4-((2,2,2-trifluoroethoxy)methyl)phenyl)acrylamide (A) 1-Bromo-2-fluoro-4-((2,2,2-trifluoroethoxy)methyl)benzene To a mixture of 60% sodium hydride (0.16 g) and DMF (5 mL), a mixture of 2,2,2-trifluoroethanol (0.42 g) and DMF (5 mL) was added under ice cooling, and the reaction mixture was stirred at room temperature for 20 minutes. A mixture of 1-bromo-4-(bromomethyl)-2-fluorobenzene (1.04 g) and DMF (5 mL) was added thereto, and the resulting mixture was stirred at room temperature for 16 hours. Saturated aqueous ammonium chloride solution was added to the reaction mixture, followed by extraction with ethyl acetate. The organic layer was washed with brine and then dried over anhydrous magnesium sulfate, and the solvent was distilled off under reduced pressure. The residue was purified by silica gel column chromatography (ethyl acetate/hexane) to obtain the title compound (1.00 g).

$^1$H NMR (300 MHz, CDCl$_3$) δ 3.86 (2H, q, J=8.6 Hz), 4.63 (2H, s), 6.94-7.07 (1H, m), 7.14 (1H, dd, J=9.1, 1.9 Hz), 7.54 (1H, dd, J=8.2, 7.0 Hz).

(B) (2E)-3-(4-(1-Cyclopropyl-1H-pyrazol-4-yl)pyridin-3-yl)-N-(2-fluoro-4-((2,2,2-trifluoroethoxy)methyl)phenyl)acrylamide A mixture of (2E)-3-(4-(1-cyclopropyl-1H-pyrazol-4-yl)pyridin-3-yl)acrylamide (302 mg), 1-bromo-2-fluoro-4-((2,2,2-trifluoroethoxy)methyl)benzene (336 mg), Xantphos (172 mg), Pd$_2$(dba)$_3$ (136 mg), sodium tert-butoxide (160 mg) and toluene (5 mL) was stirred at 130° C. for 30 minutes under microwave irradiation. The reaction mixture was filtered through Celite, and water was added to the filtrate, followed by extraction with ethyl acetate. The organic layer was washed with brine and then dried over anhydrous magnesium sulfate, and the solvent was distilled off under reduced pressure. The residue was purified by silica gel column chromatography (ethyl acetate/hexane) to obtain the title compound (184 mg).

$^1$H NMR (300 MHz, DMSO-d$_6$) δ 0.95-1.08 (2H, m), 1.09-1.16 (2H, m), 3.77-3.91 (1H, m), 4.12 (2H, d, J=9.4 Hz), 4.65 (2H, s), 7.03-7.14 (1H, m), 7.15-7.21 (1H, m), 7.24-7.32 (1H, m), 7.48-7.56 (1H, m), 7.72 (2H, d, J=0.76 Hz), 8.19 (2H, s), 8.53 (1H, d, J=5.2 Hz), 8.78 (1H, s), 10.03-10.14 (1H, m).

Example 332

(2E)-3-(4-(1-Cyclopropyl-1H-pyrazol-4-yl)-5-fluoropyridin-3-yl)-N-(2-fluoro-4-(2-hydroxy-2-methylpropyl)phenyl)acrylamide (A) 1-(4-Bromo-3-fluorophenyl)-2-methylpropan-2-ol A 3 M solution of methyl magnesium bromide in diethyl ether (23 mL) was added to a mixture of ethyl 2-(4-bromo-3-fluorophenyl)acetate (4.5 g) and THF (100 mL) under ice cooling, and the resulting mixture was stirred at room temperature for 3.5 hours. Saturated aqueous sodium bicarbonate solution was added to the reaction mixture. The insoluble matter was removed by filtration through Celite, and the filtrate was extracted with ethyl acetate. The organic layer was washed with brine and then dried over anhydrous magnesium sulfate, and the solvent was distilled off under reduced pressure to obtain the title compound (3.7 g).

$^1$H NMR (300 MHz, CDCl$_3$) δ 1.23 (6H, s), 2.73 (2H, s), 6.86-6.92 (1H, m), 6.99-7.05 (1H, m), 7.47 (1H, d, J=0.66 Hz).

(B) 1-(4-((Diphenylmethylene)amino)-3-fluorophenyl)-2-methylpropan-2-ol

A mixture of 1-(4-bromo-3-fluorophenyl)-2-methylpropan-2-ol (288 mg), diphenylmethanimine (283 mg), BINAP (212 mg), Pd$_2$(dba)$_3$ (120 mg), sodium tert-butoxide (160 mg) and toluene (10 mL) was stirred under nitrogen atmosphere at 110° C. for 16 hours. The reaction mixture was filtered through Celite, and water was added to the filtrate, followed by extraction with ethyl acetate. The organic layer was washed with brine and then dried over anhydrous magnesium sulfate, and the solvent was distilled off under reduced pressure. The residue was purified by silica gel column chromatography (ethyl acetate/hexane) to obtain the title compound as a crude product (515 mg). This compound was used in the next step without being further purified.

MS: [M+H]$^+$ 348.2.

(C) 1-(4-Amino-3-fluorophenyl)-2-methylpropan-2-ol

To a mixture of crude 1-(4-((diphenylmethylene)amino)-3-fluorophenyl)-2-methylpropan-2-ol (515 mg) and THF (10 mL), 2 N hydrochloric acid (2.2 mL) was added at room temperature, and the resulting mixture was stirred at the same temperature for 1 hour. Saturated aqueous sodium bicarbonate solution was added to the reaction mixture under ice cooling, followed by extraction with ethyl acetate. The organic layer was washed with brine and then dried over anhydrous magnesium sulfate, and the solvent was distilled off under reduced pressure. The residue was purified by silica gel column chromatography (ethyl acetate/hexane) to obtain the title compound (220 mg).

MS: [M+H]$^+$ 184.2.

(D) (2E)-3-(4-(1-Cyclopropyl-1H-pyrazol-4-yl)-5-fluoropyridin-3-yl)-N-(2-fluoro-4-(2-hydroxy-2-methylpropyl)phenyl)acrylamide HATU (110 mg) was added to a mixture of (2E)-3-(4-(1-cyclopropyl-1H-pyrazol-4-yl)-5-fluoropyridin-3-yl)acrylic acid (53 mg), 1-(4-amino-3-fluorophenyl)-2-methylpropan-2-ol (37 mg), DIEA (0.1 mL) and DMF (2 mL) at room temperature, and the resulting mixture was stirred at the same temperature for 2 days. The reaction mixture was concentrated under reduced pressure, and the residue was then purified by silica gel column chromatography (NH, ethyl acetate/hexane) to obtain the title compound (29 mg).

$^1$H NMR (300 MHz, DMSO-d$_6$) δ 0.96-1.08 (8H, m), 1.11-1.19 (2H, m), 2.64 (2H, s), 3.89 (1H, dt, J=7.5, 3.5 Hz), 4.37 (1H, s), 7.01 (1H, d, J=8.5 Hz), 7.07-7.19 (2H, m), 7.54-7.69 (2H, m), 7.94 (1H, t, J=8.4 Hz), 8.18 (1H, s), 8.63 (1H, d, J=1.7 Hz), 8.70 (1H, s), 10.01 (1H, s).

Example 333

(2E)-N-(2-((1-Fluorocyclopropyl)methyl)-2,3-dihydro-1H-isoindol-5-yl)-3-(4-(1-methyl-1H-pyrazol-4-yl)pyridin-3-yl)acrylamide (A) 1-((Dibenzylamino)methyl)cyclopropanol To a mixture of ethyl 2-(dibenzylamino)acetate (11.2 g), titanium tetraisopropoxide (2.398 mL) and THF (130 mL), a 3 M solution of ethyl magnesium bromide in diethyl ether (26.4 mL) was added dropwise at 0° C., and the resulting mixture was stirred overnight under nitrogen atmosphere at room temperature. Saturated aqueous ammonium chloride solution was added to the reaction mixture, and the aqueous layer was extracted with ethyl acetate. The extract was washed with water and brine and then dried over anhydrous magnesium sulfate, and the solvent was distilled off under reduced pressure. The residue was purified by silica gel column chromatography (ethyl acetate/hexane) to obtain the title compound (6.59 g).

$^1$H NMR (300 MHz, DMSO-d$_6$) δ 0.19-0.39 (2H, m), 0.46-0.63 (2H, m), 2.53 (2H, s), 3.66 (4H, s), 5.04 (1H, s), 7.16-7.26 (2H, m), 7.27-7.35 (4H, m), 7.36-7.43 (4H, m).

(B) N,N-Dibenzyl-1-(1-fluorocyclopropyl)methanamine

To a mixture of 1-((dibenzylamino)methyl)cyclopropanol (6.59 g) and toluene (130 mL), DAST (7.16 mL) was added at room temperature, and the resulting mixture was stirred overnight under nitrogen atmosphere at the same temperature. Saturated aqueous sodium hydroxide solution was added to the reaction mixture, and the aqueous layer was extracted with ethyl acetate. The extract was washed with water and brine and then dried over anhydrous magnesium sulfate, and the solvent was distilled off under reduced pressure. The residue was purified by silica gel column chromatography (ethyl acetate/hexane) to obtain the title compound (5.38 g).

MS: [M+H]$^+$ 270.0.

(C) (1-Fluorocyclopropyl)methanamine hydrochloride

A mixture of N,N-dibenzyl-1-(1-fluorocyclopropyl)methanamine (5.38 g), 20% palladium hydroxide (2.39 g) and methanol (150 mL) was stirred under hydrogen atmosphere (1 atm) at room temperature for 2 hours. The reaction mixture was filtered, a 4 N solution of hydrogen chloride in ethyl acetate (14.98 mL) was added to the filtrate, and the solvent was distilled off under reduced pressure. The obtained solid was washed with ethyl acetate and dried under reduced pressure at 80° C. to obtain the title compound (1.51 g).

$^1$H NMR (300 MHz, DMSO-d$_6$) δ 0.83-0.98 (2H, m), 1.02-1.23 (2H, m), 4.52 (2H, d, J=48.8 Hz), 8.78 (3H, brs).

(D) 2-((1-Fluorocyclopropyl)methyl)-5-nitroisoindoline-1,3-dione

A mixture of 4-nitrophthalic anhydride (515.2 mg), (1-fluorocyclopropyl)methanamine hydrochloride (332.5 mg), triethylamine (0.930 mL) and toluene (10 mL) was heated at reflux for 1 hour. A 1 N hydrochloric acid solution was added to the reaction mixture, and the aqueous layer was extracted with ethyl acetate. The extract was washed with water and brine and then dried over anhydrous magnesium sulfate, and the solvent was distilled off under reduced pressure. The residue was purified by silica gel column chromatography (ethyl acetate/hexane) to obtain the title compound (263 mg).

$^1$H NMR (300 MHz, DMSO-d$_6$) δ 1.11-1.23 (4H, m), 4.46 (2H, d, J=48.2 Hz), 8.12 (1H, d, J=8.1 Hz), 8.48 (1H, d, J=2.1 Hz), 8.63 (1H, dd, J=8.2, 2.0 Hz).

(E) 5-Amino-2-((1-fluorocyclopropyl)methyl)isoindoline-1,3-dione

A mixture of 2-((1-fluorocyclopropyl)methyl)-5-nitroisoindoline-1,3-dione (263 mg), 10% palladium-carbon (112.9 mg) and methanol (30 mL) was stirred under hydrogen atmosphere (1 atm) at room temperature for 2 hours. The reaction mixture was filtered, and the solvent in the filtrate was distilled off under reduced pressure. The obtained solid was washed with IPE to obtain the title compound (229.6 mg).
MS: $[M+H]^+$ 234.9.

(F) 2-((1-Fluorocyclopropyl)methyl)isoindolin-5-amine

A 1.0 M solution of THF-boron complex in THF (5.88 mL) was added to a solution of 5-amino-2-((1-fluorocyclopropyl)methyl)isoindoline-1,3-dione (229.6 mg) in THF (5 mL) at room temperature, and the mixture was heated at reflux overnight. Saturated aqueous sodium bicarbonate solution was added to the reaction mixture at room temperature, and the aqueous layer was extracted with ethyl acetate. The extract was washed with water and brine and then dried over anhydrous magnesium sulfate, and the solvent was distilled off under reduced pressure. The residue was purified by silica gel column chromatography (NH, ethyl acetate/hexane) to obtain the title compound (10.9 mg).
MS: $[M+H]^+$ 207.0.

(G) (2E)-N-(2-((1-Fluorocyclopropyl)methyl)-2,3-dihydro-1H-isoindol-5-yl)-3-(4-(1-methyl-1H-pyrazol-4-yl)pyridin-3-yl)acrylamide HATU (52.3 mg) was added to a mixture of (2E)-3-(4-(1-methyl-1H-pyrazol-4-yl)pyridin-3-yl)acrylic acid (15.4 mg), 2-((1-fluorocyclopropyl)methyl)isoindolin-5-amine (10.9 mg), DIEA (0.028 mL) and DMF (0.5 mL) at room temperature, and the resulting mixture was stirred overnight under nitrogen atmosphere at the same temperature. The solvent was distilled off under reduced pressure, and the residue was purified by silica gel column chromatography (NH, ethyl acetate/hexane). The obtained solid was washed with IPE to obtain the title compound (8.1 mg).
$^1$H NMR (300 MHz, DMSO-$d_6$) δ 0.65-0.75 (2H, m), 0.77-0.87 (2H, m), 3.94 (3H, s), 4.08 (2H, s), 4.11 (2H, s), 4.61 (2H, d, J=49.5 Hz), 6.85 (1H, d, J=15.4 Hz), 7.19 (1H, d, J=8.1 Hz), 7.42-7.53 (2H, m), 7.63-7.79 (3H, m), 8.09 (1H, s), 8.53 (1H, d, J=5.1 Hz), 8.77 (1H, s), 10.27 (1H, s).

Example 336

(2E)-3-(4-(1-Cyclopropyl-1H-pyrazol-4-yl)-5-fluoropyridin-3-yl)-N-(4-(6-oxa-3-azabicyclo[3.1.1]hept-3-ylmethyl)phenyl)acrylamide

(A) (2E)-tert-Butyl 3-(4-(1-cyclopropyl-1H-pyrazol-4-yl)-5-fluoropyridin-3-yl)acrylate A mixture of (2E)-tert-butyl 3-(4-chloro-5-fluoropyridin-3-yl)acrylate (3.51 g), 1-cyclopropyl-4-(4,4,5,5-tetramethyl-1,3,2-dioxaborolan-2-yl)-1H-pyrazole (3.88 g), 2-(dicyclohexylphosphino)biphenyl (611 mg), Pd$_2$(dba)$_3$ (749 mg), cesium carbonate (10.7 g), DME (70 mL) and water (10 mL) was stirred under nitrogen atmosphere at 85° C. for 15 hours. The reaction mixture was filtered through Celite, and water was added to the filtrate, followed by extraction with ethyl acetate. The organic layer was washed with brine and then dried over anhydrous magnesium sulfate, and the solvent was distilled off under reduced pressure. The residue was purified by silica gel column chromatography (ethyl acetate/hexane) to obtain the title compound (3.22 g).
MS: $[M+H]^+$ 330.2.

(B) (2E)-3-(4-(1-Cyclopropyl-1H-pyrazol-4-yl)-5-fluoropyridin-3-yl)acrylic acid dihydrochloride To (2E)-tert-butyl 3-(4-(1-cyclopropyl-1H-pyrazol-4-yl)-5-fluoropyridin-3-yl)acrylate (3.22 g), trifluoroacetic acid (20 mL) was added under ice cooling, and the mixture was stirred at room temperature for 1.5 hours. The solvent was distilled off under reduced pressure, a 15% solution of hydrogen chloride in CPME was added to the residue, and the mixture was concentrated under reduced pressure. Toluene was added to the residue, and the mixture was concentrated under reduced pressure. The precipitate was collected by filtration and washed with CPME to obtain the title compound (3.30 g).
MS: $[M+H]^+$ 274.1.

(C) (2E)-3-(4-(1-Cyclopropyl-1H-pyrazol-4-yl)-5-fluoropyridin-3-yl)-N-(4-(hydroxymethyl)phenyl)acrylamide HATU (696 mg) was added to a mixture of (2E)-3-(4-(1-cyclopropyl-1H-pyrazol-4-yl)-5-fluoropyridin-3-yl)acrylic acid dihydrochloride (600 mg), (4-aminophenyl)methanol (275 mg), DIEA (1.1 mL) and DMF (6 mL) at room temperature, and the resulting mixture was stirred at the same temperature for 2 hours. Water was added to the reaction mixture, and the reaction mixture was further stirred for 30 minutes. The precipitated solid was collected by filtration and washed with water to obtain the title compound (550 mg).
MS: $[M+H]^+$ 379.3.

(D) (2E)-3-(4-(1-Cyclopropyl-1H-pyrazol-4-yl)-5-fluoropyridin-3-yl)-N-(4-formylphenyl)acrylamide Manganese dioxide (1.99 g) was added to a mixture of (2E)-3-(4-(1-cyclopropyl-1H-pyrazol-4-yl)-5-fluoropyridin-3-yl)-N-(4-(hydroxymethyl)phenyl)acrylamide (550 mg) and ethyl acetate (40 mL) at room temperature, and the resulting mixture was stirred at 75° C. for 16 hours. The reaction mixture was filtered through Celite, and the filtrate was concentrated under reduced pressure to obtain the title compound as a crude product (347 mg). This compound was used in the next step without being further purified.
MS: $[M+H]^+$ 377.2.

(E) (2E)-3-(4-(1-Cyclopropyl-1H-pyrazol-4-yl)-5-fluoropyridin-3-yl)-N-(4-(6-oxa-3-azabicyclo[3.1.1]hept-3-ylmethyl)phenyl)acrylamide 6-Oxa-3-azabicyclo[3.1.1]heptane hydrochloride (27 mg) was added to a mixture of crude (2E)-3-(4-(1-cyclopropyl-1H-pyrazol-4-yl)-5-fluoropyridin-3-yl)-N-(4-formylphenyl)acrylamide (60 mg), methanol (5 mL) and acetic acid (0.5 mL) at room temperature, and the resulting mixture was stirred at the same temperature for 15 minutes. 2-Picolineboron complex (29 mg) was added to the reaction mixture, and the mixture was stirred at room temperature for 16 hours. The reaction mixture was concentrated under reduced pressure, 1 N hydrochloric acid was added to the residue, and subsequently a mixed ethyl acetate/hexane solution was added to the mixture. The aqueous layer was separated, and saturated aqueous potassium carbonate solution was added thereto, followed by extraction with a mixed ethyl acetate/THF solution. The organic layer was dried over anhydrous magnesium sulfate, and the solvent was distilled off under reduced pressure. The residue was purified by silica gel column chromatography (NH, ethyl acetate/hexane) to obtain the title compound (32 mg).

$^1$H NMR (300 MHz, DMSO-$d_6$) δ 0.99-1.07 (2H, m), 1.10-1.16 (2H, m), 2.25-2.31 (1H, m), 2.64 (2H, d, J=11.3 Hz), 2.80-2.89 (1H, m), 2.96 (2H, d, J=11.1 Hz), 3.68 (2H, s), 3.89 (1H, tt, J=7.4, 3.7 Hz), 4.41 (2H, d, J=6.1 Hz), 6.91 (1H, d, J=15.7 Hz), 7.31 (2H, d, J=8.6 Hz), 7.59 (1H, d, J=15.8 Hz), 7.63-7.70 (3H, m), 8.18 (1H, d, J=1.4 Hz), 8.62 (1H, d, J=1.7 Hz), 8.70 (1H, s), 10.33 (1H, s).

Example 343

(2E)-3-(4-(1-Cyclopropyl-1H-pyrazol-4-yl)-5-fluoropyridin-3-yl)-N-(2-fluoro-4-((3-methoxyazetidin-1-yl)methyl)phenyl)acrylamide (A) (2E)-3-(4-(1-Cyclopropyl-1H-pyrazol-4-yl)-5-fluoropyridin-3-yl)acrylamide A 28% aqueous ammonia solution (288 mg) was added to a mixture of (2E)-3-(4-(1-cyclopropyl-1H-pyrazol-4-yl)-5-fluoropyridin-3-yl)acrylic acid dihydrochloride (410 mg), HATU (704 mg), DIEA (0.9 mL) and DMF (6 mL) at room temperature, and the resulting mixture was stirred at the same temperature for 2 days. The reaction mixture was concentrated under reduced pressure, and the residue was purified by silica gel column chromatography (NH, methanol/ethyl acetate) to obtain the title compound (297 mg).

MS: [M+H]$^+$ 272.9.

(B) 1-(4-Bromo-3-fluorobenzyl)-3-methoxyazetidine

DIEA (3.5 mL) was added to a mixture of 1-bromo-4-(bromomethyl)-2-fluorobenzene (1.81 g), 3-methoxyazetidine hydrochloride (0.85 g) and acetonitrile (20 mL) at room temperature, and the resulting mixture was stirred at the same temperature for 2 hours. The reaction mixture was concentrated under reduced pressure, and saturated aqueous potassium carbonate solution was added to the residue, followed by extraction with a mixed ethyl acetate/THF solution. The organic layer was washed with brine and then dried over anhydrous magnesium sulfate, and the solvent was distilled off under reduced pressure. The residue was purified by silica gel column chromatography (ethyl acetate/hexane) to obtain the title compound (1.15 g).

MS: [M+H]$^+$ 273.8.

(C) (2E)-3-(4-(1-Cyclopropyl-1H-pyrazol-4-yl)-5-fluoropyridin-3-yl)-N-(2-fluoro-4-((3-methoxyazetidin-1-yl)methyl)phenyl)acrylamide A mixture of (2E)-3-(4-(1-cyclopropyl-1H-pyrazol-4-yl)-5-fluoropyridin-3-yl)acrylamide (504 mg), 1-(4-bromo-3-fluorobenzyl)-3-methoxyazetidine (503 mg), Xantphos (268 mg), Pd$_2$(dba)$_3$ (212 mg), sodium tert-butoxide (249 mg) and toluene (20 mL) was stirred at 130° C. for 30 minutes under microwave irradiation. The reaction mixture was filtered through Celite, and water was added to the filtrate, followed by extraction with ethyl acetate. The organic layer was washed with brine and then dried over anhydrous magnesium sulfate, and the solvent was distilled off under reduced pressure. The residue was purified by silica gel column chromatography (NH, ethyl acetate/hexane) and silica gel column chromatography (methanol/ethyl acetate) and then recrystallized from ethanol/hexane to obtain the title compound (316 mg).

$^1$H NMR (300 MHz, DMSO-$d_6$) δ 0.97-1.08 (2H, m), 1.08-1.16 (2H, m), 2.80-2.89 (2H, m), 3.14 (3H, s), 3.43-3.52 (2H, m), 3.52-3.60 (2H, m), 3.83-3.92 (1H, m), 3.92-4.02 (1H, m), 7.04-7.22 (3H, m), 7.66 (2H, d, J=0.76 Hz), 7.95-8.05 (1H, m), 8.18 (1H, d, J=1.3 Hz), 8.63 (1H, d, J=1.7 Hz), 8.70 (1H, s), 10.04 (1H, s).

Example 345

(2E)-3-(4-(1-Cyclopropyl-1H-pyrazol-4-yl)-5-fluoropyridin-3-yl)-N-(4-((3-methoxyazetidin-1-yl)methyl)phenyl)acrylamide (A) 1-(4-Bromobenzyl)-3-methoxyazetidine DIEA (2.5 mL) was added to a mixture of 1-bromo-4-(bromomethyl)benzene (1.01 g), 3-methoxyazetidine hydrochloride (0.52 g) and acetonitrile (10 mL) at room temperature, and the resulting mixture was stirred at 65° C. for 1.5 hours. The reaction mixture was concentrated under reduced pressure, and water was added to the residue, followed by extraction with a mixed ethyl acetate/THF solution. The organic layer was washed with brine and then dried over anhydrous magnesium sulfate, and the solvent was distilled off under reduced pressure. The residue was purified by silica gel column chromatography (ethyl acetate/hexane) to obtain the title compound (0.59 g).

MS: [M+H]$^+$ 256.9.

(B) (2E)-3-(4-(1-Cyclopropyl-1H-pyrazol-4-yl)-5-fluoropyridin-3-yl)-N-(4-((3-methoxyazetidin-1-yl)methyl)phenyl)acrylamide A mixture of (2E)-3-(4-(1-cyclopropyl-1H-pyrazol-4-yl)-5-fluoropyridin-3-yl)acrylamide (377 mg), 1-(4-bromobenzyl)-3-methoxyazetidine (394 mg), Xantphos (202 mg), Pd$_2$(dba)$_3$ (157 mg), sodium tert-butoxide (176 mg) and toluene (20 mL) was stirred at 130° C. for 30 minutes under microwave irradiation. The reaction mixture was filtered through Celite, and water was added to the filtrate, followed by extraction with ethyl acetate. The organic layer was washed with brine and then dried over anhydrous magnesium sulfate, and the solvent was distilled off under reduced pressure. The residue was purified by silica gel column chromatography (NH, ethyl acetate/hexane) and silica gel column chromatography (methanol/ethyl acetate) to obtain the title compound as a crude product (244 mg). The obtained crude product was separated by HPLC (C18, mobile phase: water/acetonitrile (containing 0.1% TFA)), and saturated aqueous potassium carbonate solution was added to the collected fractions, followed by extraction with ethyl acetate. The extract was dried over anhydrous magnesium sulfate and then concentrated under reduced pressure, and the residue was then recrystallized from ethyl acetate/hexane to obtain the title compound (141 mg).

$^1$H NMR (300 MHz, DMSO-$d_6$) δ 1.00-1.07 (2H, m), 1.09-1.17 (2H, m), 2.77-2.85 (2H, m), 3.14 (3H, s), 3.43-3.48 (2H, m), 3.49-3.54 (2H, m), 3.84-3.92 (1H, m), 3.92-4.00 (1H, m), 6.84-6.95 (1H, m), 7.14-7.27 (2H, m), 7.52-

7.70 (4H, m), 8.09-8.25 (1H, m), 8.57-8.64 (1H, m), 8.67-8.72 (1H, m), 10.27-10.36 (1H, m).

Example 348

(2E)-3-(4-(1-Cyclopropyl-1H-pyrazol-4-yl)-5-fluoropyridin-3-yl)-N-(4-(2-fluoro-2-methylpropyl)phenyl)acrylamide (A) 1-(4-Bromophenyl)-2-methylpropan-2-ol A 3.0 M solution of methyl magnesium bromide in diethyl ether (49 mL) was added dropwise to a mixture of ethyl 2-(4-bromophenyl)acetate (7.1 g) and THF (100 mL) under ice cooling, and the resulting mixture was stirred at room temperature for 1.5 hours. Saturated aqueous ammonium chloride solution was added to the reaction mixture under ice cooling, followed by extraction with ethyl acetate. The organic layer was washed with brine and then dried over anhydrous magnesium sulfate, and the solvent was distilled off under reduced pressure to obtain the title compound as a crude product (7.7 g). This compound was used in the next step without being further purified.
$^1$H NMR (300 MHz, CDCl$_3$) δ 1.22 (6H, s), 1.55-1.64 (1H, m), 2.72 (2H, s), 7.10 (2H, d, J=8.5 Hz), 7.43 (2H, d, J=8.4 Hz).

(B) 1-Bromo-4-(2-fluoro-2-methylpropyl)benzene

DAST (1.2 mL) was added dropwise to a mixture of crude 1-(4-bromophenyl)-2-methylpropan-2-ol (866 mg) and toluene (20 mL) under ice cooling, and the resulting mixture was stirred at room temperature 16 hours. Saturated aqueous sodium bicarbonate solution was added to the reaction mixture under ice cooling, followed by extraction with ethyl acetate. The organic layer was washed with brine and then dried over anhydrous magnesium sulfate, and the solvent was distilled off under reduced pressure. The residue was purified by silica gel column chromatography (ethyl acetate/hexane) to obtain the title compound (590 mg).
$^1$H NMR (300 MHz, CDCl$_3$) δ 1.20-1.39 (6H, m), 2.74-2.98 (2H, m), 7.09 (2H, d, J=8.2 Hz), 7.42 (2H, d, J=8.4 Hz).

(C) (2E)-3-(4-(1-Cyclopropyl-1H-pyrazol-4-yl)-5-fluoropyridin-3-yl)-N-(4-(2-fluoro-2-methylpropyl)phenyl)acrylamide A mixture of (2E)-3-(4-(1-cyclopropyl-1H-pyrazol-4-yl)-5-fluoropyridin-3-yl)acrylamide (199 mg), 1-bromo-4-(2-fluoro-2-methylpropyl)benzene (172 mg), Xantphos (111 mg), Pd$_2$(dba)$_3$ (89 mg), sodium tert-butoxide (92 mg) and toluene (5 mL) was stirred at 130° C. for 30 minutes under microwave irradiation. The reaction mixture was filtered through Celite, and water was added to the filtrate, followed by extraction with ethyl acetate. The organic layer was washed with brine and then dried over anhydrous magnesium sulfate, and the solvent was distilled off under reduced pressure. The residue was separated by silica gel column chromatography (NH, ethyl acetate/hexane) and HPLC (C18, mobile phase: water/acetonitrile (containing 0.1% TFA)), and saturated aqueous sodium bicarbonate solution was added to the collected fractions, followed by extraction with ethyl acetate. The extract was dried over anhydrous magnesium sulfate and then concentrated under reduced pressure to obtain the title compound (69 mg).
$^1$H NMR (300 MHz, DMSO-d$_6$) δ 0.94-1.08 (2H, m), 1.09-1.20 (2H, m), 1.21-1.28 (3H, m), 1.28-1.33 (3H, m), 2.77-2.93 (2H, m), 3.81-3.97 (1H, m), 6.80-7.02 (1H, m), 7.12-7.27 (2H, m), 7.52-7.76 (4H, m), 8.12-8.24 (1H, m), 8.56-8.65 (1H, m), 8.65-8.75 (1H, m), 10.28-10.38 (1H, m).

Example 352

(2E)-N-(2-(2,2-Difluoro-3-methoxypropyl)-2,3-dihydro-1H-isoindol-5-yl)-3-(5-fluoro-4-(1-methyl-1H-pyrazol-4-yl)pyridin-3-yl)acrylamide (A) N-((1H-Benzo[d][1,2,3]triazol-1-yl)methyl)-N-benzyl-1-phenylmethanamine To a mixture of 1H-benzotriazole-1-methanol (10.06 g) and ethanol (250 mL), dibenzylamine (12.97 mL) was added at room temperature, and the resulting mixture was stirred at room temperature for 1 hour. The solvent was distilled off under reduced pressure, and the precipitate was washed with IPE to obtain the title compound (19.99 g).
$^1$H NMR (300 MHz, DMSO-d$_6$) δ 3.70 (4H, s), 5.58 (2H, s), 7.18-7.46 (11H, m), 7.54 (1H, t, J=7.6 Hz), 7.70 (1H, d, J=8.5 Hz), 8.08 (1H, d, J=8.3 Hz).

(B) Ethyl 3-(dibenzylamino)-2,2-difluoropropanoate

To a mixture of a zinc powder (3.25 g) and THF (50 mL), chlorotrimethylsilane (3.02 mL) was added at room temperature, and the resulting mixture was stirred at the same temperature for 2 minutes. Ethyl bromodifluoroacetate (3.68 mL) was added dropwise to the reaction mixture at room temperature, and the mixture was stirred under nitrogen atmosphere at the same temperature for 5 minutes. A solution of N-((1H-benzo[d][1,2,3]triazol-1-yl)methyl)-N-benzyl-1-phenylmethanamine (7.85 g) in THF (60 mL) was added dropwise to the reaction mixture at room temperature, and the mixture was stirred at the same temperature for 1 hour. Saturated aqueous sodium bicarbonate solution was added to the reaction mixture at room temperature, and the mixture was stirred for 5 minutes. Then, the reaction mixture was filtered, and the filtrate was extracted with ethyl acetate. The extract was washed with brine and then dried over anhydrous magnesium sulfate, and the solvent was distilled off under reduced pressure. The residue was purified by silica gel column chromatography (NH, ethyl acetate/hexane) to obtain the title compound (5.6 g).
MS: [M+H]$^+$ 334.0.

(C) 3-(Dibenzylamino)-2,2-difluoropropan-1-ol

To a mixture of LAH (1.86 g) and diethyl ether (90 mL), a solution of ethyl 3-(dibenzylamino)-2,2-difluoropropanoate (5.6 g) in diethyl ether (30 mL) was added at 0° C., and the resulting mixture was stirred under nitrogen atmosphere at the same temperature for 10 minutes. Water (1.86 mL), a 4 N aqueous sodium hydroxide solution (1.86 mL) and water (5.58 mL) were added to the reaction mixture at 0° C., and the insoluble matter was removed by filtration. The solvent in the filtrate was distilled off under reduced pressure to obtain the title compound (4.57 g).
MS: [M+H]$^+$ 292.0.

(D) N,N-Dibenzyl-2,2-difluoro-3-methoxypropan-1-amine

To a mixture of 3-(dibenzylamino)-2,2-difluoropropan-1-ol (4.57 g) and DMF (50 mL), 60% sodium hydride (0.78 g) was added at 0° C., and the resulting mixture was stirred under nitrogen atmosphere at room temperature for 5 minutes. Iodomethane (1.471 mL) was added to the reaction mixture at 0° C., and the mixture was stirred at room temperature for 1 hour. Water was added to the reaction mixture at room temperature, and the aqueous layer was extracted with ethyl acetate. The extract was washed with water and brine and then dried over anhydrous magnesium sulfate. The solvent was distilled off under reduced pressure to obtain the title compound as a crude product (4.79 g). This compound was used in the next step without being further purified.

MS: [M+H]$^+$ 306.0.

(E) 2,2-Difluoro-3-methoxypropan-1-amine hydrochloride

A mixture of crude N,N-dibenzyl-2,2-difluoro-3-methoxypropan-1-amine (4.79 g), 20% palladium hydroxide (1.94 g), a 4 M solution of hydrogen chloride in ethyl acetate (4.71 mL) and methanol (100 mL) was stirred overnight under hydrogen atmosphere (1 atm) at room temperature. The reaction mixture was filtered, and the solvent in the filtrate was distilled off under reduced pressure to obtain the title compound as a crude product (3.04 g). This compound was used in the next step without being further purified.

MS: [M+H]$^+$ 126.0.

(F) 2-(2,2-Difluoro-3-methoxypropyl)-5-nitroisoindoline-1,3-dione

A mixture of 5-nitroisobenzofuran-1,3-dione (1.916 mg), crude 2,2-difluoro-3-methoxypropan-1-amine hydrochloride (2.92 g) and acetic acid (20 mL) was stirred at 100° C. for 16 hours. Water was added thereto at 0° C. The precipitate was collected by filtration and dissolved in acetonitrile, and the solvent was distilled off under reduced pressure to obtain the title compound (1.10 g).

$^1$H NMR (300 MHz, DMSO-d$_6$) δ 3.37 (3H, s), 3.76 (2H, t, J=13.4 Hz), 4.13 (2H, t, J=15.1 Hz), 8.19 (1H, d, J=8.1 Hz), 8.56 (1H, d, J=1.9 Hz), 8.66 (1H, dd, J=8.1, 2.1 Hz).

(G) 5-Amino-2-(2,2-difluoro-3-methoxypropyl)isoindoline-1,3-dione

A mixture of 2-(2,2-difluoro-3-methoxypropyl)-5-nitroisoindoline-1,3-dione (1.01 g), 10% palladium-carbon (240.1 mg), THF (15 mL) and methanol (15 mL) was stirred under hydrogen atmosphere (1 atm) at room temperature for 40 minutes. The reaction mixture was filtered, and the solvent in the filtrate was distilled off under reduced pressure to obtain the title compound as a crude product (908 mg). This compound was used in the next step without being further purified.

$^1$H NMR (300 MHz, DMSO-d$_6$) δ 3.36 (3H, s), 3.68 (2H, t, J=13.3 Hz), 3.98 (2H, t, J=15.3 Hz), 6.54 (2H, s), 6.82 (1H, dd, J=8.2, 2.0 Hz), 6.95 (1H, d, J=2.1 Hz), 7.52 (1H, d, J=8.1 Hz).

(H) 2-(2,2-Difluoro-3-methoxypropyl)isoindolin-5-amine

To a mixture of LAH (642.7 mg) and THF (30 mL), crude 5-amino-2-(2,2-difluoro-3-methoxypropyl)isoindoline-1,3-dione (908 mg) was added under nitrogen atmosphere at room temperature, and the resulting mixture was stirred at 50° C. for 1 hour. LAH (292.5 mg) was added to the reaction mixture at room temperature, and the mixture was heated at reflux for 1 hour. Water (0.936 mL), a 4 N aqueous sodium hydroxide solution (0.936 mL) and water (2.81 mL) were added to the reaction mixture at 0° C., and the reaction mixture was filtered. The solvent in the filtrate was distilled off under reduced pressure, and the residue was purified by silica gel column chromatography (NH, ethyl acetate/hexane) to obtain the title compound (420 mg).

MS: [M+H]$^+$ 242.9.

(I) (2E)-N-(2-(2,2-Difluoro-3-methoxypropyl)-2,3-dihydro-1H-isoindol-5-yl)-3-(5-fluoro-4-(1-methyl-1H-pyrazol-4-yl)pyridin-3-yl)acrylamide HATU (118 mg) was added to a mixture of (2E)-3-(5-fluoro-4-(1-methyl-1H-pyrazol-4-yl)pyridin-3-yl)acrylic acid dihydrochloride (53.8 mg), 2-(2,2-difluoro-3-methoxypropyl)isoindolin-5-amine (40.5 mg), DIEA (0.117 mL) and DMF (1 mL) at room temperature, and the resulting mixture was stirred overnight under nitrogen atmosphere at the same temperature. The solvent was distilled off under reduced pressure, and the residue was purified by silica gel column chromatography (NH, ethyl acetate/hexane) to obtain the title compound (28.7 mg).

1H NMR (300 MHz, DMSO-d6) δ 3.17 (2H, t, J=14.7 Hz), 3.38 (3H, s), 3.70 (2H, t, J=13.6 Hz), 3.96 (3H, s), 3.98 (2H, brs), 4.01 (2H, s), 6.90 (1H, d, J=15.8 Hz), 7.20 (1H, d, J=8.3 Hz), 7.48 (1H, d, J=8.1 Hz), 7.55-7.73 (3H, m), 8.11 (1H, d, J=1.5 Hz), 8.62 (1H, d, J=1.7 Hz), 8.69 (1H, s), 10.32 (1H, s).

Example 358

(2E)-N-(4-((3,3-Difluoroazetidin-1-yl)methyl)phenyl)-3-(5-fluoro-4-(1-methyl-1H-benzimidazol-6-yl)pyridin-3-yl)acrylamide (A) (2E)-3-(5-Fluoro-4-(1-methyl-1H-benz[d]imidazol-6-yl)pyridin-3-yl)acrylic acid dihydrochloride A mixture of (2E)-tert-butyl 3-(4-chloro-5-fluoropyridin-3-yl)acrylate (519.9 mg), 1-methyl-6-(4,4,5,5-tetramethyl-1,3,2-dioxaborolan-2-yl)-1H-benz[d]imidazole (779.5 mg), 2-(dicyclohexylphosphino)biphenyl (88 mg), Pd$_2$(dba)$_3$ (122 mg), 2 M aqueous cesium carbonate solution (2.5 mL) and DME (15 mL) was stirred under nitrogen atmosphere at 80° C. for 16 hours. The reaction mixture was diluted with ethyl acetate (50 mL) and water (50 mL), and the aqueous layer was extracted with ethyl acetate. The extract was washed with brine and then dried over anhydrous sodium sulfate, and the solvent was distilled off under reduced pressure. The residue was purified by silica gel column chromatography (NH, ethyl acetate/hexane) to obtain a solid (765 mg). A mixture of the obtained solid (whole amount) and TFA (10 mL) was stirred at room temperature for 1 hour. The reaction mixture was concentrated under reduced pressure, and a 4 M solution of hydrogen chloride in ethyl acetate (15 mL) was added to the residue. The precipitate was collected by filtration and washed with ethyl acetate to obtain the title compound (740 mg).

MS: [M+H]$^+$ 298.2.

(B) (2E)-N-(4-((3,3-Difluoroazetidin-1-yl)methyl)phenyl)-3-(5-fluoro-4-(1-methyl-1H-benzimidazol-6-yl)pyridin-3-yl)acrylamide To a solution of (2E)-3-(5-fluoro-4-(1-methyl-1H-benz[d]imidazol-6-yl)pyridin-3-yl)acrylic acid dihydrochloride (111 mg) in DMF (4 mL), 4-((3,3-difluoroazetidin-1-yl)methyl)aniline (72 mg), HATU (137 mg) and DIEA (0.233 mL) were added at room temperature, and the mixture was stirred at the same temperature for 16 hours. The solvent was distilled off under reduced pressure, and the residue was purified by silica gel column chromatography (NH, ethyl acetate/hexane), and the obtained solid was washed with ethyl acetate and then collected by filtration to obtain the title compound (85 mg).

$^1$H NMR (300 MHz, DMSO-$d_6$) δ 3.55 (4H, t, J=12.5 Hz), 3.64 (2H, s), 3.87 (3H, s), 6.94 (1H, d, J=15.8 Hz), 7.15-7.30 (4H, m), 7.58 (2H, d, J=8.6 Hz), 7.67 (1H, s), 7.82 (1H, d, J=8.3 Hz), 8.34 (1H, s), 8.71 (1H, d, J=0.8 Hz), 8.87 (1H, s), 10.30 (1H, s).

Example 359

(2E)-N-(4-((3,3-Difluoroazetidin-1-yl)methyl)phenyl)-3-(5-fluoro-4-(1-methyl-1H-pyrazol-4-yl)pyridin-3-yl)acrylamide (A) 4-Chloro-5-fluoronicotinaldehyde To a solution of diisopropylamine (9.23 g) in THF (125 mL), a 1.6 M solution of n-butyllithium in hexane (57 mL) was added dropwise over 35 minutes under nitrogen atmosphere at −30° C., and the mixture was stirred at the same temperature for 15 minutes. The reaction mixture was cooled to −78° C., a solution of 4-chloro-3-fluoropyridine (10.025 g) in THF (25 mL) was added dropwise thereto over 40 minutes under nitrogen atmosphere, and the mixture was stirred at the same temperature for 5.5 hours. DMF (7.2 mL) was added dropwise to the reaction mixture at −78° C., and the mixture was heated up to room temperature over 30 minutes and stirred under nitrogen atmosphere at the same temperature for 30 minutes. Water (100 mL) and acetic acid (10 mL) were added to the reaction mixture at room temperature, and the mixture was stirred at the same temperature for 15 minutes. The aqueous layer was extracted with ethyl acetate. The extract was washed with brine and then dried over anhydrous sodium sulfate, and the solvent was distilled off under reduced pressure to obtain the title compound as a crude product (13.6 g). This compound was used in the next step without being further purified.

$^1$H NMR (300 MHz, CDCl$_3$) δ 8.70 (1H, s), 8.88 (1H, s), 10.47 (1H, s).

(B) (2E)-tert-Butyl 3-(4-chloro-5-fluoropyridin-3-yl)acrylate

To a mixture of 60% sodium hydride (3.55 g) and THF (100 mL), a solution of tert-butyl 2-(diethoxyphosphoryl)acetate (20.7 g) in THF (20 mL) was added under ice cooling, and the resulting mixture was stirred at the same temperature for 50 minutes. A mixture of crude 4-chloro-5-fluoronicotinaldehyde (whole amount) and THF (50 mL) was added to the reaction mixture under ice cooling, and the resulting mixture was stirred at room temperature for 1.5 hours. Saturated aqueous ammonium chloride solution was added to the reaction mixture at 0° C., and the aqueous layer was extracted with ethyl acetate. The extract was washed with brine and then dried over anhydrous magnesium sulfate, and the solvent was distilled off under reduced pressure. The residue was purified by silica gel column chromatography (ethyl acetate/hexane) to obtain the title compound (13.42 g).

MS: [M+H]$^+$ 258.1.

(C) (2E)-tert-Butyl 3-(5-fluoro-4-(1-methyl-1H-pyrazol-4-yl)pyridin-3-yl)acrylate A mixture of (2E)-tert-butyl 3-(4-chloro-5-fluoropyridin-3-yl)acrylate (1.995 g), 1-methyl-4-(4,4,5,5-tetramethyl-1,3,2-dioxaborolan-2-yl)-1H-pyrazole (2.094 g), 2-(dicyclohexylphosphino)biphenyl (327 mg), Pd$_2$(dba)$_3$ (561 mg), a 2 M aqueous cesium carbonate solution (9.7 mL) and DME (40 mL) was stirred overnight under nitrogen atmosphere at 85° C. The reaction mixture was filtered through Celite, and the solvent was distilled off under reduced pressure. The residue was purified by silica gel column chromatography (NH, ethyl acetate/hexane) to obtain the title compound (2.18 g).

MS: [M+H]$^+$ 304.0.

(D) (2E)-3-(5-Fluoro-4-(1-methyl-1H-pyrazol-4-yl)pyridin-3-yl)acrylic acid dihydrochloride To (2E)-tert-butyl 3-(5-fluoro-4-(1-methyl-1H-pyrazol-4-yl)pyridin-3-yl)acrylate (2.18 g), trifluoroacetic acid (20 mL) was added at room temperature, and the mixture was stirred at the same temperature for 30 minutes. The solvent was distilled off under reduced pressure, ethyl acetate (5 mL) and a 4 N solution of hydrogen chloride in ethyl acetate (20 mL) were added to the residue at room temperature, and the mixture was stirred at the same temperature for 5 minutes. The precipitate was collected by filtration and washed with ethyl acetate to obtain the title compound (2.12 g).

MS: [M+H]$^+$ 247.9.

(E) (2E)-N-(4-((3,3-Difluoroazetidin-1-yl)methyl)phenyl)-3-(5-fluoro-4-(1-methyl-1H-pyrazol-4-yl)pyridin-3-yl)acrylamide HATU (1.489 g) was added to a mixture of (2E)-3-(5-fluoro-4-(1-methyl-1H-pyrazol-4-yl)pyridin-3-yl)acrylic acid dihydrochloride (1.06 g), 4-((3,3-difluoroazetidin-1-yl)methyl)aniline (648 mg), DIEA (2.57 mL) and DMF (10 mL) at room temperature, and the resulting mixture was stirred under nitrogen atmosphere at the same temperature for 3 hours. The solvent was distilled off under reduced pressure, and the residue was purified by silica gel column chromatography (NH, ethyl acetate/hexane), washed with IPE, and then collected by filtration to obtain the title compound as a crude product (1.108 g). The obtained crude product (whole amount) was dissolved in ethyl acetate (25 mL) at 80° C. To the solution, hexane (50 mL) was added dropwise at the same temperature. The mixture was stirred at the same temperature for 15 minutes and then stirred overnight at room temperature. The precipitate was collected by filtration, washed with ethyl acetate/hexane (1/2), and then dried under reduced pressure at 50° C. to obtain the title compound (922.4 mg).

$^1$H NMR (300 MHz, DMSO-$d_6$) δ 3.57 (4H, t, J=12.4 Hz), 3.67 (2H, s), 3.96 (3H, s), 6.90 (1H, d, J=15.6 Hz), 7.27 (2H, d, J=8.5 Hz), 7.55-7.74 (4H, m), 8.11 (1H, d, J=1.3 Hz), 8.62 (1H, d, J=1.7 Hz), 8.70 (1H, s), 10.34 (1H, s).

Example 362

(2E)-3-(4-(1-Cyclopropyl-1H-pyrazol-4-yl)pyridin-3-yl)-N-(4-(3,3-difluoroazetidin-1-yl)phenyl)acrylamide (A) 4-(3,3-Difluoroazetidin-1-yl)aniline 1-Fluoro-4-nitrobenzene (310.3 mg), 3,3-difluoroazetidine hydrochloride (326 mg), DIEA (1.149 mL) and acetonitrile (1.9 mL) were stirred at 130° C. for 30 minutes under microwave irradiation. Water was added to the reaction mixture at room temperature, and the aqueous layer was extracted with ethyl acetate. The extract was washed with water and brine and then dried over anhydrous magnesium sulfate, and the solvent was distilled off under reduced pressure. A mixture of the obtained residue, 10% palladium-carbon (228.9 mg), THF (1 mL) and methanol (3 mL) was stirred under hydrogen atmosphere (1 atm) at room temperature for 30 minutes. The reaction mixture was filtered. The solvent in the filtrate was distilled off under reduced pressure, and the residue was purified by silica gel column chromatography (ethyl acetate/hexane) to obtain the title compound (329 mg).
MS: [M+H]$^+$ 184.9.

(B) (2E)-3-(4-(1-Cyclopropyl-1H-pyrazol-4-yl)pyridin-3-yl)-N-(4-(3,3-difluoroazetidin-1-yl)phenyl)acrylamide HATU (89 mg) was added to a mixture of (2E)-3-(4-(1-cyclopropyl-1H-pyrazol-4-yl)pyridin-3-yl)acrylic acid (40 mg), 4-(3,3-difluoroazetidin-1-yl)aniline (28.9 mg), DIEA (0.082 mL) and DMF (1 mL) at room temperature, and the resulting mixture was stirred under nitrogen atmosphere at the same temperature for 3 days. The solvent was distilled off under reduced pressure, and the residue was purified by silica gel column chromatography (NH, ethyl acetate/hexane). The obtained solid was washed with IPE to obtain the title compound (46.5 mg).
$^1$H NMR (300 MHz, DMSO-d$_6$) δ 0.96-1.07 (2H, m), 1.09-1.18 (2H, m), 3.76-3.94 (1H, m), 4.24 (4H, t, J=12.3 Hz), 6.57 (2H, d, J=8.9 Hz), 6.81 (1H, d, J=15.6 Hz), 7.50 (1H, d, J=5.3 Hz), 7.59 (2H, d, J=8.9 Hz), 7.66-7.76 (2H, m), 8.18 (1H, s), 8.52 (1H, d, J=5.3 Hz), 8.76 (1H, s), 10.13 (1H, s).

Example 365

(2E)-3-(4-(1-Cyclopropyl-1H-pyrazol-4-yl)pyridin-3-yl)-N-(4-((3-fluoroazetidin-1-yl)methyl)phenyl)acrylamide (A) (2E)-3-(4-(1-Cyclopropyl-1H-pyrazol-4-yl)pyridin-3-yl)-N-(4-(hydroxymethyl)phenyl)acrylamide DIEA (1.8 mL) was added to a mixture of (2E)-3-(4-(1-cyclopropyl-1H-pyrazol-4-yl)pyridin-3-yl)acrylic acid (615 mg), (4-aminophenyl)methanol (315 mg), HATU (1.44 g) and DMF (8 mL) at room temperature, and the resulting mixture was stirred at the same temperature for 16 hours. Water was added to the reaction mixture, followed by extraction with a mixed ethyl acetate/THF solution. The organic layer was dried over anhydrous magnesium sulfate, and the solvent was distilled off under reduced pressure. The residue was purified by silica gel column chromatography (NH, methanol/ethyl acetate) to obtain the title compound (350 mg). Fractions containing impurities were recovered by the aforementioned purification operation and purified by silica gel column chromatography (NH, methanol/ethyl acetate) to obtain the title compound (215 mg).
MS: [M+H]$^+$ 361.3.

(B) (2E)-3-(4-(1-Cyclopropyl-1H-pyrazol-4-yl)pyridin-3-yl)-N-(4-formylphenyl)acrylamide Manganese dioxide (2.01 g) was added to a mixture of (2E)-3-(4-(1-cyclopropyl-1H-pyrazol-4-yl)pyridin-3-yl)-N-(4-(hydroxymethyl)phenyl)acrylamide (565 mg) and ethyl acetate (40 mL) at room temperature, and the resulting mixture was stirred at 85° C. for 24 hours. The reaction mixture was filtered through Celite, and the filtrate was concentrated under reduced pressure. Then, the obtained solid was washed with ethyl acetate to obtain the title compound (283 mg).
MS: [M+H]$^+$ 359.0.

(C) (2E)-3-(4-(1-Cyclopropyl-1H-pyrazol-4-yl)pyridin-3-yl)-N-(4-((3-fluoroazetidin-1-yl)methyl)phenyl)acrylamide 3-Fluoroazetidine hydrochloride (38 mg) was added to a mixture of (2E)-3-(4-(1-cyclopropyl-1H-pyrazol-4-yl)pyridin-3-yl)-N-(4-formylphenyl)acrylamide (95 mg), methanol (5 mL) and acetic acid (0.5 mL) at room temperature, and the resulting mixture was stirred at the same temperature for 30 minutes. To the reaction mixture was added 2-picolineborane complex (45 mg), and the mixture was stirred at room temperature for 16 hours. The reaction mixture was concentrated under reduced pressure, and saturated aqueous potassium carbonate solution was added to the residue, followed by extraction with ethyl acetate. The organic layer was dried over anhydrous magnesium sulfate, and the solvent was distilled off under reduced pressure. The residue was purified by silica gel column chromatography (NH, ethyl acetate/hexane) to obtain the title compound (47 mg).
$^1$H NMR (300 MHz, DMSO-d$_6$) δ 0.97-1.15 (4H, m), 3.03-3.19 (2H, m), 3.45-3.60 (4H, m), 3.79-3.89 (1H, m), 5.01-5.32 (1H, m), 6.79-6.91 (1H, m), 7.18-7.32 (2H, m), 7.46-7.56 (1H, m), 7.60-7.79 (4H, m), 8.19 (1H, s), 8.47-8.60 (1H, m), 8.75 (1H, s), 10.25 (1H, s).

Example 373

(2E)-3-(4-(1-Cyclopropyl-1H-pyrazol-4-yl)pyridin-3-yl)-N-(4-((3,3-difluoroazetidin-1-yl)methyl)phenyl)acrylamide sulfate To a solution of (2E)-3-(4-(1-cyclopropyl-1H-pyrazol-4-yl)pyridin-3-yl)-N-(4-((3,3-difluoroazetidin-1-yl)methyl)phenyl)acrylamide (642 mg) in dimethyl sulfoxide (10 mL), 1 M aqueous sulfuric acid solution (1.62 mL) was added at room temperature, and the mixture was stirred at the same temperature for 15 minutes. Ethyl acetate (5 mL) was added to the reaction mixture, and the mixture was stirred at the same temperature for 15 minutes. Then, ethyl acetate (5 mL) was added to the reaction mixture, and the mixture was stirred at the same temperature for 18 hours. The precipitate was collected by filtration and washed with ethyl acetate to obtain a crude product. A mixture of the obtained crude product and ethyl acetate (20 mL) was stirred at room temperature for 2 hours, and the precipitate was collected by filtration, washed with ethyl acetate, and then dried under reduced pressure at 50° C. to obtain the title compound (594 mg).
$^1$H NMR (300 MHz, DMSO-d$_6$) δ 1.00-1.17 (4H, m), 3.83-3.91 (1H, m), 4.37 (2H, brs), 4.49-4.85 (4H, m), 6.90 (1H, d, J=15.6 Hz), 7.48 (2H, d, J=5.6 Hz), 7.67-7.81 (5H, m), 8.29 (1H, s), 8.61 (1H, d, J=5.5 Hz), 8.85 (1H, s), 10.49 (1H, s).

Example 374

(2E)-3-(4-(1-Cyclopropyl-1H-pyrazol-4-yl)pyridin-3-yl)-N-(4-((3,3-difluoroazetidin-1-yl)methyl)phenyl)acrylamide diphosphate To a solution of (2E)-3-(4-(1-cyclopropyl-1H-pyrazol-4-yl)pyridin-3-yl)-N-(4-((3,3-difluoroazetidin-1-yl)methyl)

phenyl)acrylamide (50 mg) in 2-butanone (2 mL), 1 M aqueous phosphoric acid solution (0.13 mL) was added at room temperature, and the mixture was stirred at the same temperature for 5 hours. The precipitate was collected by filtration to obtain the title compound (28 mg).

$^1$H NMR (300 MHz, DMSO-d$_6$) δ 0.99-1.15 (4H, m), 3.52-3.62 (4H, m), 3.67-3.69 (2H, m), 3.84-3.88 (1H, m), 6.79-6.90 (1H, m), 7.22-7.31 (2H, m), 7.47-7.55 (1H, m), 7.63-7.78 (4H, m), 8.16-8.21 (1H, m), 8.48-8.56 (1H, m), 8.71-8.79 (1H, m), 10.30 (1H, s).

Example 375

(2E)-3-(4-(1-Cyclopropyl-1H-pyrazol-4-yl)pyridin-3-yl)-N-(4-((3,3-difluoroazetidin-1-yl)methyl)phenyl)acrylamide methanesulfonate To a solution of (2E)-3-(4-(1-cyclopropyl-1H-pyrazol-4-yl)pyridin-3-yl)-N-(4-((3,3-difluoroazetidin-1-yl)methyl)phenyl)acrylamide (101 mg) in 2-butanone (4 mL), methanesulfonic acid (0.017 mL) was added at room temperature. Ethanol (2.5 mL) was added to the reaction mixture at room temperature, subsequently heptane (2 mL) was gradually added dropwise to the mixture at the same temperature, and the resulting mixture was stirred at the same temperature for 18 hours. The precipitate was collected by filtration and dried under reduced pressure at 50° C. to obtain the title compound (104 mg).

$^1$H NMR (300 MHz, DMSO-d$_6$) δ 1.00-1.16 (4H, m), 2.33 (3H, s), 3.79-3.93 (1H, m), 4.35 (2H, brs), 4.57 (4H, brs), 6.91 (1H, d, J=15.7 Hz), 7.47 (2H, d, J=5.5 Hz), 7.66-7.80 (5H, m), 8.28 (1H, s), 8.61 (1H, d, J=5.4 Hz), 8.85 (1H, s), 10.50 (1H, s).

Example 376

(2E)-3-(4-(1-Cyclopropyl-1H-pyrazol-4-yl)pyridin-3-yl)-N-(4-((3,3-difluoroazetidin-1-yl)methyl)phenyl)acrylamide hemifumarate To a solution of fumaric acid (19.99 g) in THF/methanol (20/1, 1350 mL), (2E)-3-(4-(1-cyclopropyl-1H-pyrazol-4-yl)pyridin-3-yl)-N-(4-((3,3-difluoroazetidin-1-yl)methyl)phenyl)acrylamide (150 g) and THF/methanol (20/1, 150 mL) were added at 50° C., and the mixture was stirred at the same temperature for 10 minutes. Heptane (600 mL) was gradually added dropwise to the reaction mixture at the same temperature, and the mixture was stirred at the same temperature for 30 minutes. Heptane (2400 mL) was gradually added dropwise to the reaction mixture at the same temperature, and the mixture was stirred at the same temperature for 30 minutes. Then, the reaction mixture was cooled to room temperature and stirred overnight at room temperature. The reaction mixture was ice-cooled, and the precipitate was collected by filtration, washed with heptane/THF (5/1, 900 mL), and then dried under reduced pressure at room temperature to obtain the title compound (164.7 g).

$^1$H NMR (300 MHz, DMSO-d$_6$) δ 0.98-1.07 (2H, m), 1.07-1.15 (2H, m), 3.57 (4H, t, J=12.5 Hz), 3.67 (2H, s), 3.80-3.89 (1H, m), 6.62 (1H, s), 6.85 (1H, d, J=15.5 Hz), 7.27 (2H, d, J=5.1 Hz), 7.51 (1H, d, J=4.9 Hz), 7.64-7.76 (4H, m), 8.18 (1H, s), 8.53 (1H, d, J=5.3 Hz), 8.78 (1H, s), 10.29 (1H, s), 13.13 (1H, brs).

Example 377

(2E)-3-(4-(1-Cyclopropyl-1H-pyrazol-4-yl)pyridin-3-yl)-N-(4-((3,3-difluoroazetidin-1-yl)methyl)phenyl)acrylamide hemisuccinate To a solution of (2E)-3-(4-(1-cyclopropyl-1H-pyrazol-4-yl)pyridin-3-yl)-N-(4-((3,3-difluoroazetidin-1-yl)methyl)phenyl)acrylamide (303 mg) in ethanol (3.5 mL), succinic acid (46 mg) was added at 75° C., and the mixture was stirred at the same temperature for 15 minutes. Heptane (33 mL) was gradually added dropwise to the reaction mixture at the same temperature, and the mixture was stirred at the same temperature for 30 minutes. The reaction mixture was cooled to room temperature and stirred at room temperature for 1 hour. The precipitate was collected by filtration and dried under reduced pressure at 60° C. to obtain the title compound (309 mg).

$^1$H NMR (300 MHz, DMSO-d$_6$) δ 0.98-1.15 (4H, m), 2.41 (2H, s), 3.51-3.69 (6H, m), 3.85 (1H, tt, J=7.4, 3.8 Hz), 6.85 (1H, d, J=15.7 Hz), 7.27 (2H, d, J=8.6 Hz), 7.50 (1H, d, J=5.1 Hz), 7.63-7.76 (4H, m), 8.18 (1H, s), 8.53 (1H, d, J=5.2 Hz), 8.78 (1H, s), 10.28 (1H, s), 12.25 (1H, brs).

Example 380

2-(4-(1-Methyl-1H-pyrazol-4-yl)pyridin-3-yl)-N-(4-(morpholin-4-ylmethyl)phenyl)cyclopropanecarboxamide 60% sodium hydride (238 mg) was added to a mixture of trimethylsulfoxonium iodide (1.2 g) and DMSO (5 mL) at room temperature, and the resulting mixture was stirred at the same temperature for 1 hour. A mixture of (2E)-3-(4-(1-methyl-1H-pyrazol-4-yl)pyridin-3-yl)-N-(4-(morpholin-4-ylmethyl)phenyl)acrylamide (800 mg) and DMSO (5 mL) was added to the reaction mixture at room temperature, and the reaction mixture was stirred at the same temperature for 16 hours. Saturated aqueous ammonium chloride solution was added to the reaction mixture under ice cooling, followed by extraction with ethyl acetate. The organic layer was washed with brine and then dried over anhydrous magnesium sulfate, and the solvent was distilled off under reduced pressure. The residue was purified by preparative HPLC and preparative thin-layer chromatography to obtain the title compound (25 mg).

$^1$H NMR (300 MHz, DMSO-d$_6$) δ 1.24 (1H, brs), 1.38-1.59 (2H, m), 1.97-2.11 (1H, m), 2.33 (4H, brs), 3.40 (2H, s), 3.52-3.62 (4H, m), 3.77 (3H, s), 7.24 (2H, d, J=8.4 Hz), 7.47 (1H, d, J=5.1 Hz), 7.56 (2H, d, J=8.4 Hz), 7.85 (1H, s), 8.11 (1H, s), 8.31-8.49 (2H, m), 10.23 (1H, s).

The compounds of Examples 2, 4, 6 to 30, 33 to 36, 38, 39, 43, 46 to 48, 50 to 58, 60 to 90, 93 to 96, 100, 101, 103 to 108, 110 to 144, 146, 151 to 174, 176 to 193, 195 to 202, 206 to 208, 210 to 213, 220, 222, 225 to 227, 231, 232, 234 to 243, 245, 246, 249, 252 to 259, 261 to 264, 267, 268, 270 to 272, 274, 276 to 282, 284 to 287, 290, 293 to 301, 303 to 305, 307, 308, 310 to 315, 317, 318, 320 to 323, 325, 326, 329, 331, 334, 335, 337 to 342, 344, 346, 347, 349 to 351, 353 to 357, 360, 361, 363, 364, 366 to 372, 378, 379 and 381 were produced according to the methods shown in the Examples above or methods equivalent thereto.

The compounds of the Examples are shown in the following tables. In these tables, MS represents actually measured values (found).

TABLE 1-1

| Example No. | IUPAC name | Structural formula | Salt | MS |
|---|---|---|---|---|
| 1 | (2E)-N-(4-(2-(1,3,4-oxadiazol-2-yl)ethyl)phenyl)-3-(4-(2-thienyl)pyridin-3-yl)acrylamide | | | 403.0 |
| 2 | (2E)-3-(4-(2-furyl)pyridin-3-yl)-N-(4-(2-(1,3,4-oxadiazol-2-yl)ethyl)phenyl)acrylamide | | | 387.1 |
| 3 | (2E)-N-(4-(2-(1,3,4-oxadiazol-2-yl)ethyl)phenyl)-3-(4-(1H-pyrrol-2-yl)pyridin-3-yl)acrylamide | | | 386.0 |
| 4 | (2E)-3-(4-(1-isobutyl-1H-pyrazol-yl)pyridin-3-yl)-N-(4-(2-(1,3,4-oxadiazol-2-yl)ethyl)phenyl)acrylamide | | | 443.2 |
| 5 | (2E)-3-(4-(5-cyano-2-thienyl)pyridin-3-yl)-N-(4-(2-(1,3,4-oxadiazol-2-yl)ethyl)phenyl)acrylamide | | | 428.1 |
| 6 | (2E)-3-(4-(1-methyl-1H-pyrazol-3-yl)pyridin-3-yl)-N-(4-(2-(1,3,4-oxadiazol-2-yl)ethyl)phenyl)acrylamide | | | 401.1 |

TABLE 1-1-continued

| Example No. | IUPAC name | Structural formula | Salt | MS |
|---|---|---|---|---|
| 7 | (2E)-N-(4-(2-(1,3,4-oxadiazol-2-yl)ethyl)phenyl)-3-(4-(1H-pyrazol-4-yl)pyridin-3-yl)acrylamide | | | 387.1 |
| 8 | (2E)-3-(4-(1-methyl-1H-pyrazol-5-yl)pyridin-3-yl)-N-(4-(2-(1,3,4-oxadiazol-2-yl)ethyl)phenyl)acrylamide | | | 401.1 |
| 9 | (2E)-N-(4-(2-(1,3,4-oxadiazol-2-yl)ethyl)phenyl)-3-(4-(1H-pyrazol-3-yl)pyridin-3-yl)acrylamide | | | 387.1 |

TABLE 1-2

| Example No. | IUPAC name | Structural formula | Salt | MS |
|---|---|---|---|---|
| 10 | (2E)-3-(4-(2,4-dimethyl-1,3-thiazol-5-yl)pyridin-3-yl)-N-(4-(2-(1,3,4-oxadiazol-2-yl)ethyl)phenyl)acrylamide | | | 432.0 |
| 11 | (2E)-3-(4-(1-(2-(morpholin-4-yl)ethyl)-1H-pyrazol-4-yl)pyridin-3-yl)-N-(4-(2-(1,3,4-oxadiazol-2-yl)ethyl)phenyl)acrylamide | | | 500.2 |

TABLE 1-2-continued

| Example No. | IUPAC name | Structural formula | Salt | MS |
|---|---|---|---|---|
| 12 | ethyl(4-(3-((1E)-3-((4-(2-(1,3,4-oxadiazol-2-yl)ethyl)phenyl)amino)-3-oxoprop-1-en-1-yl)pyridin-4-yl)-1H-pyrazol-1-yl)acetate | | | 473.2 |
| 13 | (2E)-N-(4-(2-(1,3,4-oxadiazol-2-yl)ethyl)phenyl)-3-(4-(1-(pyridin-3-ylmethyl)-1H-pyrazol-4-yl)pyridin-3-yl)acrylamide | | | 478.1 |
| 14 | (2E)-N-(4-(2-(1,3,4-oxadiazol-2-yl)ethyl)phenyl)-3-(4-(1-(pyridin-2-ylmethyl)-1H-pyrazol-4-yl)pyridin-3-yl)acrylamide | | | 478.1 |
| 15 | ethyl 4-(3-((1E)-3-((4-(2-(1,3,4-oxadiazol-2-yl)ethyl)phenyl)amino)-3-oxoprop-1-en-1-yl)pyridin-4-yl)thiophene-2-carboxylate | | | 472.9 |

TABLE 1-2-continued

| Example No. | IUPAC name | Structural formula | Salt | MS |
|---|---|---|---|---|
| 16 | (2E)-3-(4-(3-methoxy-2-thienyl)pyridin-3-yl)-N-(4-(2-(1,3,4-oxadiazol-2-yl)ethyl)phenyl)acrylamide | | | 433.1 |

TABLE 1-3

| Example No. | IUPAC name | Structural formula | Salt | MS |
|---|---|---|---|---|
| 17 | (2E)-3-(4-(1-ethyl-1H-pyrazol-4-yl)pyridin-3-yl)-N-(4-(2-(1,3,4-oxadiazol-2-yl)ethyl)phenyl)acrylamide | | | 415.1 |
| 18 | (2E)-3-(4-(1,5-dimethyl-1H-pyrazol-4-yl)pyridin-3-yl)-N-(4-(2-(1,3,4-oxadiazol-2-yl)ethyl)phenyl)acrylamide | | | 415.1 |
| 19 | (2E)-3-(4-(1,3-dimethyl-1H-pyrazol-4-yl)pyridin-3-yl)-N-(4-(2-(1,3,4-oxadiazol-2-yl)ethyl)phenyl)acrylamide | | | 415.1 |
| 20 | (2E)-N-(4-(2-(1,3,4-oxadiazol-2-yl)ethyl)phenyl)-3-(4-(pyrazolo[1,5-a]pyridin-3-yl)pyridin-3-yl)acrylamide | | | 437.1 |

TABLE 1-3-continued

| Example No. | IUPAC name | Structural formula | Salt | MS |
|---|---|---|---|---|
| 21 | (2E)-N-(4-(2-(1,3,4-oxadiazol-2-yl)ethyl)phenyl)-3-(4-(1-(piperidin-4-yl)-1H-pyrazol-4-yl)pyridin-3-yl)acrylamide | | | 470.1 |
| 22 | (2E)-3-(4-(5-(morpholin-4-ylmethyl)-3-thienyl)pyridin-3-yl)-N-(4-(2-(1,3,4-oxadiazol-2-yl)ethyl)phenyl)acrylamide | | | 502.1 |
| 23 | (2E)-N-(4-(2-(1,3,4-oxadiazol-2-yl)ethyl)phenyl)-3-(4-(1-(tetrahydro-2H-pyran-4-yl)-1H-pyrazol-4-yl)pyridin-3-yl)acrylamide | | | 471.2 |

TABLE 1-4

| Example No. | IUPAC name | Structural formula | Salt | MS |
|---|---|---|---|---|
| 24 | (2E)-3-(4-(1-(2-hydroxyethyl)-1H-pyrazol-4-yl)pyridin-3-yl)-N-(4-(2-(1,3,4-oxadiazol-2-yl)ethyl)phenyl)acrylamide | | | 431.1 |

TABLE 1-4-continued

| Example No. | IUPAC name | Structural formula | Salt | MS |
|---|---|---|---|---|
| 25 | (2E)-3-(4-(1-(cyclopropylmethyl)-1H-pyrazol-4-yl)pyridin-3-yl)-N-(4-(2-(1,3,4-oxadiazol-2-yl)ethyl)phenyl)acrylamide | | | 441.1 |
| 26 | (2E)-3-(4-(1-isopropyl-1H-pyrazol-4-yl)pyridin-3-yl)-N-(4-(2-(1,3,4-oxadiazol-2-yl)ethyl)phenyl)acrylamide | | | 429.1 |
| 27 | (2E)-3-(4-(1-tert-butyl-1H-pyrazol-4-yl)pyridin-3-yl)-N-(4-(2-(1,3,4-oxadiazol-2-yl)ethyl)phenyl)acrylamide | | | 443.2 |
| 28 | (2E)-3-(4-(5-(aminomethyl)-2-furyl)pyridin-3-yl)-N-(4-(2-(1,3,4-oxadiazol-2-yl)ethyl)phenyl)acrylamide | | | 416.0 |
| 29 | (2E)-3-(4-(1-methyl-1H-pyrazol-4-yl)pyridin-3-yl)-N-(4-((methylsulfonyl)methyl)phenyl)acrylamide | | | 397.1 |

TABLE 1-4-continued

| Example No. | IUPAC name | Structural formula | Salt | MS |
|---|---|---|---|---|
| 30 | (2E)-N-(4-((2,4-dioxo-1,3-thiazolidin-5-yl)methyl)phenyl)-3-(4-(1-methyl-1H-pyrazol-4-yl)pyridin-3-yl)acrylamide | | | 434.0 |
| 31 | (2E)-3-(4-(1-methyl-1H-pyrazol-4-yl)pyridin-3-yl)-N-(4-(morpholin-4-ylmethyl)phenyl)acrylamide | | | 404.2 |

TABLE 1-5

| Example No. | IUPAC name | Structural formula | Salt | MS |
|---|---|---|---|---|
| 32 | (2E)-N-(4-((2,4-dioxo-1,3-thiazolidin-5-yl)methyl)phenyl)-3-(4-(1H-pyrazol-4-yl)pyridin-3-yl)acrylamide | | | 420.1 |
| 33 | (2E)-N-(4-(morpholin-4-ylmethyl)phenyl)-3-(4-(1H-pyrazol-4-yl)pyridin-3-yl)acrylamide | | | 390.1 |
| 34 | (2E)-N-(4-((2,4-dioxo-1,3-thiazolidin-5-yl)methyl)phenyl)-2-methyl-3-(4-(1-methyl-1H-pyrazol-4-yl)pyridin-3-yl)acrylamide | | | 448.1 |

TABLE 1-5-continued

| Example No. | IUPAC name | Structural formula | Salt | MS |
|---|---|---|---|---|
| 35 | (2E)-N-(3-methyl-4-((methylsulfonyl)methyl)phenyl)-3-(4-(1-methyl-1H-pyrazol-4-yl)pyridin-3-yl)acrylamide | | | 411.1 |
| 36 | (2E)-N-(4-(hydroxymethyl)phenyl)-3-(4-(1-methyl-1H-pyrazol-4-yl)pyridin-3-yl)acrylamide | | | 335.1 |
| 37 | (2E)-N-(4-((2,2-dimethylmorpholin-4-yl)methyl)phenyl)-3-(4-(1-methyl-1H-pyrazol-4-yl)pyridin-3-yl)acrylamide | | | 432.2 |
| 38 | (2E)-N-(4-((2,4-dioxo-1,3-oxazolidin-5-yl)methyl)phenyl)-3-(4-(1-methyl-1H-pyrazol-4-yl)pyridin-3-yl)acrylamide | | | 418.1 |
| 39 | (2E)-N-(4-((2,4-dioxo-1,3-thiazolidin-5-yl)methyl)-2-methoxyphenyl)-3-(4-(1-methyl-1H-pyrazol-4-yl)pyridin-3-yl)acrylamide | | | 464.1 |
| 40 | (2E)-3-(4-(1-methyl-1H-pyrazol-4-yl)pyridin-3-yl)-N-(5-(morpholin-4-ylmethyl)pyridin-2-yl)acrylamide | | | 405.1 |

TABLE 1-6

| Example No. | IUPAC name | Structural formula | Salt | MS |
|---|---|---|---|---|
| 41 | (2E)-N-(2-fluoro-4-(morpholin-4-ylmethyl)phenyl)-3-(4-(1-methyl-1H-pyrazol-4-yl)pyridin-3-yl)acrylamide | | | 422.1 |
| 42 | (2E)-N-(3-chloro-4-(morpholin-4-ylmethyl)phenyl)-3-(4-(1-methyl-1H-pyrazol-4-yl)pyridin-3-yl)acrylamide | | | 438.1 |
| 43 | (2E)-3-(4-(1-methyl-1H-pyrazol-4-yl)pyridin-3-yl)-N-(4-(1-(morpholin-4-yl)ethyl)phenyl)acrylamide | | | 416.1 |
| 44 | (2E)-N-(4-(morpholin-4-ylmethyl)phenyl)-3-(4-(1-(2,2,3,3,3-pentafluoropropyl)-1H-pyrazol-4-yl)pyridin-3-yl)acrylamide | | | 522.1 |
| 45 | (2E)-3-(4-(1-(cyclopropylmethyl)-1H-pyrazol-4-yl)pyridin-3-yl)-N-(4-(morpholin-4-ylmethyl)phenyl)acrylamide | | | 444.3 |

TABLE 1-6-continued

| Example No. | IUPAC name | Structural formula | Salt | MS |
|---|---|---|---|---|
| 46 | (2E)-N-(4-(morpholin-4-ylmethyl)phenyl)-3-(4-(1-(2,2,2-trifluoroethyl)-1H-pyrazol-4-yl)pyridin-3-yl)acrylamide | | | 472.1 |
| 47 | (2E)-N-(4-(morpholin-4-ylmethyl)phenyl)-3-(4-(1-(pyridin-2-ylmethyl)-1H-pyrazol-4-yl)pyridin-3-yl)acrylamide | | | 481.2 |
| 48 | (2E)-N-(1H-indazol-6-yl)-3-(4-(1-methyl-1H-pyrazol-4-yl)pyridin-3-yl)acrylamide | | | 345.2 |

TABLE 1-7

| Example No. | IUPAC name | Structural formula | Salt | MS |
|---|---|---|---|---|
| 49 | (2E)-N-(4-((cyclopropylamino)methyl)phenyl)-3-(4-(1-methyl-1H-pyrazol-4-yl)pyridin-3-yl)acrylamide | | | 374.2 |
| 50 | (2E)-3-(4-(1-methyl-1H-pyrazol-4-yl)pyridin-3-yl)-N-(4-(8-oxa-3-azabicyclo[3.2.1]oct-3-ylmethyl)phenyl)acrylamide | | | 430.2 |

TABLE 1-7-continued

| Example No. | IUPAC name | Structural formula | Salt | MS |
|---|---|---|---|---|
| 51 | (2E)-3-(4-(1-methyl-1H-pyrazol-4-yl)pyridin-3-yl)-N-(4-(2-oxa-5-azabicyclo[2.2.1]hept-5-ylmethyl)phenyl)acrylamide | | | 416.1 |
| 52 | (2E)-3-(4-(1-methyl-1H-pyrazol-4-yl)pyridin-3-yl)-N-(4-(((2-(methylsulfonyl)ethyl)amino)methyl)phenyl)acrylamide | | | 440.1 |
| 53 | (2E)-N-(4-(((2R,6S)-2,6-dimethylmorpholin-4-yl)methyl)phenyl)-3-(4-(1-methyl-1H-pyrazol-4-yl)pyridin-3-yl)acrylamide | | | 432.2 |
| 54 | (2E)-N-(4-((3-methylmorpholin-4-yl)methyl)phenyl)-3-(4-(1-methyl-1H-pyrazol-4-yl)pyridin-3-yl)acrylamide | | | 418.2 |
| 55 | (2E)-N-(4-((2-methylmorpholin-4-yl)methyl)phenyl)-3-(4-(1-methyl-1H-pyrazol-4-yl)pyridin-3-yl)acrylamide | | | 418.2 |
| 56 | (2E)-3-(4-(1-methyl-1H-pyrazol-4-yl)pyridin-3-yl)-N-(4-(3-oxa-6-azabicyclo[3.1.1]hept-6-ylmethyl)phenyl)acrylamide | | | 416.2 |

TABLE 1-7-continued

| Example No. | IUPAC name | Structural formula | Salt | MS |
|---|---|---|---|---|
| 57 | (2E)-3-(4-(1-methyl-1H-pyrazol-4-yl)pyridin-3-yl)-N-(4-(3-oxa-8-azabicyclo[3.2.1]oct-8-ylmethyl)phenyl)acrylamide | | | 430.2 |

TABLE 1-8

| Example No. | IUPAC name | Structural formula | Salt | MS |
|---|---|---|---|---|
| 58 | (2E)-3-(4-(1-methyl-1H-pyrazol-4-yl)pyridin-3-yl)-N-(4-((2,2,6,6-tetrafluoromorpholin-4-yl)methyl)phenyl)acrylamide | | | 474.2 |
| 59 | (2E)-3-(4-(1-methyl-1H-pyrazol-4-yl)pyridin-3-yl)-N-(4-(piperazin-1-ylmethyl)phenyl)acrylamide | | | 403.2 |
| 60 | (2E)-N-(4-((4-hydroxypiperidin-1-yl)methyl)phenyl)-3-(4-(1-methyl-1H-pyrazol-4-yl)pyridin-3-yl)acrylamide | | | 418.2 |
| 61 | 1-(4-(((2E)-3-(4-(1-methyl-1H-pyrazol-4-yl)pyridin-3-yl)prop-2-enoyl)amino)benzyl)piperidine-4-carboxylic acid | | | 446.2 |

TABLE 1-8-continued

| Example No. | IUPAC name | Structural formula | Salt | MS |
|---|---|---|---|---|
| 62 | (2E)-3-(4-(1-methyl-1H-pyrazol-4-yl)pyridin-3-yl)-N-(4-((3-oxopiperazin-1-yl)methyl)phenyl)acrylamide | | | 417.1 |
| 63 | (2E)-N-(4-((3-hydroxypyrrolidin-1-yl)methyl)phenyl)-3-(4-(1-methyl-1H-pyrazol-4-yl)pyridin-3-yl)acrylamide | | | 404.2 |
| 64 | (2E)-3-(4-(1-methyl-1H-pyrazol-4-yl)pyridin-3-yl)-N-(4-((tetrahydrofuran-3-ylamino)methyl)phenyl)acrylamide | | | 404.2 |
| 65 | (2E)-3-(4-(1-methyl-1H-pyrazol-4-yl)pyridin-3-yl)-N-(4-((oxetan-3-ylamino)methyl)phenyl)acrylamide | | | 390.1 |
| 66 | (2E)-N-(4-(((2-hydroxyethyl)amino)methyl)phenyl)-3-(4-(1-methyl-1H-pyrazol-4-yl)pyridin-3-yl)acrylamide | | | 378.2 |

TABLE 1-9

| Example No. | IUPAC name | Structural formula | Salt | MS |
|---|---|---|---|---|
| 67 | (2E)-N-(4-(((2-methoxyethyl)amino)methyl)phenyl)-3-(4-(1-methyl-1H-pyrazol-4-yl)pyridin-3-yl)acrylamide | | | 392.2 |
| 68 | (2E)-N-(4-((3,3-difluoropyrrolidin-1-yl)methyl)phenyl)-3-(4-(1-methyl-1H-pyrazol-4-yl)pyridin-3-yl)acrylamide | | | 422.0 |
| 69 | (2E)-N-(4-((3,3-difluoroazetidin-1-yl)methyl)phenyl)-3-(4-(1-methyl-1H-pyrazol-4-yl)pyridin-3-yl)acrylamide | | | 410.1 |
| 70 | 1-(4-(((2E)-3-(4-(1-methyl-1H-pyrazol-4-yl)pyridin-3-yl)prop-2-enoyl)amino)benzyl)piperidine-3-carboxylic acid | | | 446.1 |
| 71 | (2E)-N-(4-(((2-acetamidoethyl)amino)methyl)phenyl)-3-(4-(1-methyl-1H-pyrazol-4-yl)pyridin-3-yl)acrylamide | | | 419.1 |
| 72 | 1-(4-(((2E)-3-(4-(1-methyl-1H-pyrazol-4-yl)pyridin-3-yl)prop-2-enoyl)amino)benzyl)piperidine-4-carboxamide | | | 445.2 |

TABLE 1-9-continued

| Example No. | IUPAC name | Structural formula | Salt | MS |
|---|---|---|---|---|
| 73 | (2E)-3-(4-(1-methyl-1H-pyrazol-4-yl)pyridin-3-yl)-N-(4-(((2,2,3,3,3-pentafluoropropyl)amino)methyl)phenyl)acrylamide | | | 466.1 |
| 74 | N-(4-(((2E)-3-(4-(1-methyl-1H-pyrazol-4-yl)pyridin-3-yl)prop-2-enoyl)amino)benzyl)glycine | | | 392.1 |
| 75 | (2E)-N-(4-((3-(hydroxymethyl)pyrrolidin-1-yl)methyl)phenyl)-3-(4-(1-methyl-1H-pyrazol-4-yl)pyridin-3-yl)acrylamide | | | 418.2 |

TABLE 1-10

| Example No. | IUPAC name | Structural formula | Salt | MS |
|---|---|---|---|---|
| 76 | (2E)-N-(4-((2-(hydroxymethyl)pyrrolidin-1-yl)methyl)phenyl)-3-(4-(1-methyl-1H-pyrazol-4-yl)pyridin-3-yl)acrylamide | | | 418.1 |
| 77 | (2E)-N-(4-(((1-methyl-6-oxopiperidin-3-yl)amino)methyl)phenyl)-3-(4-(1-methyl-1H-pyrazol-4-yl)pyridin-3-yl)acrylamide | | | 445.2 |

TABLE 1-10-continued

| Example No. | IUPAC name | Structural formula | Salt | MS |
|---|---|---|---|---|
| 78 | (2E)-N-(4-(hexahydropyrrolo[1,2-a]pyrazin-2(1H)-ylmethyl)phenyl)-3-(4-(1-methyl-1H-pyrazol-4-yl)pyridin-3-yl)acrylamide | | | 443.2 |
| 79 | (2E)-N-(4-((4-(2-hydroxyethyl)piperazin-1-yl)methyl)phenyl)-3-(4-(1-methyl-1H-pyrazol-4-yl)pyridin-3-yl)acrylamide | | | 447.2 |
| 80 | (2E)-N-(4-((1,1-dioxidethiomorpholin-4-yl)methyl)phenyl)-3-(4-(1-methyl-1H-pyrazol-4-yl)pyridin-3-yl)acrylamide | | | 452.1 |
| 81 | (2E)-N-(4-(((1,1-dioxidetetrahydro-2H-thiopyran-4-yl)amino)methyl)phenyl)-3-(4-(1-methyl-1H-pyrazol-4-yl)pyridin-3-yl)acrylamide | | | 466.1 |
| 82 | (2E)-3-(4-(1-methyl-1H-pyrazol-4-yl)pyridin-3-yl)-N-(4-(((2-(methylsulfamoyl)ethyl)amino)methyl)phenyl)acrylamide | | | 455.2 |

TABLE 1-10-continued

| Example No. | IUPAC name | Structural formula | Salt | MS |
|---|---|---|---|---|
| 83 | (2E)-3-(4-(1-methyl-1H-pyrazol-4-yl)pyridin-3-yl)-N-(4-(((oxetan-3-ylmethyl)amino)methyl)phenyl)acrylamide | | | 404.2 |
| 84 | (2E)-3-(4-(1-methyl-1H-pyrazol-4-yl)pyridin-3-yl)-N-(4-(2-oxa-7-azaspiro[3.5]non-7-ylmethyl)phenyl)acrylamide | | | 444.2 |

TABLE 1-11

| Example No. | IUPAC name | Structural formula | Salt | MS |
|---|---|---|---|---|
| 85 | (2E)-N-(4-((3-hydroxypiperidin-1-yl)methyl)phenyl)-3-(4-(1-methyl-1H-pyrazol-4-yl)pyridin-3-yl)acrylamide | | | 418.2 |
| 86 | (2E)-N-(4-(aminomethyl)phenyl)-3-(4-(1-methyl-1H-pyrazol-4-yl)pyridin-3-yl)acrylamide | | | 334.2 |
| 87 | (2E)-N-(4-(((2-cyanoethyl)amino)methyl)phenyl)-3-(4-(1-methyl-1H-pyrazol-4-yl)pyridin-3-yl)acrylamide | | | 387.1 |

TABLE 1-11-continued

| Example No. | IUPAC name | Structural formula | Salt | MS |
|---|---|---|---|---|
| 88 | (2E)-N-(4-(((2-hydroxyethyl)(methyl)amino)methyl)phenyl)-3-(4-(1-methyl-1H-pyrazol-4-yl)pyridin-3-yl)acrylamide | | | 392.1 |
| 89 | (2E)-N-(4-(((3,3-difluorocyclobutyl)amino)methyl)phenyl)-3-(4-(1-methyl-1H-pyrazol-4-yl)pyridin-3-yl)acrylamide | | | 424.1 |
| 90 | (2E)-N-(4-(((2,3-dihydroxypropyl)amino)methyl)phenyl)-3-(4-(1-methyl-1H-pyrazol-4-yl)pyridin-3-yl)acrylamide | | | 408.1 |
| 91 | (2E)-3-(4-(1-methyl-1H-pyrazol-4-yl)pyridin-3-yl)-N-(4-(2-(morpholin-4-yl)ethyl)phenyl)acrylamide | | | 418.2 |
| 92 | (2E)-3-(4-(1-ethyl-1H-pyrazol-4-yl)pyridin-3-yl)-N-(4-(morpholin-4-ylmethyl)phenyl)acrylamide | | | 418.2 |

TABLE 1-11-continued

| Example No. | IUPAC name | Structural formula | Salt | MS |
|---|---|---|---|---|
| 93 | (2E)-3-(4-(1-benzyl-1H-pyrazol-4-yl)pyridin-3-yl)-N-(4-(morpholin-4-ylmethyl)phenyl)acrylamide | | | 480.2 |

TABLE 1-12

| Example No. | IUPAC name | Structural formula | Salt | MS |
|---|---|---|---|---|
| 94 | (2E)-3-(4-(1H-indol-3-yl)pyridin-3-yl)-N-(4-(morpholin-4-ylmethyl)phenyl)acrylamide | | | 439.1 |
| 95 | (2E)-N-(4-(morpholin-4-ylmethyl)phenyl)-3-(4-(1H-pyrrolo[2,3-b]pyridin-3-yl)pyridin-3-yl)acrylamide | | | 440.1 |
| 96 | (2E)-N-(4-((3-amino-1H-pyrazol-4-yl)methyl)phenyl)-3-(4-(1-methyl-1H-pyrazol-4-yl)pyridin-3-yl)acrylamide | | | 400.1 |
| 97 | (2E)-3-(4-(1-cyclopropyl-1H-pyrazol-4-yl)pyridin-3-yl)-N-(4-(morpholin-4-ylmethyl)phenyl)acrylamide | | | 430.2 |

TABLE 1-12-continued

| Example No. | IUPAC name | Structural formula | Salt | MS |
|---|---|---|---|---|
| 98 | (2E)-3-(4-(1-(difluoromethyl)-1H-pyrazol-4-yl)pyridin-3-yl)-N-(4-(morpholin-4-ylmethyl)phenyl)acrylamide | | | 440.2 |
| 99 | 3-(4-(1-ethyl-1H-pyrazol-4-yl)pyridin-3-yl)-N-(4-(morpholin-4-ylmethyl)phenyl)propanamide | | | 420.2 |
| 100 | (2E)-3-(4-(3-methoxy-2-thienyl)pyridin-3-yl)-N-(4-(morpholin-4-ylmethyl)phenyl)acrylamide | | | 436.1 |
| 101 | (2E)-N-(4-(morpholin-4-ylmethyl)phenyl)-3-(4-(pyrazolo[1,5-a]pyridin-3-yl)pyridin-3-yl)acrylamide | | | 440.1 |
| 102 | (2E)-3-(4-(1-(4-fluorobenzyl)-1H-pyrazol-4-yl)pyridin-3-yl)-N-(4-(morpholin-4-ylmethyl)phenyl)acrylamide | | | 498.1 |

TABLE 1-13

| Example No. | IUPAC name | Structural formula | Salt | MS |
|---|---|---|---|---|
| 103 | (2E)-3-(4-(3,5-dimethyl-1H-pyrazol-4-yl)pyridin-3-yl)-N-(4-(morpholin-4-ylmethyl)phenyl)acrylamide | | | 416.0 |
| 104 | (2E)-3-(4-(3-methyl-1H-pyrazol-4-yl)pyridin-3-yl)-N-(4-(morpholin-4-ylmethyl)phenyl)acrylamide | | | 404.2 |
| 105 | (2E)-N-(4-(morpholin-4-ylmethyl)phenyl)-3-(4-(1-(4-(trifluoromethyl)benzyl)-1H-pyrazol-4-yl)pyridin-3-yl)acrylamide | | | 548.2 |
| 106 | (2E)-3-(4-(1-(4-cyanobenzyl)-1H-pyrazol-4-yl)pyridin-3-yl)-N-(4-(morpholin-4-ylmethyl)phenyl)acrylamide | | | 505.2 |
| 107 | (2E)-N-(4-(morpholin-4-ylmethyl)phenyl)-3-(4-(3-(trifluoromethyl)-1H-pyrazol-4-yl)pyridin-3-yl)acrylamide | | | 458.1 |

TABLE 1-13-continued

| Example No. | IUPAC name | Structural formula | Salt | MS |
| --- | --- | --- | --- | --- |
| 108 | (2E)-3-(4-(1-(cyclopropylmethyl)-1H-pyrazol-4-yl)pyridin-3-yl)-N-(4-(2-(morpholin-4-yl)ethyl)phenyl)acrylamide | | | 458.2 |
| 109 | (2E)-N-(3-methyl-4-(morpholin-4-ylmethyl)phenyl)-3-(4-(1-methyl-1H-pyrazol-4-yl)pyridin-3-yl)acrylamide | | | 416.0 |
| 110 | (2E)-3-(4-(1-(cyclopropylmethyl)-1H-pyrazol-4-yl)pyridin-3-yl)-N-(3-methyl-4-(morpholin-4-ylmethyl)phenyl)acrylamide | | | 458.2 |
| 111 | (2E)-N-(4-((3,5-dimethyl-1H-pyrazol-4-yl)methyl)phenyl)-3-(4-(1-methyl-1H-pyrazol-4-yl)pyridin-3-yl)acrylamide | | | 413.2 |

TABLE 1-14

| Example No. | IUPAC name | Structural formula | Salt | MS |
| --- | --- | --- | --- | --- |
| 112 | (2E)-N-(4-(1,1,1,3,3,3-hexafluoro-2-hydroxypropan-2-yl)phenyl)-3-(4-(1-methyl-1H-pyrazol-4-yl)pyridin-3-yl)acrylamide | | | 471.1 |

TABLE 1-14-continued

| Example No. | IUPAC name | Structural formula | Salt | MS |
|---|---|---|---|---|
| 113 | (2E)-3-(4-(1-methyl-1H-pyrazol-4-yl)pyridin-3-yl)-N-(4-(morpholin-4-yl)phenyl)acrylamide | | | 390.1 |
| 114 | (2E)-N-(1H-benzimidazol-4-yl)-3-(4-(1-methyl-1H-pyrazol-4-yl)pyridin-3-yl)acrylamide | | | 345.1 |
| 115 | (2E)-N-(1H-indazol-4-yl)-3-(4-(1-methyl-1H-pyrazol-4-yl)pyridin-3-yl)acrylamide | | | 345.1 |
| 116 | (2E)-N-(2,3-dihydro-1-benzofuran-6-yl)-3-(4-(1-methyl-1H-pyrazol-4-yl)pyridin-3-yl)acrylamide | | | 347.2 |
| 117 | (2E)-N-(1,3-benzothiazol-5-yl)-3-(4-(1-methyl-1H-pyrazol-4-yl)pyridin-3-yl)acrylamide | | | 362.1 |
| 118 | (2E)-N-(1,3-benzoxazol-6-yl)-3-(4-(1-methyl-1H-pyrazol-4-yl)pyridin-3-yl)acrylamide | | | 346.1 |

TABLE 1-14-continued

| Example No. | IUPAC name | Structural formula | Salt | MS |
|---|---|---|---|---|
| 119 | (2E)-N-(1,3-benzoxazol-2-yl)-3-(4-(1-methyl-1H-pyrazol-4-yl)pyridin-3-yl)acrylamide | | | 346.1 |
| 120 | (2E)-3-(4-(1-methyl-1H-pyrazol-4-yl)pyridin-3-yl)-N-(4-(1H-pyrazol-3-yl)phenyl)acrylamide | | | 371.1 |

TABLE 1-15

| Example No. | IUPAC name | Structural formula | Salt | MS |
|---|---|---|---|---|
| 121 | (2E)-3-(4-(1-methyl-1H-pyrazol-4-yl)pyridin-3-yl)-N-(3-(1H-pyrazol-3-yl)phenyl)acrylamide | | | 371.1 |
| 122 | 5-(((2E)-3-(4-(1-methyl-1H-pyrazol-4-yl)pyridin-3-yl)prop-2-enoyl)amino)thiophene-2-carboxamide | | | 354.0 |
| 123 | (2E)-N-(4-(2-hydroxy-2-methylpropyl)phenyl)-3-(4-(1-methyl-1H-pyrazol-4-yl)pyridin-3-yl)acrylamide | | | 377.2 |

TABLE 1-15-continued

| Example No. | IUPAC name | Structural formula | Salt | MS |
|---|---|---|---|---|
| 124 | (2E)-3-(4-(1-methyl-1H-pyrazol-4-yl)pyridin-3-yl)-N-(4-(3,3,3-trifluoropropyl)phenyl)acrylamide | | | 401.0 |
| 125 | (2E)-3-(4-(1-methyl-1H-pyrazol-4-yl)pyridin-3-yl)-N-((2R)-2-phenylcyclopropyl)acrylamide | | | 345.1 |
| 126 | (2E)-N-(4-(hydroxymethyl)benzyl)-3-(4-(1-methyl-1H-pyrazol-4-yl)pyridin-3-yl)acrylamide | | | 349.1 |
| 127 | (2E)-N-(5-methyl-2,3-dihydro-1H-inden-2-yl)-3-(4-(1-methyl-1H-pyrazol-4-yl)pyridin-3-yl)acrylamide | | | 359.1 |
| 128 | (2E)-N-(4-acetamidephenyl)-3-(4-(1-methyl-1H-pyrazol-4-yl)pyridin-3-yl)acrylamide | | | 362.1 |
| 129 | (2E)-3-(4-(1-methyl-1H-pyrazol-4-yl)pyridin-3-yl)-N-(4-sulfamoylphenyl)acrylamide | | | 384.1 |

TABLE 1-16

| Example No. | IUPAC name | Structural formula | Salt | MS |
|---|---|---|---|---|
| 130 | 4-(((2E)-3-(4-(1-methyl-1H-pyrazol-4-yl)pyridin-3-yl)prop-2-enoyl)amino)benzamide | | | 348.2 |
| 131 | (2E)-3-(4-(1-methyl-1H-pyrazol-4-yl)pyridin-3-yl)-N-(4-(methylsulfonyl)phenyl)acrylamide | | | 383.0 |
| 132 | (2E)-N-(4-cyanobenzyl)-3-(4-(1-methyl-1H-pyrazol-4-yl)pyridin-3-yl)acrylamide | | | 344.1 |
| 133 | (2E)-N-(4-(difluoromethoxy)phenyl)-3-(4-(1-methyl-1H-pyrazol-4-yl)pyridin-3-yl)acrylamide | | | 368.9 |
| 134 | (2E)-N-(4-(difluoromethoxy)benzyl)-3-(4-(1-methyl-1H-pyrazol-4-yl)pyridin-3-yl)acrylamide | | | 385.1 |
| 135 | (2E)-N-(1-benzofuran-5-ylmethyl)-3-(4-(1-methyl-1H-pyrazol-4-yl)pyridin-3-yl)acrylamide | | | 359.1 |

TABLE 1-16-continued

| Example No. | IUPAC name | Structural formula | Salt | MS |
|---|---|---|---|---|
| 136 | (2E)-3-(4-(1-methyl-1H-pyrazol-4-yl)pyridin-3-yl)-N-((1-methylpyrrolidin-3-yl)methyl)acrylamide | | | 326.2 |
| 137 | (2E)-3-(4-(1-methyl-1H-pyrazol-4-yl)pyridin-3-yl)-N-(4-(pyridin-4-yloxy)phenyl)acrylamide | | | 398.1 |
| 138 | (2E)-3-(4-(1-methyl-1H-pyrazol-4-yl)pyridin-3-yl)-N-(4-(pyridin-3-yloxy)phenyl)acrylamide | | | 398.1 |

TABLE 1-17

| Example No. | IUPAC name | Structural formula | Salt | MS |
|---|---|---|---|---|
| 139 | (2E)-N-(1-(cyclopropylmethyl)-1H-pyrazol-4-yl)-3-(4-(1-methyl-1H-pyrazol-4-yl)pyridin-3-yl)acrylamide | | | 349.2 |
| 140 | (2E)-N-(1,3-benzodioxol-5-ylmethyl)-3-(4-(1-methyl-1H-pyrazol-4-yl)pyridin-3-yl)acrylamide | | | 363.1 |

TABLE 1-17-continued

| Example No. | IUPAC name | Structural formula | Salt | MS |
|---|---|---|---|---|
| 141 | (2E)-3-(4-(1-methyl-1H-pyrazol-4-yl)pyridin-3-yl)-N-(4-((1H-pyrazol-3-ylamino)methyl)phenyl)acrylamide | | | 400.1 |
| 142 | (2E)-3-(4-(1-cyclopropyl-1H-pyrazol-4-yl)pyridin-3-yl)-N-(3-methyl-4-(morpholin-4-ylmethyl)phenyl)acryalmide | | | 444.3 |
| 143 | (2E)-3-(4-(1-cyclopropyl-1H-pyrazol-4-yl)pyridin-3-yl)-N-(4-(2-hydroxy-2-methylpropyl)phenyl)acrylamide | | | 402.9 |
| 144 | (2E)-N-(3-methyl-4-(morpholin-4-ylmethyl)phenyl)-3-(4-(1H-pyrazol-4-yl)pyridin-3-yl)acrylamide | | | 402.0 |
| 145 | (2E)-N-(4-(morpholin-4-ylmethyl)phenyl)-3-(4-(1,2-thiazol-4-yl)pyridin-3-yl)acrylamide | | | 407.1 |
| 146 | (2E)-N-(3-methyl-4-(morpholin-4-ylmethyl)phenyl)-3-(4-(1,2-thiazol-4-yl)pyridin-3-yl)acrylamide | | | 421.1 |

TABLE 1-18

| Example No. | IUPAC name | Structural formula | Salt | MS |
|---|---|---|---|---|
| 148 | (2E)-N-(3-hydroxy-4-(morpholin-4-ylmethyl)phenyl)-3-(4-(1-methyl-1H-pyrazol-4-yl)pyridin-3-yl)acrylamide | | | 420.1 |
| 149 | (2E)-N-(3-(2-methoxyethoxy)-4-(morpholin-4-ylmethyl)phenyl)-3-(4-(1-methyl-1H-pyrazol-4-yl)pyridin-3-yl)acrylamide | | | 478.2 |
| 150 | (2E)-N-(3-cyano-4-(morpholin-4-ylmethyl)phenyl)-3-(4-(1-methyl-1H-pyrazol-4-yl)pyridin-3-yl)acrylamide | | | 429.2 |
| 151 | (2E)-3-(4-(2-methyl-1,3-thiazol-5-yl)pyridin-3-yl)-N-(4-(morpholin-4-ylmethyl)phenyl)acrylamide | | | 421.1 |
| 152 | (2E)-3-(4-(1-methyl-1H-pyrazol-4-yl)pyridin-3-yl)-N-(4-(oxetan-3-yl)phenyl)acrylamide | | | 361.1 |

TABLE 1-18-continued

| Example No. | IUPAC name | Structural formula | Salt | MS |
|---|---|---|---|---|
| 153 | (2E)-N-(1,1-dioxid-1-benzothiophen-6-yl)-3-(4-(1-methyl-1H-pyrazol-4-yl)pyridin-3-yl)acrylamide | | | 391.0 |
| 154 | (2E)-N-(isoquinolin-6-yl)-3-(4-(1-methyl-1H-pyrazol-4-yl)pyridin-3-yl)acrylamide | | | 356.1 |
| 155 | (2E)-N-(1H-indol-6-yl)-3-(4-(1-methyl-1H-pyrazol-4-yl)pyridin-3-yl)acrylamide | | | 344.1 |
| 156 | (2E)-N-(isoquinolin-7-yl)-3-(4-(1-methyl-1H-pyrazol-4-yl)pyridin-3-yl)acrylamide | | | 356.1 |

TABLE 1-19

| Example No. | IUPAC name | Structural formula | Salt | MS |
|---|---|---|---|---|
| 157 | (2E)-N-(3-hydroxy-4-methoxyphenyl)-3-(4-(1-methyl-1H-pyrazol-4-yl)pyridin-3-yl)acrylamide | | | 351.1 |

TABLE 1-19-continued

| Example No. | IUPAC name | Structural formula | Salt | MS |
|---|---|---|---|---|
| 158 | (2E)-N-(1H-indaozl-5-yl)-3-(4-(1-methyl-1H-pyrazol-4-yl)pyridin-3-yl)acrylamide | | | 345.2 |
| 159 | (2E)-N-(3-chloro-4-(morpholin-4-yl)phenyl)-3-(4-(1-methyl-1H-pyrazol-4-yl)pyridin-3-yl)acrylamide | | | 424.1 |
| 160 | (2E)-3-(4-(1-methyl-1H-pyrazol-4-yl)pyridin-3-yl)-N-(2-oxo-2,3-dihydro-1H-benzimidazol-5-yl)acrylamide | | | 361.1 |
| 161 | (2E)-N-(3-cyano-4-fluorophenyl)-3-(4-(1-methyl-1H-pyrazol-4-yl)pyridin-3-yl)acrylamide | | | 346.0 |
| 162 | (2E)-N-(4-hydroxy-3-methoxyphenyl)-3-(4-(1-methyl-1H-pyrazol-4-yl)pyridin-3-yl)acrylamide | | | 351.1 |
| 163 | (2E)-N-(1,3-benzodioxol-5-yl)-3-(4-(1-methyl-1H-pyrazole-4-yl)pyridin-3-yl)acrylamide | | | 349.1 |

TABLE 1-19-continued

| Example No. | IUPAC name | Structural formula | Salt | MS |
|---|---|---|---|---|
| 164 | (2E)-3-(4-(1-methyl-1H-pyrazole-4-yl)pyridin-3-yl)-N-(2-oxo-1,2,3,4-tetrahydroquinolin-7-yl)acrylamide | | | 374.1 |
| 165 | (2E)-N-(3-fluoro-4-hydroxyphenyl)-3-(4-(1-methyl-1H-pyrazole-4-yl)pyridin-3-yl)acrylamide | | | 336.9 |

TABLE 1-20

| Example No. | IUPAC name | Structural formula | Salt | MS |
|---|---|---|---|---|
| 166 | (2E)-N-(4-fluoro-3-methoxyphenyl)-3-(4-(1-methyl-1H-pyrazol-4-yl)pyridin-3-yl)acrylamide | | | 353.1 |
| 167 | (2E)-N-(4-chloro-3-hydroxyphenyl)-3-(4-(1-methyl-1H-pyrazol-4-yl)pyridin-3-yl)acrylamide | | | 355.1 |
| 168 | (2E)-N-(2,3-dihydro-1,4-benzodioxin-6-yl)-3-(4-(1-methyl-1H-pyrazol-4-yl)pyridin-3-yl)acrylamide | | | 363.1 |

TABLE 1-20-continued

| Example No. | IUPAC name | Structural formula | Salt | MS |
|---|---|---|---|---|
| 169 | (2E)-N-(1,3-benzothiazol-6-yl)-3-(4-(1-methyl-1H-pyrazol-4-yl)pyridin-3-yl)acrylamide | | | 362.1 |
| 170 | methyl2-hydroxy-5-(((2E)-3-(4-(1-methyl-1H-pyrazol-4-yl)pyridin-3-yl)prop-2-enoyl)amino)benzoate | | | 379.2 |
| 171 | (2E)-N-(4-hydroxy-3-methylphenyl)-3-(4-(1-methyl-1H-pyrazol-4-yl)pyridin-3-yl)acrylamide | | | 335.2 |
| 172 | (2E)-N-(2,3-dihydro-1-benzofuran-5-yl)-3-(4-(1-methyl-1H-pyrazol-4-yl)pyridin-3-yl)acrylamide | | | 347.2 |
| 173 | (2E)-N-(3-chloro-4-hydroxyphenyl)-3-(4-(1-methyl-1H-pyrazol-4-yl)pyridin-3-yl)acrylamide | | | 355.1 |
| 174 | (2E)-3-(4-(1-methyl-1H-pyrazol-4-yl)pyridin-3-yl)pyridin-3-yl)-N-(3-oxo-2,3-dihydro-1H-isoindol-5-yl)acrylamide | | | 360.1 |

TABLE 1-21

| Example No. | IUPAC name | Structural formula | Salt | MS |
|---|---|---|---|---|
| 175 | (2E)-N-(1-methyl-1H-indol-5-yl)-3-(4-(1-methyl-1H-pyrazol-4-yl)pyridin-3-yl)acrylamide | | | 358.1 |
| 176 | (2E)-3-(4-(1-methyl-1H-pyrazol-4-yl)pyridin-3-yl)-N-(1-oxo-2,3-dihydro-1H-inden-5-yl)acrylamide | | | 357.0 |
| 177 | (2E)-N-(4-hydroxy-3-(morpholin-4-ylmethyl)phenyl)-3-(4-(1-methyl-1H-pyrazol-4-yl)pyridin-3-yl)acrylamide | | | 420.2 |
| 178 | (2E)-3-(4-(1-methyl-1H-pyrazol-4-yl)pyridin-3-yl)-N-(3-(methylsulfonyl)phenyl)acrylamide | | | 383.0 |
| 179 | (2E)-N-(3-(hydroxymethyl)phenyl)-3-(4-(1-methyl-1H-pyrazol-4-yl)pyridin-3-yl)acrylamide | | | 333.0 |

TABLE 1-21-continued

| Example No. | IUPAC name | Structural formula | Salt | MS |
|---|---|---|---|---|
| 180 | (2E)-N-(3-((4-methylpiperazin-1-yl)methyl)phenyl)-3-(4-(1-methyl-1H-pyrazole-4-yl)pyridin-3-yl)acrylamide | | | 417.2 |
| 181 | (2E)-3-(4-(1-methyl-1H-pyrazol-4-yl)pyridin-3-yl)-N-(3-((methylsulfonyl)amino)phenyl)acrylamide | | | 398.1 |
| 182 | (2E)-3-(4-(1-methyl-1H-pyrazol-4-yl)pyridin-3-yl)-N-(3-(pyridin-3-yl)phenyl)acrylamide | | | 382.1 |

TABLE 1-22

| Example No. | IUPAC name | Structural formula | Salt | MS |
|---|---|---|---|---|
| 183 | (2E)-3-(4-(1-methyl-1H-pyrazol-4-yl)pyridin-3-yl)-N-(3-(morpholin-4-yl)phenyl)acrylamide | | | 390.1 |

TABLE 1-22-continued

| Example No. | IUPAC name | Structural formula | Salt | MS |
|---|---|---|---|---|
| 184 | (2E)-N-(3-ethoxyphenyl)-3-(4-(1-methyl-1H-pyrazol-4-yl)pyridin-3-yl)acrylamide | | | 349.2 |
| 185 | (2E)-3-(4-(1-methyl-1H-pyrazol-4-yl)pyridin-3-yl)-N-(3-(piperidin-1-ylmethyl)phenyl)acrylamide | | | 402.1 |
| 186 | (2E)-N-(3-((dimethylamino)methyl)phenyl)-3-(4-(1-methyl-1H-pyrazol-4-yl)pyridin-3-yl)acrylamide | | | 362.2 |
| 187 | (2E)-N-(3-acetamidephenyl)-3-(4-(1-methyl-1H-pyrazol-4-yl)pyridin-3-yl)acrylamide | | | 362.1 |
| 188 | methyl 3-(((2E)-3-(4-(1-methyl-1H-pyrazol-4-yl)pyridin-3-yl)prop-2-enoyl)amino)benzoate | | | 363.1 |
| 189 | (2E)-N-(3-(1-methyl-1H-pyrazol-5-yl)phenyl)-3-(4-(1-methyl-1H-pyrazol-4-yl)pyridin-3-yl)acrylamide | | | 385.1 |

TABLE 1-22-continued

| Example No. | IUPAC name | Structural formula | Salt | MS |
|---|---|---|---|---|
| 190 | (2E)-3-(4-(1-methyl-1H-pyrazol-4-yl)pyridin-3-yl)-N-(8-oxo-5,6,7,8-tetrahydronaphthalen-2-yl)acrylamide | | | 373.1 |
| 191 | (2E)-3-(4-(1-methyl-1H-pyrazol-4-yl)pyridin-3-yl)-N-(5-oxo-5,6,7,8-tetrahydronaphthalen-2-yl)acrylamide | | | 373.2 |

TABLE 1-23

| Example No. | IUPAC name | Structural formula | Salt | MS |
|---|---|---|---|---|
| 192 | (2E)-3-(4-(1-methyl-1H-pyrazol-4-yl)pyridin-3-yl)-N-(3-(2,2,2-trifluoromethoxy)phenyl)acrylamide | | | 403.1 |
| 193 | (2E)-3-(4-(1-methyl-1H-pyrazol-4-yl)pyridin-3-yl)-N-(4-(morpholin-4-ylcarbonyl)phenyl)acrylamide | | | 418.1 |
| 194 | (2E)-3-(4-(1-cyclopropyl-1H-pyrazol-4-yl)pyridin-3-yl)-N-(2-fluoro-4-(morpholin-4-ylmethyl)phenyl)acrylamide | | | 448.1 |

US 9,957,251 B2

TABLE 1-23-continued

| Example No. | IUPAC name | Structural formula | Salt | MS |
|---|---|---|---|---|
| 195 | (2E)-N-(4-(morpholin-4-ylmethyl)phenyl)-3-(4-(1,3-thiazol-5-yl)pyridin-3-yl)acrylamide | | | 407.1 |
| 196 | (2E)-N-(4-(morpholin-4-ylmethyl)phenyl)-3-(4-(1,2-thiazol-5-yl)pyridin-3-yl)acrylamide | | | 407.0 |
| 197 | (2E)-3-(4-(imidazo[1,2-a]pyridin-3-yl)pyridin-3-yl)-N-(4-(morpholin-4-ylmethyl)phenyl)acrylamide | | | 440.1 |
| 199 | (2E)-3-(4-(1-methyl-1H-pyrazol-4-yl)pyridin-3-yl)-N-(3-(morpholin-4-ylmethyl)phenyl)acrylamide | | | 404.2 |

TABLE 1-24

| Example No. | IUPAC name | Structural formula | Salt | MS |
|---|---|---|---|---|
| 200 | (2E)-N-(4-methyl-3-(morpholin-4-ylcarbonyl)phenyl)-3-(4-(1-methyl-1H-pyrazol-4-yl)pyridin-3-yl)acrylamide | | | 432.1 |

TABLE 1-24-continued

| Example No. | IUPAC name | Structural formula | Salt | MS |
|---|---|---|---|---|
| 201 | (2E)-3-(4-(1-methyl-1H-pyrazol-4-yl)pyridin-3-yl)-N-(2-(trifluoroacetyl)-1,2,3,4-tetrahydroisoquinolin-7-yl)acrylamide | | | 454.0 |
| 202 | (2E)-N-(2,3-dihydro-1H-isoindol-5-yl)-3-(4-(1-methyl-1H-pyrazol-4-yl)pyridin-3-yl)acrylamide | | | 346.2 |
| 203 | (2E)-N-(4-(2-hydroxypropan-2-yl)phenyl)-3-(4-(1-methyl-1H-pyrazol-4-yl)pyridin-3-yl)acrylamide | | | 363.3 |
| 204 | (2E)-3-(4-(1-methyl-1H-pyrazol-4-yl)pyridin-3-yl)-N-phenylacrylamide | | | 305.1 |
| 205 | (2E)-3-(4-(1-methyl-1H-pyrazol-4-yl)pyridin-3-yl)-N-(4-((2-oxopyridin-1(2H)-yl)methyl)phenyl)acrylamide | | | 412.2 |

TABLE 1-24-continued

| Example No. | IUPAC name | Structural formula | Salt | MS |
| --- | --- | --- | --- | --- |
| 206 | tert-butylmethyl(4-(((2E)-3-(4-(1-methyl-1H-pyrazol-4-yl)pyridin-3-yl)prop-2-enoyl)amino)benzyl)carbamate | | | 448.2 |
| 207 | (2E)-N-(4-(acetyl(methyl)amino)phenyl)-3-(4-(1-methyl-1H-pyrazol-4-yl)pyridin-3-yl)acrylamide | | | 376.1 |
| 208 | (2E)-N-(4-((acetyl(methyl)amino)methyl)phenyl)-3-(4-(1-methyl-1H-pyrazol-4-yl)pyridin-3-yl)acrylamide | | | 390.1 |

TABLE 1-25

| Example No. | IUPAC name | Structural formula | Salt | MS |
| --- | --- | --- | --- | --- |
| 209 | (2E)-N-(2-(cyclopropylcarbonyl)-1,2,3,4-tetrahydroisoquinolin-7-yl)-3-(4-(1-methyl-1H-pyrazol-4-yl)pyridin-3-yl)acrylamide | | | 428.2 |
| 210 | (2E)-3-(4-(1-methyl-1H-pyrazol-4-yl)pyridin-3-yl)-N-(3-(morpholin-4-ylcarbonyl)phenyl)acrylamide | | | 418.1 |

TABLE 1-25-continued

| Example No. | IUPAC name | Structural formula | Salt | MS |
|---|---|---|---|---|
| 211 | (2E)-N-(2-((3-methyloxetan-3-yl)carbonyl)-1,2,3,4-tetrahydroisoquinolin-7-yl)-3-(4-(1-methyl-1H-pyrazol-4-yl)pyridin-3-yl)acrylamide | | | 458.1 |
| 212 | (2E)-3(4-(1-methyl-1H-pyrazol-4-yl)pyridin-3-yl)-N-(2-methyl-1,2,3,4-tetrahydroisoquinolin-7-yl)acrylamide | | | 374.2 |
| 213 | (2E)-N-(4-(morpholin-4-ylmethyl)phenyl)-3-(4-(1-(2-phenylethyl)-1H-pyrazol-4-yl)pyridin-3-yl)acrylamide | | | 494.2 |
| 214 | tert-butyl 7-(((2E)-3-(4-(1-methyl-1H-pyrazol-4-yl)pyridin-3-yl)prop-2-enoyl)amino)-3,4-dihydrisoquinoline-2(1H)-carboxylate | | | 460.3 |
| 215 | (2E)-3-(4-(1-methyl-1H-pyrazol-4-yl)pyridin-3-yl)-N-(1,2,3,4-tetrahydroisoquinolin-7-yl)acrylamide | | 2HCl | 360.0 |

TABLE 1-25-continued

| Example No. | IUPAC name | Structural formula | Salt | MS |
|---|---|---|---|---|
| 216 | (2E)-3-(4-(1-methyl-1H-pyrazol-4-yl)pyridin-3-yl)-N-(2-(2,2,2-trifluoroethyl)-1,2,3,4-tetrahydroisoquinolin-7-yl)acrylamide | | | 442.1 |
| 217 | (2E)-N-(4-(morpholin-4-ylmethyl)phenyl)-3-(4-(1-(oxetan-3-yl)-1H-pyrazol-4-yl)pyridin-3-yl)acrylamide | | | 446.1 |

TABLE 1-26

| Example No. | IUPAC name | Structural formula | Salt | MS |
|---|---|---|---|---|
| 218 | (2E)-3-(4-(1-acetyl-1H-pyrazol-4-yl)pyridin-3-yl)-N-(4-(morpholin-4-ylmethyl)phenyl)acrylamide | | | 432.0 |
| 219 | (2E)-3-(6-amino-4-(1-methyl-1H-pyrazol-4-yl)pyridin-3-yl)-N-(4-(morpholin-4-ylmethyl)phenyl)acrylamide | | | 419.1 |
| 220 | (2E)-3-(4-(5-methoxy-2-thienyl)pyridin-3-yl)-N-(4-(morpholin-4-ylmethyl)phenyl)acrylamide | | | 436.1 |

TABLE 1-26-continued

| Example No. | IUPAC name | Structural formula | Salt | MS |
|---|---|---|---|---|
| 221 | (2E)-3-(4-(2-methoxy-1,3-thiazol-5-yl)pyridin-3-yl)-N-(4-(morpholin-4-ylmethyl)phenyl)acrylamide | | | 437.0 |
| 222 | (2E)-3-(4-(imidazo[1,2-a]pyridin-6-yl)pyridin-3-yl)-N-(4-(morpholin-4-ylmethyl)phenyl)acrylamide | | | 440.1 |
| 223 | (2E)-N-(4-bromo-3-((methylsulfonyl)methyl)phenyl)-3-(4-(1-methyl-1H-pyrazol-4-yl)pyridin-3-yl)acrylamide | | | 474.9 |
| 224 | (2E)-3-(4-(1H-imidazol-1-yl)pyridin-3-yl)-N-(4-(morpholin-4-ylmethyl)phenyl)acrylamide | | | 390.1 |
| 225 | (2E)-N-(4-((dimethylamino)methyl)phenyl)-3-(4-(1-methyl-1H-pyrazol-4-yl)pyridin-3-yl)acrylamide | | | 362.1 |
| 226 | (2E)-N-(4-(2-(dimethylamino)ethyl)phenyl)-3-(4-(1-methyl-1H-pyrazol-4-yl)pyridin-3-yl)acrylamide | | | 376.1 |

TABLE 1-27

| Example No. | IUPAC name | Structural formula | Salt | MS |
|---|---|---|---|---|
| 227 | (2E)-3-(6-chloro-4-(1-methyl-1H-pyrazol-4-yl)pyridin-3-yl)-N-(4-(morpholin-4-ylmethyl)phenyl)acrylamide | | | 438.1 |
| 228 | (2E)-N-(4-(1,1-difluoro-2-hydroxy-2-methylpropyl)phenyl)-3-(4-(1-methyl-1H-pyrazol-4-yl)pyridin-3-yl)acrylamide | | | 413.1 |
| 229 | (2E)-N-(4-cyclopropyl-3-((2,2,2-trifluoroethoxy)methyl)phenyl)-3-(4-(1-methyl-1H-pyrazol-4-yl)pyridin-3-yl)acrylamide | | | 457.1 |
| 230 | (2E)-N-(3-((acetyl(methyl)amino)methyl)-4-bromophenyl)-3-(4-(1-methyl-1H-pyrazol-4-yl)pyridin-3-yl)acrylamide | | | 467.9 |
| 231 | (2E)-3-(4-(1-(2-amino-2-oxoethyl)-1H-pyrazol-4-yl)pyridin-3-yl)-N-(4(morpholin-4-ylmethyl)phenyl)acrylamide | | | 447.0 |

TABLE 1-27-continued

| Example No. | IUPAC name | Structural formula | Salt | MS |
|---|---|---|---|---|
| 232 | (2E)-3-(4-(1-(3-amino-3-oxopropyl)-1H-pyrazol-4-yl)pyridin-3-yl)-N-(4-(morpholin-4-ylmethyl)phenyl)acrylamide | | | 459.1 |
| 233 | (2E)-N-(4-cyclopropyl-3-((methylsulfonyl)methyl)phenyl)-3-(4-(1-methyl-1H-pyrazol-4-yl)pyridin-3-yl)acrylamide | | | 437.0 |
| 234 | (2E)-3-(4-(1-methyl-1H-benzimidazol-6-yl)pyridin-3-yl)-N-(4-(morpholin-4-ylmethyl)phenyl)acrylamide | | | 454.0 |
| 235 | (2E)-N-(2,5-difluoro-4-(hydroxymethyl)phenyl)-3-(4-(1-methyl-1H-pyrazol-4-yl)pyridin-3-yl)acrylamide | | | 371.0 |

TABLE 1-28

| Example No. | IUPAC name | Structural formula | Salt | MS |
|---|---|---|---|---|
| 236 | (2E)-N-(3-fluoro-4-(hydroxymethyl)phenyl)-3-(4-(1-methyl-1H-pyrazol-4-yl)pyridin-3-yl)acrylamide | | | 353.0 |

TABLE 1-28-continued

| Example No. | IUPAC name | Structural formula | Salt | MS |
|---|---|---|---|---|
| 237 | (2E)-N-(2,5-difluoro-4-(morpholin-4-ylmethyl)phenyl)-3-(4-(1-methyl-1H-pyrazol-4-yl)pyridin-3-yl)acrylamide | | | 440.1 |
| 238 | (2E)-3-(5-fluoro-4-(1-methyl-1H-pyrazol-4-yl)pyridin-3-yl)-N-(4-(morpholin-4-ylmethyl)phenyl)acrylamide | | | 422.0 |
| 239 | (2E)-N-(4-(methoxymethyl)phenyl)-3-(4-(1-methyl-1H-pyrazol-4-yl)pyridin-3-yl)acrylamide | | | 349.1 |
| 240 | (2E)-3-(4-(1-methyl-1H-1,2,3-triazol-4-yl)pyridin-3-yl)-N-(4-(morpholin-4-ylmethyl)phenyl)acrylamide | | | 405.1 |
| 241 | (2E)-3-(4-(1H-benzimidazol-5-yl)pyridin-3-yl)-N-(4-(morpholin-4-ylmethyl)phenyl)acrylamide | | | 438.0 |
| 242 | (2E)-3-(4-(1H-indazol-5-yl)pyridin-3-yl)-N-(4-(morpholin-4-ylmethyl)phenyl)acrylamide | | | 440.1 |

TABLE 1-28-continued

| Example No. | IUPAC name | Structural formula | Salt | MS |
|---|---|---|---|---|
| 243 | (2E)-3-(4-(1H-indazol-6-yl)pyridin-3-yl)-N-(4-(morpholin-4-ylmethyl)phenyl)acrylamide | | | 440.1 |
| 244 | (2E)-3-(6-hydroxy-4-(1-methyl-1H-pyrazol-4-yl)pyridin-3-yl)-N-(4-(morpholin-4-ylmethyl)phenyl)acrylamide | | | 420.1 |

TABLE 1-29

| Example No. | IUPAC name | Structural formula | Salt | MS |
|---|---|---|---|---|
| 245 | (2E)-N-(3-((acetyl(methyl)amino)methyl)-4-cyclopropylphenyl)-3-(4-(1-methyl-1H-pyrazol-4-yl)pyridin-3-yl)acrylamide | | | 430.1 |
| 246 | (2E)-N-(3-((acetyl(methyl)amino)methyl)-4-methylphenyl)-3-(4-(1-methyl-1H-pyrazol-4-yl)pyridin-3-yl)acrylamide | | | 404.1 |
| 247 | (2E)-3-(4-(1-cyclopropyl-1H-pyrazol-4-yl)pyridin-3-yl)-N-(2-(2,2,2-trifluoroetyl)-1,2,3,4-tetrahydroisoquinolin-7-yl)acrylamide | | | 468.1 |

TABLE 1-29-continued

| Example No. | IUPAC name | Structural formula | Salt | MS |
|---|---|---|---|---|
| 248 | (2E)-3-(4-(1-cyclopropyl-1H-pyrazol-4-yl)pyridin-3-yl)-N-(2-(trifluoroacetyl)-1,2,3,4-tetrahydroisoquinolin-7-yl)acrylamide | | | 482.0 |
| 249 | (2E)-N-(3-fluoro-4-(morpholin-4-ylmethyl)phenyl)-3-(4-(1-methyl-1H-pyrazol-4-yl)pyridin-3-yl)acrylamide | | | 422.1 |
| 250 | (2E)-N-(2-fluoro-4-(morpholin-4-ylmethyl)phenyl)-3-(4-(2-methoxy-1,3-thiazol-5-yl)pyridin-3-yl)acrylamide | | | 455.0 |
| 251 | (2E)-3-(4-(1-cyclopropyl-1H-pyrazol-4-yl)pyridin-3-yl)-N-(1-methyl-1H-indol-5-yl)acrylamide | | | 384.1 |
| 252 | (2E)-N-(4-(2-(dimethylamino)ethoxy)phenyl)-3-(4-(1-methyl-1H-pyrazol-4-yl)pyridin-3-yl)acrylamide | | | 392.1 |

TABLE 1-29-continued

| Example No. | IUPAC name | Structural formula | Salt | MS |
|---|---|---|---|---|
| 253 | (2E)-N-(4-(2-methoxyethoxy)phenyl)-3-(4-(1-methyl-1H-pyrazol-4-yl)pyridin-3-yl)acrylamide | | | 379.1 |

TABLE 1-30

| Example No. | IUPAC name | Structural formula | Salt | MS |
|---|---|---|---|---|
| 254 | tert-butyl 6-(((2E)-3-(4-(1-methyl-1H-pyrazol-4-yl)pyridin-3-yl)prop-2-enoyl)amino)-3,4-dihydroisoquinoline-2(1H)-carboxylate | | | 460.2 |
| 255 | (2E)-3-(4-(1-methyl-1H-pyrazol-4-yl)pyridin-3-yl)-N-(1,2,3,4-tetrahydroisoquinolin-6-yl)acrylamide | | 3HCl | 360.0 |
| 256 | (2E)-N-(2-ethyl-1,2,3,4-tetrahydroisoquinolin-6-yl)-3-(4-(1-methyl-1H-pyrazol-4-yl)pyridin-3-yl)acrylamide | | | 388.1 |
| 257 | (2E)-N-(2-ethyl-1,2,3,4-tetrahydroisoquinolin-7-yl)-3-(4-(1-methyl-1H-pyrazol-4-yl)pyridin-3-yl)acrylamide | | | 388.2 |

TABLE 1-30-continued

| Example No. | IUPAC name | Structural formula | Salt | MS |
|---|---|---|---|---|
| 258 | (2E)-3-(4-(1-cyclobutyl-1H-pyrazol-4-yl)pyridin-3-yl)-N-(4-(morpholin-4-ylmethyl)phenyl)acrylamide | | | 444.2 |
| 259 | (2E)-3-(4-(1-cyclopropyl-1H-pyrazol-4-yl)pyridin-3-yl)-N-(4-(methoxymethyl)phenyl)acrylamide | | | 375.1 |
| 260 | (2E)-3-(5-fluoro-4-(1-methyl-1H-pyrazol-4-yl)pyridin-3-yl)-N-(2-fluoro-4-(morpholin-4-ylmethyl)phenyl)acrylamide | | | 440.0 |
| 261 | (2E)-3-(4-(2-methyl-2H-indazol-5-yl)pyridin-3-yl)-N-(4-(morpholin-4-ylmethyl)phenyl)acrylamide | | | 454.1 |
| 262 | (2E)-3-(4-(1-methyl-1H-benzimidazol-5-yl)pyridin-3-yl)-N-(4-(morpholin-4-ylmethyl)phenyl)acrylamide | | | 454.1 |

TABLE 1-31

| Example No. | IUPAC name | Structural formula | Salt | MS |
|---|---|---|---|---|
| 263 | (2E)-3-(4-(1-methyl-1H-benzimidazol-6-yl)pyridin-3-yl)-N-(1-methyl-1H-indol-5-yl)acrylamide | | | 408.1 |
| 264 | (2E)-N-(2-fluoro-4-(morpholin-4-ylmethyl)phenyl)-3-(4-(1-methyl-1H-benzimidazol-6-yl)pyridin-3-yl)acrylamide | | | 472.1 |
| 265 | (2E)-3-(6-methoxy-3,4'-bipyridin-3'-yl)-N-(4-(morpholin-4-ylmethyl)phenyl)acrylamide | | | 431.0 |
| 266 | (2E)-3-(4-(1-cyclopropyl-1H-pyrazol-4-yl)pyridin-3-yl)-N-(1-(2,2,2-trifluoroethyl)-1H-indol-5-yl)acrylamide | | | 452.0 |
| 267 | (2E)-3-(4-(1-cyclopropyl-1H-pyrazol-4-yl)pyridin-3-yl)-N-(1-(2,2,2-trifluoroethyl)-1H-indol-6-yl)acrylamide | | | 452.0 |

TABLE 1-31-continued

| Example No. | IUPAC name | Structural formula | Salt | MS |
|---|---|---|---|---|
| 268 | (2E)-3-(4-(1-cyclopropyl-1H-pyrazol-4-yl)pyridin-3-yl)-N-(1-methyl-1H-indol-6-yl)acrylamide | | | 384.0 |
| 269 | (2E)-N-(4-(morpholin-4-ylmethyl)phenyl)-3-(6-oxo-1,6-dihydro-3,4'-bipyridin-3'-yl)acrylamide | | | 415.1 |
| 270 | 5-(3-((1E)-3-((4-(morpholin-4-ylmethyl)phenyl)amino)-3-oxoprop-1-en-1-yl)pyridin-4-yl)thiophene-2-carboxamide | | | 449.0 |
| 271 | (2E)-3-(4-(1-cyclopropyl-1H-pyrazol-4-yl)pyridin-3-yl)-N-(4-(1-methoxyethyl)phenyl)acrylamide | | | 389.1 |

TABLE 1-32

| Example No. | IUPAC name | Structural formula | Salt | MS |
|---|---|---|---|---|
| 272 | (2E)-3-(4-(1-cyclopropyl-1H-pyrazol-4-yl)pyridin-3-yl)-N-(4-(2-methoxy-2-methylpropyl)phenyl)acrylamide | | | 417.0 |
| 273 | (2E)-3-(4-(1-cyclopropyl-1H-pyrazol-4-yl)-5-fluoropyridin-3-yl)-N-(2-fluoro-4-(morpholin-4-ylmethyl)phenyl)acrylamide | | | 466.1 |
| 274 | (2E)-3-(4-(1-methyl-1H-pyrazol-4-yl)pyridin-3-yl)-N-(4-(1H-pyrazol-1-ylmethyl)phenyl)acrylamide | | | 385.0 |
| 275 | (2E)-N-(4-(1H-imidazol-1-ylmethyl)phenyl)-3-(4-(1-methyl-1H-pyrazol-4-yl)pyridin-3-yl)acrylamide | | | 385.0 |
| 276 | (2E)-3-(4-(1-methyl-1H-pyrazol-4-yl)pyridin-3-yl)-N-(4-(2,2,2-trifluoroethyl)phenyl)acrylamide | | | 387.0 |

TABLE 1-32-continued

| Example No. | IUPAC name | Structural formula | Salt | MS |
|---|---|---|---|---|
| 277 | (2E)-3-(4-(1-methyl-1H-pyrazol-4-yl)pyridin-3-yl)-N'-(2-(2,2,2-trifluoroethyl)-1,2,3,4-tetrahydroisoquinolin-6-yl)acrylamide | | | 442.0 |
| 278 | (2E)-3-(4-(2-methoxypyrimidin-5-yl)pyridin-3-yl)-N-(4-(morpholin-4-ylmethyl)phenyl)acrylamide | | | 432.0 |
| 279 | tert-butyl 5-(((2E)-3-(4-(1-methyl-1H-pyrazol-4-yl)pyridin-3-yl)prop-2-enoyl)amino)indoline-1-carboxylate | | | 446.1 |
| 280 | (2E)-N-(2,3-dihydro-1H-indol-5-yl)-3-(4-(1-methyl-1H-pyrazol-4-yl)pyridin-3-yl)acrylamide | | 3HCl | 346.1 |

TABLE 1-33

| Example No. | IUPAC name | Structural formula | Salt | MS |
|---|---|---|---|---|
| 281 | (2E)-3-(4-(1-cyclopropyl-1H-pyrazol-4-yl)pyridin-3-yl)-N-(4-(1-methyl-1H-pyrazol-4-yl)phenyl)acrylamide | | | 411.1 |

TABLE 1-33-continued

| Example No. | IUPAC name | Structural formula | Salt | MS |
|---|---|---|---|---|
| 282 | (2E)-N-(1-methyl-1H-indol-5-yl)-3-(4-(1H-pyrazol-4-yl)pyridin-3-yl)acrylamide | | | 344.0 |
| 283 | (2E)-3-(4-(1-(cyclopropylmethyl)-1H-benzimidazol-6-yl)pyridin-3-yl)-N-(4-(morpholin-4-ylmethyl)phenyl)acrylamide | | | 494.1 |
| 284 | (2E)-N-(4-(cyanomethyl)phenyl)-3-(4-(1-methyl-1H-pyrazol-4-yl)pyridin-3-yl)acrylamide | | | 344.0 |
| 285 | (2E)-3-(4-(1-methyl-1H-pyrazol-4-yl)pyridin-3-yl)-N-(1-(2,2,2-trifluoroethyl)-2,3-dihydro-1H-indol-5-yl)acrylamide | | | 428.1 |
| 286 | (2E)-N-(4-(morpholin-4-ylmethyl)phenyl)-3-(4-(2-oxo-1,2-dihydropyrimidin-5-yl)pyridin-3-yl)acrylamide | | | 418.0 |

TABLE 1-33-continued

| Example No. | IUPAC name | Structural formula | Salt | MS |
|---|---|---|---|---|
| 287 | tert-butyl 5-(((2E)-3-(4-(1-methyl-1H-pyrazol-4-yl)pyridin-3-yl)prop-2-enoyl)amino)-1,3-dihydro-2H-isoindole-2-carboxylate | | | 446.1 |
| 288 | (2E)-3-(4-(1-((1-fluorocyclopropyl)methyl)-1H-pyrazol-4-yl)pyridin-3-yl)-N-(4-(morpholin-4-ylmethyl)phenyl)acrylamide | | | 462.0 |
| 289 | (2E)-3-(4-(1-methyl-1H-pyrazol-4-yl)pyridin-3-yl)-N-(2-(2,2,2-trifluoroethyl)-2,3-dihydro-1H-isoindol-5-yl)acrylamide | | | 428.1 |

TABLE 1-34

| Example No. | IUPAC name | Structural formula | Salt | MS |
|---|---|---|---|---|
| 290 | (2E)-N-(4-cyclopropylphenyl)-3-(4-(1-cyclopropyl-1H-pyrazol-4-yl)pyridin-3-yl)acetamide | | | 371.1 |

TABLE 1-34-continued

| Example No. | IUPAC name | Structural formula | Salt | MS |
|---|---|---|---|---|
| 291 | (2E)-3-(4-(1-cyclopropyl-1H-pyrazol-4-yl)pyridin-3-yl)-N-(4-(1,1-difluoro-2-methoxyethyl)phenyl)acrylamide | | | 425.0 |
| 292 | (2E)-3-(4-(1-cyclopropyl-1H-pyrazol-4-yl)pyridin-3-yl)-N-(4-((difluoromethoxy)methyl)phenyl)acrylamide | | | 411.0 |
| 293 | (2E)-3-(4-(1-cyclopropyl-1H-pyrazol-4-yl)pyridin-3-yl)-N-(4-(2-fluoro-2-methylpropyl)phenyl)acrylamide | | | 405.0 |
| 294 | (2E)-3-(4-(1-cyclopropyl-1H-pyrazol-4-yl)pyridin-3-yl)-N-(4-(5-(trifluoromethyl)-1,2,4-oxadiazol-3-yl)phenyl)acrylamide | | | 464.9 |
| 295 | (2E)-3-(4-(1-(2-methoxyethyl)-1H-benzimidazol-6-yl)pyridin-3-yl)-N-(4-(morpholin-4-ylmethyl)phenyl)acrylamide | | | 498.1 |

TABLE 1-34-continued

| Example No. | IUPAC name | Structural formula | Salt | MS |
|---|---|---|---|---|
| 296 | (2E)-N-(2-fluoro-4-methylphenyl)-3-(4-(1H-pyrazol-4-yl)pyridin-3-yl)acrylamide | | | 323.1 |
| 297 | (2E)-N-(2,3-dihydro-1,4-benzodioxin-6-yl)-3-(4-(1H-pyrazol-4-yl)pyridin-3-yl)acrylamide | | | 349.0 |
| 298 | (2E)-3-(4-(1-methyl-1H-benzimidazol-6-yl)pyridin-3-yl)-N-(1-(2,2,2-trifluoroethyl)-1H-indol-5-yl)acrylamide | | | 476.0 |

TABLE 1-35

| Example No. | IUPAC name | Structural formula | Salt | MS |
|---|---|---|---|---|
| 299 | (2E)-N-(2,3-dihydro-1-benzofuran-6-yl)-3-(4-(1H-pyrazol-4-yl)pyridin-3-yl)acrylamide | | | 333.1 |
| 300 | (2E)-3-(4-(1-cyclopropyl-1H-pyrazol-4-yl)pyridin-3-yl)-N-(2-(2,2,3,3,3-pentafluoropropyl)-1,2,3,4-tetrahydroisoquinolin-7-yl)acrylamide | | | 518.1 |

TABLE 1-35-continued

| Example No. | IUPAC name | Structural formula | Salt | MS |
|---|---|---|---|---|
| 301 | (2E)-3-(4-(1-cyclopropyl-1H-pyrazol-4-yl)pyridin-3-yl)-N-(2-(2,2,3,3-tetrafluoropropyl)-1,2,3,4-tetrahydroisoquinolin-7-yl)acrylamide | 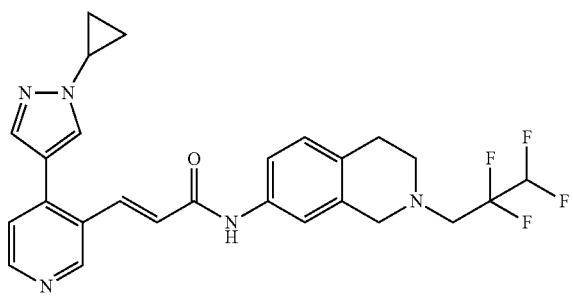 [SMILES: O=C(/C=C/c1cnccc1-c1cnn(C2CC2)c1)Nc1ccc2c(c1)CN(CC(F)(F)C(F)F)CC2] | | 500.1 |
| 302 | (2E)-N-(2-(cyclopropylmethyl)-1,2,3,4-tetrahydroisoquinolin-7-yl)-3-(4-(1-cyclopropyl-1H-pyrazol-4-yl)pyridin-3-yl)acrylamide | 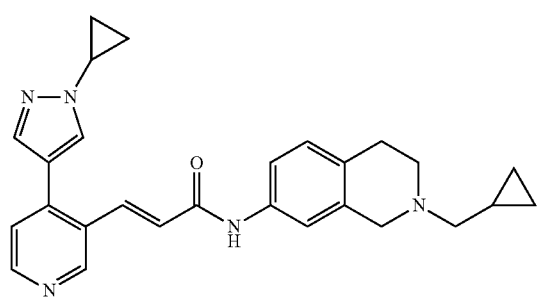 [SMILES: O=C(/C=C/c1cnccc1-c1cnn(C2CC2)c1)Nc1ccc2c(c1)CN(CC1CC1)CC2] | | 440.1 |
| 303 | (2E)-3-(4-(1H-pyrazol-4-yl)pyridin-3-yl)-N-(1-(2,2,2-trifluoroethyl)-1H-indol-5-yl)acrylamide | 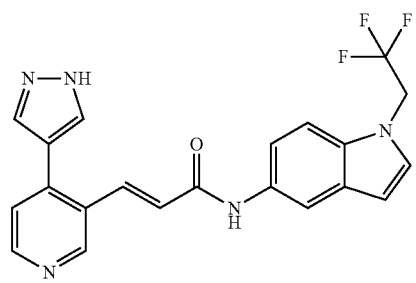 [SMILES: O=C(/C=C/c1cnccc1-c1cn[nH]c1)Nc1ccc2c(ccn2CC(F)(F)F)c1] | | 412.1 |
| 304 | (2E)-3-(4-(1-cyclopropyl-1H-pyrazol-4-yl)pyridin-3-yl)-N-(4-(2-oxa-5-azabicyclo[2.2.1]hept-5-ylmethyl)phenyl)acrylamide | 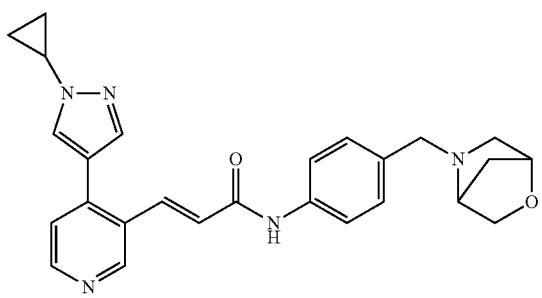 [SMILES: O=C(/C=C/c1cnccc1-c1cnn(C2CC2)c1)Nc1ccc(CN2CC3CC2CO3)cc1] | | 442.0 |
| 305 | (2E)-3-(4-(1-cyclopropyl-1H-pyrazol-4-yl)pyridin-3-yl)-N-(4-((5-methyl-2,5-diazabicyclo[2.2.1]hept-2-yl)methyl)phenyl)acrylamide | 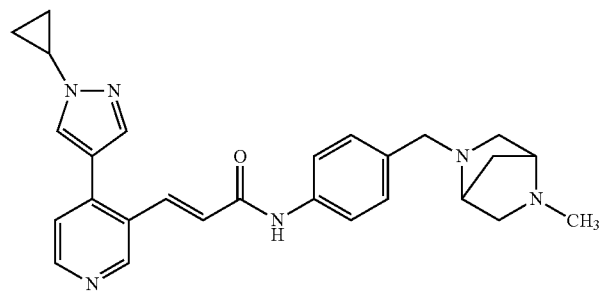 [SMILES: CN1CC2CC1CN2Cc1ccc(NC(=O)/C=C/c2cnccc2-c2cnn(C3CC3)c2)cc1] | | 455.1 |

TABLE 1-35-continued

| Example No. | IUPAC name | Structural formula | Salt | MS |
|---|---|---|---|---|
| 306 | (2E)-3-(4-(1-cyclopropyl-1H-pyrazol-4-yl)pyridin-3-yl)-N-(2-fluoro-4-(1-methyl-1H-pyrazol-5-yl)phenyl)acrylamide | 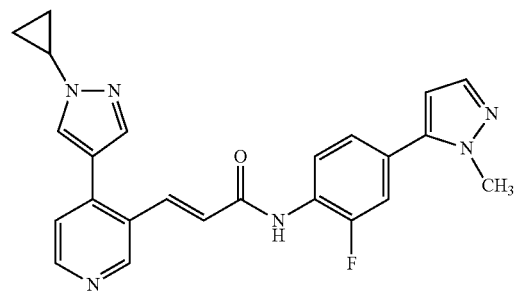 [SMILES: Cn1nccc1-c1ccc(NC(=O)/C=C/c2cnccc2-c2cnn(C3CC3)c2)c(F)c1] | | 429.0 |
| 307 | (2E)-3-(4-(1-cyclopropyl-1H-pyrazol-4-yl)pyridin-3-yl)-N-(4-(2-methylpyridin-4-yl)phenyl)acrylamide | 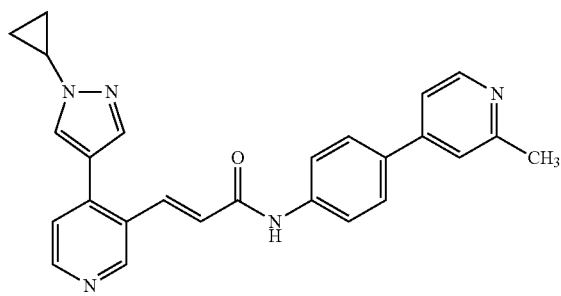 [SMILES: Cc1cc(-c2ccc(NC(=O)/C=C/c3cnccc3-c3cnn(C4CC4)c3)cc2)ccn1] | | 422.0 |

TABLE 1-36

| Example No. | IUPAC name | Structural formula | Salt | MS |
|---|---|---|---|---|
| 308 | (2E)-3-(4-(1-cyclopropyl-1H-pyrazol-4-yl)pyridin-3-yl)-N-(4-(2-oxa-6-azaspiro[3.3]hept-6-ylmethyl)phenyl)acrylamide | 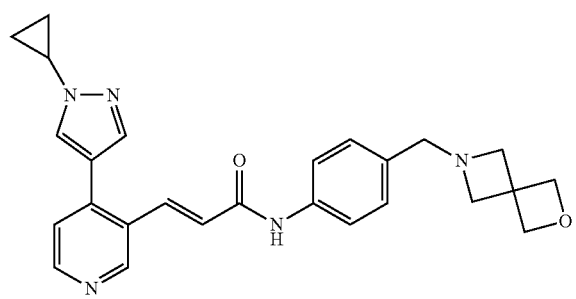 [SMILES: O=C(/C=C/c1cnccc1-c1cnn(C2CC2)c1)Nc1ccc(CN2CC3(COC3)C2)cc1] | | 442.0 |
| 309 | (2E)-3-(4-(1-cyclopropyl-1H-pyrazol-4-yl)pyridin-3-yl)-N-(4-((3,3-difluoroazetidin-1-yl)methyl)phenyl)acrylamide | 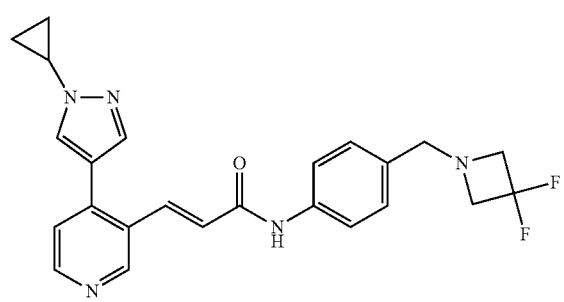 [SMILES: O=C(/C=C/c1cnccc1-c1cnn(C2CC2)c1)Nc1ccc(CN2CC(F)(F)C2)cc1] | | 436.0 |

TABLE 1-36-continued

| Example No. | IUPAC name | Structural formula | Salt | MS |
|---|---|---|---|---|
| 310 | (2E)-3-(4-(1-cyclopropyl-1H-pyrazol-4-yl)pyridin-3-yl)-N-(2-fluoro-4-methoxyphenyl)acrylamide | | | 379.1 |
| 311 | (2E)-3-(4-(1-cyclopropyl-1H-pyrazol-4-yl)pyridin-3-yl)-N-(4-(3,5-dimethyl-1,2-oxazol-4-yl)-2-fluorophenyl)acrylamide | | | 444.1 |
| 312 | (2E)-N-(2-fluoro-4-(morpholin-4-ylmethyl)phenyl)-3-(4-(1H-pyrazol-4-yl)pyridin-3-yl)acrylamide | | | 408.0 |
| 313 | (2E)-N-(4-(morpholin-4-ylmethyl)phenyl)-3-(4-(1-(oxetan-3-ylmethyl)-1H-benzimidazol-6-yl)pyridin-3-yl)acrylamide | | | 510.1 |
| 314 | (2E)-3-(4-(1H-pyrazol-4-yl)pyridin-3-yl)-N-(2-(2,2,2-trifluoroethyl)-1,2,3,4-tetrahydroisoquinolin-7-yl)acrylamide | | | 428.0 |
| 315 | (2E)-3-(4-(1H-pyrazol-4-yl)pyridin-3-yl)-N-(2-(2,2,2-trifluoroethyl)-1,2,3,4-tetrahydroisoquinolin-6-yl)acrylamide | | | 428.1 |

TABLE 1-36-continued

| Example No. | IUPAC name | Structural formula | Salt | MS |
|---|---|---|---|---|
| 316 | (2E)-3-(4-(1-cyclopropyl-1H-pyrazol-4-yl)pyridin-3-yl)-N-(2-(2,2,2-trifluoroethyl)-1,2,3,4-tetrahydroisoquinolin-6-yl)acrylamide | | | 468.0 |

TABLE 1-37

| Example No. | IUPAC name | Structural formula | Salt | MS |
|---|---|---|---|---|
| 317 | (2E)-3-(4-(1-cyclopropyl-1H-pyrazol-4-yl)pyridin-3-yl)-N-(1-(2,2,2-trifluoroethyl)-1H-indazol-5-yl)acrylamide | | | 453.0 |
| 318 | (2E)-3-(4-(1-cyclopropyl-1H-pyrazol-4-yl)pyridin-3-yl)-N-(2-(2,2,2-trifluoroethyl)-2H-indazol-5-yl)acrylamide | | | 453.0 |
| 319 | (2E)-3-(4-(1-cyclopropyl-1H-pyrazol-4-yl)pyridin-3-yl)-N-(2-(2,2,2-trifluoroethyl)-2,3-dihydro-1H-isoindol-5-yl)acrylamide | | | 452.0 |
| 320 | (2E)-3-(4-(1H-pyrazol-4-yl)pyridin-3-yl)-N-(2-(2,2,2-trifluoroethyl)-2,3-dihydro-1H-isoindol-5-yl)acrylamide | | | 414.0 |

TABLE 1-37-continued

| Example No. | IUPAC name | Structural formula | Salt | MS |
|---|---|---|---|---|
| 321 | (2E)-3-(4-(1-cyclopropyl-1H-pyrazol-4-yl)pyridin-3-yl)-N-(4-((3-methoxyazetidin-1-yl)methyl)phenyl)acrylamide | | | 430.0 |
| 322 | (2E)-3-(4-(1-cyclopropyl-1H-pyrazol-4-yl)pyridin-3-yl)-N-(4-((3-methylazetidin-1-yl)methyl)phenyl)acrylamide | | | 414.1 |
| 323 | (2E)-3-(4-(1-cyclopropyl-1H-pyrazol-4-yl)-5-fluoropyridin-3-yl)-N-(4-(morpholin-4-ylmethyl)phenyl)acrylamide | | | 448.1 |
| 324 | (2E)-3-(4-(1-cyclopropyl-1H-pyrazol-4-yl)-5-fluoropyridin-3-yl)-N-(2-(2,2,2-trifluoroethyl)-2,3-dihydro-1H-isoindol-5-yl)acrylamide | | | 471.9 |

TABLE 1-38

| Example No. | IUPAC name | Structural formula | Salt | MS |
|---|---|---|---|---|
| 325 | (2E)-N-(4-(cyclopropylmethoxy)phenyl)-3-(4-(1-cyclopropyl-1H-pyrazol-4-yl)pyridin-3-yl)acrylamide | | | 401.0 |
| 326 | (2E)-3-(4-(1-cyclopropyl-1H-pyrazol-4-yl)pyridin-3-yl)-N-(4-(6-oxa-3-azabicyclo[3.1.1]hept-3-yl)methyl)phenyl)acrylamide | | | 442.0 |
| 327 | (2E)-3-(5-fluoro-4-(1-methyl-1H-pyrazol-4-yl)pyridin-3-yl)-N-(2-(2,2,2-fluoroethyl)-2,3-dihydro-1H-isoindol-5-yl)acrylamide | | | 446.0 |
| 328 | (2E)-3-(4-(7-fluoro-1-methyl-1H-benzimidazol-6-yl)pyridin-3-yl)-N-(2-(2,2,2-trifluoroethyl)-2,3-dihydro-1H-isoindol-5-yl)acetamide | | | 495.9 |
| 329 | (2E)-3-(4-(1-methyl-1H-benzimidazol-6-yl)pyridin-3-yl)-N-(2-(2,2,2-trifluoroethyl)-2,3-dihydro-1H-isoindol-5-yl)acrylamide | | | 478.0 |

TABLE 1-38-continued

| Example No. | IUPAC name | Structural formula | Salt | MS |
|---|---|---|---|---|
| 330 | (2E)-3-(4-(1-cyclopropyl-1H-pyrazol-4-yl)pyridin-3-yl)-N-(2-fluoro-4 -((2,2,2-trifluoroethoxy)methyl)phenyl) acrylamide | | | 461.0 |
| 331 | (2E)-3 -(4-(1-cyclopropyl-1H-pyrazol-4-yl)-5-fluoropyridin-3-yl)-N-(2,3-dihydro-1,4-benzodioxin-6-yl)acrylamide | | | 406.9 |
| 332 | (2E)-3-(4-(1-cyclopropyl-1H-pyrazol-4-yl)-5-fluoropyridin-3-yl)-N-(2-fluoro-4-(2-hydroxy-2-methylpropyl)phenyl)acrylamide | | | 439.1 |

TABLE 1-39

| Example No. | IUPAC name | Structural formula | Salt | MS |
|---|---|---|---|---|
| 333 | (2E)-N-(2-((1-fluorocyclopropyl)methyl)-2,3-dihydro-1H-isoindol-5-yl)-3-(4-(1-methyl-1H-pyrazol-4-yl)pyridin-3-yl) acrylamide | | | 418.0 |
| 334 | (2E)-3-(4-(1-ethyl-1H-pyrazol-4-yl)pyridin-3-yl)-N-(2-(2,2,2-trifluoroethyl)-2,3-dihydro-1H-isoindol-5-yl) acrylamide | | | 442.0 |

TABLE 1-39-continued

| Example No. | IUPAC name | Structural formula | Salt | MS |
|---|---|---|---|---|
| 335 | tert-butyl 7-fluoro-6-(((2E)-3-(4-(1-methyl-1H-pyrazol-4-yl)pyridin-3-yl)prop-2-enoyl)amino)-3,4-dihydroisoquinoline-2(1H)-carboxylate | 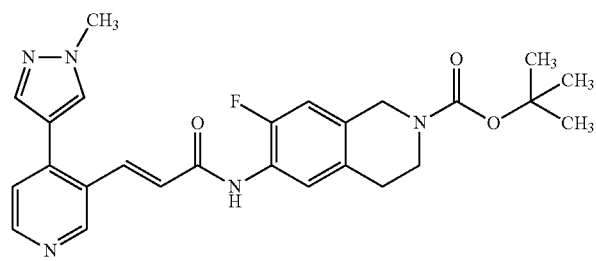 [SMILES: Cn1cc(-c2ccncc2/C=C/C(=O)Nc2cc3c(cc2F)CN(C(=O)OC(C)(C)C)CC3)cn1] | | 478.0 |
| 336 | (2E)-3-(4-(1-cyclopropyl-1H-pyrazol-4-yl)-5-fluoropyridin-3-yl)-N-(4-(6-oxa-3-azabicyclo[3.1.1]hept-3-ylmethyl)phenyl)acrylamide | 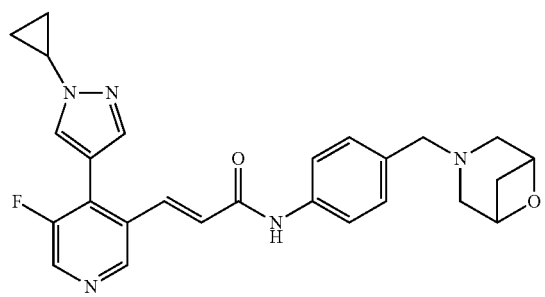 [SMILES: O=C(/C=C/c1cncc(F)c1-c1cnn(C2CC2)c1)Nc1ccc(CN2CC3CC(C2)O3)cc1] | | 460.2 |
| 337 | (2E)-3-(4-(7-fluoro-1-(oxetan-3-ylmethyl)-1H-benzimidazol-6-yl)pyridin-3-yl)-N-(2-(2,2,2-trifluoroethyl)-2,3-dihydro-1H-isoindol-5-yl)acrylamide | 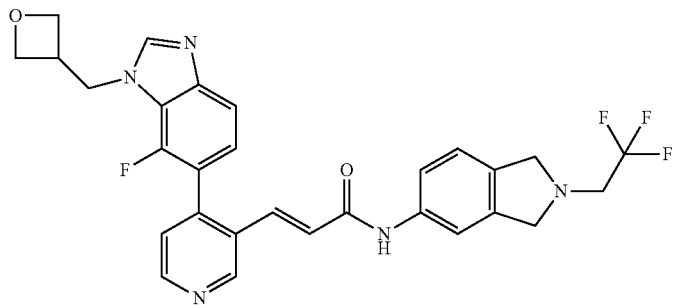 [SMILES: O=C(/C=C/c1cnccc1-c1ccc2ncn(CC3COC3)c2c1F)Nc1ccc2c(c1)CN(CC(F)(F)F)C2] | | 552.2 |
| 338 | (2E)-N-(7-fluoro-1,2,3,4-tetrahydroisoquinolin-6-yl)-3-(4-(1-methyl-1H-pyrazol-4-yl)pyridin-3-yl)acrylamide | 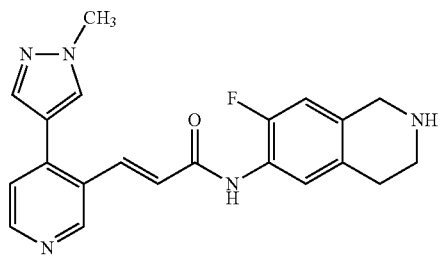 [SMILES: Cn1cc(-c2ccncc2/C=C/C(=O)Nc2cc3c(cc2F)CNCC3)cn1] | 3HCl | 378.2 |
| 339 | (2E)-N-(7-fluoro-2-(2,2,2-trifluoroethyl)-1,2,3,4-tetrahydroisoquinolin-6-yl)-3-(4-(1-methyl-1H-pyrazol-4-yl)pyridin-3-yl)acrylamide | 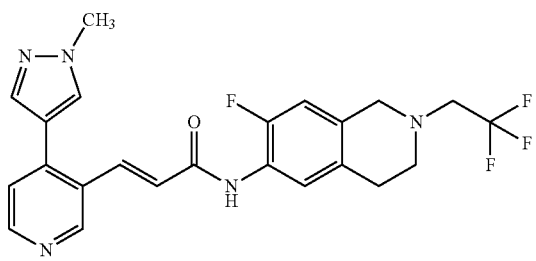 [SMILES: Cn1cc(-c2ccncc2/C=C/C(=O)Nc2cc3c(cc2F)CN(CC(F)(F)F)CC3)cn1] | | 460.2 |

TABLE 1-39-continued

| Example No. | IUPAC name | Structural formula | Salt | MS |
|---|---|---|---|---|
| 340 | (2E)-3-(4-(1-cyclopropyl-1H-pyrazol-4-yl)pyridin-3-yl)-N-(2-(2,2-difluoro-3-hydroxypropyl)-2,3-dihydro-1H-isoindol-5-yl)acrylamide | | | 466.1 |

TABLE 1-40

| Example No. | IUPAC name | Structural formula | Salt | MS |
|---|---|---|---|---|
| 341 | (2E)-N-(2-(2,2-difluoro-3-hydroxypropyl)-2,3-dihydro-1H-isoindol-5-yl)-3-(4-(1-methyl-1H-pyrazol-4-yl)pyridin-3-yl)acrylamide | | | 440.2 |
| 342 | (2E)-N-(2-(2,2-difluoroethyl)-2,3-dihydro-1H-isoindol-5-yl)-3-(4-(1-methyl-1H-pyrazol-4-yl)pyridin-3-yl)acrylamide | | | 410.1 |
| 343 | (2E)-3-(4-(1-cyclopropyl-1H-pyrazol-yl)-5-fluoropyridin-3-yl)-N-(2-fluoro-4-((3-methoxyazetidin-1-yl)methyl)phenyl)acrylamide | | | 466.2 |
| 344 | (2E)-3-(4-(1-cyclopropyl-1H-pyrazol-4-yl)-5-fluoropyridin-3-yl)-N-(4-((3,3-difluoroazetidin-1-yl)methyl)phenyl)acrylamide | | | 454.2 |

TABLE 1-40-continued

| Example No. | IUPAC name | Structural formula | Salt | MS |
|---|---|---|---|---|
| 345 | (2E)-3-(4-(1-cyclopropyl-1H-pyrazol-4-yl)-5-fluoropyridin-3-yl)-N-(4-((3-methoxyazetidin-1-yl)methyl)phenyl)acrylamide | 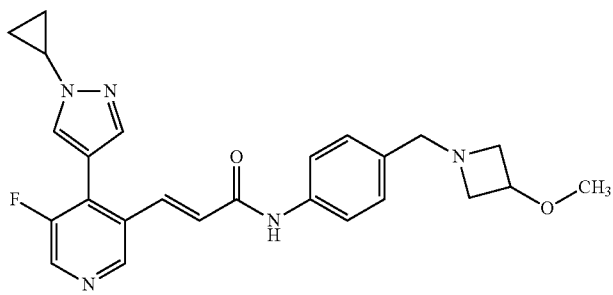 [SMILES: COC1CN(Cc2ccc(NC(=O)/C=C/c3cncc(F)c3-c3cnn(C4CC4)c3)cc2)C1] | | 448.2 |
| 346 | (2E)-3-(4-(1-cyclopropyl-1H-pyrazol-4-yl)-5-fluoropyridin-3-yl)-N-(4-((33-difluoroazetidin-1-yl)methyl)-2-fluorophenyl)acrylamide | 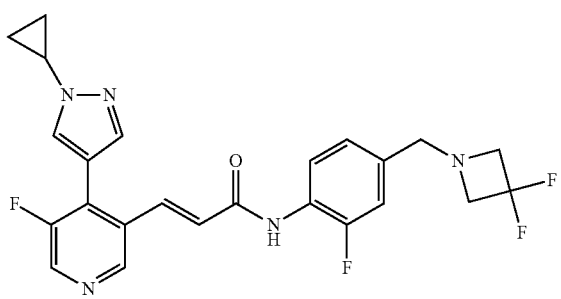 [SMILES: O=C(/C=C/c1cncc(F)c1-c1cnn(C2CC2)c1)Nc1ccc(CN2CC(F)(F)C2)cc1F] | | 472.1 |
| 347 | (2E)-3 -(4-(1-cyclopropyl-1H-pyrazol-4-yl)-5-fluoropyridin-3-yl)-N-(2-fluoro-4-(6-oxa-3-azabicyclo[3.1.1]hept-3-ylmethyl)phenyl)acrylamide | 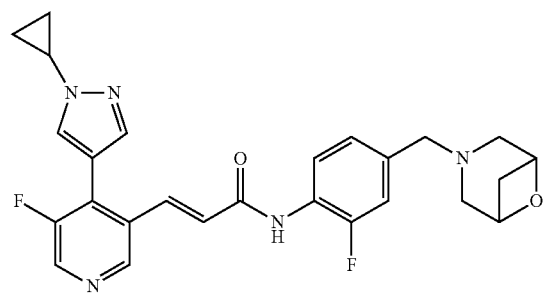 [SMILES: O=C(/C=C/c1cncc(F)c1-c1cnn(C2CC2)c1)Nc1ccc(CN2CC3CC(C2)O3)cc1F] | | 478.2 |
| 348 | (2E)-3-(4-(1-cyclopropyl-1H-pyrazol-4-yl)-5-fluoropyridin-3-yl)-N-(4-(2-fluoro-2-methylpropyl)phenyl)acrylamide | 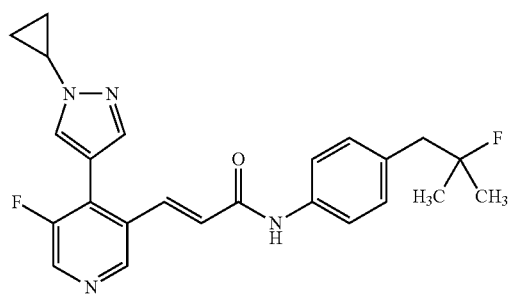 [SMILES: CC(C)(F)Cc1ccc(NC(=O)/C=C/c2cncc(F)c2-c2cnn(C3CC3)c2)cc1] | | 423.2 |

TABLE 1-41

| Example No. | IUPAC name | Structural formula | Salt | MS |
|---|---|---|---|---|
| 349 | (2E)-3-(4-(1-cyclopropyl-1H-pyrazol-4-yl)-5-fluoropyridin-3-yl)-N-(4-(1-methyl-1H-pyrazol-3-yl)phenyl)acrylamide | 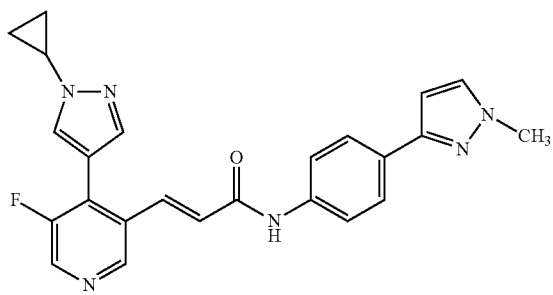 [SMILES: Cn1ccc(-c2ccc(NC(=O)/C=C/c3cncc(F)c3-c3cnn(C4CC4)c3)cc2)n1] | | 429.2 |
| 350 | (2E)-N-(2-(2,2-difluoropropyl)-2,3-dihydro-1H-isoindol-5-yl)-3-(4-(1-methyl-1H-pyrazol-4-yl)pyridin-3-yl)acrylamide | 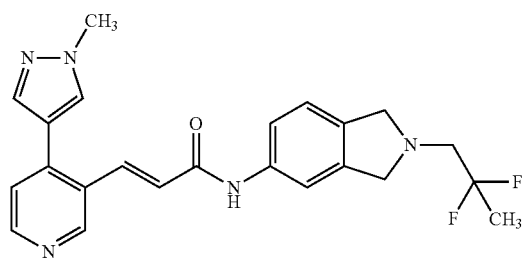 [SMILES: Cn1cc(-c2ccncc2/C=C/C(=O)Nc2ccc3c(c2)CN(CC(C)(F)F)C3)cn1] | | 424.1 |
| 351 | (2E)-N-(2-(2,2-difluoropropyl)-2,3-dihydro-1H-isoindol-5-yl)-3-(5-fluoro-4-(1-methyl-1H-pyrazol-4-yl)pyridin-3-yl)acrylamide | 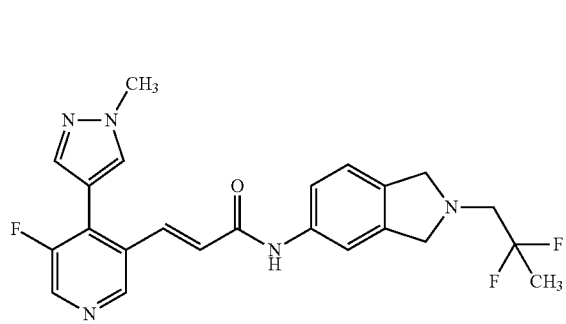 [SMILES: Cn1cc(-c2c(F)cncc2/C=C/C(=O)Nc2ccc3c(c2)CN(CC(C)(F)F)C3)cn1] | | 442.2 |
| 352 | (2E)-N-(2-(2,2-difluoro-3-methoxypropyl)-2,3-dihydro-1H-isoindol-5-yl)-3-(5-fluoro-4-(1-methyl-1H-pyrazol-4-yl)pyridin-3-yl)acrylamide | 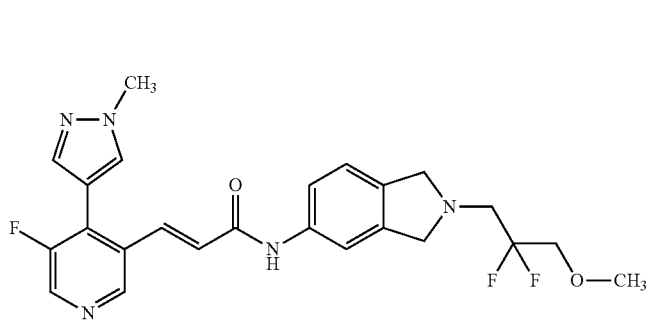 [SMILES: COCC(F)(F)CN1Cc2ccc(NC(=O)/C=C/c3cncc(F)c3-c3cnn(C)c3)cc2C1] | | 470.2 |
| 353 | (2E)-N-(2-(2,2-difluoro-3-methoxypropyl)-2,3-dihydro-1H-isoindol-5-yl)-3-(4-(1-methyl-1H-pyrazol-4-yl)pyridin-3-yl)acrylamide | 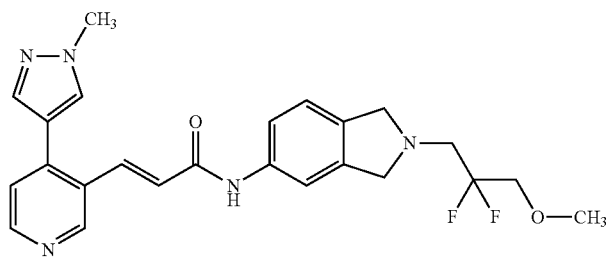 [SMILES: COCC(F)(F)CN1Cc2ccc(NC(=O)/C=C/c3cnccc3-c3cnn(C)c3)cc2C1] | | 454.2 |

TABLE 1-41-continued

| Example No. | IUPAC name | Structural formula | Salt | MS |
|---|---|---|---|---|
| 354 | (2E)-N-(2-(2,2-difluoroethyl)-2,3-dihydro-1H-isoindol-5-yl)-3-(5-fluoro-4-(1-methyl-1H-pyrazol-4-yl)pyridin-3-yl)acrylamide | | | 428.2 |
| 355 | (2E)-N-(2-(2,2-difluoro-3-methoxypropyl)-2,3-dihydro-1H-isoindol-5-yl)-3-(5-fluoro-4-(1-methyl-1H-benzimidazol-6-yl)pyridin-3-yl)acrylamide | | | 522.2 |
| 356 | (2E)-N-(2-(2,2-difluoro-3-methoxypropyl)-2,3-dihydro-1H-isoindol-5-yl)-3-(4-(1-methyl-1H-benzimidazol-6-yl)pyridin-3-yl)acrylamide | | | 504.4 |

TABLE 1-42

| Example No. | IUPAC name | Structural formula | Salt | MS |
|---|---|---|---|---|
| 357 | (2E)-3-(5-fluoro-4-(1-methyl-1H-benzimidazol-6-yl)pyridin-3-yl)-N-(2-(2,2,2-trifluoroethyl)-2,3-dihydro-1H-isoindol-5-yl)acrylamide | | | 496.1 |
| 358 | (2E)-N-(4-((3,3-difluoroazetidin-1-yl)methyl)phenyl)-3-(5-fluoro-4-(1-methyl-1H-benzimidazol-6-yl)pyridin-3-yl)acrylamide | | | 478.1 |

TABLE 1-42-continued

| Example No. | IUPAC name | Salt | MS |
|---|---|---|---|
| 359 | (2E)-N-(4-((3,3-difluoroazetidin-1-yl)methyl)phenyl)-3-(5-fluoro-4-(1-methyl-1H-pyrazol-4-yl)pyridin-3-yl)acrylamide | | 426.1 |
| 360 | (2E)-3-(4-(1-cyclopropyl-1H-pyrazol-4-yl)-5-fluoropyridin-3-yl)-N-(4-(3,3-difluoroazetidin-1-yl)phenyl)acetamide | | 440.1 |
| 361 | (2E)-N-(4-(3,3-difluoroazetidin-1-yl)phenyl)-3-(5-fluoro-4-(1-methyl-1H-pyrazol-4-yl)pyridin-3-yl)acrylamide | | 414.1 |
| 362 | (2E)-3-(4-(1-cyclopropyl-1H-pyrazol-4-yl)pyridin-3-yl)-N-(4-(3,3-difluoroazetidin-1-yl)phenyl)acrylamide | | 422.1 |
| 363 | (2E)-N-(4-(3,3-difluoroazetidin-1-yl)phenyl)-3-(4-(1-methyl-1H-pyrazol-4-yl)pyridin-3-yl)acrylamide | | 396.2 |

TABLE 1-42-continued

| Example No. | IUPAC name | Structural formula | Salt | MS |
|---|---|---|---|---|
| 364 | (2E)-3-(4-(1-cyclopropyl-1H-pyrazol-4-yl)-5-fluoropyridin-3-yl)-N-(4-(2-hydroxy-2-methylpropyl)phenyl)acrylamide | | | 421.2 |
| 365 | (2E)-3-(4-(1-cyclopropyl-1H-pyrazol-4-yl)pyridin-3-yl)-N-(4-((3-fluoroazetidin-1-yl)methyl)phenyl)acrylamide | | | 418.1 |

TABLE 1-43

| Example No. | IUPAC name | Structural formula | Salt | MS |
|---|---|---|---|---|
| 366 | (2E)-N-(4-(3,3-difluoropyrrolidin-1-yl)phenyl)-3-(5-fluoro-4-(1-methyl-1H-pyrazol-4-yl)pyridin-3-yl)acrylamide | | | 428.2 |
| 367 | (2E)-N-(4-(4,4-difluoropiperidin-1-yl)phenyl)-3-(5-fluoro-4-(1-methyl-1H-pyrazol-4-yl)pyridin-3-yl)acrylamide | | | 442.1 |
| 368 | (2E)-3-(4-(1-cyclopropyl-1H-pyrazol-yl)-5-fluoropyridin-3-yl)-N-(4-(2,2,2-trifluoroethyl)phenyl)acrylamide | | | 431.1 |

TABLE 1-43-continued

| Example No. | IUPAC name | Structural formula | Salt | MS |
|---|---|---|---|---|
| 369 | (2E)-3-(4-(1-cyclopropyl-1H-pyrazol-4-yl)pyridin-3-yl)-N-(4-((3,3-dimethylazetidin-1-yl)methyl)phenyl)acrylamide | | | 428.3 |
| 370 | (2E)-3-(4-(1-cyclopropyl-1H-pyrazol-4-yl)pyridin-3-yl)-N-(4-((3,3-difluoroazetidin-1-yl)methyl)-2-fluorophenyl)acrylamide | | | 454.2 |
| 371 | (2E)-N-(4-((3-fluoroazetidin-1-yl)methyl)phenyl)-3-(5-fluoro-4-(1-methyl-1H-pyrazol-4-yl)pyridin-3-yl)acrylamide | | | 410.1 |
| 372 | (2E)-3-(4-(1-cyclopropyl-1H-pyrazol-4-yl)-5-fluoropyridin-3-yl)-N-(4-((3-fluoroazetidin-1-yl)methyl)phenyl)acrylamide | | | 436.1 |

TABLE 1-44

| Example No. | IUPAC name | Structural formula | Salt | MS |
|---|---|---|---|---|
| 373 | (2E)-3-(4-(1-cyclopropyl-1H-pyrazol-yl)pyridin-3-yl)-N-(4-((3,3-difluoroazetidin-1-yl)methyl)phenyl)acrylamide | | $H_2SO_4$ | 436.1 |

TABLE 1-44-continued

| Example No. | IUPAC name | Structural formula | Salt | MS |
|---|---|---|---|---|
| 374 | (2E)-3-(4-(1-cyclopropyl-1H-pyrazol-4-yl)pyridin-3-yl)-N-(4-((3,3-difluoroazetidin-1-yl)methyl)phenyl)acrylamide | | H₃PO₄ | 436.1 |
| 375 | (2E)-3-(4-(1-cyclopropyl-1H-pyrazol-4-yl)pyridin-3-yl)-N-(4-((3,3-difluoroazetidin-1-yl)methyl)phenyl)acrylamide | | MsOH | 436.0 |
| 376 | (2E)-3-(4-(1-cyclopropyl-1H-pyrazol-4-yl)pyridin-3-yl)-N-(4-((3,3-difluoroazetidin-1-yl)methyl)phenyl)acrylamide | | 1/2 fumarate | 436.1 |
| 377 | (2E)-3-(4-(1-cyclopropyl-1H-pyrazol-4-yl)pyridin-3-yl)-N-(4-((3,3-difluoroazetidin-1-yl)methyl)phenyl)acrylamide | | 1/2 succinate | 436.1 |
| 378 | 3-(4-(1-methyl-1H-pyrazol-4-yl)pyridin-3-yl)-N-(4-(morpholin-4-ylmethyl)phenyl)propaneamide | | | 406.2 |

TABLE 1-44-continued

| Example No. | IUPAC name | Structural formula | Salt | MS |
|---|---|---|---|---|
| 379 | 3-(4-(1-cyclopropyl-1H-pyrazol-4-yl)pyridin-3-yl)-N-(4-morpholin-4-ylmethyl)phenyl)propaneamide | | | 432.2 |
| 380 | 2-(4-(1-methyl-1H-pyrazol-4-yl)pyridin-3-yl)-N-(4-(morpholin-4-ylmethyl)phenyl)cyclopropanecarboxamide | | | 418.2 |
| 381 | 2-(4-(1-cyclopropyl-1H-pyrazol-4-yl)pyridin-3-yl)-N-(4-(morpholin-4-ylmethyl)phenyl)cyclopropanecarboxamide | | | 444.3 |

Formulation Example 1

A medicament containing the compound of the present invention as an active ingredient can be produced by, for example, the following formulation:

[Formula 1]
1. Capsule

| | | |
|---|---|---|
| (1) | Compound obtained in Example 1 | 40 mg |
| (2) | Lactose | 70 mg |
| (3) | Microcrystalline cellulose | 9 mg |
| (4) | Magnesium stearate | 1 mg |
| | | 120 mg per capsule |

Ingredients (1), (2) and (3) and ½ of ingredient (4) are mixed and then granulated. The remaining portion of the ingredient (4) is added thereto, and the whole portion is encapsulated in a gelatin shell.

[Formula 2]
2. Tablet

| | | |
|---|---|---|
| (1) | Compound obtained in Example 1 | 40 mg |
| (2) | Lactose | 58 mg |
| (3) | Corn starch | 18 mg |

-continued

[Formula 2]
2. Tablet

| | | |
|---|---|---|
| (4) | Microcrystalline cellulose | 3.5 mg |
| (5) | Magnesium stearate | 0.5 mg |
| | | 120 mg per tablet |

Ingredients (1), (2) and (3), ⅔ of ingredient (4) and ½ of ingredient (5) are mixed and then granulated. The remaining portions of the ingredients (4) and (5) are added to the granules, and the mixture is molded into a tablet under pressure.

Formulation Example 2

In 50 mL of Japanese Pharmacopoeia distilled water for injection, 50 mg of the compound obtained in Example 1 is dissolved, followed by addition of Japanese Pharmacopoeia distilled water for injection to adjust the amount of the solution to 100 mL. This solution is filtered under sterile conditions. Next, each vial for injection is filled with a 1 mL aliquot of this solution under sterile conditions, freeze-dried and hermetically sealed.

Test Example 1

The compound of the present invention was evaluated for its CDK8 inhibitory activity and CDK19 inhibitory activity by the following method.

The test compound dissolved in dimethyl sulfoxide was diluted with an assay buffer (25 mM HEPES, 10 mM $MgCl_2$, 2 mM DL-dithiothreitol, and 0.01% Tween-20) to obtain a primary diluted solution having a DMSO concentration of 3%. The primary diluted solution was dispensed in the amount of 2 μL/well to a 384-well plate, and then, a mixed solution of $Eu^{3+}$ Cryptate conjugated mouse monoclonal antibody anti-glutathione S-transferase (Cisbio) diluted 267-fold with an assay buffer and 60 nM Kinase Tracer-236 (Life technologies) was added thereto at 2 μL/well. After the addition, each kinase solution (84 ng/mL CDK8/CycC (Carna Biosciences) diluted with an assay buffer used for CDK8 inhibitory activity measurement, and 87 ng/mL CDC2L6/CycC (Carna Biosciences) diluted with an assay buffer used for CDK19 inhibitory activity measurement) was further added thereto at 2 μL/well. After the addition, the plate was left standing at room temperature for 1 hour, and then, the fluorescence intensity (excitation wavelength 320 nm, fluorescence wavelength 615 nm, 665 nm, delay time 50 μsec) was measured using an EnVision plate reader (PerkinElmer).

The percent inhibition of CDK8 or CDK19 activity by the test compound can be calculated according to the following formula, wherein the fluorescence intensity of a reaction solution in the absence of compound is defined as the control, and the fluorescence intensity of a reaction solution in the presence of 10 μM of control compound is defined as the blank.

Percent inhibition (%)=(1−(fluorescence intensity of the test compound−blank)÷(control−blank))×100.

Commercially available 4-(4-(2,3-dihydro-1,4-benzodioxin-6-yl)-1H-pyrazol-3-yl)benzene-1,3-diol can be used as the control compound. For reference, the concentrations necessary for the control compound to exhibit 50% percent inhibition of CDK8 or CDK19 ($IC_{50}$ value) are shown in Table 2.

TABLE 2

| CDK8 inhibition $IC_{50}$ (μM) | CDK19 inhibition $IC_{50}$ (μM) |
|---|---|
| 0.12 | 0.13 |

The percent inhibition (%) of CDK8 and the percent inhibition (%) of CDK19 by 1 μM of the test compounds are shown in Table 3.

Test Example 2

The compound of the present invention was evaluated for its inhibitory activity against human multiple myeloma RPMI8226 cell growth by the following method.

A suspension of human multiple myeloma RPMI8226 cells (purchased from the Health Protection Agency) was inoculated at 40 μL (300 cells/well) to a 384-well plate and cultured at 37° C. for 1 day in a 5% $CO_2$ incubator. After the culture, each test compound solution was added thereto at a test concentration of 1 μM using TECAN D300, and the cells were further cultured for 8 days. After the culture, CellTiter-Glo™ Luminescent Cell Viability Assay reagent (Promega) was added at 40 μL/well to a 384-well plate, and the amount of luminescence was measured using a luminometer. Inhibitory activity against human multiple myeloma RPMI8226 cell growth (percent inhibition (%)) of the test compound was calculated according to the following formula, which is based on the hypothesis that the amount of residual ATP reflects the number of cells. In this formula, 100% control represents the amount of luminescence from a well with only 0.1% DMSO added.

Percent inhibition (%)=(1−(amount of luminescence of the test compound)÷(100% control))×100

Percent inhibition (%) for 1 μM of the test compounds is shown in Table 3.

TABLE 3

| Example | Percent inhibition of CDK8 activity (%) | Percent inhibition of CDK19 activity (%) | Percent inhibition of RPMI8226 cell growth (%) |
|---|---|---|---|
| 1 | 101 | 100 | 59 |
| 19 | 100 | 98 | 54 |
| 31 | 100 | 98 | 60 |
| 33 | 100 | 99 | 61 |
| 37 | 97 | 101 | 61 |
| 41 | 99 | 97 | 56 |
| 42 | 99 | 99 | 53 |
| 43 | 96 | 98 | 57 |
| 45 | 98 | 99 | 55 |
| 47 | 101 | 98 | 57 |
| 49 | 95 | 96 | 56 |
| 50 | 96 | 97 | 61 |
| 51 | 100 | 96 | 58 |
| 53 | 101 | 97 | 58 |
| 54 | 100 | 95 | 55 |
| 55 | 99 | 97 | 55 |
| 58 | 97 | 98 | 55 |
| 68 | 99 | 100 | 62 |
| 69 | 99 | 99 | 48 |
| 73 | 101 | 99 | 56 |
| 76 | 104 | 93 | 52 |
| 78 | 100 | 74 | 59 |
| 84 | 97 | 97 | 60 |
| 89 | 96 | 97 | 63 |
| 91 | 96 | 101 | 59 |
| 92 | 96 | 100 | 63 |
| 93 | 101 | 101 | 63 |
| 97 | 92 | 102 | 53 |
| 98 | 98 | 100 | 53 |
| 99 | 90 | 85 | 62 |
| 100 | 97 | 100 | 52 |
| 101 | 98 | 97 | 55 |
| 108 | 94 | 97 | 58 |
| 109 | 96 | 98 | 58 |
| 116 | 100 | 94 | 55 |
| 123 | 99 | 101 | 62 |
| 124 | 98 | 99 | 53 |
| 137 | 95 | 96 | 54 |
| 142 | 98 | 99 | 62 |
| 143 | 100 | 103 | 61 |
| 145 | 90 | 94 | 51 |
| 148 | 97 | 99 | 54 |
| 150 | 100 | 99 | 54 |
| 151 | 95 | 95 | 54 |
| 154 | 96 | 99 | 62 |
| 155 | 98 | 93 | 54 |
| 156 | 94 | 94 | 55 |
| 159 | 102 | 100 | 60 |
| 163 | 96 | 94 | 53 |
| 168 | 100 | 97 | 59 |
| 169 | 94 | 90 | 53 |
| 172 | 96 | 95 | 55 |
| 175 | 98 | 99 | 55 |
| 176 | 92 | 87 | 54 |
| 182 | 84 | 78 | 58 |
| 191 | 96 | 92 | 56 |
| 194 | 99 | 99 | 53 |
| 195 | 94 | 97 | 52 |

TABLE 3-continued

| Example | Percent inhibition of CDK8 activity (%) | Percent inhibition of CDK19 activity (%) | Percent inhibition of RPMI8226 cell growth (%) |
|---|---|---|---|
| 196 | 101 | 98 | 54 |
| 212 | 100 | 98 | 52 |
| 216 | 102 | 100 | 59 |
| 218 | 96 | 101 | 65 |
| 220 | 93 | 96 | 58 |
| 221 | 99 | 98 | 63 |
| 222 | 101 | 100 | 52 |
| 226 | 98 | 98 | 66 |
| 234 | 102 | 102 | 65 |
| 237 | 94 | 91 | 66 |
| 238 | 100 | 100 | 67 |
| 239 | 100 | 100 | 65 |
| 241 | 99 | 101 | 66 |
| 242 | 96 | 97 | 55 |
| 246 | 95 | 93 | 49 |
| 247 | 98 | 102 | 63 |
| 248 | 98 | 98 | 57 |
| 249 | 99 | 97 | 62 |
| 250 | 99 | 96 | 63 |
| 251 | 100 | 97 | 61 |
| 252 | 99 | 93 | 60 |
| 253 | 98 | 97 | 62 |
| 256 | 96 | 95 | 58 |
| 257 | 99 | 95 | 56 |
| 258 | 96 | 96 | 54 |
| 260 | 98 | 99 | 53 |
| 261 | 97 | 93 | 52 |
| 266 | 99 | 98 | 57 |
| 271 | 102 | 93 | 62 |
| 272 | 101 | 94 | 67 |
| 273 | 101 | 96 | 64 |
| 274 | 102 | 97 | 53 |
| 275 | 102 | 98 | 64 |
| 276 | 99 | 92 | 60 |
| 277 | 98 | 101 | 65 |
| 280 | 97 | 96 | 58 |
| 281 | 92 | 97 | 58 |
| 283 | 95 | 96 | 60 |
| 284 | 92 | 95 | 57 |
| 288 | 99 | 101 | 57 |
| 289 | 98 | 102 | 64 |
| 290 | 95 | 89 | 53 |
| 292 | 97 | 93 | 52 |
| 293 | 102 | 95 | 61 |
| 295 | 103 | 97 | 62 |
| 296 | 100 | 97 | 59 |
| 298 | 85 | 84 | 63 |
| 300 | 97 | 94 | 57 |
| 308 | 110 | 98 | 56 |
| 309 | 105 | 101 | 58 |
| 311 | 103 | 98 | 58 |
| 316 | 103 | 98 | 49 |
| 319 | 103 | 101 | 47 |
| 321 | 101 | 99 | 59 |
| 322 | 102 | 97 | 55 |
| 324 | 104 | 100 | 58 |
| 327 | 106 | 104 | 56 |
| 330 | 101 | 96 | 53 |
| 331 | 103 | 98 | 65 |
| 332 | 102 | 99 | 60 |
| 336 | 102 | 101 | 59 |
| 340 | 102 | 96 | 65 |
| 342 | 105 | 94 | 63 |
| 343 | 103 | 96 | 63 |
| 345 | 101 | 100 | 63 |
| 348 | 99 | 101 | 62 |
| 351 | 106 | 100 | 63 |
| 357 | 101 | 96 | 69 |
| 358 | 87 | 101 | 67 |
| 359 | 103 | 102 | 65 |
| 363 | 105 | 99 | 50 |
| 365 | 107 | 99 | 58 |
| 370 | 105 | 74 | 51 |
| 373 | 101 | 101 | 70 |
| 374 | 100 | 100 | 69 |
| 375 | 102 | 101 | 70 |
| 376 | 99 | 100 | 70 |
| 377 | 102 | 100 | 66 |

It is shown in Table 3 that the compound of the present invention strongly inhibits CDK8 and CDK19 and inhibits the growth of human multiple myeloma.

Test Example 3

The compound of the present invention was evaluated for its antitumor efficacy in mice bearing cancer derived from SW480 human colorectal cancer cells by the following method.

SW480 human colorectal cancer cells were transplanted into 6- to 7-week-old BALB/c female nude mice (CLEA Japan) by subcutaneous injection of $2.0 \times 10^6$ cells per mouse. At 7 to 14 days after the transplantation, the size of the engrafted tumor was measured, and the tumor volume was calculated according to the following formula.

Tumor volume=major axis×minor axis×minor axis× (½)

Test subjects having an engrafted tumor with a tumor volume of approximately 100 mm³ were selected and used in the experiment (6 subjects per group). A suspension of each test compound in a 0.5% methylcellulose solution (Wako Pure Chemical Industries) was orally administered to the mice for 14 days at the dose (mg/kg body weight, indicating the amount per dose) and the number of doses shown in Table 4. On the day before the start of the administration and the day before the completion of the administration, the tumor size was measured, and the tumor volume was calculated.

Percent tumor growth (T/C (%)) of the test compound administration group relative to the control administration group was calculated according to the following formula.

T/C(%)=(tumor volume of the test compound administration group after the completion of the administration−tumor volume of the test compound administration group at the day before the start of the administration)/(tumor volume of the control administration group after the completion of the administration−tumor volume of the control administration group at the day before the start of the administration))×100

The T/C (%) of each administered test compound is shown in Table 4.

TABLE 4

| Example No. | Dose (mg/kg) | Number of doses per day (times) | T/C (%) |
|---|---|---|---|
| 97 | 50 | 1 | 37 |
| 194 | 50 | 1 | 36 |
| 216 | 50 | 1 | 43 |
| 273 | 50 | 1 | 36 |
| 289 | 50 | 1 | 31 |
| 309 | 30 | 1 | 51 |
| 324 | 30 | 1 | 29 |
| 359 | 30 | 1 | 36 |

It is shown in Table 4 that the compound of the present invention strongly inhibits the growth of colorectal cancer cells.

INDUSTRIAL APPLICABILITY

The compound of the present invention has excellent inhibitory activity against CDK8/19. Thus, the compound of the present invention can be used as a CDK8/19 inhibitor and is useful as a preventive or therapeutic agent for diseases associated with CDK8/19, including cancer, etc.

The present application is based on Japanese Patent Application No. 2014-086927 filed in Japan, the content of which is incorporated herein in its entirety.

The invention claimed is:

1. A compound capable of inhibiting CDK8 and/or CDK19 represented by the formula:

[Formula 1]

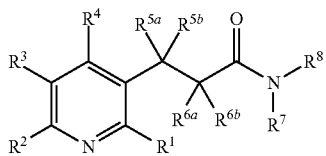

(I)

or a salt thereof, wherein
 $R^1$ is a hydrogen atom;
 $R^2$ is a hydrogen atom, a halogen atom, an amino group or a hydroxy group;
 $R^3$ is a hydrogen atom or a halogen atom;
 $R^4$ is a 5- or 6-membered monocyclic aromatic heterocyclic group or an 8- to 14-membered fused polycyclic aromatic heterocyclic group, optionally substituted by 1 to 3 substituents selected from the following substituents (1) to (11):
  (1) a $C_{1-6}$ alkyl group optionally having 1 to 7 halogen atoms,
  (2) a $C_{1-6}$ alkyl group substituted by 1 to 7 substituents selected from
   (i) a hydroxy group,
   (ii) an amino group,
   (iii) a $C_{1-6}$ alkoxy group,
   (iv) an optionally halogenated $C_{3-10}$ cycloalkyl group,
   (v) a 5- to 14-membered aromatic heterocyclic group,
   (vi) a 3- to 14-membered non-aromatic heterocyclic group,
   (vii) a $C_{1-6}$ alkoxy-carbonyl group, and
   (viii) a carbamoyl group,
  (3) a $C_{3-10}$ cycloalkyl group,
  (4) a $C_{7-16}$ aralkyl group optionally substituted by 1 to 7 substituents selected from the following (i) to (iii):
   (i) a halogen atom,
   (ii) an optionally halogenated $C_{1-6}$ alkyl group, and
   (iii) a cyano group,
  (5) a 3- to 14-membered non-aromatic heterocyclic group,
  (6) a $C_{1-6}$ alkyl-carbonyl group,
  (7) a $C_{1-6}$ alkoxy group,
  (8) a $C_{1-6}$ alkoxy-carbonyl group,
  (9) a carbamoyl group,
  (10) a cyano group, and
  (11) a halogen atom;
 $R^{5a}$ and $R^{6a}$ are each independently a hydrogen atom or a $C_{1-6}$ alkyl group;
 $R^{5b}$ and $R^{6b}$ are both hydrogen atoms, or $R^{5b}$ and $R^{6b}$ together (i) form a double bond or (ii) form a $C_{3-4}$ cycloalkyl including the carbon atom to which they are mutually bound; and
 either $R^7$ or $R^8$ is a hydrogen atom, and the other is a substituent, wherein the substituent is
 (I) a $C_{6-14}$ aryl group optionally having 1 to 3 substituents selected from the following (i) to (xvii):
  (i) a halogen atom,
  (ii) a cyano group,
  (iii) a hydroxy group,
  (iv) a $C_{1-6}$ alkoxy group optionally having 1 to 3 substituents selected from a halogen atom, a $C_{1-6}$ alkoxy group, a mono- or di-$C_{1-6}$ alkyl-amino group and a $C_{3-10}$ cycloalkyl group,
  (v) a 5- to 14-membered aromatic heterocyclyloxy group,
  (vi) a 3- to 14-membered non-aromatic heterocyclic group optionally having 1 to 5 halogen atoms,
  (vii) a 5- to 14-membered aromatic heterocyclic group optionally having 1 to 3 optionally halogenated $C_{1-6}$ alkyl groups,
  (viii) a 3- to 14-membered non-aromatic heterocyclyl-carbonyl group,
  (ix) a $C_{1-6}$ alkoxy-carbonyl group,
  (x) a carbamoyl group,
  (xi) a $C_{1-6}$ alkylsulfonyl group,
  (xii) a $C_{1-6}$ alkyl-carbonylamino group,
  (xiii) a ($C_{1-6}$ alkyl)($C_{1-6}$ alkyl-carbonyl)amino group,
  (xiv) a $C_{1-6}$ alkylsulfonylamino group,
  (xv) a sulfamoyl group,
  (xvi) a $C_{3-10}$ cycloalkyl group, and
  (xvii) a $C_{1-6}$ alkyl group optionally having 1 to 7 substituents selected from the following (1) to (10):
   (1) a halogen atom,
   (2) a cyano group,
   (3) a hydroxy group,
   (4) a 3- to 14-membered non-aromatic heterocyclic group optionally having 1 to 5 substituents selected from an optionally hydroxy group-substituted $C_{1-6}$ alkyl group, a halogen atom, a hydroxy group, a carboxy group, a carbamoyl group, a $C_{1-6}$ alkoxy group and an oxo group,
   (5) an optionally halogenated $C_{1-6}$ alkoxy group,
   (6) a $C_{1-6}$ alkylsulfonyl group,
   (7) 2-oxa-7-azaspiro[3.5]nonyl or 2-oxa-6-azaspiro[3.3]heptanyl,
   (8) a 5- to 14-membered aromatic heterocyclic group optionally having 1 to 3 substituents selected from an amino group and a $C_{1-6}$ alkyl group,
   (9) a 7- to 10-membered bridged heterocyclic group optionally having 1 to 3 $C_{1-6}$ alkyl groups, and
   (10) an amino group optionally mono- or di-substituted by a substituent selected from the following (a) to (f):
    (a) a $C_{1-6}$ alkyl-carbonyl group,
    (b) a $C_{1-6}$ alkoxy-carbonyl group, (c) a $C_{1-6}$ alkyl group optionally having 1 to 5 substituents selected from a halogen atom, a cyano group, a hydroxy group, a $C_{1-6}$ alkoxy group, a carboxy group, a $C_{1-6}$ alkylsulfonyl group, a $C_{1-6}$ alkyl-carbonylamino group, a $C_{1-6}$ alkyl-sulfamoyl group and a 3- to 14-membered non-aromatic heterocyclic group,
(d) an optionally halogenated $C_{3-10}$ cycloalkyl group,
(e) a 5- to 14-membered aromatic heterocyclic group, and
(f) a 3- to 14-membered non-aromatic heterocyclic group optionally having 1 to 3 substituents selected from a $C_{1-6}$ alkyl group and an oxo group;
(II) a 5- to 14-membered aromatic heterocyclic group optionally having 1 to 3 substituents selected from the following (i) to (iv):
(i) a carbamoyl group,
(ii) an optionally halogenated $C_{1-6}$ alkyl group,
(iii) a $C_{3-10}$ cycloalkyl-$C_{1-6}$ alkyl group, and
(iv) a 3- to 14-membered non-aromatic heterocyclyl-$C_{1-6}$ alkyl group;
(III) a 3- to 14-membered non-aromatic heterocyclic group optionally having 1 to 3 substituents selected from the following (i) to (viii):
(i) a halogen atom,
(ii) an oxo group,
(iii) a $C_{1-6}$ alkyl group optionally having 1 to 5 substituents selected from a halogen atom, a hydroxy group and a $C_{1-6}$ alkoxy group,
(iv) a $C_{3-10}$ cycloalkyl-$C_{1-6}$ alkyl group optionally having 1 to 5 halogen atoms,
(v) an optionally halogenated $C_{1-6}$ alkyl-carbonyl group,
(vi) a $C_{1-6}$ alkoxy-carbonyl group,
(vii) a $C_{3-10}$ cycloalkyl-carbonyl group, and
(viii) a 3- to 14-membered non-aromatic heterocyclyl-carbonyl group optionally having 1 to 3 $C_{1-6}$ alkyl groups;
(IV) a $C_{6-14}$ aryl-$C_{3-10}$ cycloalkyl group;
(V) a $C_{7-16}$ aralkyl group optionally having 1 to 3 substituents selected from the following (i) to (iii):
(i) a cyano group,
(ii) an optionally hydroxy group-substituted $C_{1-6}$ alkyl group, and
(iii) an optionally halogenated $C_{1-6}$ alkoxy group;
(VI) a 5- to 14-membered aromatic heterocyclyl-$C_{1-6}$ alkyl group;
(VII) a 3- to 14-membered non-aromatic heterocyclyl-$C_{1-6}$ alkyl group optionally having 1 to 3 $C_{1-6}$ alkyl groups; or
(VIII) dihydroindenyl or tetrahydronaphthalenyl optionally having a substituent selected from a $C_{1-6}$ alkyl group and an oxo group.

2. (2E)-3-(4-(1-Methyl-1H-pyrazol-4-yl)pyridin-3-yl)-N-(2-(2,2,2-trifluoroethyl)-2,3-dihydro-1H-isoindol-5-yl)acrylamide or a salt thereof.

3. (2E)-3-(4-(1-Cyclopropyl-1H-pyrazol-4-yl)pyridin-3-yl)-N-(4-((3,3-difluoroazetidin-1-yl)methyl)phenyl)acrylamide or a salt thereof.

4. (2E)-3-(4-(1-Cyclopropyl-1H-pyrazol-4-yl)-5-fluoropyridin-3-yl)-N-(2-fluoro-4-((3-methoxyazetidin-1-yl)methyl)phenyl)acrylamide or a salt thereof.

5. (2E)-3-(4-(1-Cyclopropyl-1H-pyrazol-4-yl)-5-fluoropyridin-3-yl)-N-(4-((3-methoxyazetidin-1-yl)methyl)phenyl)acrylamide or a salt thereof.

6. (2E)-N-(4-((3,3-Difluoroazetidin-1-yl)methyl)phenyl)-3-(5-fluoro-4-(1-methyl-1H-pyrazol-4-yl)pyridin-3-yl)acrylamide or a salt thereof.

7. A medicament comprising a compound according to claim 1 or a salt thereof.

8. A method for inhibiting CDK8 and/or CDK19 in a mammal, comprising administering an effective amount of a compound according to claim 1 or a salt thereof to the mammal.

9. A method for treating cancer, comprising administering an effective amount of a compound according to claim 1 or a salt thereof to the mammal, wherein the cancer is selected from the group consisting of colorectal cancer, pancreatic cancer, prostate cancer, sarcoma, and blood cancer.

10. The method of claim 9, wherein the blood cancer is multiple myeloma or leukemia.

* * * * *